United States Patent
Zhao

(10) Patent No.: US 9,603,980 B2
(45) Date of Patent: Mar. 28, 2017

(54) LAYER-BY-LAYER STEREOCOMPLEXED POLYMERS AS DRUG DEPOT CARRIERS OR COATINGS IN MEDICAL DEVICES

(75) Inventor: Jonathon Z. Zhao, Belle Mead, NJ (US)

(73) Assignee: Cardinal Health Switzerland 515 GmbH (CH)

( * ) Notice: Subject to any disclaimer, the term of this patent is extended or adjusted under 35 U.S.C. 154(b) by 1223 days.

(21) Appl. No.: 12/037,307

(22) Filed: Feb. 26, 2008

(65) Prior Publication Data

US 2009/0214615 A1    Aug. 27, 2009

(51) Int. Cl.
   *A61L 31/16* (2006.01)
   *A61L 31/10* (2006.01)

(52) U.S. Cl.
   CPC ........... *A61L 31/16* (2013.01); *A61L 31/10* (2013.01); *A61L 2300/45* (2013.01); *A61L 2300/604* (2013.01); *A61L 2300/61* (2013.01)

(58) Field of Classification Search
   None
   See application file for complete search history.

(56) References Cited

U.S. PATENT DOCUMENTS

| | | | | |
|---|---|---|---|---|
| 6,153,252 | A | * | 11/2000 | Hossainy et al. ............ 427/2.3 |
| 2002/0007209 | A1 | * | 1/2002 | Scheerder et al. ........... 623/1.15 |
| 2003/0068355 | A1 | * | 4/2003 | Shanley et al. ............ 424/426 |
| 2003/0219562 | A1 | * | 11/2003 | Rypacek et al. ........... 428/36.91 |
| 2006/0246108 | A1 | * | 11/2006 | Pacetti et al. ............ 424/426 |
| 2007/0043434 | A1 | | 2/2007 | Meerkin et al. |
| 2008/0014240 | A1 | * | 1/2008 | Gale et al. ............... 424/422 |

FOREIGN PATENT DOCUMENTS

| | | |
|---|---|---|
| JP | 8-33718 | 2/2008 |
| WO | 2007/116646 | 10/2007 |
| WO | 2008008495 | 1/2008 |

OTHER PUBLICATIONS

Serizawa, Takeshi, et al., Macromolecules, 2001, 34, pp. 1996-2001.*
Examiner's Decision of Refusal dated Nov. 25, 2014 in corresponding Japanese Patent Application No. 2009-042284.
Notification of Reasons for Refusal dated Aug. 20, 2014 in corresponding Japanese Patent Application No. 2009-042284.
Office Action dated Apr. 11, 2013 in corresponding Canadian Patent Application No. 2,654,479.
Extended European Search Report dated Aug. 21, 2013 in corresponding European Patent Application No. 09152298.7.
Office Action dated Jun. 12, 2014 in corresponding European Patent Application No. 09152298.7.
Serizawa et al. Stepwise Assemply of Enantiomeric Poly(lactide)s on Surfaces. Macromolecules 2001, vol. 34, No. 6, Mar. 1, 2001, pp. 1996-2001.
Finkelstein et al. "Local Druge Delivery via a Coronary Stent With Programmable Release Pharmacokinetics." Circulation, 2003, vol. 107 No. 5, pp. 777-784.

* cited by examiner

*Primary Examiner* — Dennis J Parad
*Assistant Examiner* — Lyndsey Beckhardt

(57) ABSTRACT

Medical devices, and in particular implantable medical devices, may be coated to minimize or substantially eliminate a biological organism's reaction to the introduction of the medical device to the organism. The medical devices may be coated with any number of biocompatible materials. Therapeutic drugs, agents or compounds may be mixed with the biocompatible materials and affixed to at least a portion of the medical device. These therapeutic agents or compounds may also further reduce a biological organism's reaction to the introduction of the medical device to the organism. In addition, these therapeutic drugs, agents and/or compounds may be utilized to promote healing, including the prevention of thrombosis. The drugs, agents, and/or compounds may also be utilized to treat specific disorders, including vulnerable plaque, and atherosclerosis in type 2 diabetic patients. Therapeutic agents may also be delivered to the region of a disease site. In regional delivery, liquid formulations may be desirable to increase the efficacy and deliverability of the particular drug. Various materials and coating methodologies may be utilized to maintain the agents or compounds on the medical device until delivered and positioned.

4 Claims, 74 Drawing Sheets

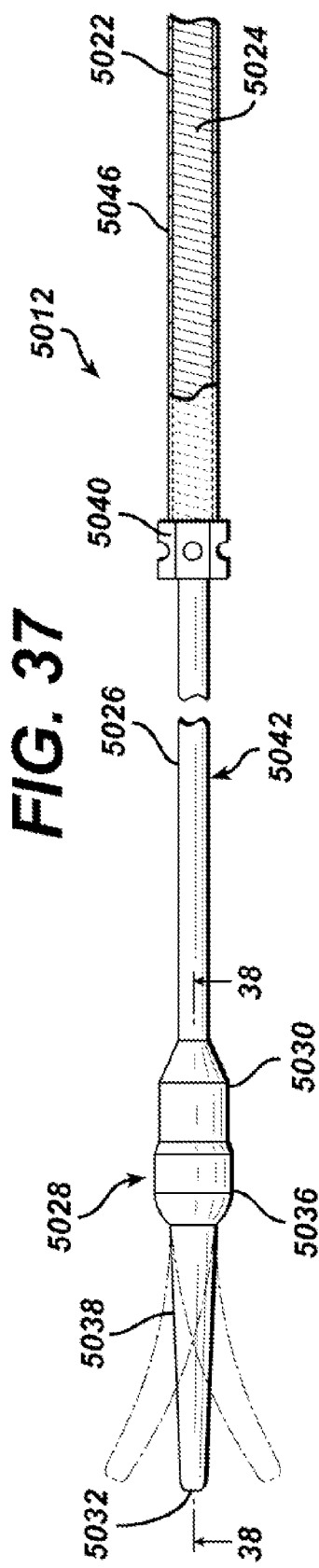
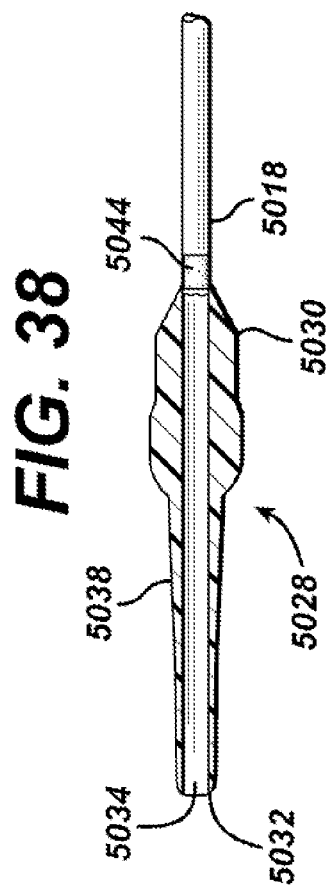
FIG. 37
FIG. 38

Inhibition of CA-SMC proliferation by sirolimus

% Inhibition vs Log [PX-867 (M)], labeled 8707

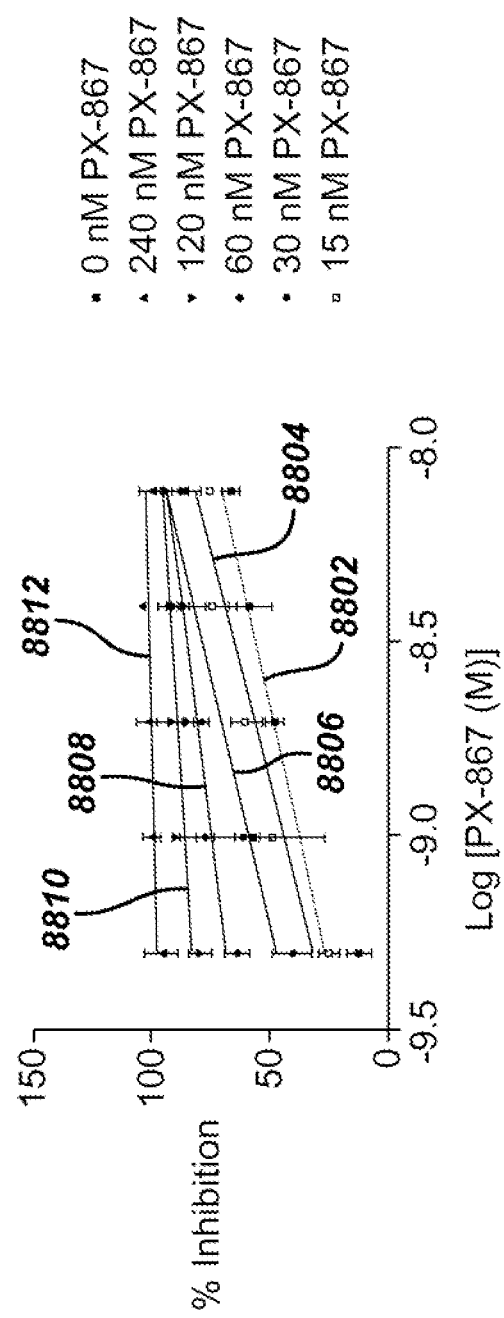

Probucol

Butylated hydroxytoluene

SS or L-lactide

RR or D-lactide

RS or meso-lactide poly (L-lactide)

poly (D-lactide)

LAYER-BY-LAYER STEREOCOMPLEXED POLYMERS AS DRUG DEPOT CARRIERS OR COATINGS IN MEDICAL DEVICES

BACKGROUND OF THE INVENTION

1. Field of the Invention

The present invention relates to the local administration of therapeutic agents and/or therapeutic agent combinations for the prevention and treatment of vascular disease, and more particularly to intraluminal medical devices for the local delivery of therapeutic agents and/or therapeutic agent combinations. The present invention also relates to polymer constructs for optimizing therapeutic agent loading and therapeutic agent release in coated medical devices or medical devices having depots therein.

2. Discussion of the Related Art

Many individuals suffer from circulatory disease caused by a progressive blockage of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans, which are believed to be responsible for maintaining smooth muscle cells in the contractile phenotypic state (Campbell and Campbell, 1985).

Upon pressure expansion of an intracoronary balloon catheter during angioplasty, smooth muscle cells and endothelial cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days' post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed anti-proliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), steroids (Colburn, M. D. et al., J. Vasc. Surg. 15: 510-518, 1992), see also Berk, B. C. et al., J. Am. Coll. Cardiol. 17: 111B-117B, 1991), ionizing radiation (Weinberger, J. et al., lnt. J. Rad. Onc. Biol. Phys. 36: 767-775, 1996), fusion toxins (Farb, A. et al., Circ. Res. 80: 542-550, 1997) antisense oligionucleotides (Simons, M. et al., Nature 359: 67-70, 1992) and gene vectors (Chang, M. W. et al., J. Clin. Invest. 96: 2260-2268, 1995). Anti-proliferative action on smooth muscle cells in vitro has been demonstrated for many of these agents, including heparin and heparin conjugates, taxol, tranilast, colchicine, ACE inhibitors, fusion toxins, antisense oligionucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP $II_b/III_a$ receptor, antagonist, Reopro® is still under study but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxident agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty. In addition, there exists a need for maintaining the drug/drug combinations on the local delivery device through delivery and positioning as well as ensuring that the drug/drug combination is released in therapeutic dosages over a given period of time.

A variety of stent coatings and compositions have been proposed for the prevention and treatment of injury causing intimal thickening. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The mechanism for delivery of the agent is through diffusion of the agent through either a bulk polymer or through pores that are created in the polymer structure, or by erosion of a biodegradable coating.

Both bioabsorbable and biostable compositions have been reported as coatings for stents. They generally have been polymeric coatings that either encapsulate a pharmaceutical/therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

It would be advantageous to develop coatings for implantable medical devices that will reduce thrombosis, restenosis, or other adverse reactions, that may include, but do not require, the use of pharmaceutical or therapeutic agents or drugs to achieve such affects, and that possess physical and mechanical properties effective for use in such devices even when such coated devices are subjected to relatively low maximum temperatures. It would also be advantageous to develop implantable medical devices in combination with various drugs, agents and/or compounds which treat disease and minimize or substantially eliminate a living organisms' reaction to the implantation of the medical device. In certain circumstances, it may be advantageous to develop implantable medical devices in combination with various drugs, agents and/or compounds which promote wound healing and endothelialization of the medical device.

It would also be advantageous to develop delivery devices that provide for the delivery of the coated implantable medical devices without adversely affecting the coating or the medical device itself. In addition, such delivery devices should provide the physician with a means for easily and accurately positioning the medical device in the target area.

It would also be advantageous to develop coatings for implantable medical devices that allow for the precise control of the elution rate of drugs, agents and/or compounds from the implantable medical devices.

It would also be advantageous to develop delivery devices that provide for the release of one or more agents that act through different molecular mechanisms affecting cell proliferation.

It would also be advantageous to develop delivery devices that provide for the regional administration of one or more agents for the treatment of atherosclerotic plaque.

Another type of vascular disease of considerable concern is atherosclerosis. Atherosclerosis is a thickening and hardening of the arteries and is generally believed to be caused by the progressive buildup of fatty substances, e.g. cholesterol, inflammatory cells, cellular waste products, calcium and other substances in the inner lining or intima of the arteries. The buildup of these irritating substances may in turn stimulate cells in the walls of the affected arteries to produce additional substances that result in the further buildup of cells leading to the growth of a lesion. This buildup or lesion is generally referred to as plaque.

Recent studies have lead to a shift in the understanding of atherosclerosis and uncovered another major vascular problem not yet well treated. Scientists theorize that at least some coronary disease is an inflammatory process, in which inflammation causes plaque to destabilize and rupture. This inflamed plaque is known as atherosclerotic vulnerable plaque.

Vulnerable plaque consists of a lipid-rich core covered by a thin layer of smooth muscle cells. These vulnerable plaques are prone to rupture and erosion, and can cause significant infarcts if the thin cellular layer ruptures or ulcerates. When the inflammatory cells erode or rupture, the lipid core is exposed to the blood flow, forming thrombi in the artery. These thrombi may grow rapidly and block the artery, or detach and travel downstream, leading to embolic events, unstable angina, myocardial infarction, and/or sudden death. In fact, some recent studies have suggested that plaque rupture may trigger sixty to seventy percent of all fatal myocardial infarctions. See U.S. Pat. No. 5,924,997 issued to Campbell and U.S. Pat. No. 6,245,026 issued to Campbell et al. for further descriptions of vulnerable plaques.

Early methods used to detect atherosclerosis lacked the diagnostic tools to visualize and identify vulnerable plaque in cardiac patients. However, new diagnostic technologies are under development to identify the location of vulnerable plaques in the coronary arteries. These new devices include refined magnetic resonance imaging (MRI), thermal sensors that measure the temperature of the arterial wall on the premise that the inflammatory process generates heat, elasticity sensors, intravascular ultrasound, optical coherence tomography (OCT), contrast agents, and near-infrared and infrared light. What is not currently clear, however, is how to treat these vulnerable plaque lesions once they are found.

Treating vulnerable plaque by using balloon angioplasty followed by traditional stenting would provide less than satisfactory results. Balloon angioplasty by itself may rupture the vulnerable plaque exposing the underlying fresh tissue cells, collagen or damaged endothelium, to the blood flow. This condition ultimately leads to the formation of a thrombi or blood clot that may partially or completely occlude the vessel. In addition, while bare or uncoated stents will induce neointimal hyperplasia that will provide a protective cover over the vulnerable plaque, restenosis remains a major problem that may create more risk to the patient than the original vulnerable plaque.

Accordingly, it would be advantageous to develop a drug eluting stent or other medical device that effectively treats vulnerable plaque and related vascular disease such as restenosis, abdominal aortic aneurysms and stroke.

Diabetes is a disease in which the body fails to provide enough insulin (type 1 diabetes) or cannot properly use the insulin it makes (type 2 diabetes). Insulin is a hormone that is required to convert sugar, starches and other foods into energy for normal cellular activity or function. In healthy individuals insulin is released or secreted from the beta cells of the Islets of Langerhans, located in the pancreas, after ingesting food and/or drink and it signals insulin-sensitive tissues in the body, for example, muscle, to absorb glucose thereby lowering blood glucose levels in the blood.

Approximately five to ten percent of the population diagnosed with diabetes has type 1 diabetes. As briefly described above and as known in the medical art, type 1 diabetes results from the body's inability to produce enough or even any insulin. Therefore, without sufficient insulin, glucose cannot enter the cells of the body to provide the required metabolic fuel. The remaining ninety to ninety-five percent of the population diagnosed with diabetes have type 2 diabetes. As briefly described above and as known in the medical art, type 2 diabetes results from insulin resistance combined with relative insulin deficiency. Insulin resistance is a condition in which normal amounts of insulin are inadequate to produce a normal insulin response from muscle, liver and fats cells in the body. Insulin resistance in muscle cells reduces glucose uptake and insulin resistance in liver cells reduces glucose storage with the combined effect leading to elevated blood glucose levels resulting in various deleterious effects, including metabolic diseases. Insulin resistance in fat cells results in the hydrolysis of stored triglycerides which elevates free fatty acids in the blood which in turn causes other deleterious effects.

Atherogenic dyslipidemia or diabetic dyslipidemia is a condition associated with insulin resistance that is characterized by high levels of triglycerides, high levels of low-density lipoproteins and low levels of high-density lipoproteins. Evidence suggests that the high levels of triglycerides, the high levels of low-density lipoproteins and the low levels of high-density lipoproteins contribute to atherosclerosis, i.e. fatty buildup in the artery walls. Essentially, atherosclerosis begins with damage to the inner layer or endothelium of the artery and is followed by plaque buildup that may in turn stimulate the cells that comprise the artery to produce substances that may lead to further plaque buildup. The initial damage is at least partially caused by the lipid imbalance described above. This process significantly increases the thickness of the endothelium and may eventually develop to a point where the plaque buildup ruptures. Once the plaque ruptures, there is a chance that blood clots may form and block off the flow of blood through the diseased artery. The lack of blood flow may be to a major organ such as the heart, thereby causing a myocardioinfarction, or the brain, thereby causing a stroke.

Accordingly, it would be advantageous to develop a drug eluting stent or other medical device that effectively treats vascular disease in patients with type 2 diabetes.

Regardless of the disease state and the medical devices utilized for the local and/or regional delivery of the therapeutic agent and/or agents, the therapeutic agent and/or agents should preferably be precisely delivered in the correct therapeutic dosage, over the correct dosing time and at the correct dosing rate. In addition, the therapeutic agent and/or agents, the medical device and the carrier or matrix should preferably be made as biocompatible as possible. Biocompatibility lessens the potential for a reaction by the body to the introduction of the medical device.

Accordingly, it would be advantageous to develop a drug eluting stent or any other drug eluting medical device that ensures the above positive attributes while minimizing potential reactions.

SUMMARY OF THE INVENTION

Drugs, agents or compounds may be affixed to any number of medical devices to treat various diseases. The drugs, agents or compounds may also be affixed to minimize or substantially eliminate the biological organism's reaction to the introduction of the medical device utilized to treat a separate condition. For example, stents may be introduced to open coronary arteries or other body lumens such as biliary ducts. The introduction of these stents cause a smooth muscle cell proliferation effect as well as inflammation. Accordingly, the stents may be coated with drugs, agents or compounds to combat these reactions. Anastomosis devices, routinely utilized in certain types of surgery, may also cause a smooth muscle cell proliferation effect as well as inflammation. Stent-grafts and systems utilizing stent-grafts, for example, aneurysm bypass systems may be coated with drugs, agents and/or compounds which prevent adverse affects caused by the introduction of these devices as well as to promote healing and incorporation. Therefore, the devices may also be coated with drugs, agents and/or compounds to combat these reactions. In addition, devices such as aneurysm bypass systems may be coated with drugs, agents and/or compounds that promote would healing and endothelialization, thereby reducing the risk of endoleaks or other similar phenomena.

The drugs, agents or compounds will vary depending upon the type of medical device, the reaction to the introduction of the medical device and/or the disease sought to be treated. The type of coating or vehicle utilized to immobilize the drugs, agents or compounds to the medical device may also vary depending on a number of factors, including the type of medical device, the type of drug, agent or compound and the rate of release thereof.

In order to be effective, the drugs, agents or compounds should preferably remain on the medical devices during delivery and implantation. Accordingly, various coating techniques for creating strong bonds between the drugs, agents or compounds may be utilized. In addition, various materials may be utilized as surface modifications to prevent the drugs, agents or compounds from coming off prematurely.

The layer-by-layer stereocomplexed polymer construct of the present invention overcomes the disadvantages described above and provides a therapeutic agent and/or agents carrier or coating that is highly biocompatible and allows for controlled release for the therapeutic agent and/or agents.

The present invention utilizes layer-by-layer sterocomplexed biodegradable polymers as therapeutic agent and/or agents depot carriers and/or coatings for medical devices. The use of a layer-by-layer construct of sterocomplexed biodegradable polymers such as poly(D-lactic acid) and poly(L-lactic acid) as a therapeutic agent and/or agents carrier in drug eluting medical devices, for example, drug eluting stents, offer a number of advantages over existing constructs. The identical chemical properties of the two stereo-specific polymers and variable physical properties enable a broader range of therapeutic agent and/or agents stability and release controls. Layered poly(D-lactic acid) and poly(L-lactic acid) would create sterocomplexes in situ and thereby provide a better control of therapeutic agent and/or agents drug release pharmakinetics with a smaller amount of therapeutic agent and/or agents carrier matrix. This may be especially important to medical devices that comprise therapeutic agent and/or agents depots, such as through-holes, to reduce the number of deposition cycles. Changes of the rheologica properties of these sterocomplexed biodegradable polymers makes these materials denser and thus lead to the use of a thinner overall coating. This in turn would improve the long term biocompatibility of the coating. In addition, the use of a comparatively smaller molecular weight sterocomplexed poly(D-lactic acid) and poly(L-lactic acid) preferably achieves the same control of therapeutic agent and/or agents release as compared to the higher molecular weight racemic poly(D-lactic acid). This is turn leads to a shorter resorption time and potentially better biocompatibility of the coating or carrier.

An exemplary process or construct that takes advantage of such sterocomplexes of poly(D-lactic acid) and poly(L-lactic acid) is to mix one of the stereospecific and optically pure poly lactic acids with one or more therapeutic agents and coat at least a portion of the surface of a medical device utilizing any number of known coating methods, such as spray coating, dip coating or ink-jet deposition. Once this first coating is applied and while still "wet" a mixture of the other sterospecifc and optically pure poly lactic acid with opposite optical rotation and the same and/or other therapeutic agent and/or agents is made and applied as a second coating or layer on top of the first layer utilizing any of the known coating techniques described above. These polymers of opposite stereospecificity will bind in situ to form a sterocomplex that holds and releasably controls the elution of the therapeutic agent and/or agents. This layering process may be repeated until a proper or desired therapeutic agent and/or agents loading is achieved. A top layer of any or either of the two optically active polymers or a combination of the polymers may be applied to further regulate the release rate of the therapeutic agent or agents from the coating.

What is described above is only one of a multiplicity of combinations that are possible utilizing this approach or construct. For example, the therapeutic agent and/or agents may be mixed with the polymeric material forming each layer or deposited thereon after the coating is applied. In addition, some layers may not compromise any therapeutic agent and/or agents at all.

In another alternate exemplary embodiment, the combination of poly lactic acids and therapeutic agent or agents may be deposited in a receptacle, well, depot or through-hole in a medical device to accomplish the layer-by-layer therapeutic agents loading configuration described above.

Essentially, the layer-by-layer approach described herein may be utilized in any number of ways, including varying the ratios between the poly(D-lactic acid) and the poly(L-lactic acid), utilizing various combinations of therapeutic agents as described herein, utilizing the layer-by-layer sterocomplex as a drug carrier for coating medical devices, utilizing the layer-by-layer sterocomplex as a top coat and utilizing the layer-by-layer sterocomplex as a therapeutic agent and/or agents carrier for filling openings or reservoirs in medical devices or any combination thereof.

In accordance with one aspect, the resent invention is directed to an implantable medical device. The implantable medical devices comprising a structure configured for implantation in an organ of the body, a first stereospecific and optically pure biodegradable polymer affixed to at least a portion of the structure, and a second stereospecific and optically pure biodegradable polymer having an opposite optical rotation from that of the first stereospecific and optically pure biodegradable polymer, the second stereospecific and optically pure biodegradable polymer being affixed to the first stereospecific and optically pure biodegradable polymer.

In accordance with another aspect, the present invention is directed to a polymer complex. The polymeric complex comprising a layer of a first stereospecific and optically pure biodegradable polymer and a layer of a second stereospecific and optically pure biodegradable polymer affixed to the layer of the first stereospecific and optically pure biodegradable polymer, the second stereospecific and optically pure biodegradable polymer having an opposite optical rotation from that of the first stereospecific and optically pure biodegradable polymer.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 37 is a simplified elevational view of the distal end of the inner shaft made in accordance with the present invention.

FIG. 38 is a cross-sectional view of FIG. 37 taken along lines 38-38.

FIG. 88 is a graphical representation of the percent inhibition of coronary artery smooth muscle cells versus concentration of PX-867 and sirolimus in accordance with the present invention.

DETAILED DESCRIPTION OF THE PREFERRED EMBODIMENTS

Figure 1:
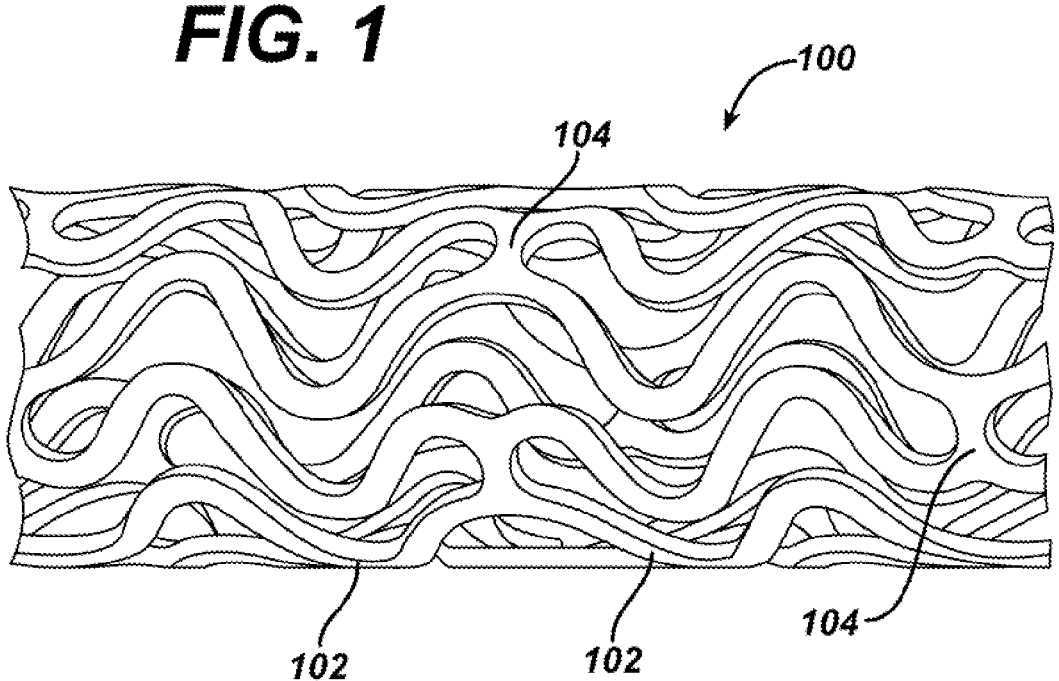
FIG. 1 is a view along the length of a stent (ends not shown) prior to expansion showing the exterior surface of the stent and the characteristic banding pattern.

The drug/drug combinations and delivery devices of the present invention may be utilized to effectively prevent and treat vascular disease, and in particular, vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, as stated above, the procedure typically causes a certain degree of damage to the vessel wall, thereby potentially exacerbating the problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures, including the joining of arteries, veins and other fluid carrying conduits. In addition, various methods and devices will be described for the effective delivery of the coated medical devices.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of drugs, agents or compounds which prevents smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systemic use of drugs, agents or compounds in combination with the local delivery of the same or different drug/drug combinations may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

FIG. 1 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one exemplary embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 2:
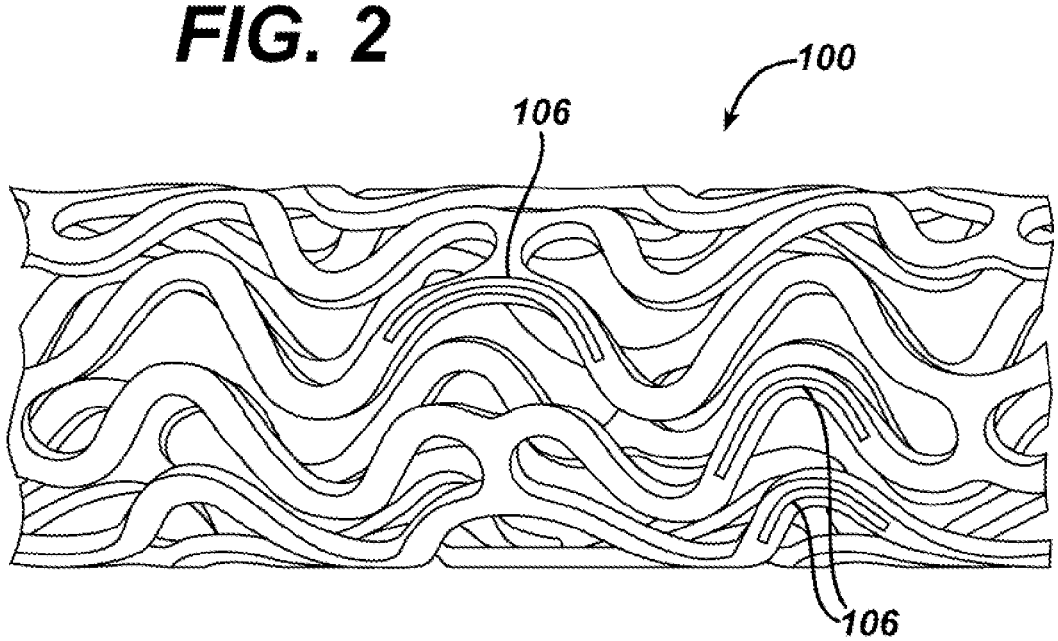
FIG. 2 is a perspective view along the length of the stent of FIG. 1 having reservoirs in accordance with the present invention.

FIG. 2 illustrates an exemplary embodiment of the present invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with drug/drug combinations in therapeutic dosage amounts. A detailed description of a drug for treating restenosis, as well as exemplary coating techniques, is described below. It is, however, important to note that the coating techniques may vary depending on the drug/drug combinations. Also, the coating techniques may vary depending on the material comprising the stent or other intraluminal medical device.

Rapamycin is a macrocyclic triene antibiotic produced by Streptomyces hygroscopicus as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

As used herein, rapamycin includes rapamycin and all analogs, derivatives and conjugates that bind to FKBP12, and other immunophilins and possesses the same pharmacologic properties as rapamycin including inhibition of TOR.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 100, illustrated in FIG. 1, where the stent 100 makes contact with the lumen wall.

Rapamycin may be incorporated onto or affixed to the stent in a number of ways. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months, and more preferably between seven and thirty days.

Any number of non-erodible polymers may be utilized in conjunction with rapamycin. In one exemplary embodiment, the rapamycin or other therapeutic agent may be incorporated into a film-forming polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, wherein the relative amounts of the first moiety and the second moiety are effective to provide the coating and film produced therefrom with properties effective for use in treating implantable medical devices.

The present invention provides polymeric coatings comprising a polyfluoro copolymer and implantable medical devices, for example, stents coated with a film of the polymeric coating in amounts effective to reduce thrombosis and/or restenosis when such stents are used in, for example, angioplasty procedures. As used herein, polyfluoro copolymers means those copolymers comprising an amount of a first moiety selected from the group consisting of polymerized vinylidenefluoride and polymerized tetrafluoroethylene, and an amount of a second moiety other than the first moiety and which is copolymerized with the first moiety to produce the polyfluoro copolymer, the second moiety being capable of providing toughness or elastomeric properties to the polyfluoro copolymer, wherein the relative amounts of the first moiety and the second moiety are effective to provide coatings and film made from such polyfluoro copolymers with properties effective for use in coating implantable medical devices.

The coatings may comprise pharmaceutical or therapeutic agents for reducing restenosis, inflammation, and/or thrombosis, and stents coated with such coatings may provide sustained release of the agents. Films prepared from certain polyfluoro copolymer coatings of the present invention provide the physical and mechanical properties required of conventional coated medical devices, even where maximum temperature, to which the device coatings and films are exposed, are limited to relatively low temperatures. This is particularly important when using the coating/film to deliver pharmaceutical/therapeutic agents or drugs that are heat sensitive, or when applying the coating onto temperature-sensitive devices such as catheters. When maximum exposure temperature is not an issue, for example, where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked by standard methods described in, e.g., *Modern Fluoropolymers*, (J. Shires ed.), John Wiley & Sons, New York, 1997, pp. 77-87.

The present invention comprises polyfluoro copolymers that provide improved biocompatible coatings or vehicles for medical devices. These coatings provide inert biocompatible surfaces to be in contact with body tissue of a mammal, for example, a human, sufficient to reduce restenosis, or thrombosis, or other undesirable reactions. While many reported coatings made from polyfluoro homopolymers are insoluble and/or require high heat, for example, greater than about one hundred twenty-five degrees centigrade, to obtain films with adequate physical and mechanical properties for use on implantable devices, for example, stents, or are not particularly tough or elastomeric, films prepared from the polyfluoro copolymers of the present invention provide adequate adhesion, toughness or elasticity, and resistance to cracking when formed on medical devices. In certain exemplary embodiments, this is the case even where the devices are subjected to relatively low maximum temperatures.

The polyfluoro copolymers used for coatings according to the present invention are preferably film-forming polymers that have molecular weight high enough so as not to be waxy or tacky. The polymers and films formed therefrom should preferably adhere to the stent and not be readily deformable after deposition on the stent as to be able to be displaced by hemodynamic stresses. The polymer molecular weight should preferably be high enough to provide sufficient toughness so that films comprising the polymers will not be rubbed off during handling or deployment of the stent. In certain exemplary embodiments the coating will not crack where expansion of the stent or other medical devices occurs.

Coatings of the present invention comprise polyfluoro copolymers, as defined hereinabove. The second moiety polymerized with the first moiety to prepare the polyfluoro copolymer may be selected from those polymerized, biocompatible monomers that would provide biocompatible polymers acceptable for implantation in a mammal, while maintaining sufficient elastomeric film properties for use on medical devices claimed herein. Such monomers include, without limitation, hexafluoropropylene (HFP), tetrafluoroethylene (TFE), vinylidenefluoride, 1-hydropentafluoropropylene, perfluoro(methyl vinyl ether), chlorotrifluoroethylene (CTFE), pentafluoropropene, trifluoroethylene, hexafluoroacetone and hexafluoroisobutylene.

Polyfluoro copolymers used in the present invention typically comprise vinylidinefluoride copolymerized with hexafluoropropylene, in the weight ratio in the range of from about fifty to about ninety-two weight percent vinylidinefluoride to about fifty to about eight weight percent HFP. Preferably, polyfluoro copolymers used in the present invention comprise from about fifty to about eighty-five weight percent vinylidinefluoride copolymerized with from about fifty to about fifteen weight percent HFP. More preferably, the polyfluoro copolymers will comprise from about fifty-five to about seventy weight percent vinylidinefluoride copolymerized with from about forty-five to about thirty weight percent HFP. Even more preferably, polyfluoro copolymers comprise from about fifty-five to about sixty-five weight percent vinylidinefluoride copolymerized with from about forty-five to about thirty-five weight percent HFP. Such polyfluoro copolymers are soluble, in varying degrees, in solvents such as dimethylacetamide (DMAc), tetrahydrofuran, dimethyl formamide, dimethyl sulfoxide and n-methyl pyrrolidone. Some are soluble in methylethylketone (MEK), acetone, methanol and other solvents commonly used in applying coatings to conventional implantable medical devices.

Conventional polyfluoro homopolymers are crystalline and difficult to apply as high quality films onto metal surfaces without exposing the coatings to relatively high temperatures that correspond to the melting temperature (Tm) of the polymer. The elevated temperature serves to provide films prepared from such PVDF homopolymer coatings that exhibit sufficient adhesion of the film to the device, while preferably maintaining sufficient flexibility to resist film cracking upon expansion/contraction of the coated medical device. Certain films and coatings according to the present invention provide these same physical and mechanical properties, or essentially the same properties, even when the maximum temperatures to which the coatings and films are exposed is less than about a maximum predetermined temperature. This is particularly important when the coatings/films comprise pharmaceutical or therapeutic agents or drugs that are heat sensitive, for example, subject to chemical or physical degradation or other heat-induced negative affects, or when coating heat sensitive substrates of medical devices, for example, subject to heat-induced compositional or structural degradation.

Depending on the particular device upon which the coatings and films of the present invention are to be applied and the particular use/result required of the device, polyfluoro copolymers used to prepare such devices may be crystalline, semi-crystalline or amorphous.

Where devices have no restrictions or limitations with respect to exposure of same to elevated temperatures, crystalline polyfluoro copolymers may be employed. Crystalline polyfluoro copolymers tend to resist the tendency to flow under applied stress or gravity when exposed to temperatures above their glass transition (Tg) temperatures. Crystalline polyfluoro copolymers provide tougher coatings and films than their fully amorphous counterparts. In addition, crystalline polymers are more lubricious and more easily handled through crimping and transfer processes used to mount self-expanding stents, for example, nitinol stents.

Semi-crystalline and amorphous polyfluoro copolymers are advantageous where exposure to elevated temperatures is an issue, for example, where heat-sensitive pharmaceutical or therapeutic agents are incorporated into the coatings and films, or where device design, structure and/or use preclude exposure to such elevated temperatures. Semi-crystalline polyfluoro copolymer elastomers comprising relatively high levels, for example, from about thirty to about forty-five weight percent of the second moiety, for example, HFP, copolymerized with the first moiety, for example, VDF, have the advantage of reduced coefficient of friction and self-blocking relative to amorphous polyfluoro copolymer elastomers. Such characteristics may be of significant value when processing, packaging and delivering medical devices coated with such polyfluoro copolymers. In addition, such polyfluoro copolymer elastomers comprising such relatively high content of the second moiety serves to control the solubility of certain agents, for example, rapamycin, in the polymer and therefore controls permeability of the agent through the matrix.

Polyfluoro copolymers utilized in the present inventions may be prepared by various known polymerization methods. For example, high pressure, free-radical, semi-continuous emulsion polymerization techniques such as those disclosed in *Fluoroelastomers-dependence of relaxation phenomena on compositions*, POLYMER 30, 2180, 1989, by Ajroldi, et al., may be employed to prepare amorphous polyfluoro copolymers, some of which may be elastomers. In addition, free-radical batch emulsion polymerization techniques disclosed herein may be used to obtain polymers that are semi-crystalline, even where relatively high levels of the second moiety are included.

As described above, stents may comprise a wide variety of materials and a wide variety of geometrics. Stents may be made of biocomptible materials, including biostable and bioabsorbable materials. Suitable biocompatible metals include, but are not limited to, stainless steel, tantalum, titanium alloys (including nitinol), and cobalt alloys (including cobalt-chromium nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and blends thereof).

The film-forming biocompatible polymer coatings generally are applied to the stent in order to reduce local turbulence in blood flow through the stent, as well as adverse tissue reactions. The coatings and films formed therefrom also may be used to administer a pharmaceutically active material to the site of the stent placement. Generally, the amount of polymer coating to be applied to the stent will vary depending on, among other possible parameters, the particular polyfluoro copolymer used to prepare the coating, the stent design and the desired effect of the coating. Generally, the coated stent will comprise from about 0.1 to about fifteen weight percent of the coating, preferably from about 0.4 to about ten weight percent. The polyfluoro copolymer coatings may be applied in one or more coating steps, depending on the amount of polyfluoro copolymer to be applied. Different polyfluoro copolymers may be used for different layers in the stent coating. In fact, in certain exemplary embodiments, it is highly advantageous to use a diluted first coating solution comprising a polyfluoro copolymer as a primer to promote adhesion of a subsequent polyfluoro copolymer coating layer that may include pharmaceutically active materials. The individual coatings may be prepared from different polyfluoro copolymers.

Additionally, a top coating may be applied to delay release of the pharmaceutical agent, or they could be used as the matrix for the delivery of a different pharmaceutically active material. Layering of coatings may be used to stage release of the drug or to control release of different agents placed in different layers.

Blends of polyfluoro copolymers may also be used to control the release rate of different agents or to provide a desirable balance of coating properties, i.e. elasticity, toughness, etc., and drug delivery characteristics, for example, release profile. Polyfluoro copolymers with different solubilities in solvents may be used to build up different polymer layers that may be used to deliver different drugs or to control the release profile of a drug. For example, polyfluoro copolymers comprising 85.5/14.5 (wt/wt) of poly(vinylidinefluoride/HFP) and 60.6/39.4 (wt/wt) of poly(vinylidinefluoride/HFP) are both soluble in DMAc. However, only the 60.6/39.4 PVDF polyfluoro copolymer is soluble in methanol. So, a first layer of the 85.5/14.5 PVDF polyfluoro copolymer comprising a drug could be over coated with a topcoat of the 60.6/39.4 PVDF polyfluoro copolymer made with the methanol solvent. The top coating may be used to delay the drug delivery of the drug contained in the first layer. Alternately, the second layer could comprise a different drug to provide for sequential drug delivery. Multiple layers of different drugs could be provided by alternating layers of first one polyfluoro copolymer, then the other. As will be readily appreciated by those skilled in the art, numerous layering approaches may be used to provide the desired drug delivery.

Coatings may be formulated by mixing one or more therapeutic agents with the coating polyfluoro copolymers in a coating mixture. The therapeutic agent may be present as a liquid, a finely divided solid, or any other appropriate physical form. Optionally, the coating mixture may include one or more additives, for example, nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a polyfluoro copolymer coating to modify the release profile. Appropriate relative amounts may be determined by monitoring the in vitro and/or in vivo release profiles for the therapeutic agents.

The best conditions for the coating application are when the polyfluoro copolymer and pharmaceutical agent have a common solvent. This provides a wet coating that is a true solution. Less desirable, yet still usable, are coatings that contain the pharmaceutical agent as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that need to remain essentially free of coating. In cases where a dispersion is applied to the stent and the smoothness of the coating film surface requires improvement, or to be ensured that all particles of the drug are fully encapsulated in the polymer, or in cases where the release rate of the drug is to be slowed, a clear (polyfluoro copolymer only) topcoat of the same polyfluoro copolymer used to provide sustained release of the drug or another polyfluoro copolymer that further restricts the diffusion of the drug out of the coating may be applied. The topcoat may be applied by dip coating with mandrel to clear the slots. This method is disclosed in U.S. Pat. No. 6,153,252. Other methods for applying the topcoat include spin coating and spray coating. Dip coating of the topcoat can be problematic if the drug is very soluble in the coating solvent, which swells the polyfluoro copolymer, and the clear coating solution acts as a zero concentration sink and redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001 percent to about seventy percent of the total coating weight, more typically about 0.001 percent to about sixty percent of the total coating weight. It is possible that the drug may represent as little as 0.0001 percent to the total coating weight.

The quantity and type of polyfluoro copolymers employed in the coating film comprising the pharmaceutic agent will vary depending on the release profile desired and the amount of drug employed. The product may contain blends of the same or different polyfluoro copolymers having different molecular weights to provide the desired release profile or consistency to a given formulation.

Polyfluoro copolymers may release dispersed drug by diffusion. This can result in prolonged delivery (over, say approximately one to two-thousand hours, preferably two to eight-hundred hours) of effective amounts (0.001 $\mu g/cm^2$-min to 1000 $\mu g/cm^2$-min) of the drug. The dosage may be tailored to the subject being treated, the severity of the affliction, the judgment of the prescribing physician, and the like.

Individual formulations of drugs and polyfluoro copolymers may be tested in appropriate in vitro and in vivo models to achieve the desired drug release profiles. For example, a drug could be formulated with a polyfluoro copolymer, or blend of polyfluoro copolymers, coated onto a stent and placed in an agitated or circulating fluid system, for example, twenty-five percent ethanol in water. Samples of the circulating fluid could be taken to determine the release profile (such as by HPLC, UV analysis or use of radiotagged molecules). The release of a pharmaceutical compound from a stent coating into the interior wall of a lumen could be modeled in appropriate animal system. The drug release profile could then be monitored by appropriate means such as, by taking samples at specific times and assaying the samples for drug concentration (using HPLC to detect drug concentration). Thrombus formation can be modeled in animal models using the In-platelet imaging methods described by Hanson and Harker, Proc. Natl. Acad. Sci. USA 85:3184-3188 (1988). Following this or similar procedures, those skilled in the art will be able to formulate a variety of stent coating formulations.

While not a requirement of the present invention, the coatings and films may be crosslinked once applied to the medical devices. Crosslinking may be affected by any of the known crosslinking mechanisms, such as chemical, heat or light. In addition, crosslinking initiators and promoters may be used where applicable and appropriate. In those exemplary embodiments utilizing crosslinked films comprising pharmaceutical agents, curing may affect the rate at which the drug diffuses from the coating. Crosslinked polyfluoro copolymers films and coatings of the present invention also may be used without drug to modify the surface of implantable medical devices.

EXAMPLES

Example 1

A PVDF homopolymer (Solef® 1008 from Solvay Advanced Polymers, Houston, Tex., Tm about 175° C.) and polyfluoro copolymers of poly(vinylidenefluoride/HFP), 92/8 and 91/9 weight percent vinylidenefluoride/HFP as determined by $F^{19}$ NMR, respectively (eg: Solef® 11010 and 11008, Solvay Advanced Polymers, Houston, Tex., Tm about 159 degrees C. and 160 degrees C., respectively) were examined as potential coatings for stents. These polymers are soluble in solvents such as, but not limited to, DMAc, N,N-dimethylformamide (DMF), dimethyl sulfoxide (DMSO), N-methylpyrrolidone (NMP), tetrahydrofuran (THF) and acetone. Polymer coatings were prepared by dissolving the polymers in acetone, at five weight percent as a primer, or by dissolving the polymer in 50/50 DMAc/acetone, at thirty weight percent as a topcoat. Coatings that were applied to the stents by dipping and dried at 60 degrees C. in air for several hours, followed by 60 degrees C. for three hours in a <100 mm Hg vacuum, resulted in white foamy films. As applied, these films adhered poorly to the stent and flaked off, indicating they were too brittle. When stents coated in this manner were heated above 175 degrees C., i.e. above the melting temperature of the polymer, a clear, adherent film was formed. Since coatings require high temperatures, for example, above the melting temperature of the polymer, to achieve high quality films. As mentioned above, the high temperature heat treatment is unacceptable for the majority of drug compounds due to their thermal sensitivity.

Example 2

A polyfluoro copolymer (Solef® 21508) comprising 85.5 weight percent vinylidenefluoride copolymerized with 14.5 weight percent HFP, as determined by $F^{19}$ NMR, was evaluated. This copolymer is less crystalline than the polyfluoro homopolymer and copolymers described in Example 1. It also has a lower melting point reported to be about 133 degrees C. Once again, a coating comprising about twenty weight percent of the polyfluoro copolymer was applied from a polymer solution in 50/50 DMAc/MEK. After drying (in air) at 60 degrees C. for several hours, followed by 60 degrees C. for three hours in a <100 mtorr Hg vacuum, clear adherent films were obtained. This eliminated the need for a high temperature heat treatment to achieve high quality films. Coatings were smoother and more adherent than those of Example 1. Some coated stents that underwent expansion show some degree of adhesion loss and "tenting" as the film pulls away from the metal. Where necessary, modification of coatings containing such copolymers may be made, e.g. by addition of plasticizers or the like to the coating compositions. Films prepared from such coatings may be used to coat stents or other medical devices, particularly where those devices are not susceptible to expansion to the degree of the stents.

The coating process above was repeated, this time with a coating comprising the 85.5/14.6 (wt/wt) (vinylidenefluoride/HFP) and about thirty weight percent of rapamycin (Wyeth-Ayerst Laboratories, Philadelphia, Pa.), based on total weight of coating solids. Clear films that would occasionally crack or peel upon expansion of the coated stents resulted. It is believed that inclusion of plasticizers and the like in the coating composition will result in coatings and films for use on stents and other medical devices that are not susceptible to such cracking and peeling.

Example 3

Polyfluoro copolymers of still higher HFP content were then examined. This series of polymers were not semicrystalline, but rather are marketed as elastomers. One such copolymer is Fluorel™ FC2261Q (from Dyneon, a 3M-Hoechst Enterprise, Oakdale, Minn.), a 60.6/39.4 (wt/wt) copolymer of vinylidenefluoride/HFP. Although this copolymer has a Tg well below room temperature (Tg about minus twenty degrees C.) it is not tacky at room temperature or even at sixty degrees C. This polymer has no detectable crystallinity when measured by Differential Scanning Calorimetry (DSC) or by wide angle X-ray diffraction. Films formed on stents as described above were non-tacky, clear, and expanded without incident when the stents were expanded.

The coating process above was repeated, this time with coatings comprising the 60.6/39.4 (wt/wt) (vinylidenefluoride/HFP) and about nine, thirty and fifty weight percent of rapamycin (Wyeth-Ayerst Laboratories, Philadelphia, Pa.), based on total weight of coating solids, respectively. Coatings comprising about nine and thirty weight percent rapamycin provided white, adherent, tough films that expanded without incident on the stent. Inclusion of fifty percent drug, in the same manner, resulted in some loss of adhesion upon expansion.

Changes in the comonomer composition of the polyfluoro copolymer also can affect the nature of the solid state coating, once dried. For example, the semicrystalline copolymer, Solef® 21508, containing 85.5 percent vinylidenefluoride polymerized with 14.5 percent by weight HFP forms homogeneous solutions with about 30 percent rapamycin (drug weight divided by total solids weight, for example, drug plus copolymer) in DMAc and 50/50 DMAc/MEK. When the film is dried (60 degrees C./16 hours followed by 60 degrees C./3 hours in vacuum of 100 mm Hg) a clear coating, indicating a solid solution of the drug in the polymer, is obtained. Conversely, when an amorphous copolymer, Fluorel™ FC2261Q, of PDVF/HFP at 60.6/39.5 (wt/wt) forms a similar thirty percent solution of rapamycin in DMAc/MEK and is similarly dried, a white film, indicating phase separation of the drug and the polymer, is obtained. This second drug containing film is much slower to release the drug into an in vitro test solution of twenty-five percent ethanol in water than is the former clear film of crystalline Solef® 21508. X-ray analysis of both films indicates that the drug is present in a non-crystalline form. Poor or very low solubility of the drug in the high HFP containing copolymer results in slow permeation of the drug through the thin coating film. Permeability is the product of diffusion rate of the diffusing species (in this case the drug) through the film (the copolymer) and the solubility of the drug in the film.

Example 4

In Vitro Release Results of Rapamycin from Coating

Figure 3:
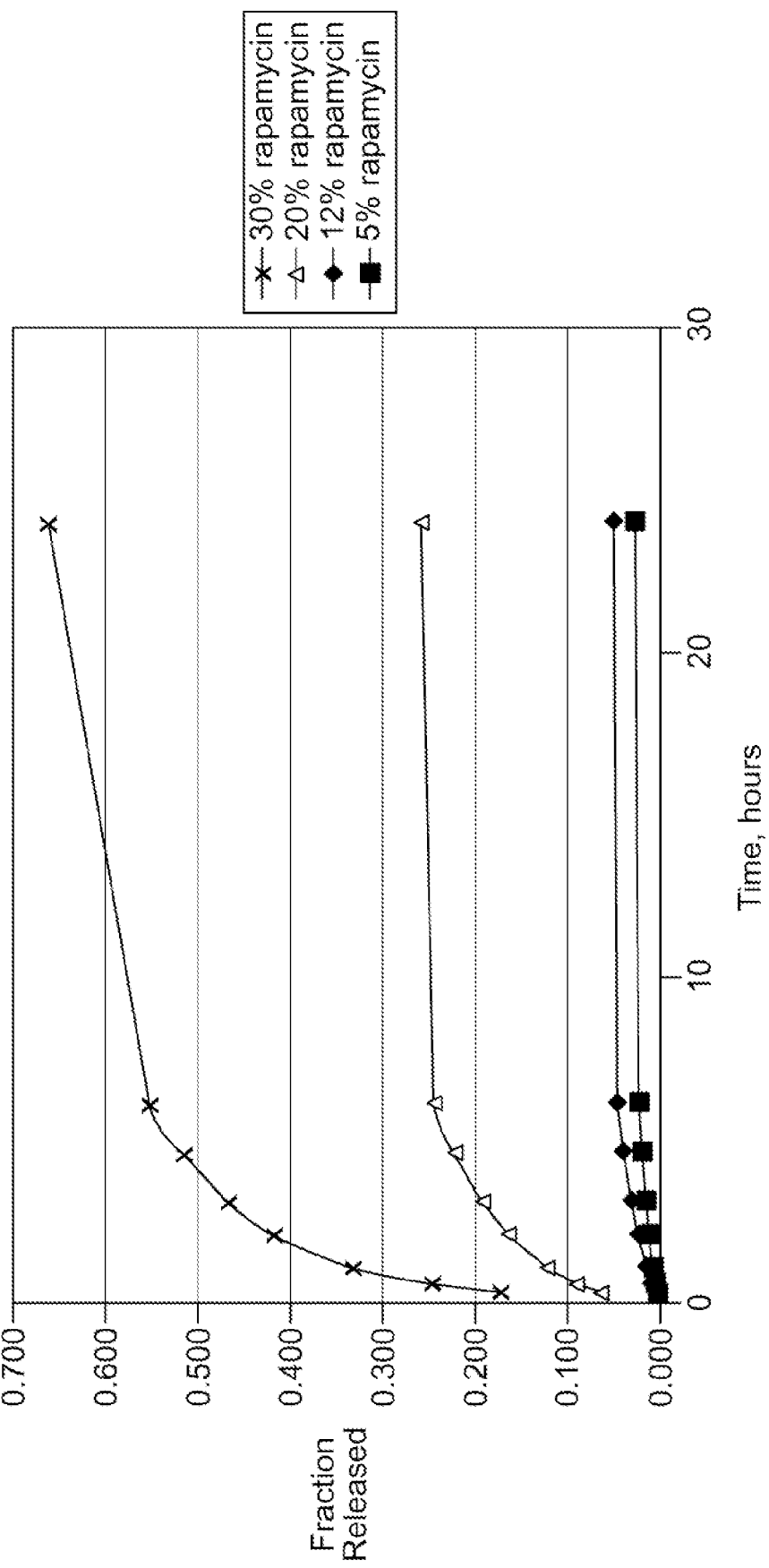
FIG. 3 indicates the fraction of drug released as a function of time from coatings of the present invention over which no topcoat has been disposed.
Figure 4:
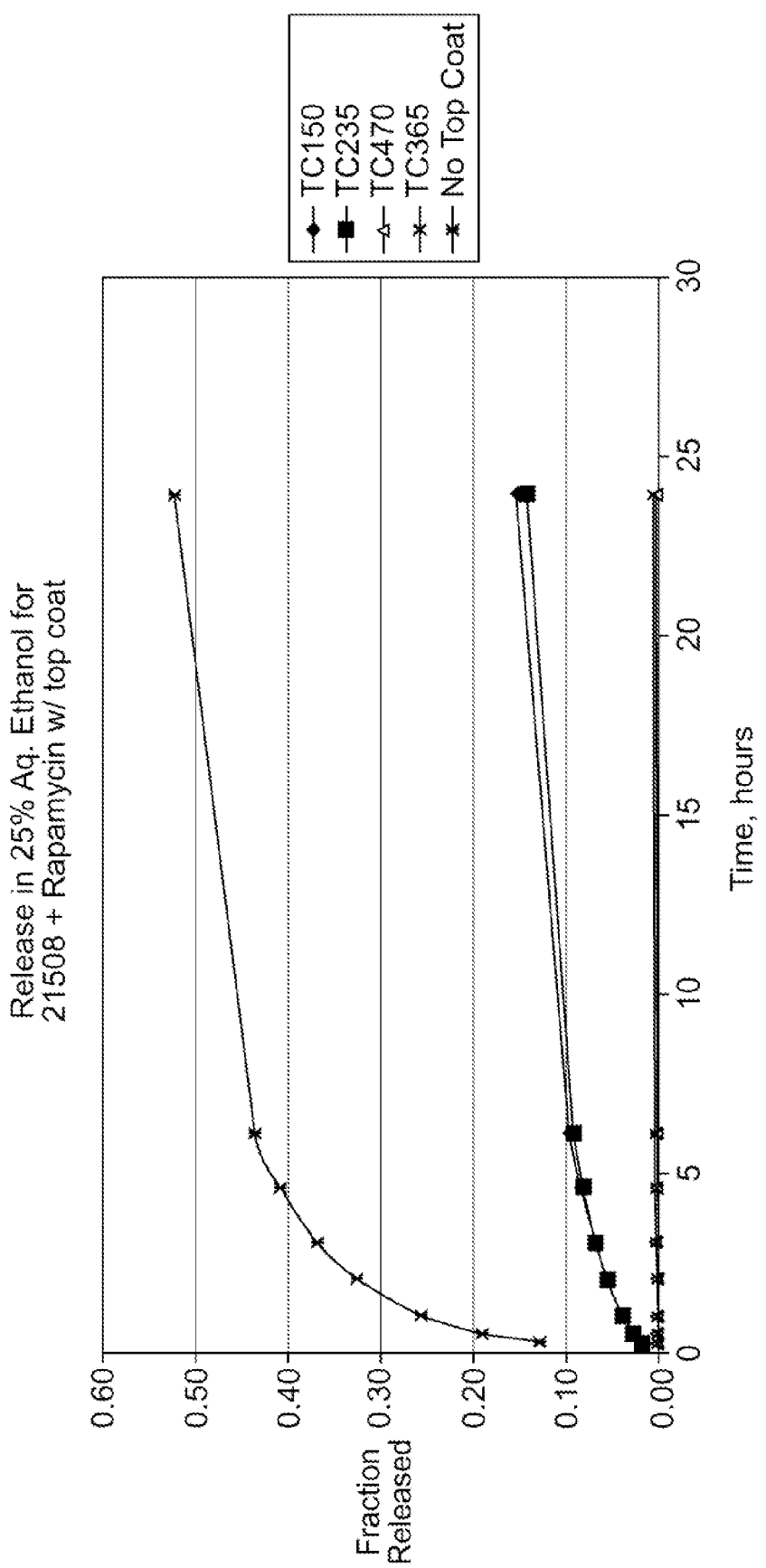
FIG. 4 indicates the fraction of drug released as a function of time from coatings of the present invention including a topcoat disposed thereon.
Figure 5:
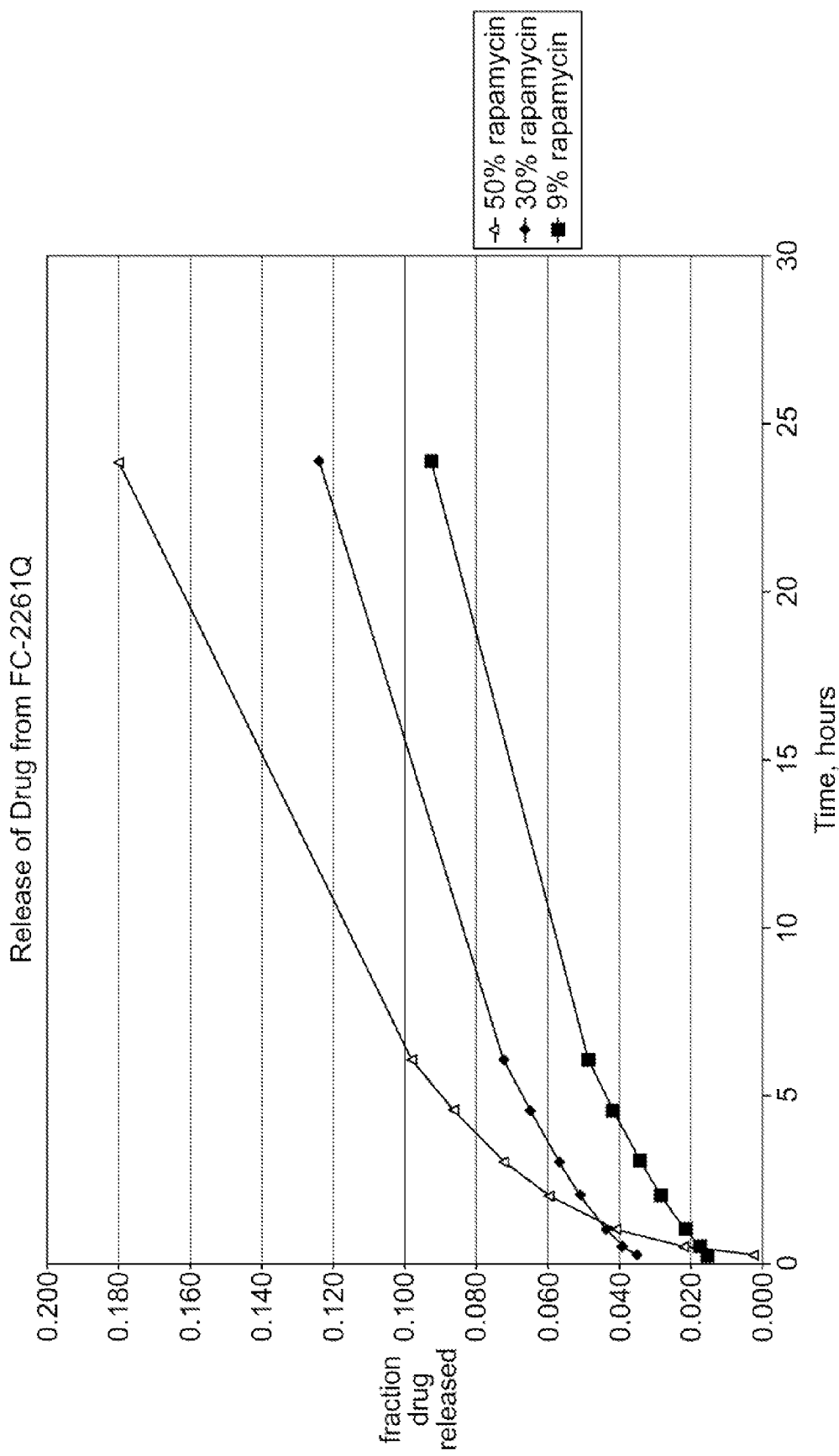
FIG. 5 indicates the fraction of drug released as a function of time from coatings of the present invention over which no topcoat has been disposed.
Figure 6:
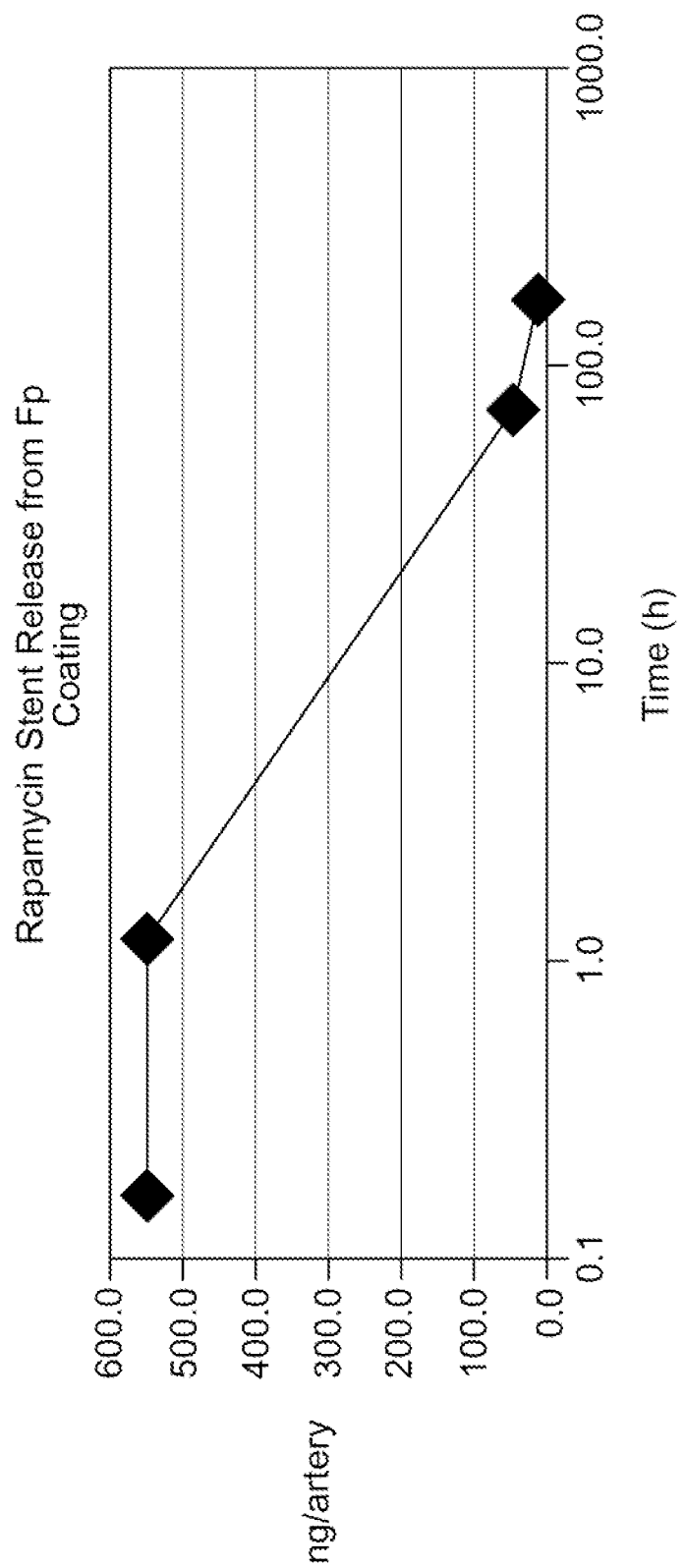
FIG. 6 indicates in vivo stent release kinetics of rapamycin from poly(VDF/HFP).

FIG. 3 is a plot of data for the 85.5/14.5 vinylidenefluoride/HFP polyfluoro copolymer, indicating fraction of drug released as a function of time, with no topcoat. FIG. 4 is a plot of data for the same polyfluoro copolymer over which a topcoat has been disposed, indicating that most effect on release rate is with a clear topcoat. As shown therein, TC150 refers to a device comprising one hundred fifty micrograms of topcoat, TC235 refers to two hundred thirty-five micrograms of topcoat, etc. The stents before topcoating had an average of seven hundred fifty micrograms of coating containing thirty percent rapamycin. FIG. 5 is a plot for the 60.6/39.4 vinylidenefluoride/HFP polyfluoro copolymer, indicating fraction of drug released as a function of time, showing significant control of release rate from the coating without the use of a topcoat. Release is controlled by loading of drug in the film.

Example 5

In Vivo Stent Release Kinetics of Rapamycin from Poly(VDF/HFP)

Nine New Zealand white rabbits (2.5-3.0 kg) on a normal diet were given aspirin twenty-four hours prior to surgery, again just prior to surgery and for the remainder of the study. At the time of surgery, animals were premedicated with Acepromazine (0.1-0.2 mg/kg) and anesthetized with a Ketamine/Xylazine mixture (40 mg/kg and 5 mg/kg, respectively). Animals were given a single intraprocedural dose of heparin (150 IU/kg, i.v.)

Arteriectomy of the right common carotid artery was performed and a 5 F catheter introducer (Cordis, Inc.) placed in the vessel and anchored with ligatures. Iodine contrast agent was injected to visualize the right common carotid artery, brachlocephalic trunk and aortic arch. A steerable guide wire (0.014 inch/180 cm, Cordis, Inc.) was inserted via the introducer and advanced sequentially into each iliac artery to a location where the artery possesses a diameter closest to 2 mm using the angiographic mapping done previously. Two stents coated with a film made of poly (VDF/HFP):(60.6/39.4) with thirty percent rapamycin were deployed in each animal where feasible, one in each iliac artery, using 3.0 mm balloon and inflation to 8-10 ATM for thirty seconds followed after a one minute interval by a second inflation to 8-10 ATM for thirty seconds. Follow-up angiographs visualizing both iliac arteries are obtained to confirm correct deployment position of the stent.

At the end of procedure, the carotid artery was ligated and the skin is closed with 3/0 vicryl suture using a one layered interrupted closure. Animals were given butoropanol (0.4 mg/kg, s.c.) and gentamycin (4 mg/kg, i.m.). Following recovery, the animals were returned to their cages and allowed free access to food and water.

Due to early deaths and surgical difficulties, two animals were not used in this analysis. Stented vessels were removed from the remaining seven animals at the following time points: one vessel (one animal) at ten minutes post implant; six vessels (three animals) between forty minutes and two hours post-implant (average, 1.2 hours); two vessels (two animals) at three days post implant; and two vessels (one animal) at seven days post-implant. In one animal at two hours, the stent was retrieved from the aorta rather than the iliac artery. Upon removal, arteries were carefully trimmed at both the proximal and distal ends of the stent. Vessels were then carefully dissected free of the stent, flushed to remove any residual blood, and both stent and vessel frozen immediately, wrapped separately in foil, labeled and kept frozen at minus eighty degrees C. When all samples had been collected, vessels and stents were frozen, transported and subsequently analyzed for rapamycin in tissue and results are illustrated in FIG. 4.

Example 6

Purifying the Polymer

The Fluorel™ FC2261Q copolymer was dissolved in MEK at about ten weight percent and was washed in a 50/50 mixture of ethanol/water at a 14:1 of ethanol/water to MEK solution ratio. The polymer precipitated out and was separated from the solvent phase by centrifugation. The polymer again was dissolved in MEK and the washing procedure repeated. The polymer was dried after each washing step at sixty degrees C. in a vacuum oven (<200 mtorr) over night.

Example 7

In Vivo Testing of Coated Stents in Porcine Coronary Arteries

CrossFlex® stents (available from Cordis, a Johnson & Johnson Company) were coated with the "as received" Fluorel™ FC2261Q PVDF copolymer and with the purified polyfluoro copolymer of Example 6, using the dip and wipe approach. The coated stents were sterilized using ethylene oxide and a standard cycle. The coated stents and bare metal stents (controls) were implanted in porcine coronary arteries, where they remained for twenty-eight days.

Angiography was performed on the pigs at implantation and at twenty-eight days. Angiography indicated that the control uncoated stent exhibited about twenty-one percent restenosis. The polyfluoro copolymer "as received" exhibited about twenty-six percent restenosis (equivalent to the control) and the washed copolymer exhibited about 12.5 percent restenosis.

Histology results reported neointimal area at twenty-eight days to be 2.89±0.2, 3.57±0.4 and 2.75±0.3, respectively, for the bare metal control, the unpurified copolymer and the purified copolymer.

Since rapamycin acts by entering the surrounding tissue, it s preferably only affixed to the surface of the stent making contact with one tissue. Typically, only the outer surface of the stent makes contact with the tissue. Accordingly, in one exemplary embodiment, only the outer surface of the stent is coated with rapamycin.

The circulatory system, under normal conditions, has to be self-sealing, otherwise continued blood loss from an injury would be life threatening. Typically, all but the most catastrophic bleeding is rapidly stopped though a process known as hemostasis. Hemostasis occurs through a progression of steps. At high rates of flow, hemostasis is a combination of events involving platelet aggregation and fibrin formation. Platelet aggregation leads to a reduction in the blood flow due to the formation of a cellular plug while a cascade of biochemical steps leads to the formation of a fibrin clot.

Fibrin clots, as stated above, form in response to injury. There are certain circumstances where blood clotting or clotting in a specific area may pose a health risk. For example, during percutaneous transluminal coronary angioplasty, the endothelial cells of the arterial walls are typically injured, thereby exposing the sub-endothelial cells. Platelets adhere to these exposed cells. The aggregating platelets and the damaged tissue initiate further biochemical process resulting in blood coagulation. Platelet and fibrin blood clots may prevent the normal flow of blood to critical areas. Accordingly, there is a need to control blood clotting in various medical procedures. Compounds that do not allow blood to clot are called anti-coagulants. Essentially, an anti-coagulant is an inhibitor of thrombin formation or function. These compounds include drugs such as heparin and hirudin. As used herein, heparin includes all direct or indirect inhibitors of thrombin or Factor Xa.

In addition to being an effective anti-coagulant, heparin has also been demonstrated to inhibit smooth muscle cell growth in vivo. Thus, heparin may be effectively utilized in conjunction with rapamycin in the treatment of vascular disease. Essentially, the combination of rapamycin and heparin may inhibit smooth muscle cell growth via two different mechanisms in addition to the heparin acting as an anti-coagulant.

Because of its multifunctional chemistry, heparin may be immobilized or affixed to a stent in a number of ways. For example, heparin may be immobilized onto a variety of surfaces by various methods, including the photolink methods set forth in U.S. Pat. Nos. 3,959,078 and 4,722,906 to Guire et al. and U.S. Pat. Nos. 5,229,172; 5,308,641; 5,350,800 and 5,415,938 to Cahalan et al. Heparinized surfaces have also been achieved by controlled release from a polymer matrix, for example, silicone rubber, as set forth in U.S. Pat. Nos. 5,837,313; 6,099,562 and 6,120,536 to Ding et al.

Unlike rapamycin, heparin acts on circulating proteins in the blood and heparin need only make contact with blood to be effective. Accordingly, if used in conjunction with a medical device, such as a stent, it would preferably be only on the side that comes into contact with the blood. For example, if heparin were to be administered via a stent, it would only have to be on the inner surface of the stent to be effective.

Figure 7:
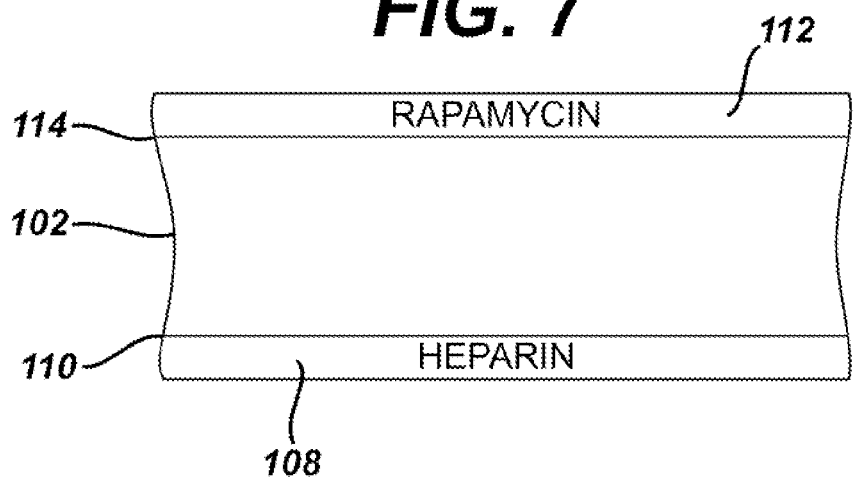
FIG. 7 is a cross-sectional view of a band of the stent of FIG. 1 having drug coatings thereon in accordance with a first exemplary embodiment of the invention.

In an exemplary embodiment of the invention, a stent may be utilized in combination with rapamycin and heparin to treat vascular disease. In this exemplary embodiment, the heparin is immobilized to the inner surface of the stent so that it is in contact with the blood and the rapamycin is immobilized to the outer surface of the stent so that it is in contact with the surrounding tissue. FIG. 7 illustrates a cross-section of a band 102 of the stent 100 illustrated in FIG. 1. As illustrated, the band 102 is coated with heparin 108 on its inner surface 110 and with rapamycin 112 on its outer surface 114.

Figure 8:
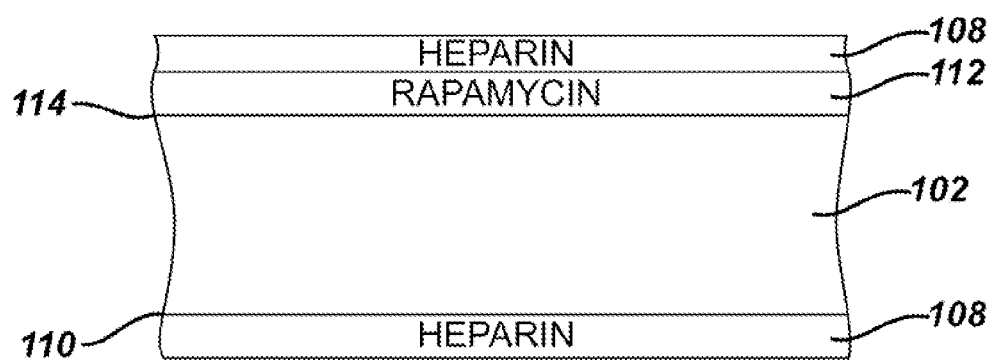
FIG. 8 is a cross-sectional view of a band of the stent of FIG. 1 having drug coatings thereon in accordance with a second exemplary embodiment of the invention.

In an alternate exemplary embodiment, the stent may comprise a heparin layer immobilized on its inner surface, and rapamycin and heparin on its outer surface. Utilizing current coating techniques, heparin tends to form a stronger bond with the surface it is immobilized to then does rapamycin. Accordingly, it may be possible to first immobilize the rapamycin to the outer surface of the stent and then immobilize a layer of heparin to the rapamycin layer. In this embodiment, the rapamycin may be more securely affixed to the stent while still effectively eluting from its polymeric matrix, through the heparin and into the surrounding tissue. FIG. 8 illustrates a cross-section of a band 102 of the stent 100 illustrated in FIG. 1. As illustrated, the band 102 is coated with heparin 108 on its inner surface 110 and with rapamycin 112 and heparin 108 on its outer surface 114.

Figure 9:
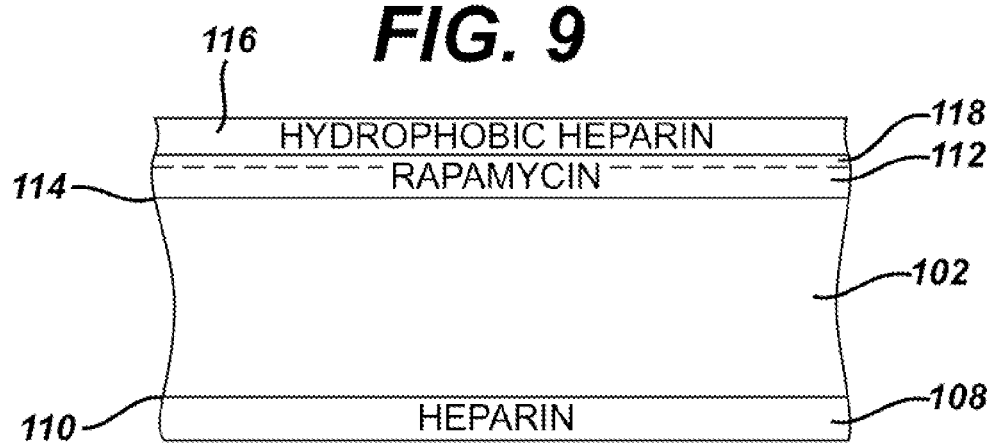
FIG. 9 is a cross-sectional view of a band of the stent of FIG. 1 having drug coatings thereon in accordance with a third exemplary embodiment of the present invention.
Figure 10:
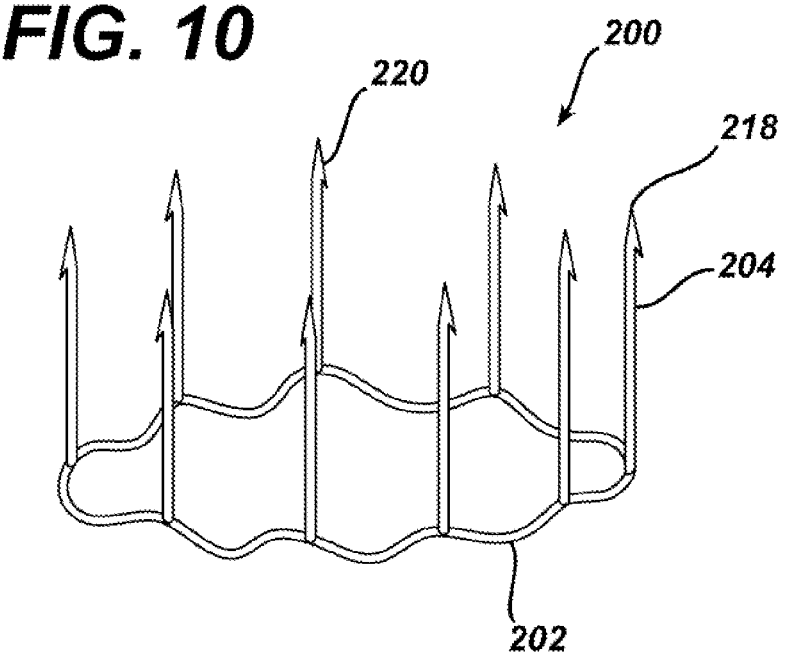
FIGS. 10-13 illustrate an exemplary one-piece embodiment of an anastomosis device having a fastening flange and attached staple members in accordance with the present invention.
Figure 11:
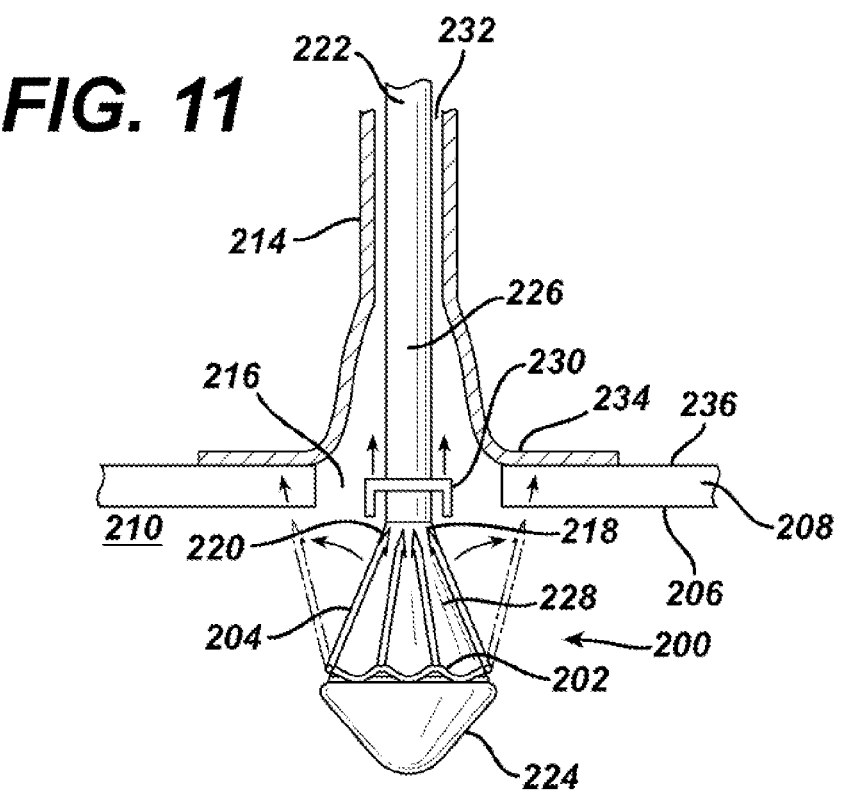
Figure 12:
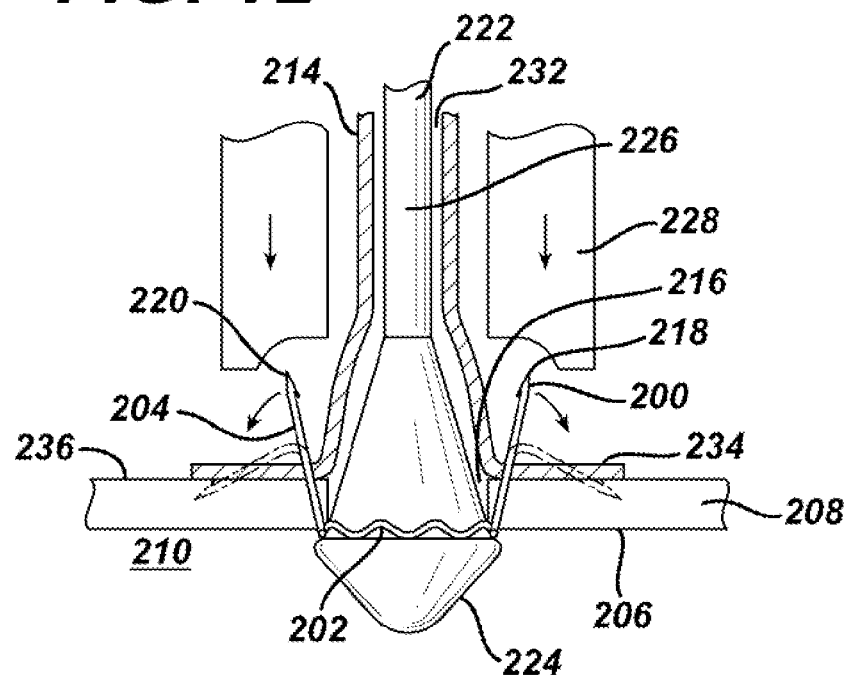
Figure 13:
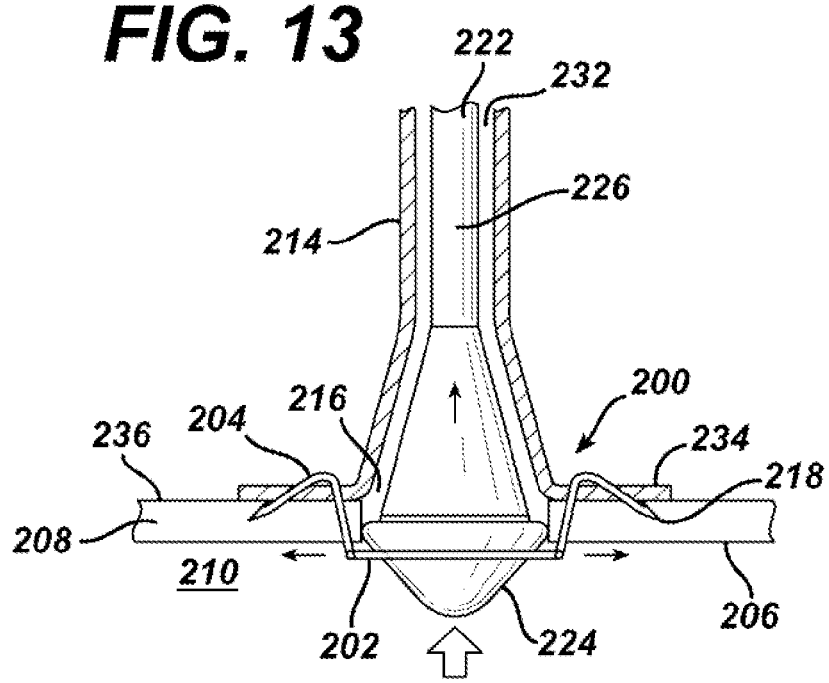

There are a number of possible ways to immobilize, i.e., entrapment or covalent linkage with an erodible bond, the heparin layer to the rapamycin layer. For example, heparin may be introduced into the top layer of the polymeric matrix. In other embodiments, different forms of heparin may be directly immobilized onto the top coat of the polymeric matrix, for example, as illustrated in FIG. 9. As illustrated, a hydrophobic heparin layer 116 may be immobilized onto the top coat layer 118 of the rapamycin layer 112. A hydrophobic form of heparin is utilized because rapamycin and heparin coatings represent incompatible coating application technologies. Rapamycin is an organic solvent-based coating and heparin, in its native form, is a water-based coating.

As stated above, a rapamycin coating may be applied to stents by a dip, spray or spin coating method, and/or any combination of these methods. Various polymers may be utilized. For example, as described above, poly(ethylene-co-vinyl acetate) and polybutyl methacrylate blends may be utilized. Other polymers may also be utilized, but not limited to, for example, polyvinylidene fluoride-co-hexafluoropropylene and polyethylbutyl methacrylate-co-hexyl methacrylate. Also as described above, barrier or top coatings may also be applied to modulate the dissolution of rapamycin from the polymer matrix. In the exemplary embodiment described above, a thin layer of heparin is applied to the surface of the polymeric matrix. Because these polymer systems are hydrophobic and incompatible with the hydrophilic heparin, appropriate surface modifications may be required.

The application of heparin to the surface of the polymeric matrix may be performed in various ways and utilizing various biocompatible materials. For example, in one embodiment, in water or alcoholic solutions, polyethylene imine may be applied on the stents, with care not to degrade the rapamycin (e.g., pH<7, low temperature), followed by the application of sodium heparinate in aqueous or alcoholic solutions. As an extension of this surface modification, covalent heparin may be linked on polyethylene imine using amide-type chemistry (using a carbondiimide activator, e.g. EDC) or reductive amination chemistry (using CBAS-heparin and sodium cyanoborohydride for coupling). In another exemplary embodiment, heparin may be photolinked on the surface, if it is appropriately grafted with photo initiator moieties. Upon application of this modified heparin formulation on the covalent stent surface, light exposure causes cross-linking and immobilization of the heparin on the coating surface. In yet another exemplary embodiment, heparin may be complexed with hydrophobic quaternary ammonium salts, rendering the molecule soluble in organic solvents (e.g. benzalkonium heparinate, troidodecylmethylammonium heparinate). Such a formulation of heparin may be compatible with the hydrophobic rapamycin coating, and may be applied directly on the coating surface, or in the rapamycin/hydrophobic polymer formulation.

It is important to note that the stent, as described above, may be formed from any number of materials, including various metals, polymeric materials and ceramic materials. Accordingly, various technologies may be utilized to immobilize the various drugs, agent, compound combinations thereon. Specifically, in addition to the polymeric matricies described above biopolymers may be utilized. Biopolymers may be generally classified as natural polymers, while the above-described polymers may be described as synthetic polymers. Exemplary biopolymers, which may be utilized include, agarose, alginate, gelatin, collagen and elastin. In addition, the drugs, agents or compounds may be utilized in conjunction with other percutaneously delivered medical devices such as grafts and profusion balloons.

In addition to utilizing an anti-proliferative and anti-coagulant, anti-inflammatories may also be utilized in combination therewith. One example of such a combination would be the addition of an anti-inflammatory corticosteroid such as dexamethasone with an anti-proliferative, such as rapamycin, cladribine, vincristine, taxol, or a nitric oxide donor and an anti-coagulant, such as heparin. Such combination therapies might result in a better therapeutic effect, i.e., less proliferation as well as less inflammation, a stimulus for proliferation, than would occur with either agent alone. The delivery of a stent comprising an anti-proliferative, anti-coagulant, and an anti-inflammatory to an injured vessel would provide the added therapeutic benefit of limiting the degree of local smooth muscle cell proliferation, reducing a stimulus for proliferation, i.e., inflammation and reducing the effects of coagulation thus enhancing the restenosis-limiting action of the stent.

In other exemplary embodiments of the inventions, growth factor inhibitor or cytokine signal transduction inhibitor, such as the ras inhibitor, R115777, or P38 kinase inhibitor, RWJ67657, or a tyrosine kinase inhibitor, such as tyrphostin, might be combined with an anti-proliferative agent such as taxol, vincristine or rapamycin so that proliferation of smooth muscle cells could be inhibited by different mechanisms. Alternatively, an anti-proliferative agent such as taxol, vincristine or rapamycin could be combined with an inhibitor of extracellular matrix synthesis such as halofuginone. In the above cases, agents acting by different mechanisms could act synergistically to reduce smooth muscle cell proliferation and vascular hyperplasia. This invention is also intended to cover other combinations of two or more such drug agents. As mentioned above, such drugs, agents or compounds could be administered systemically, delivered locally via drug delivery catheter, or formulated for delivery from the surface of a stent, or given as a combination of systemic and local therapy.

In addition to anti-proliferatives, anti-inflammatories and anti-coagulants, other drugs, agents or compounds may be utilized in conjunction with the medical devices. For example, immunosuppressants may be utilized alone or in combination with these other drugs, agents or compounds. Also gene therapy delivery mechanisms such as modified genes (nucleic acids including recombinant DNA) in viral vectors and non-viral gene vectors such as plasmids may also be introduced locally via a medical device. In addition, the present invention may be utilized with cell based therapy.

In addition to all of the drugs, agents, compounds and modified genes described above, chemical agents that are not ordinarily therapeutically or biologically active may also be utilized in conjunction with the present invention. These chemical agents, commonly referred to as pro-drugs, are agents that become biologically active upon their introduction into the living organism by one or more mechanisms. These mechanisms include the addition of compounds supplied by the organism or the cleavage of compounds from the agents caused by another agent supplied by the organism. Typically, pro-drugs are more absorbable by the organism. In addition, pro-drugs may also provide some additional measure of time release.

As stated above, rapamycin may be utilized alone or in combination with one or more drugs, agents and/or compounds for the prevention of restenosis following vascular injury.

Histone proteins are part of cellular chromatin that aid in the packaging of DNA and transcription of genes. Several histone proteins exist, each expressing net positive charges capable of interacting with anionic DNA. These histone proteins form nucleosome subunits around which DNA is wound. Chemical modification of the histones through acetylation/deacetylation by acetyltransferase and deacetylase enzymes as well as other post-translational modifications help regulate the shape of the histone proteins, and subsequently, the accessibility of DNA to transcription enzymes. In resting cells, gene transcription is, at least in part, regulated by a balance of acetylation (transcription ON) and deacetylation (transcription OFF) of histone proteins that bind to DNA. Therefore, affecting the balance between acetylation and deacetylation can ultimately impact gene transcription, and subsequently, cell proliferation as proliferative pathways depend to a significant degree on gene transcription. Histone deacetylase are of two general classes, RPd3-like and Hda1-like proteins.

Other drugs, agents and or compounds that may be utilized include other histone deacetylase inhibitors, which include trichostatin A, its analogs and derivatives as well as similar agents. These agents include short-chain fatty acids, such as butyrate, phenylbutyrate and valproate, hydroxamic acids, such as trichostatins, SAHA and its derivatives, oxamflatin, ABHA, scriptaid, pyroxamide, and propenamides, epoxyketone-containing cyclic tetrapeptides, such as trapoxins, HC-toxin, chlamydocin, diheteropeptin, WF-3161 and Cyl-1 and Cyl-2, non-epoxyketone-containing cyclic tetrapeptides such as, FR901228 and apicidin, benzamides, such as MS-275 (MS-27-275), CI-994 and other benzamide analogs, and various miscellaneous structures, such as depudecin and organosulfur compounds.

Trichostatin A is a histone deacetylase inhibitor that arrests tumor cell proliferation predominantly in the G1 and G2 phases of the cell cycle. The G1 and G2 phases of the cell cycle are the phases characterized by gene transcription. The anti-proliferative activity and point of cell cycle arrest profile of trichostatin A have been characterized primarily in tumor cell lines with anti-proliferative IC50's in the low nM range (Woo et al., *J. Med Chem*, 45: 2877-2885, 2002). In addition, trichostatin A has been shown to have anti-angiogenic activity (Deroanne et al., Oncogene 21 (3): 427-436, 2002).

Figure 51:
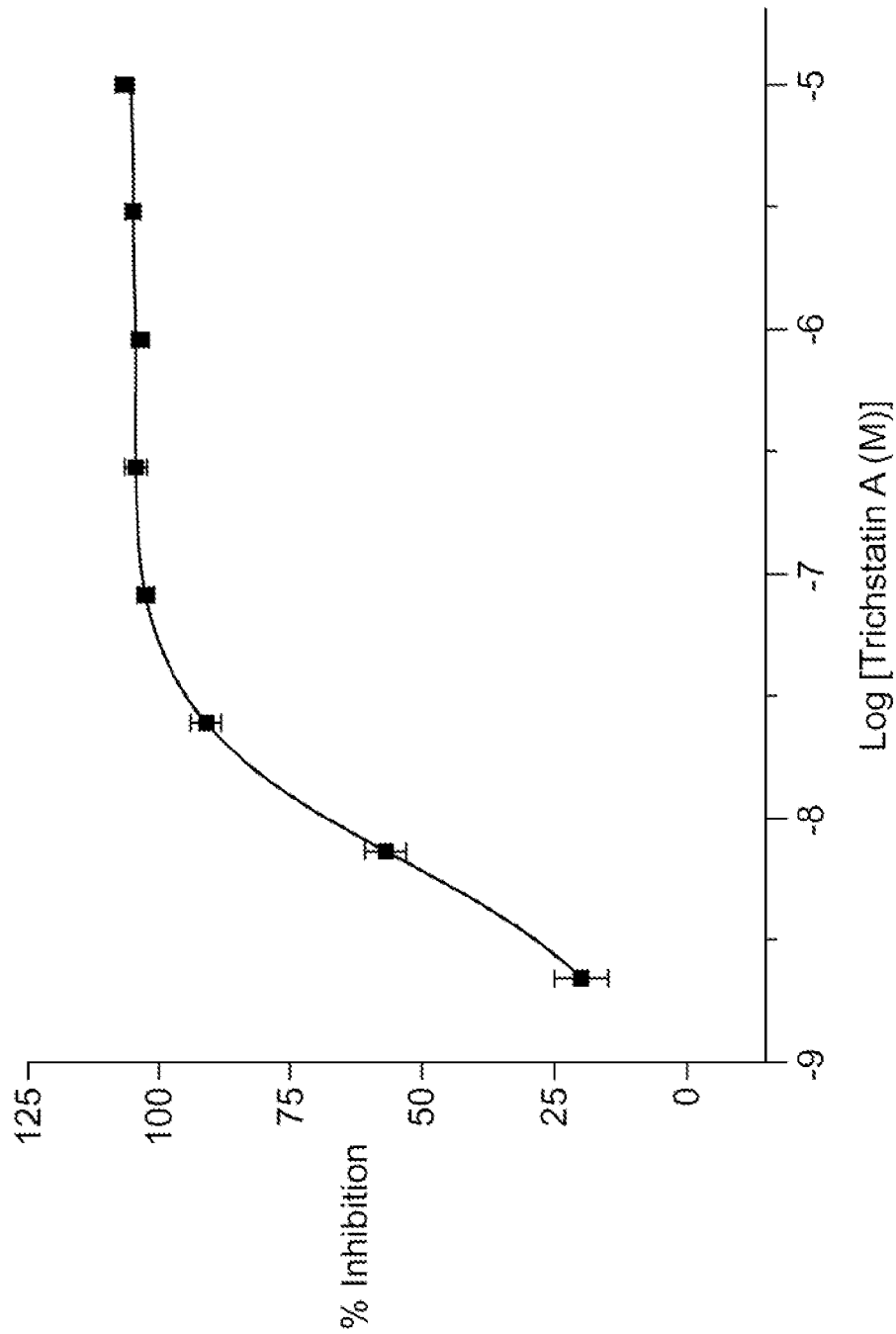
FIG. 51 is a graphical representation of the inhibition of coronary artery smooth muscle cell proliferation utilizing trichostatin A in an in vitro cell culture study.

In in vitro cell culture studies, trichostatin A has been shown to completely inhibit human coronary artery smooth muscle cell proliferation and has an anti-proliferative IC50 of approximately 6 nM. FIG. 51 is a graph of the inhibition of coronary artery smooth muscle cells by trichostatin A in a cell culture study. It is therefore possible that trichostatin A, delivered locally, may substantially inhibit neointimal formation following vascular injury.

Rapamycin, as described above, is a macroyclic triene antibiotic produced by streptomyces hygroscopicus as disclosed in U.S. Pat. No. 3,929,992. It has been found that rapamycin inhibits the proliferation of vascular smooth muscle cells in vivo. Accordingly, rapamycin may be utilized in treating intimal smooth muscle cell hyperplasia, restenosis and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin functions to inhibit smooth muscle cell proliferation through a number of mechanisms. In addition, rapamycin reduces the other effects caused by vascular injury, for example, inflammation. The mechanisms of action and various functions of rapamycin are described in detail below. Rapamycin as used throughout this application shall include rapamycin, rapamycin analogs, derivatives and congeners that bind FKBP12 and possess the same pharmacologic properties as rapamycin, as described in detail below.

Rapamycin reduces vascular hyperplasia by antagonizing smooth muscle proliferation in response to mitogenic signals that are released during angioplasty. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

The molecular events that are responsible for the actions of rapamycin, a known anti-proliferative, which acts to reduce the magnitude and duration of neointimal hyperplasia, are still being elucidated. It is known, however, that rapamycin enters cells and binds to a high-affinity cytosolic protein called FKBP12. The complex of rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that rapamycin reduces restenosis by inhibiting neointimal hyperplasia. However, there is evidence that rapamycin may also inhibit the other major component of restenosis, namely, negative remodeling. Remodeling is a process whose mechanism is not clearly understood but which results in shrinkage of the external elastic lamina and reduction in lumenal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural timepoint to four-month and twelve-month follow-ups are reflective of remodeling changes.

Evidence that rapamycin exerts an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that rapamycin is preventing vascular remodeling.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

Angiographic In-Lesion Percent Diameter Stenosis (%, mean ± SD and "n=") In Patients Who Received a Rapamycin-Coated Stent

| Coating Group | Post Placement | 4-6 month Follow Up | 12 month Follow Up |
|---|---|---|---|
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n =) | 4-Month Follow-Up (n =) | 12-Month Follow-Up (n =) |
|---|---|---|---|
| Mean proximal vessel area ($mm^2$) | 16.53 ± 3.53 (27) | 16.31 ± 4.36 (28) | 13.96 ± 2.26 (13) |
| Mean distal vessel area ($mm^2$) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycin may also affect the translation of key proteins involved in collagen formation or metabolism.

Rapamycin used in this context includes rapamycin and all analogs, derivatives and congeners that bind FKBP12 and possess the same pharmacologic properties as rapamycin.

In a preferred embodiment, the rapamycin is delivered by a local delivery device to control negative remodeling of an arterial segment after balloon angioplasty as a means of reducing or preventing restenosis. While any delivery device may be utilized, it is preferred that the delivery device comprises a stent that includes a coating or sheath which elutes or releases rapamycin. The delivery system for such a device may comprise a local infusion catheter that delivers rapamycin at a rate controlled by the administrator. In other embodiments, an injection need may be utilized.

Rapamycin may also be delivered systemically using an oral dosage form or a chronic injectible depot form or a patch to deliver rapamycin for a period ranging from about seven to forty-five days to achieve vascular tissue levels that are sufficient to inhibit negative remodeling. Such treatment is to be used to reduce or prevent restenosis when administered several days prior to elective angioplasty with or without a stent.

Data generated in porcine and rabbit models show that the release of rapamycin into the vascular wall from a nonerodible polymeric stent coating in a range of doses (35-430 ug/15-18 mm coronary stent) produces a peak fifty to fifty-five percent reduction in neointimal hyperplasia as set forth in Table 3 below. This reduction, which is maximal at about twenty-eight to thirty days, is typically not sustained in the range of ninety to one hundred eighty days in the porcine model as set forth in Table 4 below.

TABLE 3.0

Animal Studies with Rapamycin-coated stents.
Values are mean ± Standard Error of Mean

| Study | Duration | Stent[1] | Rapamycin | N | Neointimal Area (mm$^2$) | % Change From Polyme | % Change From Metal |
|---|---|---|---|---|---|---|---|
| | Porcine | | | | | | |
| 98009 | 14 days | Metal | | 8 | 2.04 ± 0.17 | | |
| | | 1X + rapamycin | 153 μg | 8 | 1.66 ± 0.17* | −42% | −19% |
| | | 1X + TC300 + rapamycin | 155 μg | 8 | 1.51 ± 0.19* | −47% | −26% |
| 99005 | 28 days | Metal | | 10 | 2.29 ± 0.21 | | |
| | | | | 9 | 3.91 ± 0.60** | | |
| | | 1X + TC30 + rapamycin | 130 μg | 8 | 2.81 ± 0.34 | | +23% |
| | | 1X + TC100 + rapamycin | 120 μg | 9 | 2.62 ± 0.21 | | +14% |
| 99006 | 28 days | Metal | | 12 | 4.57 ± 0.46 | | |
| | | EVA/BMA 3X | | 12 | 5.02 ± 0.62 | | +10% |
| | | 1X + rapamycin | 125 μg | 11 | 2.84 ± 0.31* ** | −43% | −38% |
| | | 3X + rapamycin | 430 μg | 12 | 3.06 ± 0.17* ** | −39% | −33% |
| | | 3X + rapamycin | 157 μg | 12 | 2.77 ± 0.41* ** | −45% | −39% |
| 99011 | 28 days | Metal | | 11 | 3.09 ± 0.27 | | |
| | | | | 11 | 4.52 ± 0.37 | | |
| | | 1X + rapamycin | 189 μg | 14 | 3.05 ± 0.35 | | −1% |
| | | 3X + rapamycin/dex | 182/363 μg | 14 | 2.72 ± 0.71 | | −12% |
| 99021 | 60 days | Metal | | 12 | 2.14 ± 0.25 | | |
| | | 1X + rapamycin | 181 μg | 12 | 2.95 ± 0.38 | | +38% |
| 99034 | 28 days | Metal | | 8 | 5.24 ± 0.58 | | |
| | | 1X + rapamycin | 186 μg | 8 | 2.47 ± 0.33** | | −53% |
| | | 3X + rapamycin/dex | 185/369 μg | 6 | 2.42 ± 0.64** | | −54% |
| 20001 | 28 days | Metal | | 6 | 1.81 ± 0.09 | | |
| | | 1X + rapamycin | 172 μg | 5 | 1.66 ± 0.44 | | −8% |
| 20007 | 30 days | Metal | | 9 | 2.94 ± 0.43 | | |
| | | 1XTC + rapamycin | 155 μg | 10 | 1.40 ± 0.11* | | −52%* |
| | Rabbit | | | | | | |
| 99019 | 28 days | Metal | | 8 | 1.20 ± 0.07 | | |
| | | EVA/BMA 1X | | 10 | 1.26 ± 0.16 | | +5% |
| | | 1X + rapamycin | 64 μg | 9 | 0.92 ± 0.14 | −27% | −23% |
| | | 1X + rapamycin | 196 μg | 10 | 0.66 ± 0.12* ** | −48% | −45% |
| 99020 | 28 days | Metal | | 12 | 1.18 ± 0.10 | | |
| | | EVA/BMA 1X + rapamycin | 197 μg | 8 | 0.81 ± 0.16 | | −32% |

[1]Stent nomenclature: EVA/BMA 1X, 2X, and 3X signifies approx. 500 μg, 1000 μg, and 1500 μg total mass (polymer + drug), respectively. TC, top coat of 30 μg, 100 μg, or 300 μg drug-free BMA; Biphasic; 2 × 1X layers of rapamycin in EVA/BMA spearated by a 100 μg drug-free BMA layer.
[2]0.25 mg/kg/d × 14 d preceeded by a loading dose of 0.5 mg/kg/d × 3 d prior to stent implantation.
*p < 0.05 from EVA/BMA control.
**p < 0.05 from Metal;
Inflammation score: (0 = essentially no intimal involvement; 1 = <25% intima involved; 2 = ≥25% intima involved; 3 = >50% intima involved).

TABLE 4.0

180 day Porcine Study with Rapamycin-coated stents.
Values are mean ± Standard Error of Mean

| Study | Duration | Stent[1] | Rapamycin | N | Neointimal Area (mm$^2$) | % Change From Polyme | % Change From Metal | Inflammation Score # |
|---|---|---|---|---|---|---|---|---|
| 20007 | 3 days | Metal | | 10 | 0.38 ± 0.06 | | | 1.05 ± 0.06 |
| (ETP-2-002233-P) | | 1XTC + rapamycin | 155 μg | 10 | 0.29 ± 0.03 | | −24% | 1.08 ± 0.04 |
| | 30 days | Metal | | 9 | 2.94 ± 0.43 | | | 0.11 ± 0.08 |
| | | 1XTC + rapamycin | 155 μg | 10 | 1.40 ± 0.11* | | −52%* | 0.25 ± 0.10 |
| | 90 days | Metal | | 10 | 3.45 ± 0.34 | | | 0.20 ± 0.08 |
| | | 1XTC + rapamycin | 155 μg | 10 | 3.03 ± 0.29 | | −12% | 0.80 ± 0.23 |
| | | 1X + rapamycin | 171 μg | 10 | 2.86 ± 0.35 | | −17% | 0.60 ± 0.23 |
| | 180 days | Metal | | 10 | 3.65 ± 0.39 | | | 0.65 ± 0.21 |
| | | 1XTC + rapamycin | 155 μg | 10 | 3.34 ± 0.31 | | −8% | 1.50 ± 0.34 |
| | | 1X + rapamycin | 171 μg | 10 | 3.87 ± 0.28 | | +6% | 1.68 ± 0.37 |

The release of rapamycin into the vascular wall of a human from a nonerodible polymeric stent coating provides superior results with respect to the magnitude and duration of the reduction in neointimal hyperplasia within the stent as compared to the vascular walls of animals as set forth above.

Humans implanted with a rapamycin coated stent comprising rapamycin in the same dose range as studied in animal models using the same polymeric matrix, as described above, reveal a much more profound reduction in neointimal hyperplasia than observed in animal models, based on the magnitude and duration of reduction in neointima. The human clinical response to rapamycin reveals essentially total abolition of neointimal hyperplasia inside the stent using both angiographic and intravascular ultrasound measurements. These results are sustained for at least one year as set forth in Table 5 below.

These results may be due to a number of factors. For example, the greater effectiveness of rapamycin in humans is due to greater sensitivity of its mechanism(s) of action toward the pathophysiology of human vascular lesions compared to the pathophysiology of animal models of angioplasty. In addition, the combination of the dose applied to the stent and the polymer coating that controls the release of the drug is important in the effectiveness of the drug.

As stated above, rapamycin reduces vascular hyperplasia by antagonizing smooth muscle proliferation in response to mitogenic signals that are released during angioplasty injury. Also, it is known that rapamycin prevents T-cell proliferation and differentiation when administered systemically. It has also been determined that rapamycin exerts a local inflammatory effect in the vessel wall when administered from a stent in low doses for a sustained period of time

TABLE 5.0

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| Procedure Success (QCA) | 100.0% (45/45) | [92.1%, 100.0%] |
| 4-month In-Stent Diameter Stenosis (%) | | |
| Mean ± SD (N) | 4.8% ± 6.1% (30) | [2.6%, 7.0%] |
| Range (min, max) | (−8.2%, 14.9%) | |
| 6-month In-Stent Diameter Stenosis (%) | | |
| Mean ± SD (N) | 8.9% ± 7.6% (13) | [4.8%, 13.0%] |
| Range (min, max) | (−2.9%, 20.4%) | |
| 12-month In-Stent Diameter Stenosis (%) | | |
| Mean ± SD (N) | 8.9% ± 6.1% (15) | [5.8%, 12.0%] |
| Range (min, max) | (−3.0%, 22.0%) | |
| 4-month In-Stent Late Loss (mm) | | |
| Mean ± SD (N) | 0.00 ± 0.29 (30) | [−0.10, 0.10] |
| Range (min, max) | (−0.51, 0.45) | |
| 6-month In-Stent Late Loss (mm) | | |
| Mean ± SD (N) | 0.25 ± 0.27 (13) | [0.10, 0.39] |
| Range (min, max) | (−0.51, 0.91) | |
| 12-month In-Stent Late Loss (mm) | | |
| Mean ± SD (N) | 0.11 ± 0.36 (15) | [−0.08, 0.29] |
| Range (min, max) | (−0.51, 0.82) | |
| 4-month Obstruction Volume (%) (IVUS) | | |
| Mean ± SD (N) | 10.48% ± 2.78% (28) | [9.45%, 11.51%] |
| Range (min, max) | (4.60%, 16.35%) | |
| 6-month Obstruction Volume (%) (IVUS) | | |
| Mean ± SD (N) | 7.22% ± 4.60% (13) | [4.72%, 9.72%], |
| Range (min, max) | (3.82%, 19.88%) | |
| 12-month Obstruction Volume (%) (IVUS) | | |
| Mean ± SD (N) | 2.11% ± 5.28% (15) | [0.00%, 4.78%], |
| Range (min, max) | (0.00%, 19.89%) | |
| 6-month Target Lesion Revascularization (TLR) | 0.0% (0/30) | [0.0%, 9.5%] |
| 12-month Target Lesion Revascularization (TLR) | 0.0% (0/15) | [0.0%, 18.1%] |

QCA = Quantitative Coronary Angiography
SD = Standard Deviation
IVUS = Intravascular Ultrasound Rapamycin produces an unexpected benefit in humans when delivered from a stent by causing a profound reduction in in-stent neointimal hyperplasia that is sustained for at least one year. The magnitude and duration of this benefit in humans is not predicted from animal model data. Rapamycin used in this context includes rapamycin and all analogs, derivatives and congeners that bind FKBP12 and possess the same pharmacologic properties as rapamycin.

(approximately two to six weeks). The local anti-inflammatory benefit is profound and unexpected. In combination with the smooth muscle anti-proliferative effect, this dual mode of action of rapamycin may be responsible for its exceptional efficacy.

Accordingly, rapamycin delivered from a local device platform, reduces neointimal hyperplasia by a combination of anti-inflammatory and smooth muscle anti-proliferative effects. Rapamycin used in this context means rapamycin and all analogs, derivatives and congeners that bind FKBP12 and possess the same pharmacologic properties as rapamycin. Local device platforms include stent coatings, stent sheaths, grafts and local drug infusion catheters or porous balloons or any other suitable means for the in situ or local delivery of drugs, agents or compounds.

The anti-inflammatory effect of rapamycin is evident in data from an experiment, illustrated in Table 6, in which rapamycin delivered from a stent was compared with dexamethasone delivered from a stent. Dexamethasone, a potent steroidal anti-inflammatory agent, was used as a reference standard. Although dexamethasone is able to reduce inflammation scores, rapamycin is far more effective than dexamethasone in reducing inflammation scores. In addition, rapamycin significantly reduces neointimal hyperplasia, unlike dexamethasone.

TABLE 6.0

| Group Rapamycin Rap | N = | Neointimal Area ($mm^2$) | % Area Stenosis | Inflammation Score |
|---|---|---|---|---|
| Uncoated | 8 | 5.24 ± 1.65 | 54 ± 19 | 0.97 ± 1.00 |
| Dexamethasone (Dex) | 8 | 4.31 ± 3.02 | 45 ± 31 | 0.39 ± 0.24 |
| Rapamycin (Rap) | 7 | 2.47 ± 0.94* | 26 ± 10* | 0.13 ± 0.19* |
| Rap + Dex | 6 | 2.42 ± 1.58* | 26 ± 18* | 0.17 ± 0.30* |

*= significance level $P < 0.05$

Rapamycin has also been found to reduce cytokine levels in vascular tissue when delivered from a stent. The data in FIG. 1 illustrates that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycin may be shown to inhibit local inflammatory events in the vessel it is believed that this could explain the unexpected superiority of rapamycin in inhibiting neointima.

As set forth above, rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycin suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving rapamycin delivered locally from a stent. The present invention expands upon the mechanism of rapamycin to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs, agents or compounds that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as P27$^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

Any of the drugs, agents or compounds discussed above may be administered either systemically, for example, orally, intravenously, intramuscularly, subcutaneously, nasally or intradermally, or locally, for example, stent coating, stent covering or local delivery catheter. In addition, the drugs or agents discussed above may be formulated for fast-release or slow release with the objective of maintaining the drugs or agents in contact with target tissues for a period ranging from three days to eight weeks.

As set forth above, the complex of rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

The inhibitor may be a small organic molecule (approximate mw<1000), which is either a synthetic or naturally derived product. Wortmanin may be an agent which inhibits the function of this class of proteins. It may also be a peptide or an oligonucleotide sequence. The inhibitor may be administered either sytemically (orally, intravenously, intramuscularly, subcutaneously, nasally, or intradermally) or locally (stent coating, stent covering, local drug delivery catheter). For example, the inhibitor may be released into the vascular wall of a human from a nonerodible polymeric stent coating. In addition, the inhibitor may be formulated for fast-release or slow release with the objective of maintaining the rapamycin or other drug, agent or compound in contact with target tissues for a period ranging from three days to eight weeks.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

Further, insulin supplemented diabetic patients receiving rapamycin eluting vascular devices, such as stents, may exhibit a higher incidence of restenosis than their normal or non-insulin supplemented diabetic counterparts. Accordingly, combinations of drugs may be beneficial.

The local delivery of drugs, agents or compounds from a stent has the following advantages; namely, the prevention of vessel recoil and remodeling through the scaffolding action of the stent and the drugs, agents or compounds and the prevention of multiple components of neointimal hyperplasia. This local administration of drugs, agents or compounds to stented coronary arteries may also have additional therapeutic benefit. For example, higher tissue concentrations would be achievable than that which would occur with systemic administration, reduced systemic toxicity, and single treatment and ease of administration. An additional benefit of drug therapy may be to reduce the dose of the therapeutic compounds, thereby limiting their toxicity, while still achieving a reduction in restenosis.

As rapamycin and trichostatin A act through different molecular mechanisms affecting cell proliferation, it is possible that these agents, when combined on a medical device such as a drug eluting stent, may potentiate each other's anti-restenotic activity by downregulating both smooth muscle and immune cell proliferation (inflammatory cell proliferation) by distinct multiple mechanisms. This potentiation of rapamycin anti-proliferative activity by trichostatin A may translate to an enhancement in anti-restenotic efficacy following vascular injury during revascularization and other vascular surgical procedures and a reduction in the required amount of either agent to achieve the anti-restenotic effect.

Trichostatin A may be affixed to any of the medical devices described herein utilizing any of the techniques and materials described herein. For example, trichostatin A may be affixed to a stent, with or without polymers, or delivered locally via a catheter-based delivery system. The trichostatin A may substantially block neointimal formation by local vascular application by virtue of a substantially complete and potent blockade of human coronary artery smooth muscle cell proliferation. The combination of rapamycin and trichostatin A, as well as other agents within its pharmacologic class, represents a new therapeutic combination that may be more efficacious against restenosis/neointimal thickening then rapamycin alone. In addition, different doses of the combination may lead to additional gains of inhibition of the neointimal growth than the simple additive effects of rapamycin plus trichostatin A. The combination of rapamycin and trichostatin A may be efficacious towards other cardiovascular diseases such as vulnerable atherosclerotic plaque.

In yet another alternate exemplary embodiment, rapamycin may be utilized in combination with mycophenolic acid. Like rapamycin, mycophenolic acid is an antibiotic, an anti-inflammatory and an immunosuppressive agent. Rapamycin, as previously stated, acts to reduce lymphocyte proliferation by arresting cells in the G1 phase of the cell cycle through the inhibition of the mammalian target of rapamycin. The downstream effects of rapamycin on the mammalian target of rapamycin block subsequent activity of cell cycle associated protein kinases. In contrast, mycophenolic acid inhibits immune cell proliferation in the S phase of the cell cycle through the inhibition of inosine monophosphate dehydrogenase, an enzyme necessary for purine biosynthesis. In addition to their immunosuppressive and anti-inflammatory effects, rapamycin and mycophenolic acid are each potent inhibitors of human coronary artery smooth muscle cell proliferation.

As rapamycin and mycophenolic acid act through different molecular mechanisms affecting cell proliferation at different phases of the cell cycle, it is possible that these agents, when combined on a drug eluting stent or any other medical device as defined herein, my potentiate each others anti-restenotic activity by down regulating both smooth muscle and immune cell proliferation by different mechanisms.

Figure 52:
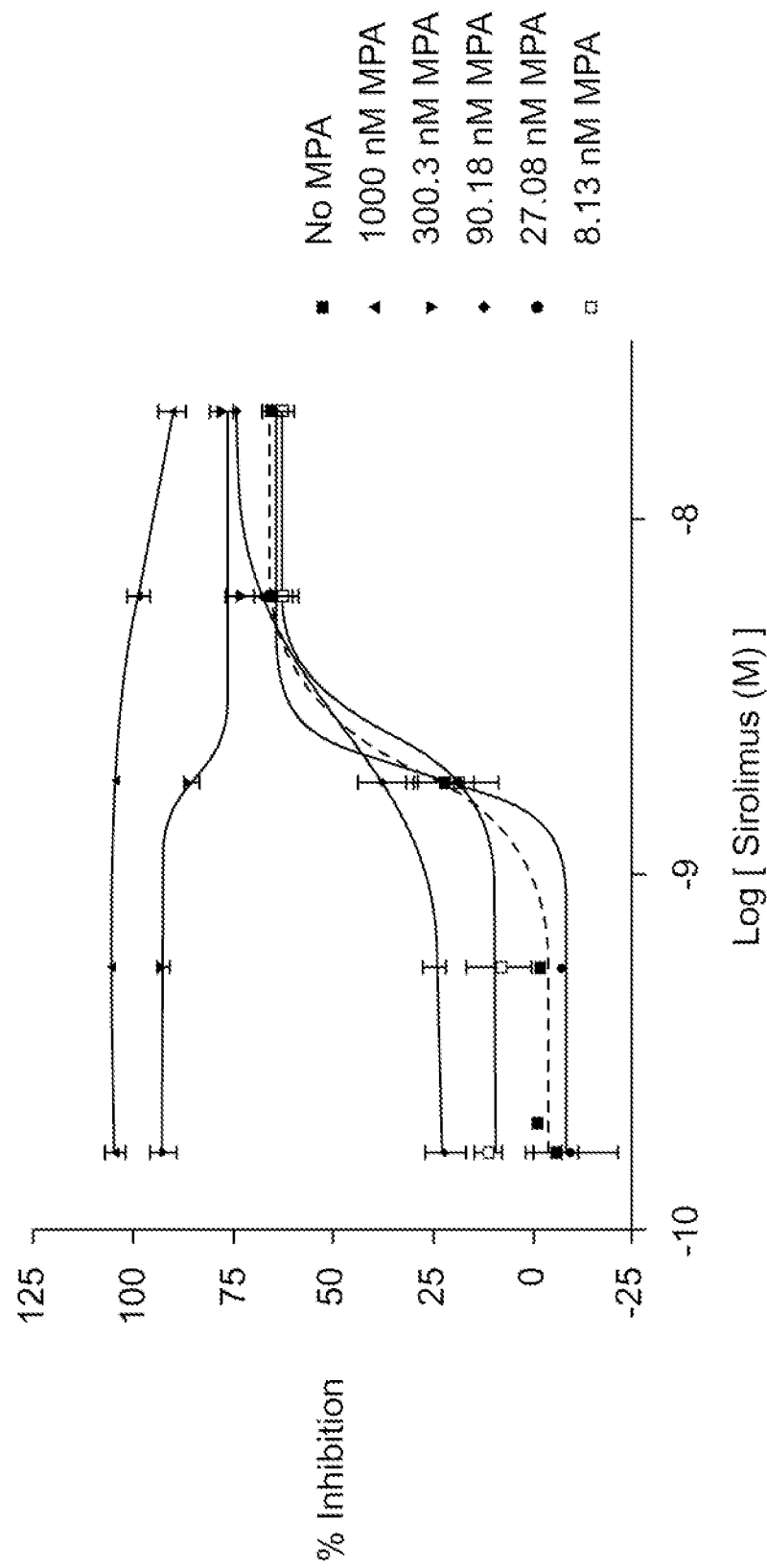
FIG. 52 is a graphical representation of the anti-proliferative activity of rapamycin with varying concentrations of mycophenolic acid in non-synchronized cultured human coronary artery smooth muscle cells stimulated with two percent fetal bovine serum in accordance with the present invention.

Referring to FIG. 52, there is illustrated, in graphical format, the anti-proliferative activity of rapamycin, with varying concentrations of mycophenolic acid in non-synchronized cultured human coronary artery smooth muscle cells stimulated with two percent fetal bovine serum. The multiple curves represent various concentrations of mycophenolic acid ranging from zero to one thousand nanomolar concentrations. As seen in FIG. 52, the addition of mycophenolic acid to cells treated with rapamycin resulted in a leftward and upward shift of the anti-proliferative rapamycin dose response curve, indicating that mycophenolic acid potentiates the anti-proliferative activity of rapamycin in coronary artery smooth muscle cells. This potentiation observed in cultured coronary artery smooth muscle cells preferably translates to an enhancement in anti-restenotic efficacy following vascular injury and a reduction in the required amount of either agent to achieve the desired anti-restenotic effect.

Figure 53:
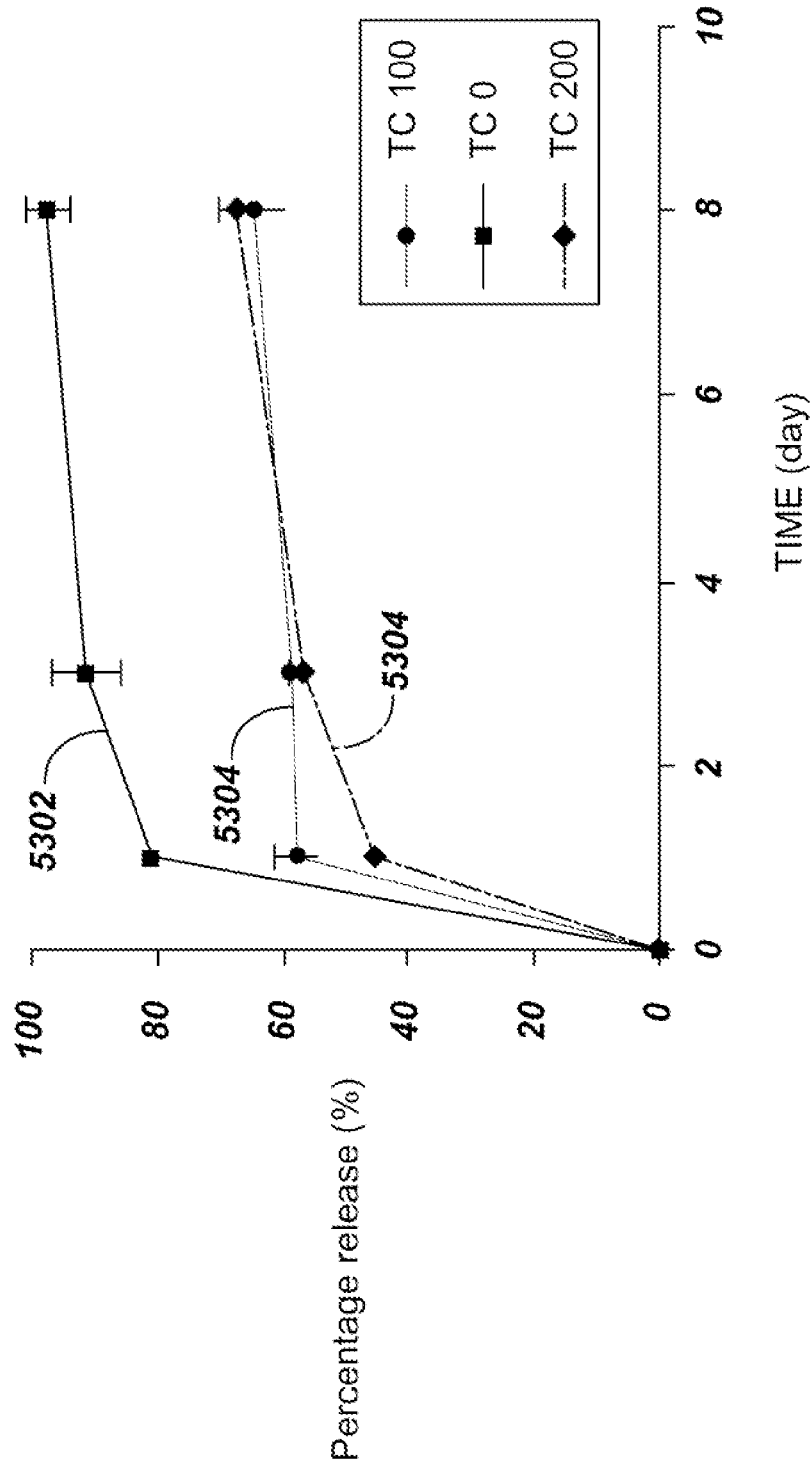
FIG. 53 is a graphical representation of the in vivo release kinetics of rapamycin from a combination of rapamycin, mycophenolic acid and a polymer in porcine pharmacokinetics studies in accordance with the present invention.

FIG. 53 is a graphical representation of the in vivo release kinetics of rapamycin from a combination of rapamycin, mycophenolic acid and a polymer in porcine pharmacokinetics studies. In the study, the rapamycin and mycophenolic acid are incorporated into an EVA/BMA polymer basecoat. The total weight of the basecoat is six hundred micro grams, with both the rapamycin and mycophenolic acid comprising thirty percent, by weight, of the basecoat (one hundred eighty micro grams rapamycin, one hundred eighty micro grams mycophenolic acid and two hundred forty micro grams EVA/BMA). Curve 5302 represents the release of rapamycin from the basecoat when no topcoat is utilized. Curve 5304 represents the release of rapamycin from the basecoat when a one hundred micro grams BMA topcoat is utilized. Curve 5306 represents the release of rapamycin from the basecoat when a two hundred micro grams BMA topcoat is utilized. The BMA topcoat does slow the release of rapamycin from the basecoat, which in turn provides a mechanism for greater drug release control.

Figure 54:
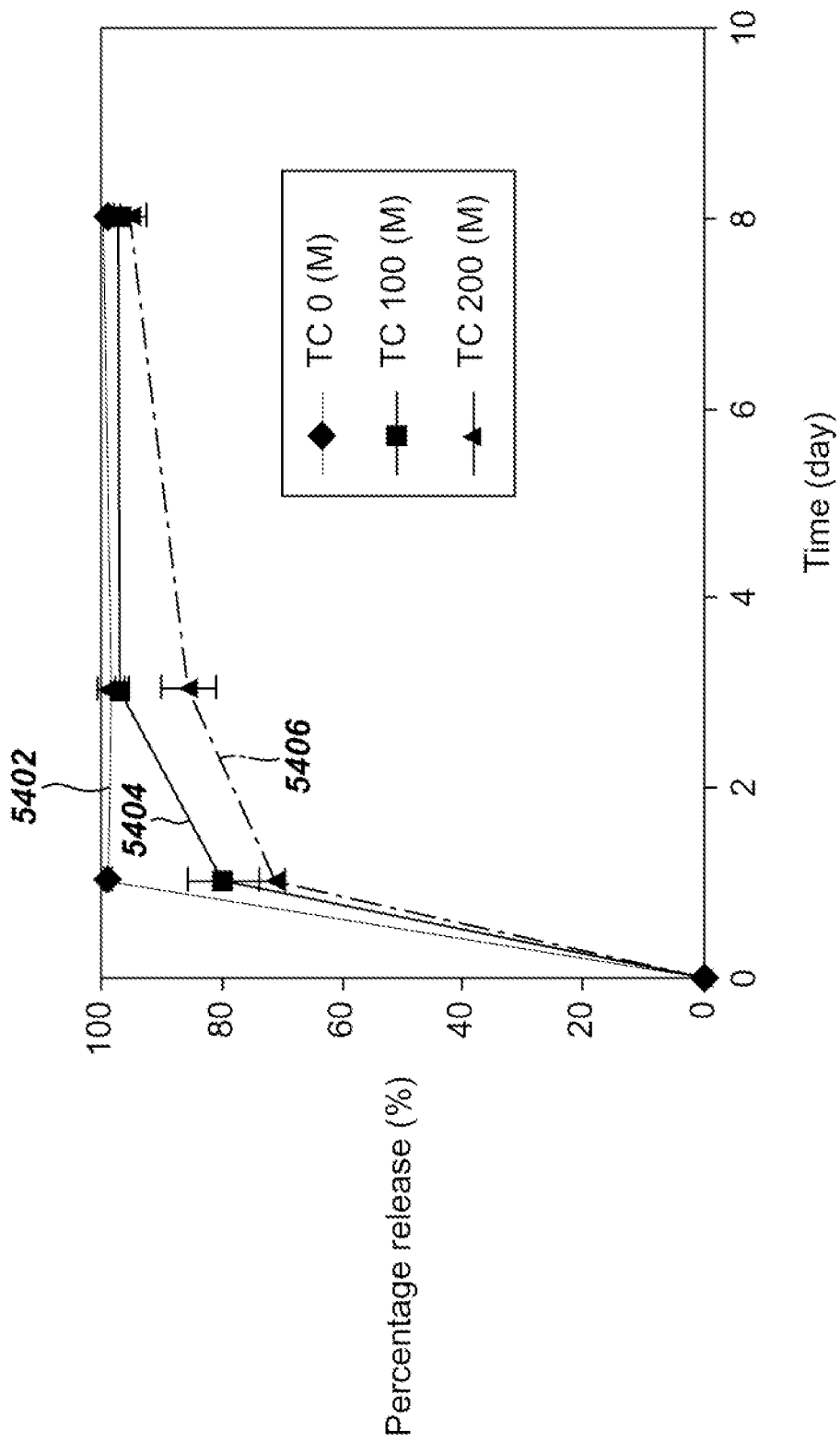
FIG. 54 is a graphical representation of the in vivo release kinetics of mycophenolic acid from a combination of rapamycin, mycophenolic acid and a polymer in porcine pharmacokinetics studies in accordance with the present invention.

FIG. 54 is a graphical representation of the in vivo release kinetics of mycophenolic acid from a combination of rapamycin, mycophenolic acid and a polymer in porcine pharmacokinetics studies. In the study, the rapamycin and mycophenolic acid are incorporated into an EVA/BMA polymer basecoat. The total weight of the basecoat is six hundred micro grams, with both the rapamycin and mycophenolic acid comprising thirty percent, by weight, of the basecoat (one hundred eighty micro grams rapamycin, one hundred eighty micro grams mycophenolic acid and two hundred forty micro grams EVA/BMA). Curve 5402 represents the release of mycophenolic acid from the basecoat when no topcoat is utilized. Curve 5404 represents the release of mycophenolic acid from the basecoat when a one hundred micro grams BMA topcoat is utilized. Curve 5406 represents the release of mycophenolic acid from the basecoat when a two hundred micro gram BMA topcoat is utilized. Similarly to the rapamycin pharmacokinetics, the BMA topcoat does slow the release of mycophenolic acid from the basecoat, which in turn provides a mechanism for greater drug release control. However, mycophenolic acid elutes more completely over a shorter duration than the rapamycin.

Figure 55:
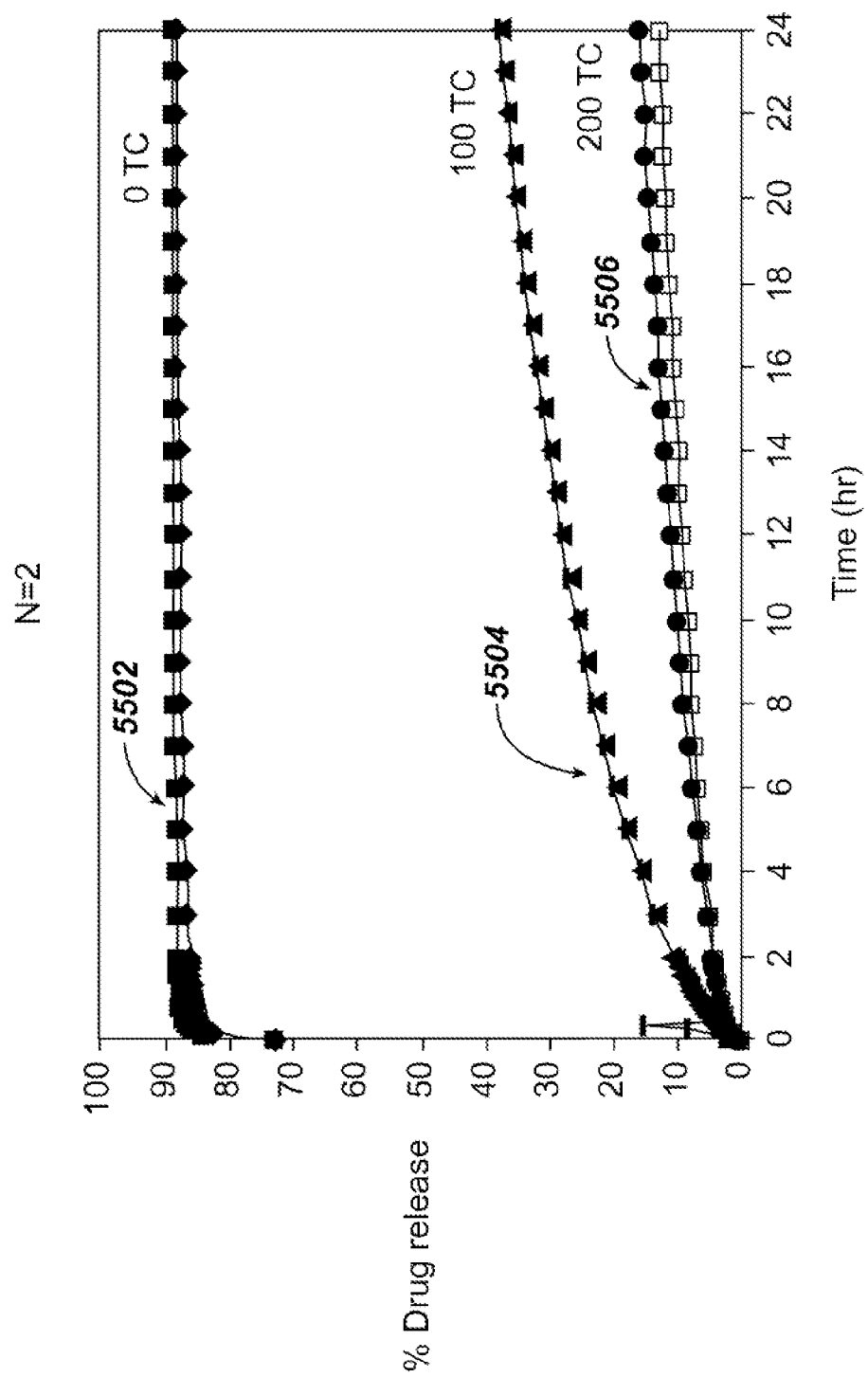
FIG. 55 is a graphical representation of the in vitro release kinetics of rapamycin from a combination of rapamycin and mycophenolic acid in accordance with the present invention.

FIG. 55 is a graphical representation of the in vitro release kinetics of rapamycin from a combination of rapamycin and mycophenolic acid. In the study, the rapamycin and mycophenolic acid are incorporated into an EVA/BMA polymer basecoat. The total weight of the basecoat is six hundred micro grams, with both the rapamycin and mycophenolic acid comprising thirty percent, by weight, of the basecoat (one hundred eighty micro grams rapamycin, one hundred eighty micro grams mycophenolic acid and two hundred forty micro grams EVA/BMA). The in vitro tests were run twice for each coating scenario. Curves 5502 represent the release of rapamycin from the basecoat when no topcoat is utilized. Curves 5504 represent the release of rapamycin from the basecoat when a one hundred micro grams BMA topcoat is utilized. Curves 5506 represent the release of rapamycin from the basecoat when a two hundred micro grams BMA topcoat is utilized. The BMA topcoat does slow the release of rapamycin from the basecoat in in vitro testing; however, the release rates are faster than in the in vivo testing.

Figure 56:
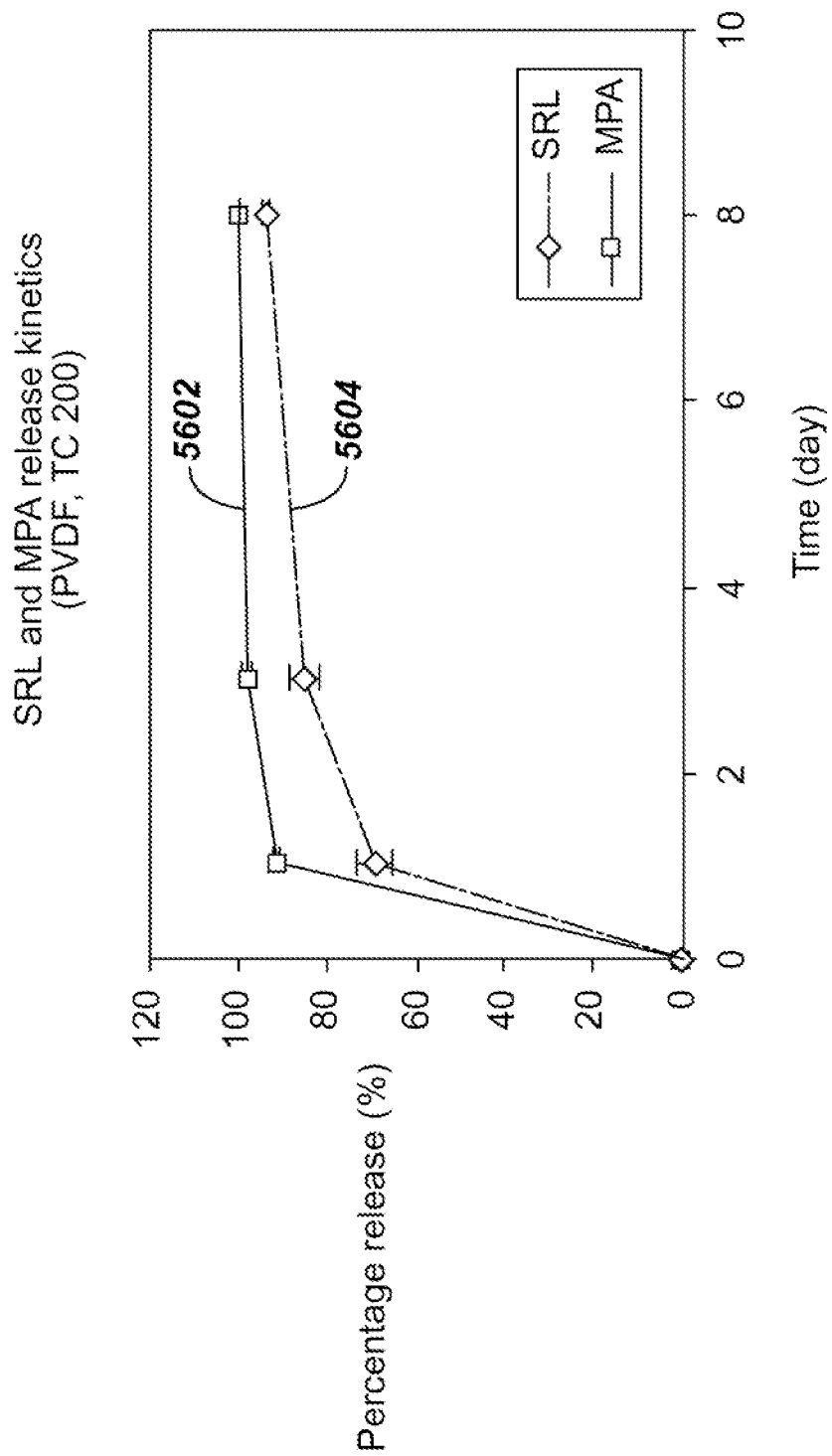
FIG. 56 is a graphical representation of the in vivo release kinetics of both rapamycin and mycophenolic acid in porcine pharmacokinetics studies in accordance with the present invention.

FIG. 56 is a graphical representation of the in vivo release kinetics of both rapamycin and mycophenolic acid in porcine pharmacokinetics studies. In this study, the rapamycin and mycophenolic acid are incorporated in a PVDF polymer basecoat with a PVDF topcoat. The total weight of the basecoat is six hundred micro grams with the rapamycin and mycophenolic acid equally comprising two thirds, by weight, of the basecoat. The topcoat is two hundred micro grams. Curve 5602 represents the release rate of mycophenolic acid and curve 5604 represents the release rate of rapamycin. As can be readily seen from the figure, rapamycin has a slower release rate than that of mycophenolic acid, which is consistent with the results found with an EVA/BMA basecoat and BMA topcoat. However, an EVA/BMA basecoat with a BMA topcoat appears to slow the release rate and thereby provide more control of the release rate or elution rate than a PVDF basecoat and PVDF topcoat.

In yet another alternate exemplary embodiment, rapamycin may be utilized in combination with cladribine. Cladribine (2-chlorodeoxyadenosine or 2-CdA) is the 2-chloro-2'-deoxy derivative of the purine nucleoside, adenosine. Cladribine is resistant to degradation by adenosine deaminase, one of two intracellular adenine nucleotide regulatory enzymes, found in most cells. The other enzyme, 5'-nucleotidase, is present in variable amounts in different cell types (Carson et al., 1983). After initial phosphorylation to its monophosphate derivative by the intracellular enzyme, deoxycytidine kinase, 2-CdA is converted to a 5'-triphosphate (2-CdATP) which accumulates in levels which may be fifty fold greater than normal dATP levels. Thus, in cells such as leukocytes, which contain a high ratio (>0.04) of deoxycytidine kinase to 5'-nucleotidase, 2-CdA and its subsequent metabolites will tend to accumulate in pharmacological concentrations (Carson et al., 1983). Such high levels of a nucleoside triphosphate are known to inhibit the enzyme ribonucleotide reductase in rapidly dividing cells, thus preventing synthesis of deoxynucleotides required for DNA synthesis.

In resting cells, 2-CdATP is incorporated into DNA which results in single strand breaks. Breaks in DNA results in the activation of poly(ADP-ribose) polymerase which in turn leads to a depletion of NAD, ATP and a disruption of cell metabolism (Carson et al., 1986; Seto et al., 1985). Further activation of a $Ca^{2+}/Mg^{2+}$-dependent endonuclease results in cleavage of the damaged DNA into fragments leading to programmed cell death (apoptosis). Thus, 2-CdA may be cytotoxic to both resting and dividing cells (Beutler, 1992). Cladribine has shown activity in other cell types known to play a role in the inflammatory process which accompanies restenosis. Additionally, data presented herein demonstrate that cladribine also possesses an ability to inhibit smooth muscle cell proliferation, an action previously unknown for cladribine (see Cladribine Example). Therefore, cladribine may possess a unique spectrum of therapeutic action, including the prevention of the leukocyte accumulation known to occur at sites of arterial injury and inflammation and the prevention of smooth muscle hyperplasia which results from angioplasty and stent implantation.

Cladribine Example

To assess the ability of cladribine to prevent cell proliferation, human smooth muscle or endothelial cells (Clonetics, Walkersville, Md.) were seeded at a density of 2000 cells/cm$^2$ (approximately 3600 cells/well) into each well of 12-well plates and cultured with 1.5 ml of growth medium containing five percent fetal calf serum (FCS). After twenty-four hours, the growth medium was changed and fresh medium containing 10 ng/ml platelet-derived growth factor AB (PDGF AB; LIFE Technologies), as well as various concentrations of cladribine (0.001-10,000 nM) were added with triplicate wells. Medium was replaced with fresh cladribine-containing medium after three days. On day six, cells were detached by trypsinization to yield a cell suspension, lightly centrifuged to pellet and then counted manually using a Neubauer hemocytometer system. Cell viability was assessed by trypan blue exclusion.

Table 7 provides the percent inhibition of the various tested concentrations of cladribine on human smooth muscle and endothelial cells in culture. Cladribine produced a concentration-related decrease in the proliferation of both smooth muscle and endothelial cells in this model system. $IC_{50}$ values (concentration required to produce a reduction in proliferation to 50 percent of the vehicle-treated cell count) for the inhibition of smooth muscle cell and endothelial cell growth were 23 nanomolar and 40 nanomolar, respectively. Cladribine was thus approximately twice as potent as an inhibitor of smooth muscle cells as it was as an inhibitor of endothelial cells. Both $IC_{50}$ values are within the range of inhibitory concentrations reported for cladribine on human monocytes (Carrera et al., J. Clin. Invest. 86:1480-1488, 1990) and normal bone marrow, lymphocytic and lymphoblastic cell lines (Carson, D. A. et al., Blood 62: 737-743, 1983). Thus, concentrations of cladribine known to be effective at inhibiting peripheral leukemic blood cell proliferation and bone marrow cells are also effective at inhibiting proliferating vascular smooth muscle and endothelial cells. Cladribine may therefore be therapeutically useful for inhibition of the intimal smooth muscle cell proliferation which accompanies stent implantation.

TABLE 7

Inhibition of human vascular cell proliferation with cladribine.

| | Con-trol | Vehi-cle | Cladribine (nM) | | | | | | | |
|---|---|---|---|---|---|---|---|---|---|---|
| | | | 0.001 | 0.01 | 0.1 | 1 | 10 | 100 | 1000 | 10,000 |
| SMC | 100 | 108 | — | 104 | 86 | 85 | 54 | 58 | 12 | −4 |
| EC | 100 | 100 | 100 | 90 | 79 | 75 | 59 | 57 | 35 | 10 |

Values represent % of PDGF-stimulated increase in cell count. Each % is the mean of triplicate determinations.
SMC, smooth muscle cells;
EC, endothelial cells.

Cladribine or 2-chlorodeoxyadenosine is a purine antimetabolite prodrug that undergoes intracellular phosphorylation and incorporation into the DNA of proliferating cells. This leads to DNA strand breaks and inhibition of DNA synthesis. Cladribine is capable of arresting cells at the G1/S phase interface. Thus it is possible that cladribine may inhibit vascular smooth muscle cell proliferation and inhibit inflammatory cell function secondary to revascularization procedures.

Figure 58:
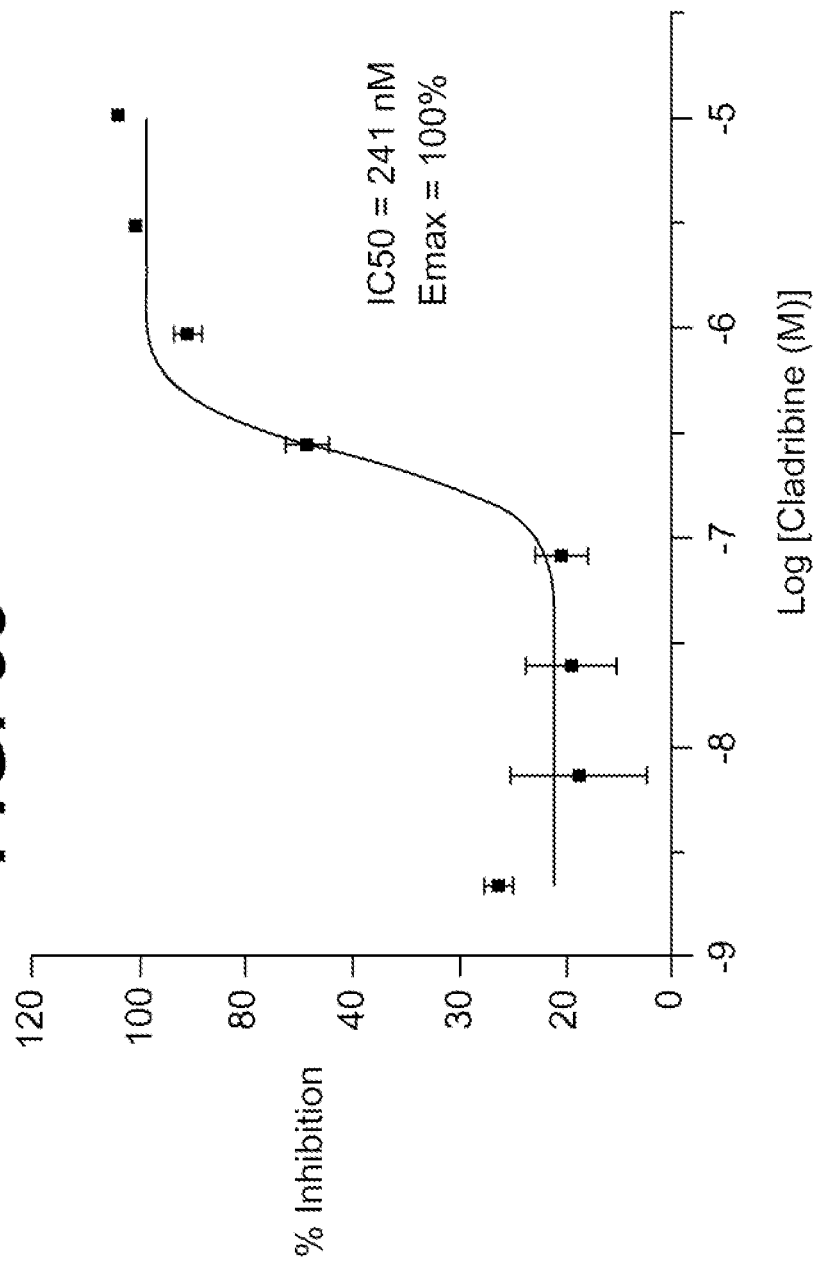
FIG. 58 is a graphical representation of the anti-proliferative activity of cladribine in non-synchronized cultured human coronary artery smooth muscle cells stimulated with two percent fetal bovine serum in accordance with the present invention.

FIG. 58 illustrates, in graphical format, the anti-proliferative activity of cladribine in non-synchronized cultured human coronary artery smooth muscle cells stimulated with two percent fetal bovine serum. As illustrated, cladribine completely inhibits human coronary artery smooth muscle cell proliferation and has an anti-proliferative IC50 of approximately 241 nanomolar. It is therefore possible that cladribine itself, delivered locally, may substantially inhibit neointimal formation following vascular injury.

As rapamycin and cladribine act through different molecular mechanisms affecting cell proliferation at different phases of the cell cycle, it is possible that these agents, when combined on a drug eluting stent or any other medical device as defined herein, may potentiate each other's anti-restenotic activity by downregulating both smooth muscle cell and immune cell proliferation by different mechanisms. In non-synchronized cultured human coronary artery smooth muscle cells studies, the addition of cladribine to cells treated with rapamycin resulted in a leftward and upward shift of the anti-proliferative rapamycin dose response curves, as set forth in detail below, suggesting that cladribine does in fact potentiate the anti-proliferative activity of rapamycin in coronary artery smooth muscle cells. The combination of rapamycin and cladribine may be utilized to enhance the anti-restenotic efficacy following vascular injury and a reduction in the required amount of either agent to achieve the anti-restenotic effect. The combination may be particularly relevant to the subpopulations of patients that are resistant to single drugs regimens such as rapamycin or paclitaxel coated stents.

Figure 57:
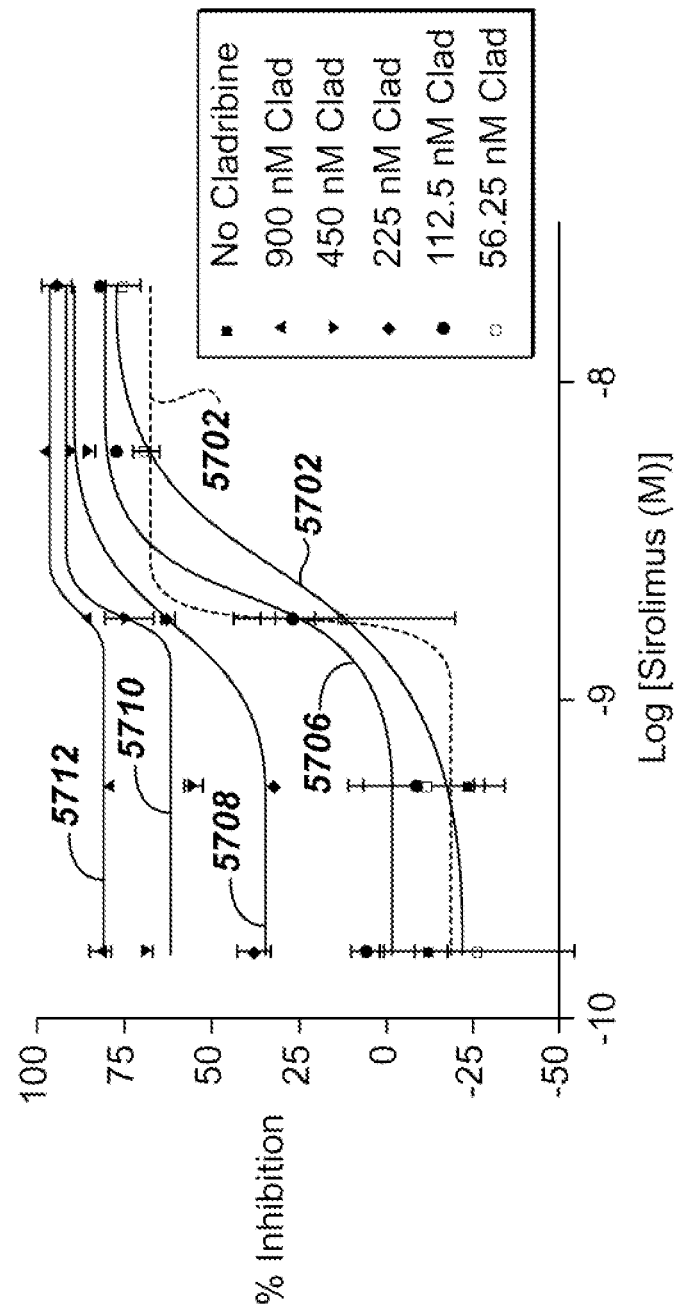
FIG. 57 is a graphical representation of the anti-proliferative activity of rapamycin with varying concentrations of cladribine in non-synchronized cultured human coronary artery smooth muscle cells stimulated with two percent fetal bovine serum in accordance with the present invention.

Referring to FIG. 57, there is illustrated, in graphical format, the anti-proliferative activity of rapamycin, with varying concentrations of cladribine in non-synchronized cultured human coronary artery smooth muscle cells stimulated with two percent fetal bovine serum. The multiple curves represent various concentrations of cladribine ranging from zero to nine hundred nanomolar concentrations. As seen in FIG. 57, the addition of cladribine to cells treated with rapamycin increases the percent inhibition of rapamycin alone. Curve 5702 represents the response of just rapamycin. Curve 5704 represents the response of rapamycin in combination with a 56.25 nanomolar concentration of cladribine. Curve 5706 represents the response of rapamycin in combination with a 112.5 nanomolar concentration of cladribine. Curve 5708 represents the response of rapamycin in combination with a 225 nanomolar concentration cladribine. Curve 5710 represents the response of rapamycin in combination with a 450 nanomolar concentration of cladribine. Curve 5712 represents the response of rapamycin in combination with a 900 nanomolar concentration of cladribine. As illustrated, the percent inhibition increases substantially as the dose of cladribine increases.

Figure 59:
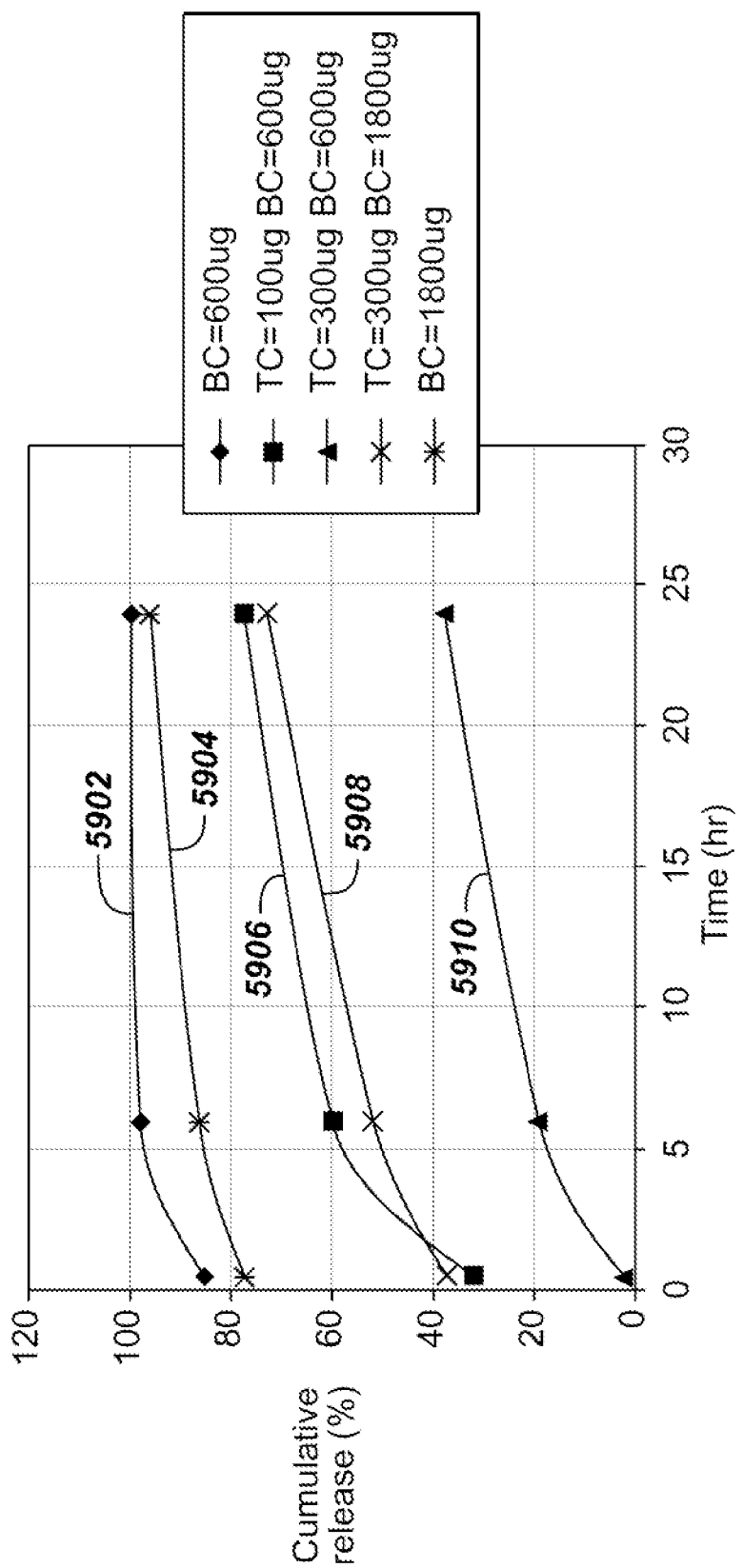
FIG. 59 is a graphical representation of the in vitro release kinetics of cladribine from non-sterile cladribine coatings in a PVDF/HFP basecoat incorporated in a twenty-five percent ethanol/water release medium at room temperature in accordance with the present invention.

FIG. 59 is a graphical representation of the in vitro release kinetics of cladribine from non-sterile cladribine coatings in a PVDF/HFP basecoat incorporated in a twenty-five percent ethanol/water release medium at room temperature. The basecoat comprises a ratio of PVDF/HFP (85/15) and cladribine. Cladribine comprises thirty percent of the basecoat. The topcoat also comprises an 85/15 ratio of PVDF and HFP, but no cladribine. Curve 5902 represents the release kinetics of cladribine wherein the basecoat weight is six hundred micrograms (one hundred eighty micrograms cladribine). Curve 5904 represents the release kinetics of cladribine wherein the basecoat weight is one thousand eight hundred micrograms (five hundred forty micrograms cladribine). Curve 5906 represents the release kinetics of cladribine wherein the basecoat weight is six hundred micrograms (one hunded eighty micrograms cladribine) and the topcoat weight is one hundred micrograms. Curve 5908 represents the release kinetics of cladribine wherein the basecoat weight is one thousand eight hundred micrograms (five hundred forty micrograms cladribine) and the topcoat is three hundred micrograms. Curve 5910 represents the release kinetic of cladribine wherein the basecoat weight is six hundred micrograms (one hundred eighty micrograms cladribine) and the topcoat is three hundred micrograms. As can be seen from the various curves, an increase in topcoat weight or thickness led to a decrease in the release rate of cladribine from the coating.

Figure 60:
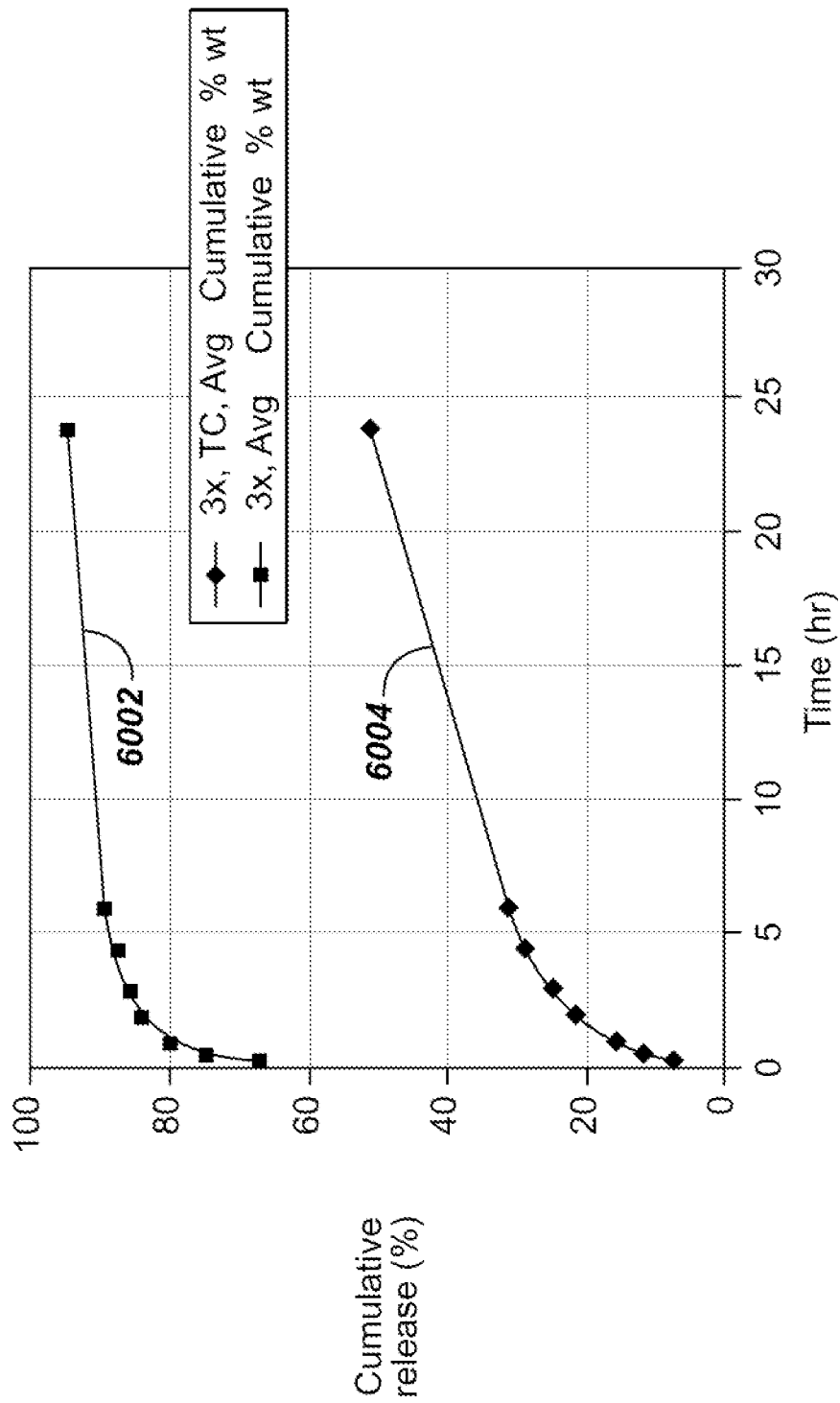
FIG. 60 is a graphical representation of the in vitro release kinetics of cladribine from sterile cladribine coatings in a PVDF/HFP basecoat incorporated in a twenty-five percent ethanol/water release medium at room temperature in accordance with the present invention.

FIG. 60 is a graphical representation of the in vitro release kinetics of cladribine from a sterile PVDF/HFP coating incorporated in a twenty-five percent ethanol/water release medium at room temperature. Curve 6002 represents the release kinetics where no topcoat is utilized and curve 6004 represents the release kinetics where a topcoat is utilized. As seen from the figure, a three-times topcoat led to a drastic decrease of release rate of cladribine.

Figure 61:
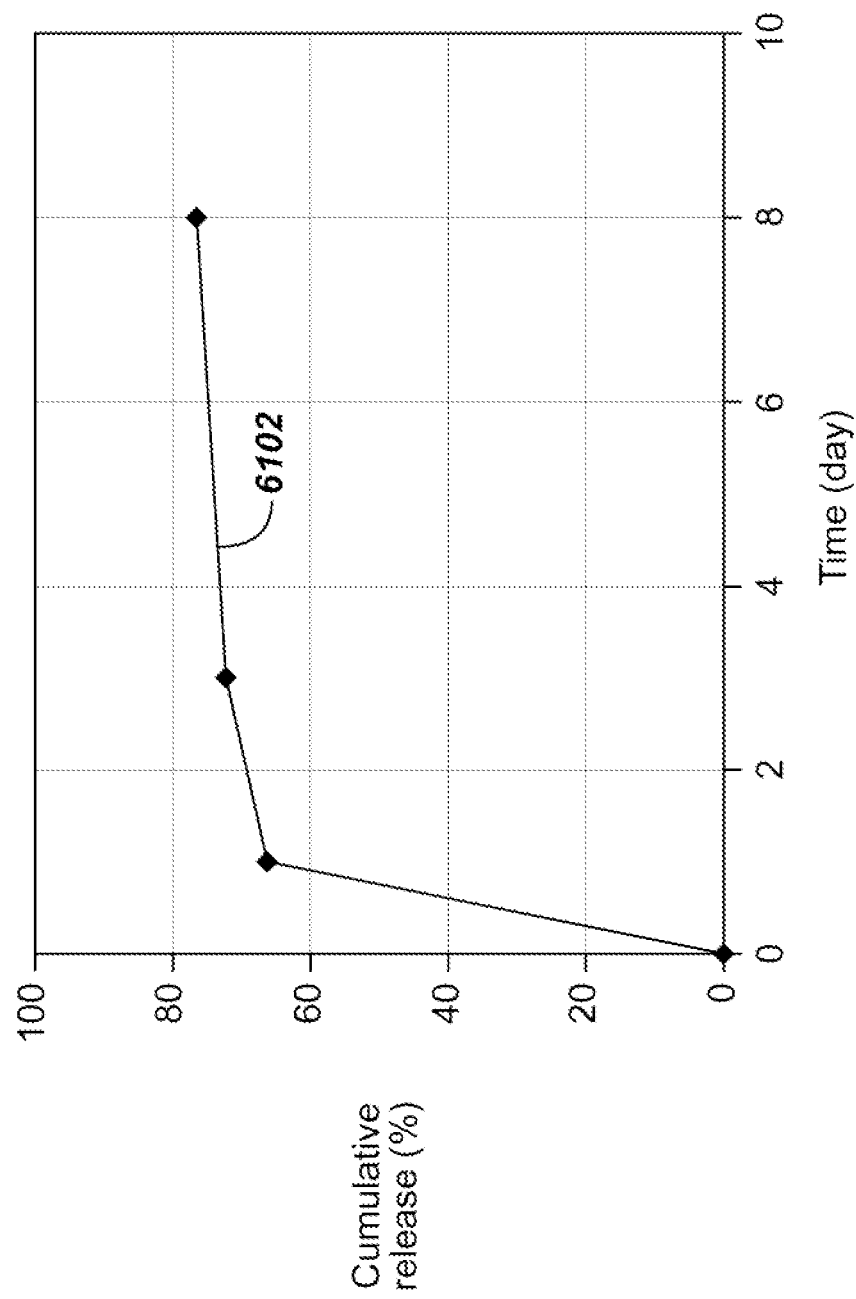
FIG. 61 is a graphical representation of the in vivo release kinetics of cladribine from a polymeric coating in porcine pharmacokinetics studies in accordance with the present invention.

FIG. 61 is a graphical representation of the in vivo release kinetics of cladribine from a polymeric coating on BxVelocity® stents, available from Cordis Corporation, implanted in a Yorkshire pig. The basecoat comprises an 85/15 ratio of PVDF and HFP and cladribine for a total combined weight of one thousand eight hundred micrograms (cladribine comprising thirty percent of the total weight). The topcoat comprises an 85/15 ratio of PVDF/HFP and no cladribine. The total weight of the topcoat is three hundred micrograms. As can be seen from curve 6102, after the first day, the elution of cladribine levels off significantly.

Figure 62:
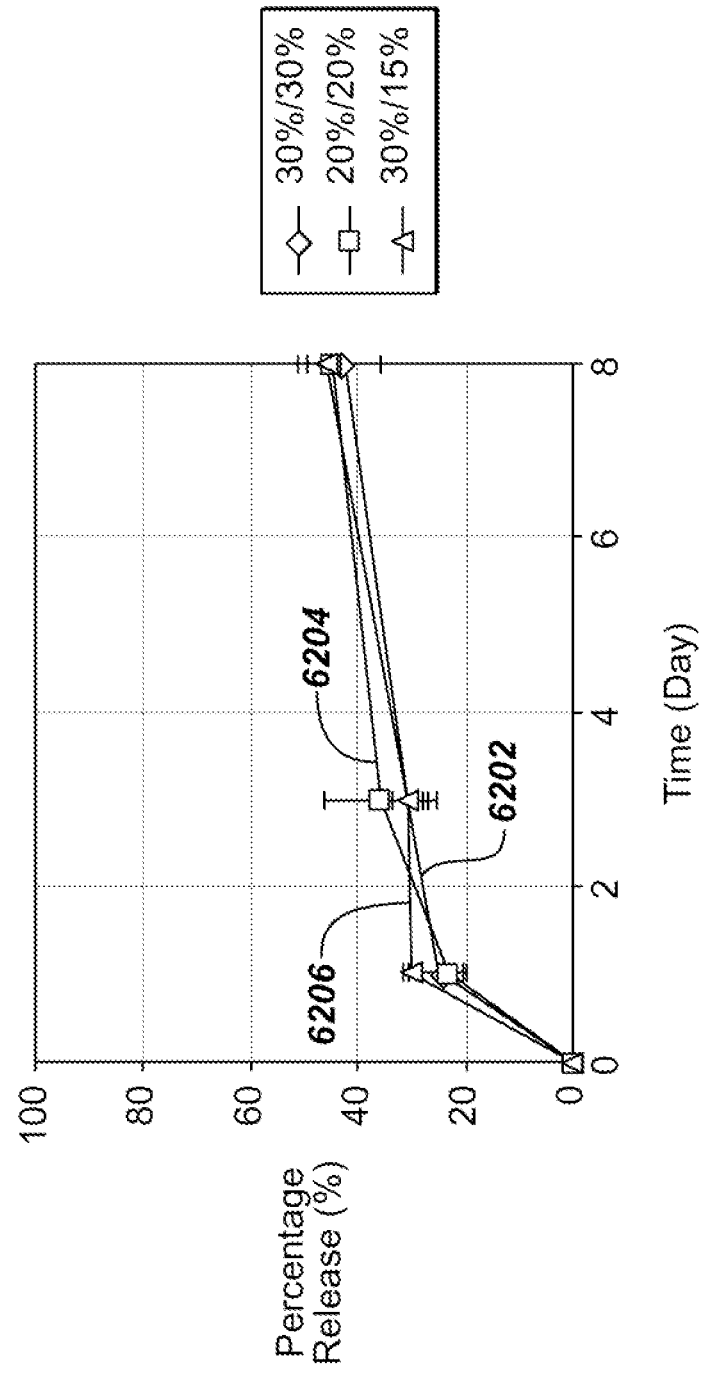
FIG. 62 is a graphical representation of the in vivo release kinetics of rapamycin from a combination of rapamycin, cladribine and a polymer in porcine pharmacokinetics studies in accordance with the present invention.

FIG. 62 is a graphical representation of the in vivo release kinetics of rapamycin from a combination of rapamycin, cladribine and a polymer in porcine pharmacokinetics studies. In the study, the rapamycin and cladribine are incorporated into an EVA/BMA (50/50) polymer basecoat. The basecoat is applied to Bx Velocity® stents and implanted into Yorkshire pigs. Curve 6202 represents the release kinetics of rapamycin from a six hundred microgram basecoat comprising one hundred eighty micrograms rapamycin, one hundred eighty micrograms cladribine and two hundred forty micrograms EVA/BMA with a two hundred microgram topcoat of BMA. Curve 6204 represents the release kinetics of rapamycin from a six hundred microgram basecoat comprising one hundred twenty micrograms rapamycin, one hundred twenty micrograms cladribine and three hundred sixty micrograms EVA/BMA with a two hundred microgram topcoat of BMA. Curve 6206 represents the release kinetics of rapamycin from a six hundred microgram basecoat comprising one hundred eighty micrograms rapamycin, ninety micrograms cladribine and three hundred thirty micrograms EVA/BMA with a two hundred microgram topcoat of BMA. The release rates of rapamycin from the polymeric coating are substantially similar to one another.

Figure 63:
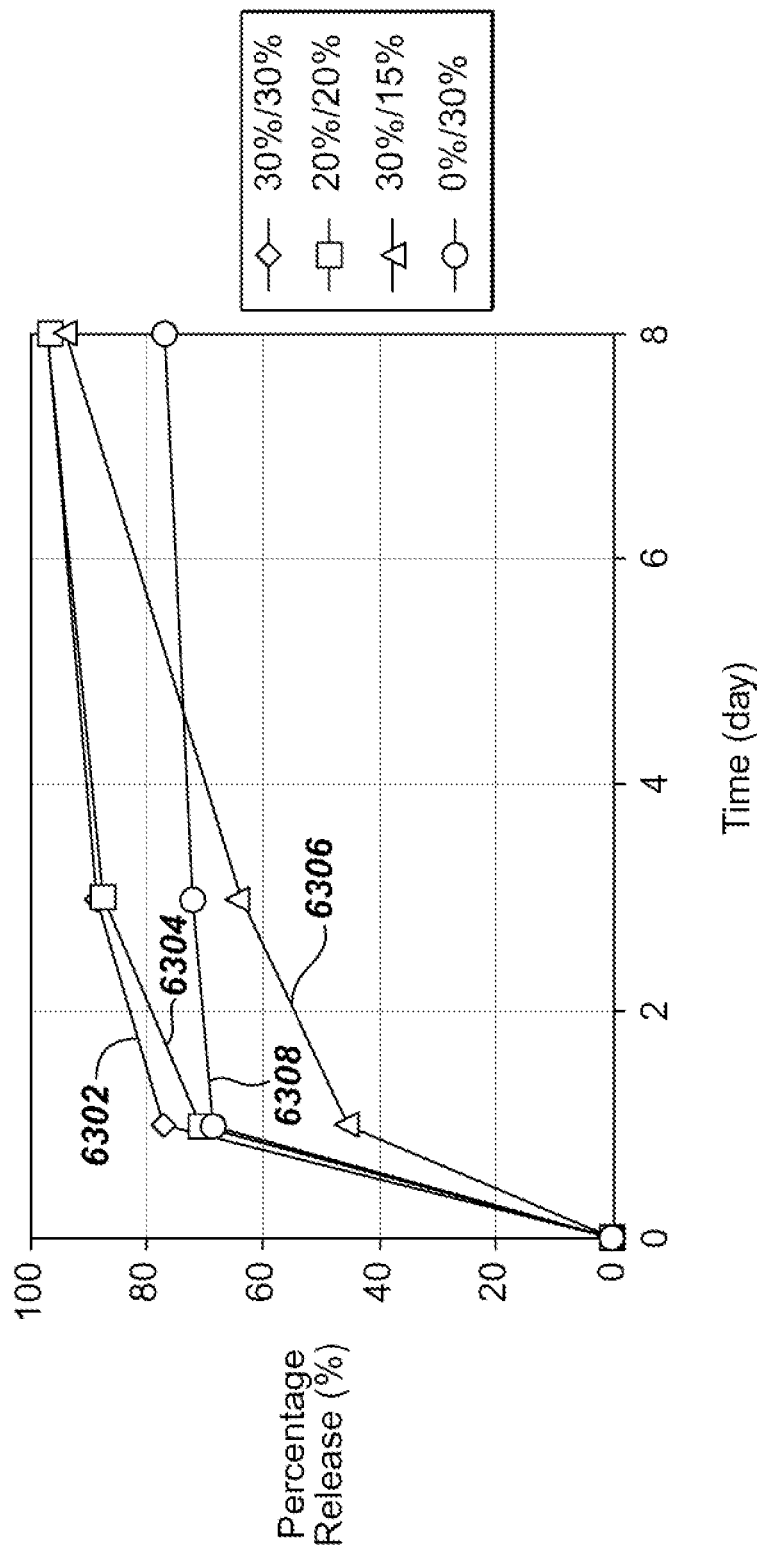
FIG. 63 is a graphical representation of the in vivo release kinetics of cladribine from a combination of rapamycin, cladribine and a polymer in porcine pharmacokinetics studies in accordance with the present invention.

FIG. 63 is a graphical representation of the in vivo release kinetics of cladribine from a combination of rapamycin, cladribine and a polymer in porcine pharmacokinetics studies. In the study, the rapamycin and cladribine are incorporated into an EVA/BMA polymer basecoat. The basecoat is applied to Bx Velocity® stents and implanted into Yorkshire pigs. Curve 6302 represents the release kinetics of cladribine from a six hundred microgram basecoat comprising one hundred eighty micrograms rapamycin, one hundred eighty micrograms cladribine and two hundred forty micrograms EVA/BMA with a two hundred microgram topcoat of BMA. Curve 6304 represents the release kinetics of cladribine from a six hundred microgram basecoat comprising one hundred twenty micrograms rapamycin, one hundred twenty micrograms cladribine and three hundred sixty micrograms EVA/BMA with a two hundred microgram topcoat of BMA. Curve 6306 represents the release kinetics of cladribine from a six hundred microgram basecoat comprising one hundred eighty micrograms rapamycin, ninety micrograms cladribine and three hundred thirty micrograms EVA/BMA with a two hundred microgram topcoat of BMA. Curve 6308 represents the release kinetics of cladribine from a six hundred microgram basecoat comprising no rapamycin, one hundred eighty micrograms of cladribine and four hundred micrograms EVA/BMA with a two hundred microgram BMA topcoat. As illustrated in FIG. 63, there appears to be some degree of controlled cladribine elution from the polymeric stent coating; however, it may be generally concluded that cladribine elutes more rapidly than rapamycin as is seen from a comparison to the results presented with respect to FIG. 62. In general, it appears that the thicker or heavier the topcoat, the slower the elution rate, regardless of the agent.

In yet another alternate exemplary embodiment, topotecan in combination with rapamycin may be utilized to prevent restenosis following vascular injury. Rapamycin acts to reduce lymphocyte and smooth muscle cell proliferation by arresting cells in the G1 phase of the cell cycle through the inhibition of the mammalian target of rapamycin. Subsequent activity of cell cycle associated protein kinases is blocked by the downstream effects of rapamycin on the mammalian target of rapamycin. Topotecan is an analog of camptothecin that interfaces with DNA synthesis through the inhibition of topoisomerase I. This inhibition leads to an accumulation of DNA double strand breaks and an arrest of cell division at the S phase of the cell cycle. Topotecan has been shown to inhibit human coronary artery smooth muscle cell proliferation (Brehm et al., 2000).

Camptothecin is a quinoline-based alkaloid found in the barks of the Chinese camptotheca tree and the Asian nothapodytes tree. Camptothecin, aminocamptothecin, amerogentin, CPT-11 (irinotecan), DX-8951f and topotecan are all DNA topoisomerase I inhibitors. Topotecan, irinotecan and camptothecin belong to the group of medicines or agents generally referred to as anti-neoplastics and are utilized to treat various forms of cancer, including cancer of the ovaries and certain types of lung cancer. Camptothecin may be particularly advantageous in local delivery because of its high lipid solubility and poor water solubility. Poor water solubility may help retain the drug near the release site for a longer period of action time, potentially covering more cells as they cycle. High lipid solubility may lead to increased penetration of the drug through the lipid cellular membrane, resulting in better efficacy.

As rapamycin and topotecan (and the analogs camptothecin and irinotecan) act through different molecular mechanisms affecting cell proliferation at different phases of the cell cycle, it is possible that these agents, when combined on a drug eluting stent or any other medical device as defined herein, may potentiate each other's anti-restenotic activity by downregulating both smooth muscle cell and immune cell proliferation (inflammatory cell proliferation) by distinct multiple mechanisms. In synchronized cultured human coronary artery smooth muscle cells studies, the addition of topotecan to cells treated with rapamycin resulted in a leftward and upward shift of the anti-proliferative rapamycin dose response curves, as set forth in detail below, suggesting that topotecan, and by extension, other agents in the topoisomerase I inhibitor class, does in fact potentiate the anti-proliferative activity of rapamycin in coronary artery smooth muscle cells. The combination of rapamycin and topotecan may be utilized to enhance the anti-restenotic efficacy following vascular injury and a reduction in the required amount of either agent to achieve the anti-restenotic effect. The combination may be particularly relevant to the subpopulations of patients that are resistant to single drug regimens such as rapamycin or paclitaxel coated stents.

Figure 64:
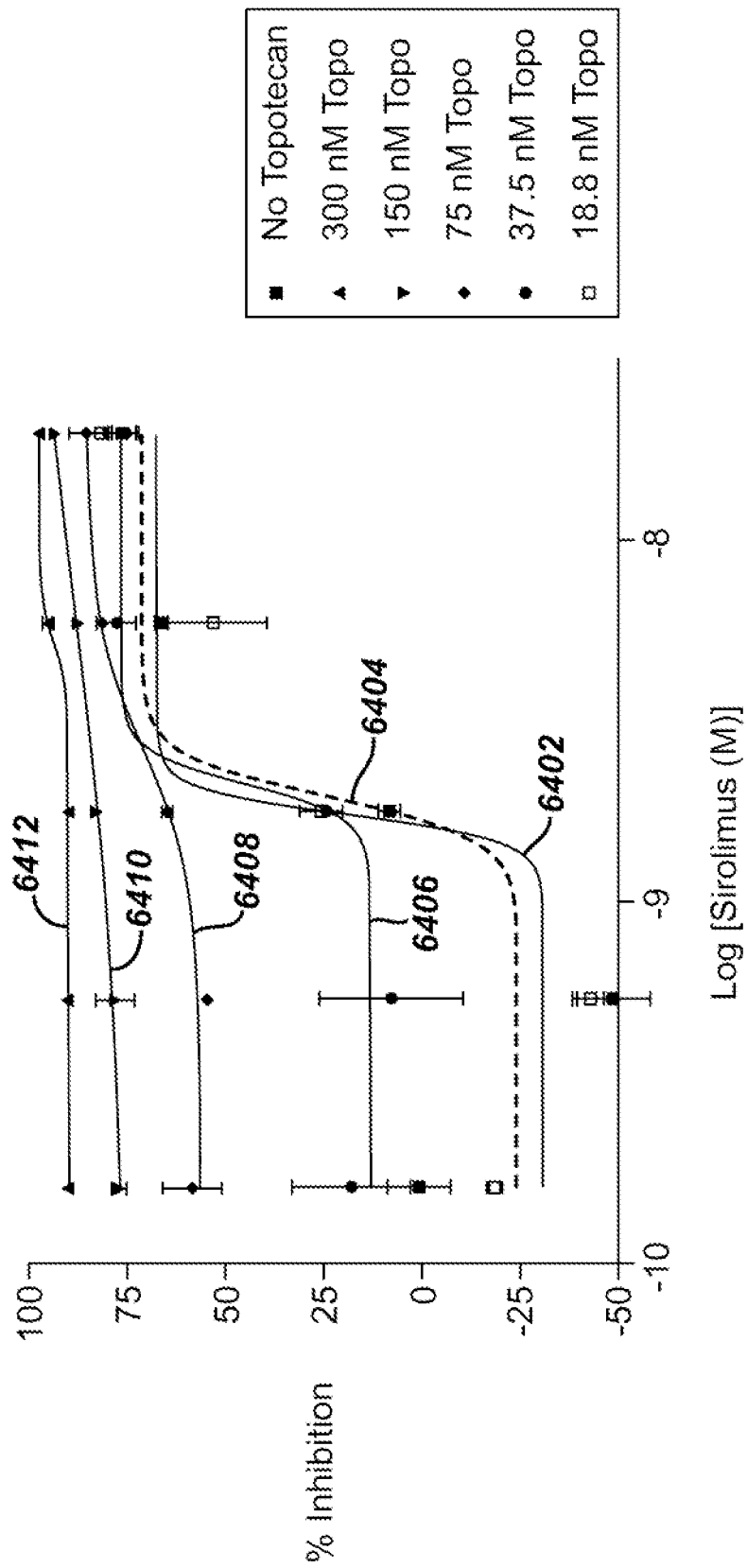
FIG. 64 is a graphical representation of the anti-proliferative activity of rapamycin with varying concentrations of topotecan in synchronized cultured human coronary artery smooth muscle cells stimulated with two percent fetal bovine serum in accordance with the present invention.

Referring to FIG. 64, there is illustrated, in graphical format, the anti-proliferative activity of rapamycin, with varying concentrations of topotecan in synchronized cultured human coronary artery smooth muscle cells stimulated with two percent fetal bovine serum. The multiple curves represent various concentrations of topotecan ranging from zero to three hundred nanomolar concentrations. Topotecan was found to be non-cytotoxic in a separate cell viability assay at concentrations up to one micromolar. As seen in FIG. 64, the addition of topotecan to cells treated with rapamycin increases the percent inhibition of rapamycin alone. Curve 6402 represents the response of just rapamycin. Curve 6404 represents the response of rapamycin in combination with a 18.8 nanomolar concentration of topotecan. Curve 6406 represents the response of rapamycin in combination with a 37.5 nanomolar concentration of topotecan. Curve 6408 represents the response of rapamycin in combination with a 75 nanomolar concentration of topotecan. Curve 6410 represents the response of rapamycin in combination with a 150 nanomolar concentration of topotecan. Curve 6412 represents the response of rapamycin in combination with a 300 nanomolar concentration of topotecan.

The combination of rapamycin and topotecan, as well as other topoisomerase I inhibitors, may provide a new therapeutic combination that may be more efficacious against restenosis/neointimal thickening than rapamycin alone. Different doses of rapamycin and topotecan, as well as other topoisomerase I inhibitors, may lead to additional gains of inhibition of the neointimal growth than the simple additive effects of rapamycin and topotecan. In addition, the combination of topotecan, as well as other topoisomerase I inhibitors, may be efficacious in the treatment of other cardiovascular diseases such as vulnerable atherosclerotic plaque.

The combination of rapamycin and topotecan, as well as other topoisomerase I inhibitors, may be delivered to the target tissue through any number of means including stents and catheters. The delivery of the drug combination may be achieved at different dose rates to achieve the desired effect, and as explained in more detail subsequently, each drug may be loaded into different levels of the polymeric matrix.

In yet another alternate exemplary embodiment, etoposide in combination with rapamycin may be utilized to prevent restenosis following vascular injury. Rapamycin acts to reduce smooth muscle cell proliferation and lymphocyte proliferation by arresting cells in the G1 phase of the cell cycle through inhibition of the mammalian target of rapamycin. Subsequent activity of cell cycle associated protein kinases is blocked by the downstream effects of rapamycin on the mammalian target of rapamycin. Etoposide is a cytostatic glucoside derivative of podophyllotoxin that interferes with DNA synthesis through inhibition of topoisomerase II. This inhibition leads to DNA strand breaks and an accumulation of cells in the G2/M phase of the cell cycle, G2/M checkpoint dysregulation and subsequent apoptosis.

Podophyllotoxin (podofilox) and its derivatives, etoposide and teniposide, are all cytostatic (antimitotic) glucosides. Podofilox is an extract of the mayapple. Proliferating cells are particularly vulnerable to podofilox. Etoposide is utilized to treat cancer of the testicles, lungs and other kinds of cancer. Etoposide and teniposide both block the cell cycle in two specific places. Etoposide and teniposide block the phase between the last division and the start of DNA replication and also block the replication of DNA.

As rapamycin and etoposide act through different molecular mechanisms affecting cell proliferation at different phases of the cell cycle, it is likely that these agents, when combined on a drug eluting stent or any other medical device as defined herein may potentiate each other's anti-restenotic activity by downregulating both smooth muscle cell and immune cell proliferation (inflammatory cell proliferation) by distinct multiple mechanisms. In non-synchronized cultured human coronary artery smooth muscle cell studies, the addition of etoposide to cells treated with rapamycin resulted in a leftward and upward shift of the anti-proliferative rapamycin dose response curves, as set forth in detail below, suggesting that etoposide, and by extension, other agents in the topoisomerase II inhibitor class, potentiate the anti-proliferative activity of rapamycin in coronary artery smooth muscle cells. The combination of rapamycin and etoposide may be utilized to enhance the anti-restenotic efficacy following vascular injury and a reduction in the required amount of either agent to achieve the anti-restenotic effect. The combination may be particularly relevant to the subpopulation of patients that are resistant to single drug regimens such as rapamycin or paclitaxel coated stents.

Figure 65:
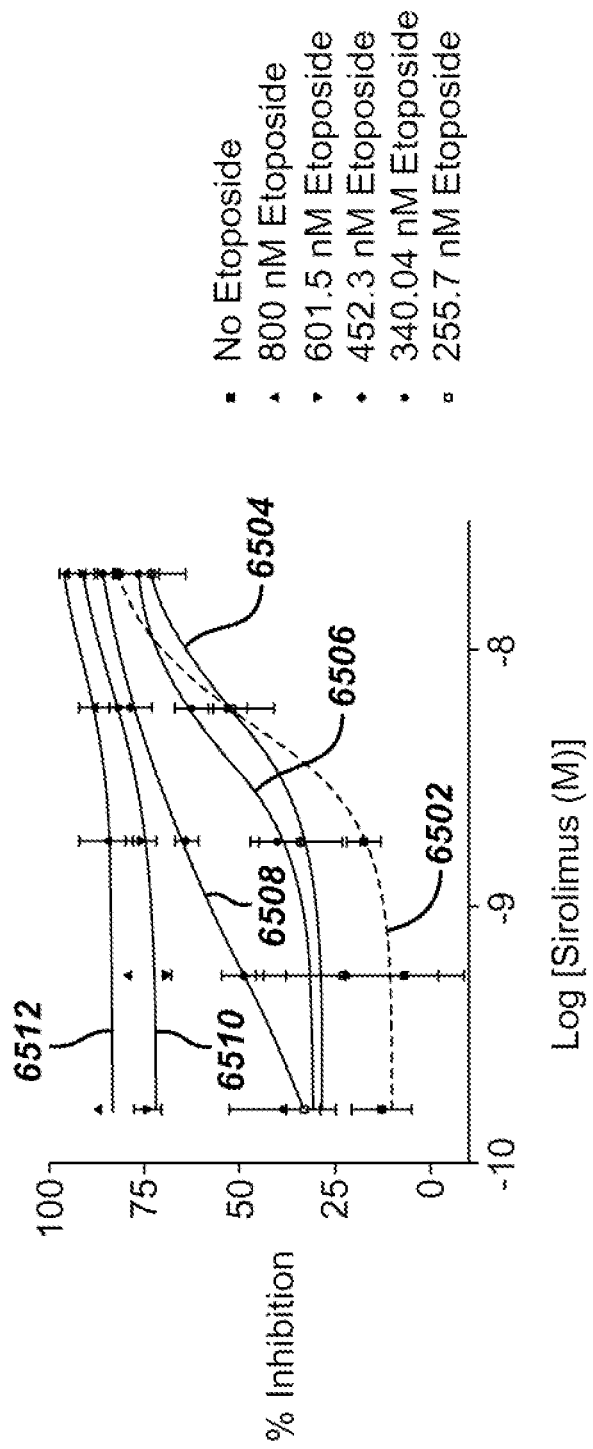
FIG. 65 is a graphical representation of the anti-proliferative activity of rapamycin with varying concentrations of etoposide in synchronized cultured human coronary smooth muscle cells stimulated with two percent fetal bovine serum in accordance with the present invention.

Referring to FIG. 65, there is illustrated, in graphical format, the anti-proliferative activity of rapamycin with varying concentrations of etoposide in synchronized cultured human coronary artery smooth muscle cells stimulated with two percent fetal bovine serum. The multiple curves represent various concentrations of etoposide ranging from zero to eight hundred nanomolar concentrations. Etoposide was found to be non-cytotoxic in a cell viability assay at concentrations up to ten micromolar. As seen in FIG. 65, the addition of etoposide to cells treated with rapamycin increases the percent inhibition of rapamycin alone. Curve 6502 represents the response of just rapamycin. Curve 6504 represents the response of rapamycin in combination with a 255.7 nanomolar concentration of etoposide. Curve 6506 represents the response of rapamycin in combination with a 340.04 nanomolar concentration of etoposide. Curve 6508 represents the response of rapamycin in combination with a 452.3 nanomolar concentration of etoposide. Curve 6510 represents the response of rapamycin in combination with a 601.5 nanomolar concentration of etoposide. Curve 6512 represents the response of rapamycin in combination with an eight-hundred nanomolar concentration of etoposide.

The combination of rapamycin and etoposide, as well as other cytostatic glucosides, including podophyllotoxin, its derivatives and teniposide, may provide a new therapeutic combination that may be more efficacious against restenosis/neointimal thickening than rapamycin alone. Different doses of rapamycin and etoposide, as well as other cytostatic glucosides, including podophyllotoxin, its derivatives and teniposide, may lead to additional gains of inhibition of the neointimal growth than the simple additive effects of rapamycin and etoposide. In addition, the combination of etoposide, as well as other cytostatic glucosides, including podophyllotoxin, its derivatives and teniposide, may be efficacious in the treatment of other cardiovascular diseases such as vulnerable atherosclerotic plaque.

The combination of rapamycin and etoposide, as well as other cytostatic glucosides, including podophyllotoxin, its derivatives and teniposide, may be delivered to the target tissue through any number of means including stents and catheters. The delivery of the drug combination may be achieved at different dose rates to achieve the desired effect, and as explained in more detail subsequently, each drug may be loaded into different levels of the polymeric matrix.

In yet another alternate exemplary embodiment, Panzem® may be utilized alone or in combination with rapamycin to prevent restenosis following vascular injury. Rapamycin or sirolimus acts to reduce lymphocyte and smooth muscle cell proliferation by arresting cells in the G1 phase of the cell cycle through the inhibition of the mammalian target of rapamycin (mTOR). Rapamycin or sirolimus has shown excellent anti-restenotic effects when administered during revascularization procedures using drug eluting stents. In recent clinical trials, the Cypher® stent, available from Cordis Corporation, which contains rapamycin or sirolimus in a polymer coating, consistently demonstrated superior efficacy against restenosis after the implantation of the stent as compared to a bare metal stent. Although the local delivery of rapamycin from a drug eluting stent or other medical device is effective in reducing restenosis, further reductions in neointimal hyperplasia would benefit certain patient populations. Thus, the combination of rapamycin with another agent, for example, another anti-proliferative agent from a stent or other medical device may further reduce fibroproliferative vascular responses secondary to procedures involving vascular injury.

Panzem®, or 2-methoxyestradiol (2ME2) is a naturally occurring metabolite of endogenous estrogen. Its many properties provide for a wide range of potential formulations for drug delivery to treat numerous indications. Panzem® has been shown to exhibit anti-cancer activity in patients with breast cancer, prostate cancer and multiple myeloma. Panzem® is a by-product of the metabolism estrogen and is normally present in the body in small amounts. Panzem®; however, does not act like a hormone. Panzem® is a potent inhibitor of angiogenesis, which is what makes it such an effective anti-tumor agent. Essentially, Panzem® inhibits the formation of new blood vessels that supply oxygen and nutrients to tumor cells. Panzem® also appears to have multiple direct and indirect anti-myeloma effects as briefly described above.

Panzem®, 2-methoxyestradiol (2ME2) or methoxy-β-estradiol is, as described above, a product of estrogen metabolism and is currently being evaluated clinically for a variety of oncologic indications. Panzem® has anti-angiogenic activity, blocks the production of vascular endothelial growth factor and directly inhibits the growth of a number of tumor cell types. Panzem® is also proapoptotic (programmed cell death) to myeloma cells. Panzem® has been found to upregulate the DR-5 receptor (of the TNF receptor family) number responsible for TRAIL-mediated apoptosis (AACR, 2003) and has microtubule stabilizing properties and reduces hypoxia-inducible factor-1 (AACR, 2003). In addition, as illustrated in detail below, Panzem® reduces human coronary artery smooth muscle cell proliferation without negatively impacting coronary artery smooth muscle cell viability.

Figure 66:
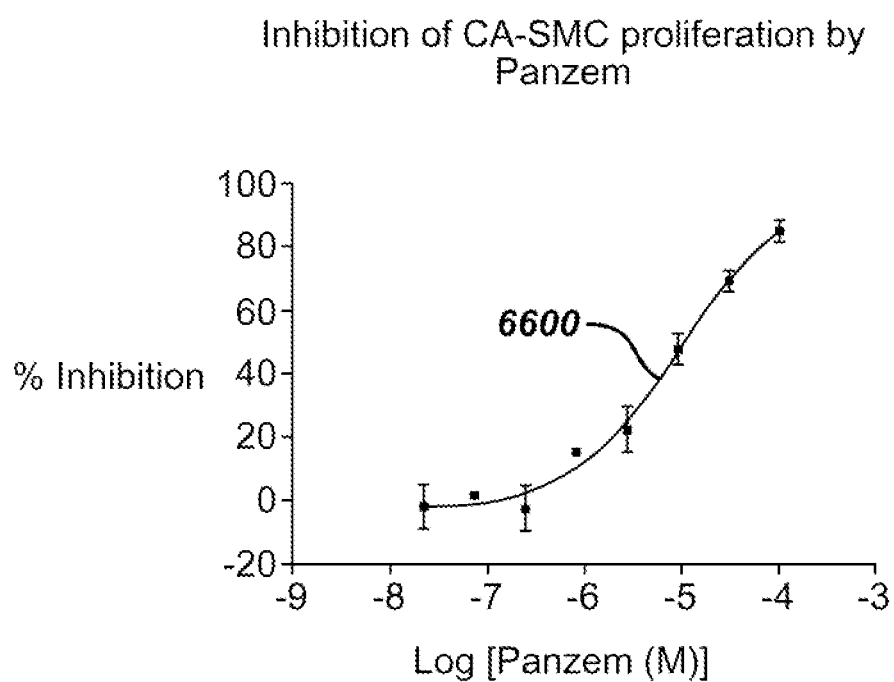
FIG. 66 is a graphical representation of the anti-proliferative activity of Panzem® in synchronized cultured human coronary artery smooth muscle cells stimulated with two percent fetal bovine serum in accordance with the present invention.
Figure 67:
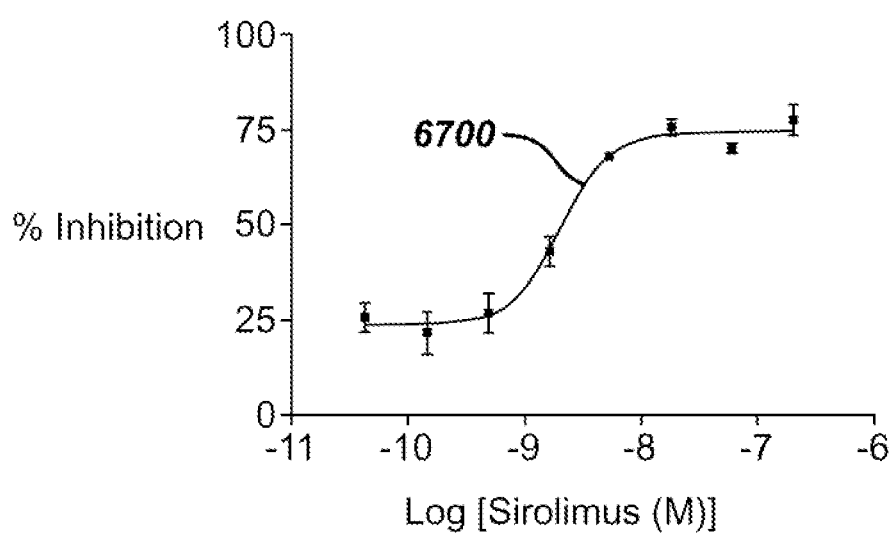
FIG. 67 is a graphical representation of the anti-proliferative activity of rapamycin in synchronized cultured human coronary artery smooth muscle cells stimulated with two percent fetal bovine serum in accordance with the present invention.

Referring to FIG. 66, there is illustrated, in graphical format, the anti-proliferative activity of Panzem® in synchronized cultured human coronary artery smooth muscle cells stimulated with two percent fetal bovine serum. As illustrated by curve 6600, Panzem® is an extremely effective inhibitor of human coronary artery smooth muscle cell proliferation in vitro. FIG. 67 illustrates, in graphical format, the anti-proliferative activity of rapamycin or sirolimus in synchronized cultured human coronary artery smooth muscle cells stimulated with two percent fetal bovine serum. As can be seen between a comparison between curves 6700 and 6600, both agents are effective in the in vitro studies.

Figure 68:
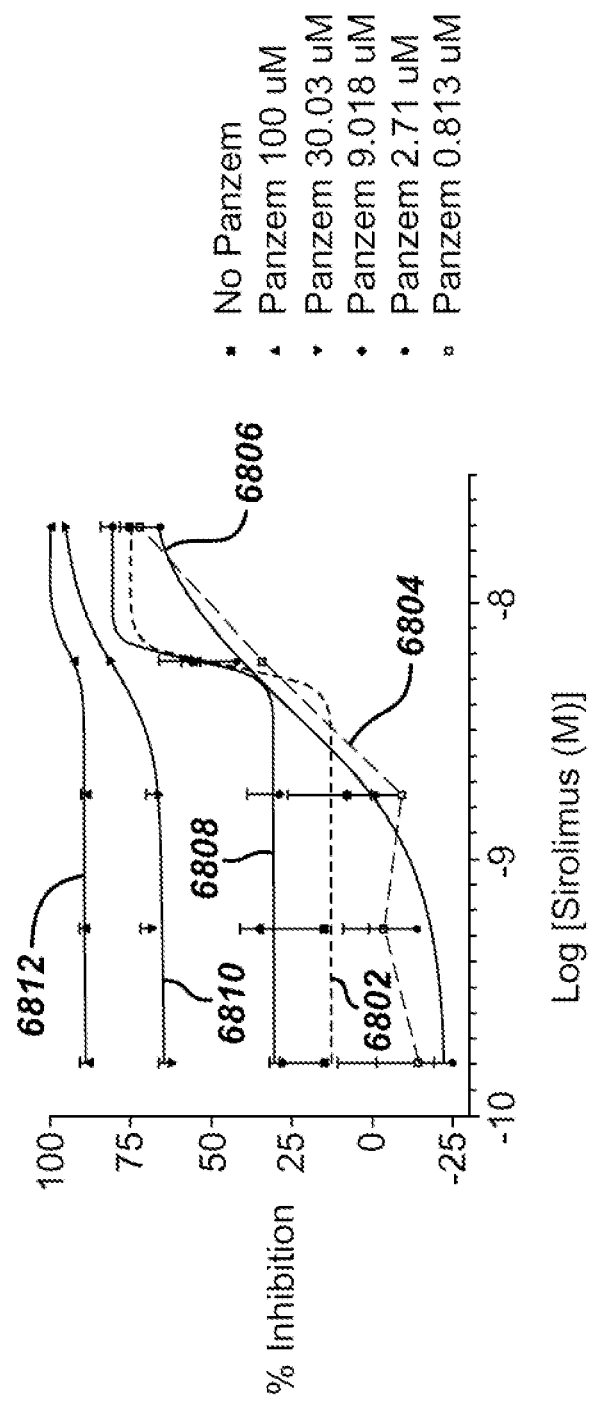
FIG. 68 is a graphical representation of the anti-proliferative activity of rapamycin with varying concentrations of Panzem® in synchronized cultured human coronary artery smooth muscle cells stimulated with two percent fetal bovine serum in accordance with the present invention.

As rapamycin or sirolimus and Panzem® or other estrogen receptor modulators act to inhibit cell proliferation through different molecular mechanisms, it is possible that these agents, when combined on a drug eluting stent or other medical device as defined herein, may potentiate each other's anti-restenotic activity by downregulating both smooth muscle and immune cell proliferation (inflammatory cell proliferation) by distinct multiple mechanisms. FIG. 68 illustrates the potentiation of rapamycin by Panzem® on the anti-proliferative effects of rapamycin in coronary artery smooth muscle cells. This potentiation of rapamycin antiproliferative activity by Panzem® and related compounds may translate into an enhancement in anti-restenotic efficacy following vascular injury during revascularization and other vascular surgical procedures and a reduction in the required amount of either agent to achieve the anti-restenotic effect. In addition, the local application of Panzem® and related compounds, alone or in combination with rapamycin may be therapeutically useful in treating vulnerable plaque.

Referring to FIG. 68, there is illustrated, in graphical format, the anti-proliferative activity of rapamycin with varying concentrations of Panzem® in synchronized cultured human coronary artery smooth muscle cells stimulated with two percent fetal bovine serum. The multiple curves represent various concentrations of Panzem® ranging from zero to 100 micromolar concentrations. As seen in FIG. 68, the addition of Panzem® to cells treated with rapamycin increases the percent of inhibition of rapamycin alone. Curve 6802 represents the response of just rapamycin. Curve 6804 represents the response of rapamycin in combination with a 0.813 micromolar concentration of Panzem®. Curve 6806 represents the response of rapamycin in combination with a 2.71 micromolar concentration of Panzem®. Curve 6808 represents the response of rapamycin in combination with a 9.018 micromolar concentration of Panzem®. Curve 6810 represents the response of rapamycin in combination with a 30.03 micromolar concentration of Panzem®. Curve 6812 represents the response of rapamycin in combination with a 100 micromolar concentration of Panzem®.

Figure 69:
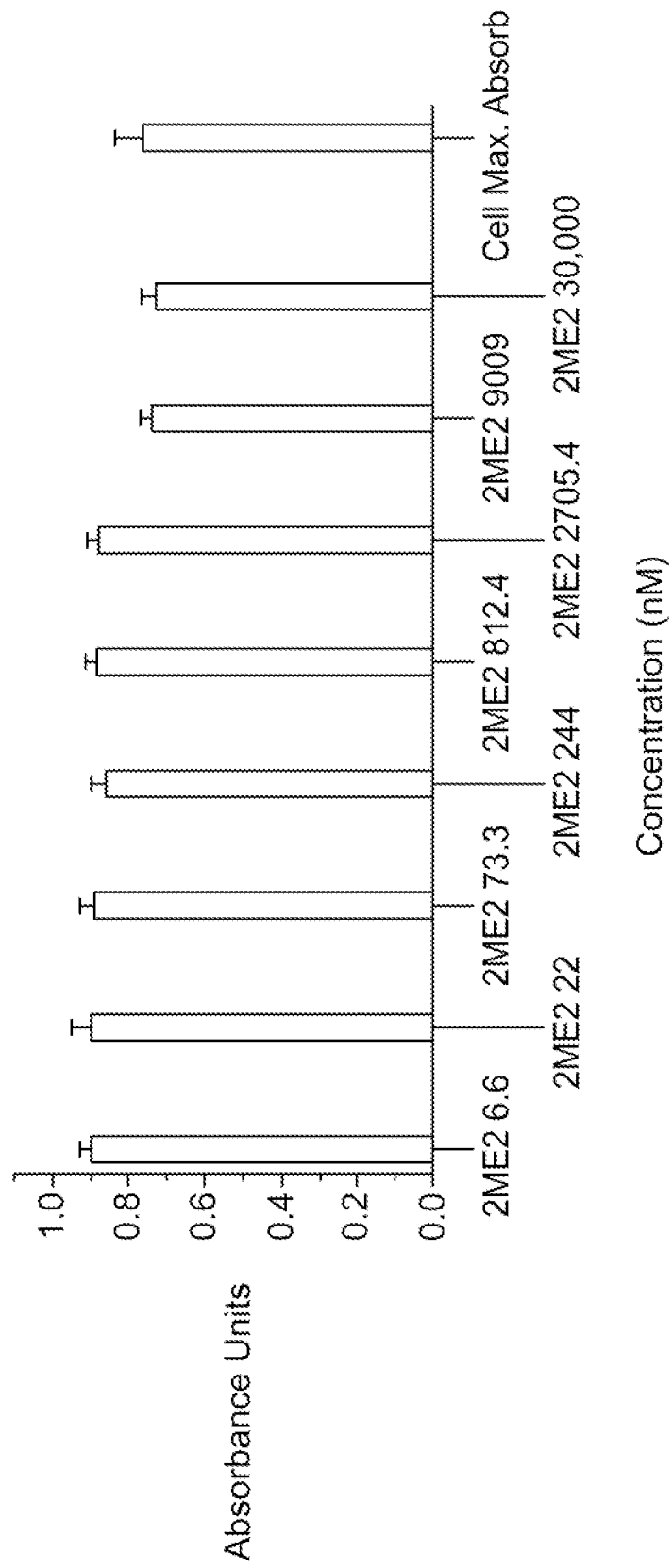
FIG. 69 is a graphical representation of a MTS assay of Panzem® in accordance with the present invention.

In vitro cytotoxicity tests or assays may be utilized to determine if drugs, agents and/or compounds are potentially toxic and the level of toxicity. Essentially, in vitro cytotoxicity assays determine acute necrotic effects by a drug causing direct cellular damage. The idea behind these assays is that toxic chemicals affect basic functions of cells which are common to all cells. Typically, a control is utilized to determine baseline toxicity. There are a number of different assays that may be utilized. In the present invention, the cytotoxicity assay utilized is based upon the measurement of cellular metabolic activity. A reduction in metabolic activity is an indication of cellular damage. Tests that can measure metabolic function measure cellular ATP levels or mitochondrial activity via MTS metabolism. FIG. 69 is a graphical representation of the results of an MTS assay of Panzem®. As illustrated, concentrations of Panzem® ranging from 6.6 nanomolar to 30,000.00 nanomolar concentrations were tested without any significant fluctuations in cytotoxicity. The results of the assay indicate that Panzem® concentrations up to 30,000.00 nanomolar do not reduce human coronary artery smooth muscle cell survival.

Figure 70:
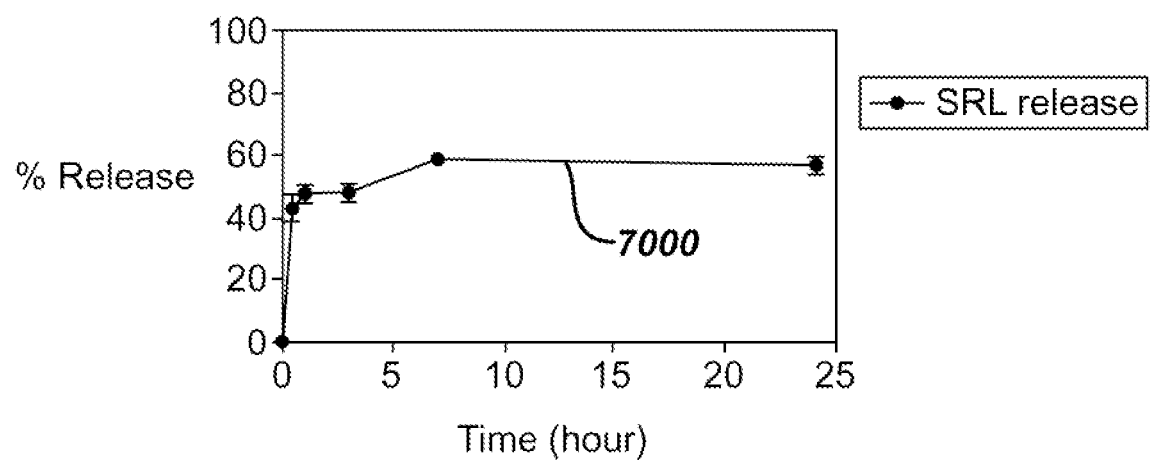
FIG. 70 is a graphical representation of the in vitro release kinetics of rapamycin from a layered rapamycin, Panzem® and polymeric coating in accordance with the present invention.

FIG. 70 is a graphical representation of the in vitro release kinetics of rapamycin or sirolimus from a combination of rapamycin and Panzem®. In the study, the rapamycin and Panzem® are incorporated into different layers of a polymeric coating. In this study, a Bx Velocity stent is coated with a four hundred microgram inner layer and a three hundred microgram outer layer. The inner layer comprises forty-five percent Panzem® and fifty-five percent EVA/BMA (50/50). The outer layer comprises forty percent rapamycin and sixty percent EVA/BMA (50/50). There is no topcoat of just polymer in this study. Curve 7000 illustrates the release kinetics of rapamycin from the combination.

Figure 71:
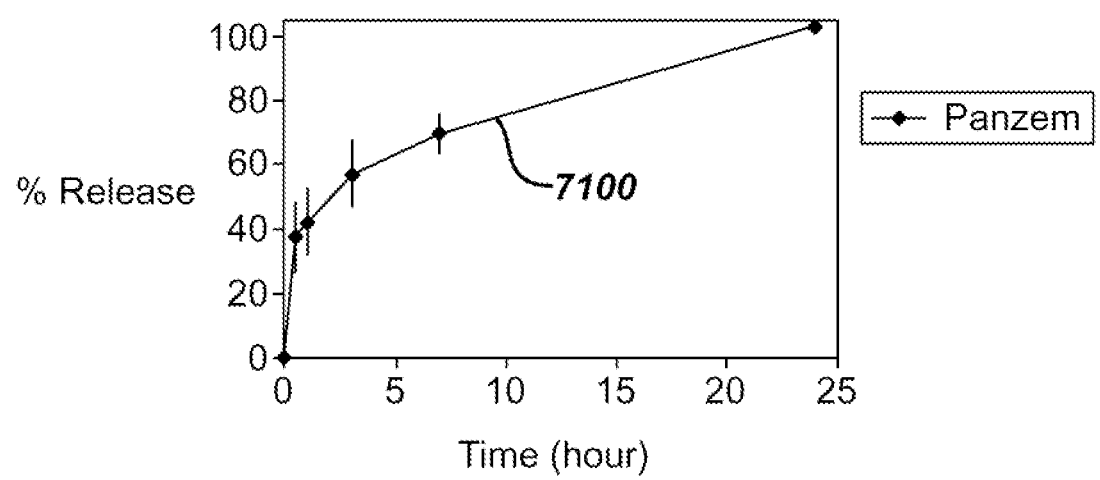
FIG. 71 is a graphical representation of the in vitro release kinetics of Panzem® from a layered rapamycin, Panzem® and polymeric coating in accordance with the present invention.
Figure 72A:
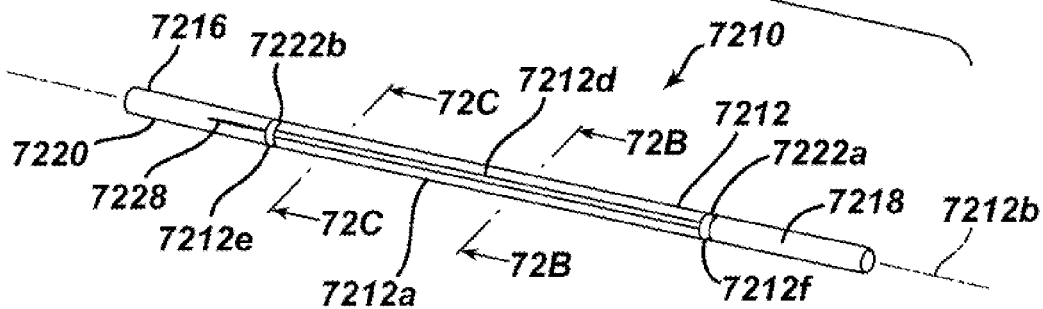
FIG. 72A is a schematic, perspective view of a microfabricated surgical device for interventional procedures in an unactuated condition in accordance with the present invention.
Figure 72B:
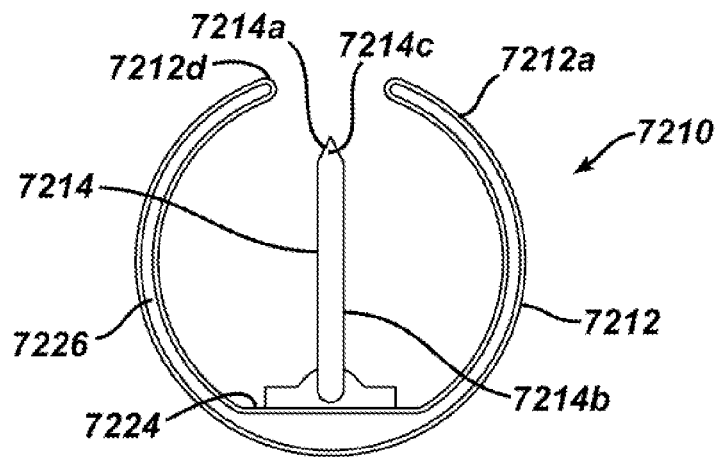
FIG. 72B is a schematic view along line 72B-72B of FIG. 72A.
Figure 72C:
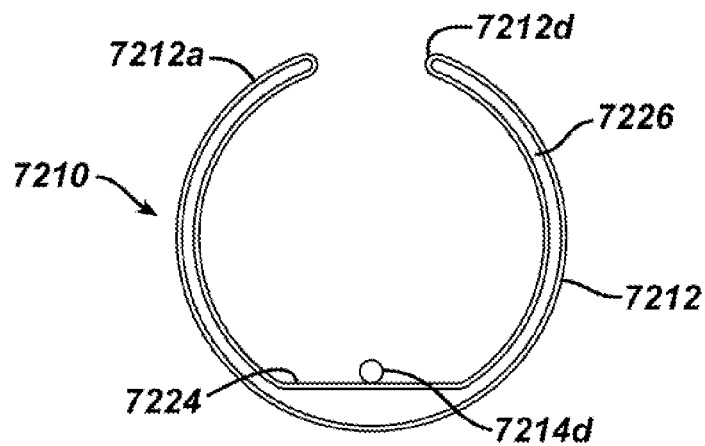
FIG. 72C is a schematic view along line 72C-72C of FIG. 72A.

FIG. 71 is a graphical representation of the in vitro release kinetics of Panzem® from a combination of rapamycin or sirolimus and Panzem®. In the study, the rapamycin and Panzem® are incorporated into different layers of a polymeric coating. In this study, a Bx Velocity stent is coated with a four hundred microgram inner layer and a three hundred microgram outer layer. The inner layer comprises forty-five percent Panzem® and fifty-five percent EVA/BMA (50/50). The outer layer comprises forty percent rapamycin and sixty percent EVA/BMA (50/50). There is no topcoat of just polymer in this study. Curve 7100 illustrates the release kinetics of Panzem® from the coating. As may be seen from a comparison of FIGS. 70 and 71, rapamycin elutes more slowly than Panzem® under the conditions of the test.

In yet another alternate exemplary embodiment, rapamycin may be utilized in combination with cilostazol. Cilostazol {6[4-(1-cyclohexyl-1H-tetrazol-5-yl)-butoxy]-3,4-dihydro-2-(1H)-quinolinone} is an inhibitor of type III (cyclic GMP-inhibited) phosphodiesterase and has anti-platelet and vasodilator properties. Cilostazol was originally developed as a selective inhibitor of cyclic nucleotide phosphodiesterase 3. Phosphodiesterase 3 inhibition in platelets and vascular smooth muscle cells was expected to provide an anti-platelet effect and vasodilation; however, recent preclinical studies have demonstrated that cilostazol also possesses the ability to inhibit adenosine uptake by various cells, a property that distinguishes cilastazol from other phosphodiesterase 3 inhibitors, such as milrinone. Accordingly, cilostazol has been shown to have unique antithrombotic and vasodilatory properties based upon a number of novel mechanisms of action.

Studies have also shown the efficacy of cilostazol in reducing restenosis after the implantation of a stent. See, for example, Matsutani M., Ueda H. et al.: "Effect of cilostazol in preventing restenosis after percutaneous transluminal coronary angioplasty, Am. J. Cardiol 1997, 79:1097-1099, Kunishima T., Musha H., Eto F., et al.: A randomized trial of aspirin versus cilostazol therapy after successful coronary stent implantation, Clin Thor 1997, 19:1058-1066, and Tsuchikane E. Fukuhara A., Kobayashi T., et al.: Impact of cilostazol on restenosis after percutaneous coronary balloon angioplasty, Circulation 1999, 100:21-26.

In accordance with the present invention, cilostazol may be configured for sustained release from a medical device or medical device coating to help reduce platelet deposition and thrombosis formation on the surface of the medical device. As described herein, such medical devices include any short and long term implant in constant contact with blood such as cardiovascular, peripheral and intracranial stents. Optionally, cilostazol may be incorporated in an appropriate polymeric coating or matrix in combination with a rapamycin or other potent anti-restenotic agents.

The incorporation and subsequent sustained release of cilostazol from a medical device or a medical device coating will preferably reduce platelet deposition and thrombosis formation on the surface of the medical device. There is, as described above, pre-clinical and clinical evidence that indicates that cilostazol also has anti-restenotic effects partly due to its vasodilating action. Accordingly, cilostazol is efficacious on at least two aspects of blood contacting devices such as drug eluting stents. Therefore, a combination of cilostazol with another potent anti-restenotic agent including a rapamycin, such as sirolimus, its analogs, derivatives, congeners and conjugates or paclitoxel, its analogs, derivatives, congeners and conjugates may be utilized for the local treatment of cardiovascular diseases and reducing platelet deposition and thrombosis formation on the surface of the medical device. Although described with respect to stents, it is important to note that the drug combinations described with respect to this exemplary embodiment may be utilized in connection with any number of medical devices, some of which are described herein.

Figure 75:
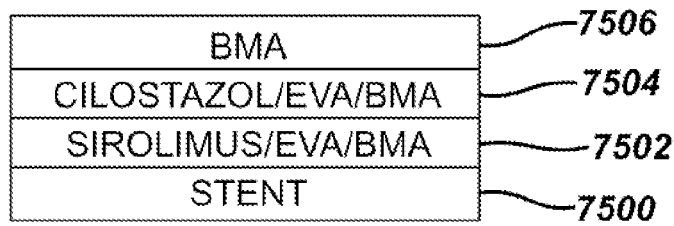
FIG. 75 is a diagrammatic representation of a first exemplary embodiment of a stent coated with a combination of sirolimus and cilostazol in accordance with the present invention.

FIG. 75 illustrates a first exemplary configuration of a combination of cilostazol and a rapamycin on a stent. In this exemplary embodiment, the stent is a Bx Velocity® stent available from Cordis Corporation. In this particular configuration, the stent 7500 is coated with three layers. The first layer or inner layer 7502 comprises one hundred eighty (180 μg) micrograms of sirolimus which is equivalent to forty-five (45) percent by weight of the total weight of the inner layer 7502 and a copolymer matrix of, polyethelene-co-vinylacetate and polybutylmethacrylate, EVA/BMA which is equivalent to fifty-five (55) percent by weight of the total weight of the inner layer 7502. The second layer or outer layer 7504 comprises one hundred (100 μg) micrograms of cilostazol which is equivalent to forty-five (45) percent by weight of the total weight of the outer layer 7504 and a copolymer matrix of EVA/BMA which is equivalent to fifty-five (55) percent by weight of the total weight of the outer layer 7504. The third layer or diffusion overcoat 7506 comprises two hundred (200 μg) micrograms of BMA. The range of content recovery was eighty-five (85) percent of nominal drug content for the sirolimus and ninety-eight (98) percent of nominal drug content for cilostazol. The in vitro release kinetics for both cilostazol and sirolimus are illustrated in FIG. 76 and are described in more detail subsequently.

Figure 77:
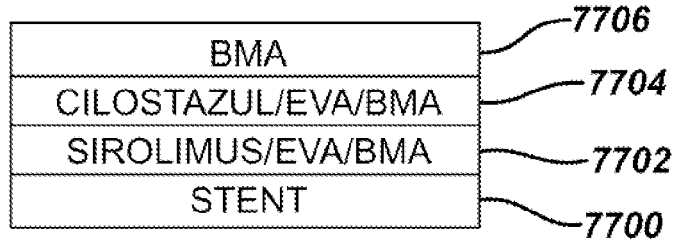
FIG. 77 is a diagrammatic representation of a second exemplary embodiment of a stent coated with a combination of sirolimus and cilostazol in accordance with the present invention.

FIG. 77 illustrates a second exemplary configuration of a combination of cilostazol and a rapamycin on a stent. As described above, the stent is a Bx Velocity® stent available from Cordis Corporation. In this exemplary embodiment, the stent 7700 is coated with three layers. The first layer or inner layer 7702 comprises one hundred eighty (180 μg) micrograms of sirolimus which is equivalent to forty-five (45) percent by weight of the total weight of the inner layer 7702 and a copolymer matrix of EVA/BMA which is equivalent to fifty-five (55) percent by weight of the total weight of the inner layer 7702. The second layer or outer layer 7704 comprises one hundred (100 μg) micrograms of cilostazol which is equivalent to forty-five (45) percent by weight of the total weight of the outer layer 7704 and a copolymer matrix of EVA/BMA which is equivalent to fifty-five (55) percent by weight of the outer layer 7704. The third layer or diffusion overcoat 7706 comprises one hundred (100 μg) micrograms of BMA. Once again, the range of content recovery was eighty-five (85) percent of nominal drug content for the sirolimus and ninety-eight (98) percent of nominal drug content in cilostazol. The in-vitro release kinetic for both cilostazol and sirolimus are illustrated in FIG. 78 and are described in more detail subsequently.

Figure 76:
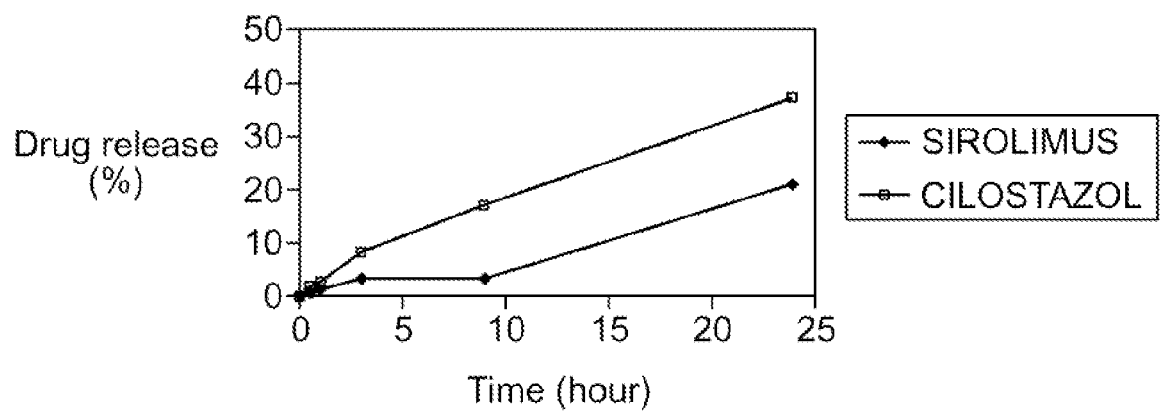
FIG. 76 is a graphical representation of the in vitro release kinetics of a first exemplary sirolimus and cilostazol combination stent coating in accordance with the present invention.
Figure 78:
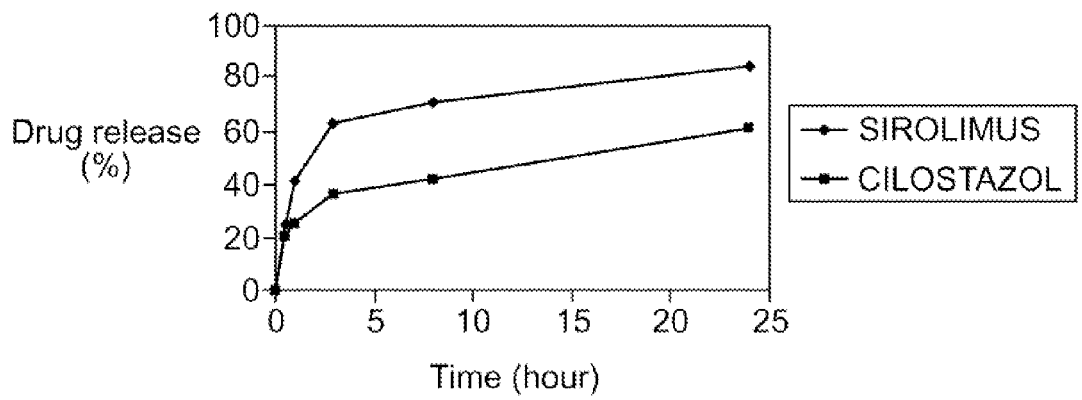
FIG. 78 is a graphical representation of the in vitro release kinetics of a second exemplary sirolimus and cilostazol combination stent coating in accordance with the present invention.

As may be readily seen from a comparison of FIGS. 76 and 78, the drug release rate of both sirolimus and cilostazol was comparatively slower from the configuration comprising the thicker diffusion overcoat of BMA, i.e. two hundred micrograms rather than one hundred micrograms. Accordingly, additional control over the drug elution rates for both drugs may be achieved through the selective use of diffusion overcoats as described more fully herein. The selective use of diffusion overcoats includes thickness as well as other features, including chemical incompatibility.

Figure 79:
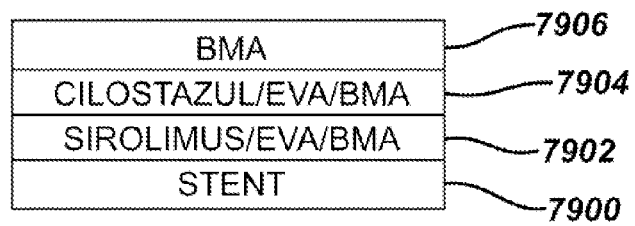
FIG. 79 is a diagrammatic representation of a third exemplary embodiment of a stent coated with a combination of sirolimus and cilostazol in accordance with the present invention.

FIG. 79 illustrates a third exemplary configuration of a combination of cilostazol and a rapamycin on a stent. This configuration is identical in structure to that of the configuration of FIG. 75, but with the amount of cilostazol reduced to fifty (50 μg) micrograms. As with the previous exemplary embodiment, there is a stent 7900 and three additional layers 7902, 7904 and 7906. The percentage by weight, however, remains the same.

Figure 80:
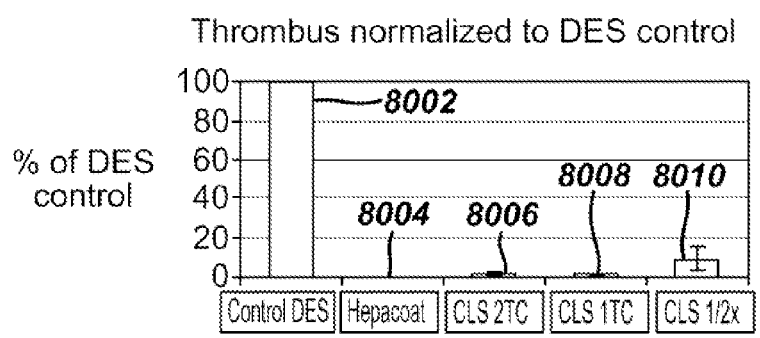
FIG. 80 is a graphical representation of the anti-thrombotic activity of a combination sirolimus and cilostazol drug eluting stent in an in vitro bovine blood loop model in accordance with the present invention.

The anti-thrombotic efficacy of the above-described three configurations is illustrated in FIG. 80. FIG. 80 illustrates the anti-thrombotic properties of the sirolimus/cilostazol combination coatings described above in an in vitro bovine blood loop model. In the in vitro bovine blood loop model, fresh bovine blood is heparinized to adjust for acute clotting time (ACT) of about two hundred (200) seconds. The platelet content in the blood is labeled through the use of Indium 111. In the study, a stent is deployed in a silicone tube, which is part of a closed loop system for blood circulation. The heparinzed blood is circulated through the closed loop system by means of a circulating pump. Blood clots and thrombus builds up on a stent surface over time and reduces the flow rate of blood through the stented loop. The flow is stopped when the flow rate is reduced to fifty (50) percent of the starting value or at ninety (90) minutes if none of the tested stent reduces the flow by fifty (50) percent. The total radioactivity (In 111) on the stent surface is counted by a beta counter and normalized with the control unit, set as one hundred (100) percent in the chart. A smaller number indicates that the surface is less thrombogenic. All three sirolimus/cilostazol dual drug coating groups reduced platelet deposition and thrombus formation on the stent surface by more than ninety (90) percent compared to the control drug eluting stent without the additional cilostazol compound. Bar 8002 represents the control drug eluting stent which has been normalized to one hundred (100) percent. The control drug eluting stent is the Cypher® sirolimus eluting coronary stent available from Cordis Corporation. Bar 8004 is a stent coated with heparin and is available from Cordis Corporation under the HEPACOAT® on the Bx Velocity® coronary stent trademark. Bar 8006 is a stent configured as set forth with respect to the architecture illustrated in FIG. 75. Bar 8008 is a stent configured as set forth with respect to the architecture illustrated in FIG. 77. Bar 8010 is a stent configured as set forth with respect to the architecture illustrated in FIG. 79. As may be readily seen from FIG. 80, cilostazol significantly reduces thrombus formation.

Figure 81:
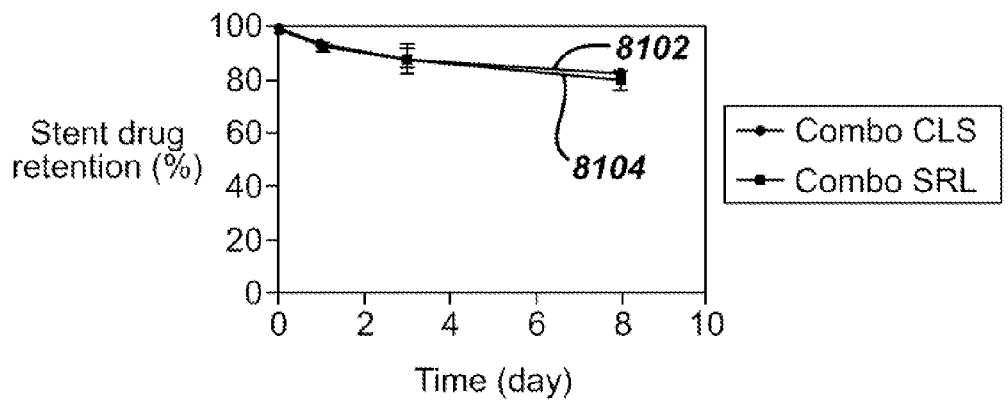
FIG. 81 is a graphical representation of the in vivo release kinetics of sirolimus and cilostazol from the stent illustrated in FIG. 83.
Figure 82:
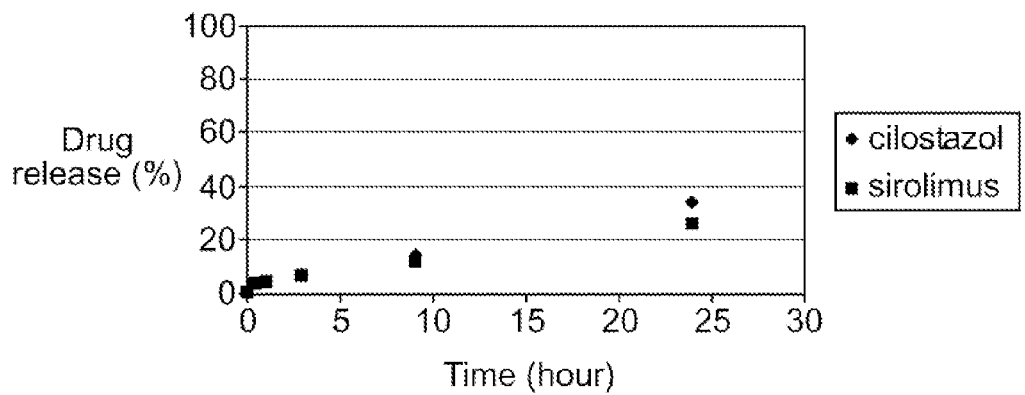
FIG. 82 is a graphical representation of the in vitro release kinetics of sirolimus and cilostazol from the stent illustrated in FIG. 83.
Figure 83:
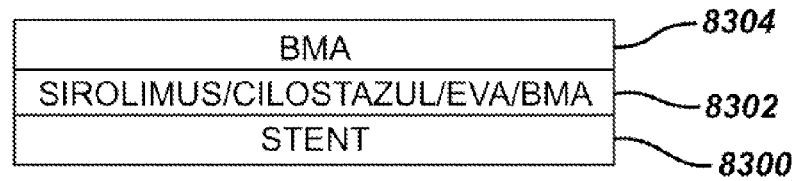
FIG. 83 is a diagrammatic representation of a fourth exemplary embodiment of a stent coated with a combination of sirolimus and cilostazol in accordance with the present invention.

Another critical parameter for the performance of the thrombus resistance of a device coated with cilostazol is the duration of the drug release from the coating. This is of particular significance in the two weeks after device implantation. In the porcine drug elution PK studies of the dual drug eluting coating, both cilostazol and sirolius were slowly released from the coating, resulting in a sustained drug release profile. The purpose of the porcine PK study is to assess the local pharmacokinetics of a drug eluting stent at a given implantation time. Normally three stents are implanted in three different coronary arteries in a pig for a given time point and then retrieved for total drug recovery analysis. The stents are retrieved at predetermined time points; namely, 1, 3 and 8 days. The stents are extracted and the total amount of drug remaining on the stents is determined by analysis utilizing HPLC (high performance liquid chromatography) for total drug amount. The difference between the original amount of drug on the stent and the amount of drug retrieved at a given time represents the amount of drug released in that period. The continuous release of drug into surrounding arterial tissue is what prevents the neointimal growth and restenosis in the coronary artery. A normal plot represents the percentage of total drug released (%, y-axis) vs. time of implantation (day, x-axis). As illustrated in FIG. 81, approximately eighty percent (80%) of the two drugs remained in the drug coating after eight (8) days of implantation. In addition, both drugs were released at a similar rate, despite the relatively large difference between their respective log P values and water solubility. Curve 8102 represents cilostazol and curve 8104 represents sirolimus. Their respective in vitro release profiles are illustrated in FIG. 82. Similar to the in vivo release profile, both sirolimus, represented by squares, and cilostazol, represented by diamonds, were released rather slowly, with only about thirty-five (35) percent release from both drugs. FIGS. 81 and 82 represent the in vivo and in vitro release rates from a stent coated in accordance with the configuration of FIG. 83 respectively, wherein the sirolimus and cilostazol are in one single layer, rather than in two separate layers. In this exemplary configuration, the stent 8300 is coated with two layers. The first layer 8302 comprises a combination of sirolimus, cilostazol and a copolymer matrix of EVA/BMA. The second layer or diffusion overcoat 8304 comprises only BMA. More specifically, in this embodiment, the first layer 8302 comprises a combination of sirolimus and cilastazol that is forty-five (45) percent by weight of the total weight of the first layer 8302 and an EVA/BMA copolymer matrix that is fifty-five (55) percent by weight of the total weight of the first layer 8302. The diffusion overcoat comprises one hundred (100 µg) micrograms of BMA.

Figure 84:
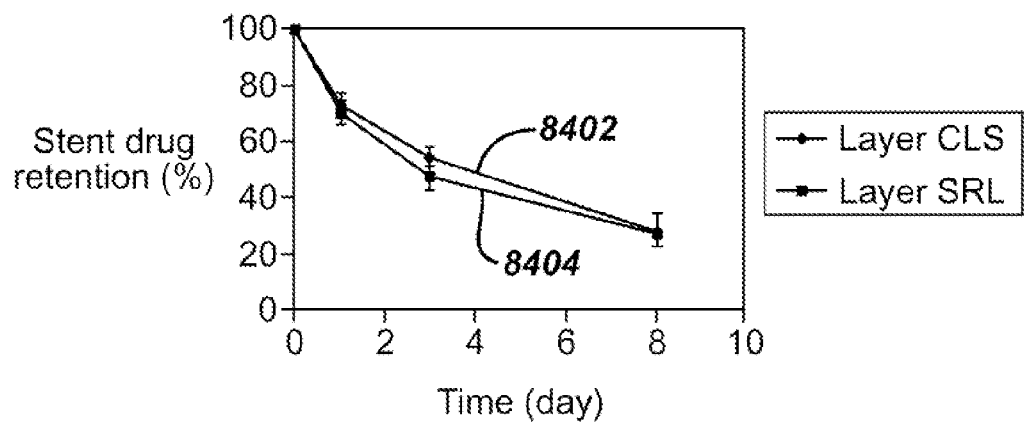
FIG. 84 is a graphical representation of the in vivo release kinetics of sirolimus and cilost6azol from the stent illustrated in FIG. 75.
Figure 85:
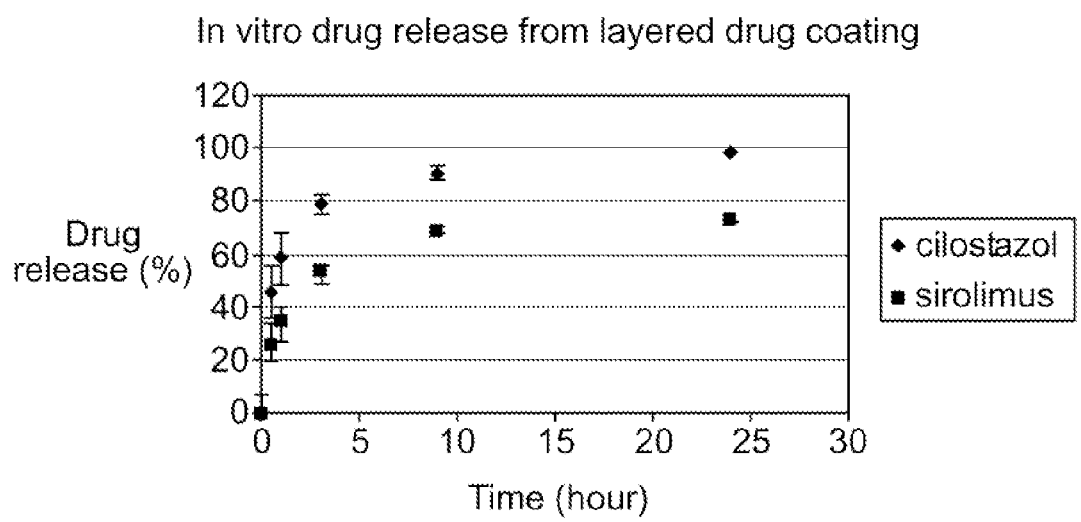
FIG. 85 is a graphical representation of the in vitro release kinetics of sirolimus and cilostazol from the stent illustrated in FIG. 75.

FIGS. 84 and 85 represent the in vivo and in vitro release rate from a stent coated in accordance with the configuration in FIG. 75, respectively. The layered dual drug eluting coating had a relatively faster release rate in the same procine PK model compared to the dual drug base coating as may be readily seen from a comparison of FIGS. 84 and 81. In FIG. 84, curve 8402 represents the cilostazol and curve 8404 represents the sirolimus. However, the percentage release of both drugs were comparable at each time point. The respective in vitro release rate profiles are shown in FIG. 84, with the diamonds representing cilostazol and the squares representing sirolimus. In a comparison to the dual drug base coating, both drugs were released at a much faster rate, mirroring the fast release profiles shown in the in vivo PK study. Accordingly, combining the drugs in a single layer results in a higher degree of control over the elution rate.

The combination of a rapamycin, such as sirolimus, and cilostazol, as described above, may be more efficacious than either drug alone in reducing both smooth muscle cell proliferation and migration. In addition, as shown herein, cilostazol release from the combination coating may be controlled in a sustained fashion to achieve prolonged anti-platelet deposition and thrombosis formation on the stent surface or the surface of other blood contacting medical devices. The incorporation of cilostazol in the combination coating may be arranged in both a single layer with sirolimus or in a separate layer outside of the sirolimus containing layer. With its relatively low solubility in water, cilostazol has a potential to be retained in the coating for a relatively long period of time inside the body after deployment of the stent or other medical device. The relatively slow in vitro elution as compared to sirolimus in the inner layer suggests such a possibility. Cilostazol is stable, soluble in common organic solvents and is compatible with the various coating techniques described herein. It is also important to note that both sirolimus and cilostazol may be incorporated in a non-absorbable polymeric matrix or an absorbable matrix.

In yet another alternate exemplary embodiment, a rapamycin may be utilized in combination with a class of agents that inhibit phosphoinositide 3-kinases. The family of phosphoinositide 3-kinases (PI3 kinase) is ubiquitously expressed in cells, and their activation plays a major role in intracellular signal transduction. Activators of this enzyme include many cell surface receptors, especially those linked to tyrosine kinases. PI3 kinase catalyzes the phosphorylation of membrane inositol lipids, with different family members producing different lipid products. Two of these products, phosphatidylinositol (3,4)-bisphosphate [Ptdins $(3,4)P_2$] and phosphatidylinositol (3,4,5)-triphosphate [Ptdins $(3,4,5)P_3$] act as secondary messengers that influence a variety of cellular processes and events.

PI3 kinase was first identified as a heteromeric complex of two subunits: a 110 kDa cata-lytic subunit (p110α) and a 85 kDa regulatory subunit (p85α). Since then, eight additional PI3 kinase have been identified. These PI3 kinases are grouped into three main classes based on differences in their subunit structure and substrate preference in vitro. p110α falls into Class I, and is further categorized into Class Ia based on its mechanism of action in vivo. Two other close members in this group are p110β and p110δ. The p85 adapter subunit has two SH2 domains that allow PI3 kinase to associate with cell surface receptors of the tyrosine kinase family, and are thereby critical to activate the enzyme, although a detailed mechanism of action is unknown.

Once PI3 kinase is activated, it generates lipid products that act to stimulate many different cellular pathways. Many of these pathways have been described for the Class Ia group in a number of different cell types. It is evident that the cellular effects observed upon PI3 kinase activation are the result of downstream targets of this enzyme. For example, protein kinase B (PKB) or AKT, and the related kinases, protein kinases A and C (PKA and PKC), are activated by two phosphorylation events catalyzed by PDK1, an enzyme that is activated by PI3 kinase.

A number of observations that link PI3 kinase function with cell proliferation and inflammation point to a therapeutic role for PI3 kinase inhibitors. In the area of oncology, results show that the p110α subunit of PI3K is amplified in ovarian tumors (L. Shayesteh et al., *Nature Genetics* (1999) 21:99-102). Further investigations have also shown that PI3 kinase activity is elevated in ovarian cancer cell lines, and treatment with the known PI3 kinase inhibitor LY 294002 decreases proliferation and increases apoptosis. These studies suggest that PI3K is an oncogene with an important role in ovarian cancer.

A malignant tumor of the central nervous system, glioblastoma, is highly resistant to radiation and chemotherapy treatments (S. A. Leibel et al., *J Neurosurg* (1987) 66:1-22). The PI3 kinase signal transduction pathway inhibits apoptosis induced by cytokine withdrawal and the detachment of cells from the extracellular matrix (T. F. Franke et al., Cell (1997) 88:435-37). D. Haas-Kogan et al., *Curr Biol* (1998) 8:1195-98 have demonstrated that glioblastoma cells, in contrast to primary human astrocytes, have high PKB/AKT activity, and subsequently high levels of the lipid second messengers produced by PI3 kinase activity. Addition of the known PI3 kinase inhibitor LY 294002 reduced the levels of the lipid products and abolished the PKB/AKT activity in the glioblastoma cells. Additionally, evidence exists to support the misregulation of the PI3-kinase-PKB pathway in these cells. The glioblastoma cells contain a mutant copy of the putative 3' phospholipid phosphatase PTEN. This phosphatase normally removes the phosphate group from the lipid product, thus acting to regulate signaling through the PI3 kinase pathways. When wild-type PTEN was expressed in the tumor cells PKB/AKT activity was abolished. These experiments suggest a role for PTEN in regulating the activity of the PI3 kinase pathway in malignant human cells. In further work these investigators also observed that inhibition of PDK1 reduced PKB/AKT activity. PDK1, as described above, is a protein kinase activated by PI3 kinase, and is likely responsible for inducing the events that lead to the activation of PKB/AKT activity. In addition, cell survival was dramatically reduced following treatment with antisense oligonucleotides against PDK1. Thus inhibitors of the PI3 kinase pathway including PI 3-kinase, PDK1, and PKB/AKT are all potential targets for therapeutic intervention for glioblastoma.

Another potential area of therapeutic intervention for inhibitors of PI3K is juvenile myelomonocytic leukemia. The NF1 gene encodes the protein neurofibromin, a GTPase activating ("GAP") protein for the small GTPase Ras. Immortalized immature myelomonocytic cells from NF1 −/− mice have been generated that have deregulated signaling through the Ras pathway, including the PI3 kinase/PKB pathway. These cells undergo apoptosis when incubated with known inhibitors of PI3 kinase, LY294002 and wortmannin, indicating a normal role for the protein in cell survival.

Wortmannin and other PI3 kinase inhibitors inhibit the phosphatidylinositol 3-kinase (PI3 kinase)-FKBP-rapamycin-associated protein (FRAP) signal transduction pathway. PI3 kinase is activiated by growth factors and hormones to deliver cell proliferation and survival signals. Upon activation, PI3 kinase phosphorylates the D3 position of Pis, which then act as secondary messengers to effect the different functions of the PI3 kinase. Wortmannin inhibits PI3 kinase by binding irreversibly to its catalytic subunit. The immunosuppressive drug rapamycin is a potent inhibitor of FRAP (mTOR/RAFT), a member of a PI3 kinase-related family, which is thought to be a downstream target of PI3 kinase.

Wortmannin was isolated in 1957 by Brian and co-workers from the broth of *Penicilium wortmani* klocker (Frank, T. F. D. R. Kaplan, and L. C. Cantley, 1997, PI3K: downstream AKT ion blocks apoptosis, Cell 88: 435-437). It was subsequently shown to be a potent anti-fungal compound. Wortmannin is a member of the structurally closely related class of steroidal furanoids which include viridian, viridiol, demethoxyviridin, demethoxyviridiol and wortmannolone. Other compounds such as Halenaquinol, halenaquinone, and xestoquinone and their analogs are also included for similar PI3 Kinase inhibition functions. In 1998, noelaquinone was obtained from an Indonesian *Xestopongia* sp: this compound is clearly closely related to the halenaquinones, but no specific biological activities have been reported. Wortmannin interacts with many biological targets, but binds in vitro most strongly to PI3 kinase. Wortmannin is thus a potent anti-proliferative agent, especially important for treating vascular restenosis which is thought to be caused by the migration and proliferation of vascular SMC. Even prior to PI3 kinase inhibition findings, wortmannin was also shown to inhibit other kinases in the PI3 kinase family, such as mTOR.

Most wortmannin and its derivatives are potent PI3 kinase inhibitors. The clinical uses of wortmannin and its many derivatives are limited by its substantial toxicity. PX867, is a modified wortmannin that turned out to be potent inhibitor of smooth muscle cells (SMC) which plays a significant role of arterial restenosis after an interventional procedure.

As described herein, sirolimus, a rapamycin, acts to reduce lymphocyte and smooth muscle cell proliferation by arresting cells in the G1 phase of the cell cycle through the inhibition of the mammalian target of rapamycin or mTOR. The subsequent activity of cell cycle associated protein kinases is blocked by the downstream effects of sirolimus on mTOR. Sirolimus has shown excellent antirestenotic effects when administered during revascularization procedures utilizing drug eluting stents. Although the local delivery of sirolimus is effective in reducing restenosis, further reductions in neointimal hyperplasia may benefit certain patient populations. Accordingly, the combination of sirolums with another antiproliferative agent within a stent coating or via other local drug delivery techniques could reduce further fibroproliferative vascular responses secondary to procedures involving vascular injury.

Figures 86, 87:
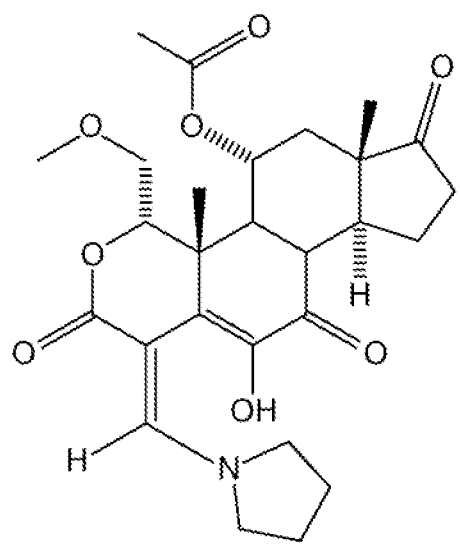
FIG. 86 is the structural formulation of the PI3 kinase inhibitor, PX-867, in accordance with the present invention.
FIG. 87 is a graphical representation of the percent inhibition of coronary artery smooth muscle cells versus concentration of PX-867 in accordance with the present invention.

The present invention is directed to the use of a PI3 kinase inhibitor, for example, PX867, alone or in combination with sirolimus for preventing neointimal hyperplasia in vascular injury applications. PX867 is a prototype PI3 kinase inhibitor whose structure is illustrated in FIG. 86. As sirolimus and PI3 kinase inhibitors act through divergent antiproliferative mechanisms, it is possible that these agents, when combined on a drug eluting stent or other intraluminal device, may potentiate each others' antirestenotic activity by downregulating both smooth muscle and immune cell proliferation (inflammatory cell proliferation) by distinct multiple mechanisms. This potentiation of sirolimus antiproliferative activity by PI3 kinase inhibitors may translate to an enhancement in antirestenotic efficacy following vascular injury during revascularization and other vascular procedures and a reduction in the required amount of either agent to achieve the antirestenotic effect.

A PI3 kinase inhibitor can affect restinosis when administered by local or systemic delivery alone or in combination with sirolimus. FIGS. 87 and 88 illustrate the antiproliferative effects of PX867 on cultured human coronary artery smooth muscle cells alone (FIG. 87) or in combination with sirolimus (FIG. 88). Referring specifically to FIG. 87, one can see that at a concentration of about $10^{-6}$, there is close to one hundred percent inhibition of coronary artery smooth muscle cell proliferation for PX867 alone. Curve 8702 illustrates the percent inhibition for various concentrations. In FIG. 88, the six curves 8802, 8804, 8806, 8808, 8810 and 8812 represent various concentrations of PX867 with various concentrations of sirolimus. What FIG. 88 shows is that with higher concentrations of sirolimus and lower concentrations of PX867 one can achieve higher percent inhibition. In other words, there is a synergistic affect between PX867 and sirolimus. More specifically, curve 8812 illustrates the percent inhibition for a 240 nM PX-867 concentration. As one can see from this curve, increasing the concentration of sirolimus has no significant effect. This may be compared to curve 8804 which represents a 15 nM PX-867 concentration. As one can see, the percent inhibition increases as the concentration of sirolimus increases. Accordingly, a potent PI3 kinase inhibitor, such as PX-867, can improve the inhibition of coronary artery smooth muscle cell proliferation either as a stand alone treatment or via combination with another restenotic agent, such as sirolimus. In addition, as the figures illustrate, there is a strong synergistic effect between PX-867 and sirolimus.

Turning to Table 8 below, one can readily see that PX-867 has a percent recovery of greater than eighty percent. Essentially, what this means is that once the drug is loaded into the polymeric coating and applied to the stent or other medical device as described herein, and processed as described herein, at least eighty percent of the drug remains in the coating on the stent and is available as a therapeutic agent. Similar results are obtained after sterilization, thereby indicating how robust the drug is.

TABLE 8

Drug recovery of PX 867 at 33 percent loading of coating

| | PX-867 | | | |
|---|---|---|---|---|
| Stent ID# | Eluted PX 867 (ug) | Residual PX 867 in coating (ug) | Total PX 867 recovery (ug) | % Recovery |
| 195-41 | 11.56 | 128.86 | 140.42 | 83.93 |
| 195-42 | 16.67 | 117.61 | 134.28 | 82.70 |
| 195-45 | 19.78 | 116.27 | 136.05 | 84.83 |
| 195-47 | 12.98 | 138.14 | 151.12 | 85.28 |
| 195-48 | 17.17 | 126.54 | 143.71 | 83.75 |

Note:
1. Theoretical drug loading is around 167 ug (33% of 500 ug of coating weight, standard pEVAc/pBMA at 1:1 weight ratio was used as the coating matrix.
2. Drug elution study was done is a proprietary Sotax 4 device.

The combination of sirolimus and a PI3 kinase inhibitor may be constructed in a manner similar to that of sirolimus and cilostizol and/or any of the drug or drug combinations described herein. For example, both sirolimus and the PI3 kinase inhibitor may be directly affixed to the medical device in a single layer or multiple layer architecture. In another alternate embodiment, both drugs may be incorporated into a polymer and then affixed to the medical device. In these embodiments, both sirolimus and the PI3 kinase inhibitor may be incorporated in a single polymer layer, in different polymer layers, with a top coat or elution controlling layer or without a top coat or elution controlling layer. Any type of polymers may be utilized. Different and/or dissimilar polymers may be utilized to control elution rates. Essentially, any type of architecture may be utilized to effectively release both agents at the appropriate times.

It is important to reiterate that as used herein, that rapamycin includes rapamycin and all analogs, derivatives, congeners and conjugates that bind to FK3P12 and other immunophilins and possesses the same pharmacologic properties as rapamycin including inhibition of mTOR.

As is explained in more detail subsequently, a combination of incompatible polymers may be utilized in combination with rapamycin and mycophenolic acid, rapamycin and trichostatin A, rapamycin and cladribine, rapamycin and topotecan, rapamycin and etoposide, rapamycin and Panzem, rapamycin and cilostazol and/or any of the drugs, agents and/or compounds described herein to provide for the controlled local delivery of these drugs, agents and/or compounds or combinations thereof from a medical device. In addition, these incompatible polymers may be utilized in various combinations to control the release rates of individual agents from combinations of agents. For example, from the tests described above, it is seen that mycophenolic acids elute more quickly than rapamycin. Accordingly, the correct combination of incompatible polymers may be utilized to ensure that both agents elute at the same rate if so desired.

The coatings and drugs, agents or compounds described above may be utilized in combination with any number of medical devices, and in particular, with implantable medical devices such as stents and stent-grafts. Other devices such as vena cava filters and anastomosis devices may be used with coatings having drugs, agents or compounds therein. The exemplary stent illustrated in FIGS. 1 and 2 is a balloon expandable stent. Balloon expandable stents may be utilized in any number of vessels or conduits, and are particularly well suited for use in coronary arteries. Self-expanding stents, on the other hand, are particularly well suited for use in vessels where crush recovery is a critical factor, for example, in the carotid artery. Accordingly, it is important to note that any of the drugs, agents or compounds, as well as the coatings described above, may be utilized in combination with self-expanding stents which are known in the art.

Surgical anastomosis is the surgical joining of structures, specifically the joining of tubular organs to create an intercommunication between them. Vascular surgery often involves creating an anastomosis between blood vessels or between a blood vessel and a vascular graft to create or restore a blood flow path to essential tissues. Coronary artery bypass graft surgery (CABG) is a surgical procedure to restore blood flow to ischemic heart muscle whose blood supply has been compromised by occlusion or stenosis of one or more of the coronary arteries. One method for performing CABG surgery involves harvesting a saphenous vein or other venous or arterial conduit from elsewhere in the body, or using an artificial conduit, such as one made of Dacron® or GoreTex® tubing, and connecting this conduit as a bypass graft from a viable artery, such as the aorta, to the coronary artery downstream of the blockage or narrowing. It is preferable to utilize natural grafts rather than synthetic grafts. A graft with both the proximal and distal ends of the graft detached is known as a "free graft." A second method involves rerouting a less essential artery, such as the internal mammary artery, from its native location so that it may be connected to the coronary artery downstream of the blockage. The proximal end of the graft vessel remains attached in its native position. This type of graft is known as a "pedicled graft." In the first case, the bypass graft must be attached to the native arteries by an end-to-side anastomosis at both the proximal and distal ends of the graft. In the second technique at least one end-to-side anastomosis must be made at the distal end of the artery used for the bypass. In the description of the exemplary embodiment given below reference will be made to the anastomoses on a free graft as the proximal anastomosis and the distal anastomosis. A proximal anastomosis is an anastomosis on the end of the graft vessel connected to a source of blood, for example, the aorta and a distal anastomosis is an anastomosis on the end of the graft vessel connected to the destination of the blood flowing through it, for example, a coronary artery. The anastomoses will also sometimes be called the first anastomosis or second anastomosis, which refers to the order in which the anastomoses are performed regardless of whether the anastomosis is on the proximal or distal end of the graft.

At present, essentially all vascular anastomoses are performed by conventional hand suturing. Suturing the anastomoses is a time-consuming and difficult task, requiring much skill and practice on the part of the surgeon. It is important that each anastomosis provide a smooth, open flow path for the blood and that the attachment be completely free of leaks. A completely leak-free seal is not always achieved on the very first try. Consequently, there is a frequent need for resuturing of the anastomosis to close any leaks that are detected.

The time consuming nature of hand sutured anastomoses is of special concern in CABG surgery for several reasons. Firstly, the patient is required to be supported on cardiopulmonary bypass (CPB) for most of the surgical procedure, the heart must be isolated from the systemic circulation (i.e. "cross-clamped"), and the heart must usually be stopped, typically by infusion of cold cardioplegia solution, so that the anastomosis site on the heart is still and blood-free during the suturing of the anastomosis. Cardiopulminary bypass, circulatory isolation and cardiac arrest are inherently very traumatic, and it has been found that the frequency of certain post-surgical complications varies directly with the duration for which the heart is under cardioplegic arrest (frequently referred to as the "crossclamp time"). Secondly, because of the high cost of cardiac operating room time, any prolongation of the surgical procedure can significantly increase the cost of the bypass operation to the hospital and to the patient. Thus, it is desirable to reduce the duration of the crossclamp time and of the entire surgery by expediting the anastomosis procedure without reducing the quality or effectiveness of the anastomoses.

The already high degree of manual skill required for conventional manually sutured anastomoses is even more elevated for closed-chest or port-access thoracoscopic bypass surgery, a newly developed surgical procedure designed to reduce the morbidity of CABG surgery as compared to the standard open-chest CABG procedure. In the closed-chest procedure, surgical access to the heart is made through narrow access ports made in the intercostal spaces of the patient's chest, and the procedure is performed under thoracoscopic observation. Because the patient's chest is not opened, the suturing of the anastomoses must be performed at some distance, using elongated instruments positioned through the access ports for approximating the tissues and for holding and manipulating the needles and sutures used to make the anastomoses. This requires even greater manual skill than the already difficult procedure of suturing anastomoses during open-chest CABG surgery.

In order to reduce the difficulty of creating the vascular anastomoses during either open or closed-chest CABG surgery, it would be desirable to provide a rapid means for making a reliable end-to-side anastomosis between a bypass graft or artery and the aorta or the native vessels of the heart. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery. Various surgical stapling instruments have been developed for end-to-end, side-to-side, and end-to-side anastomoses of hollow or tubular organs, such as the bowel. These instruments, unfortunately, are not easily adaptable for use in creating vascular anastomoses. This is partially due to the difficulty in miniaturizing the instruments to make them suitable for smaller organs such as blood vessels. Possibly even more important is the necessity of providing a smooth, open flow path for the blood. Known gastrointestinal stapling instruments for end-to-side or end-to-end anastomosis of tubular organs are designed to create an inverted anastomosis, that is, one where the tissue folds inward into the lumen of the organ that is being attached. This is acceptable in gastrointestinal surgery, where it is most important to approximate the outer layers of the intestinal tract (the serosa). This is the tissue which grows together to form a strong, permanent connection. However, in vascular surgery this geometry is unacceptable for several reasons. Firstly, the inverted vessel walls would cause a disruption in the blood flow. This could cause decreased flow and ischemia downstream of the disruption, or, worse yet, the flow disruption or eddies created could become a locus for thrombosis which could shed emboli or occlude the vessel at the anastomosis site. Secondly, unlike the intestinal tract, the outer surfaces of the blood vessels (the adventitia) will not grow together when approximated. The sutures, staples, or other joining device may therefore be needed permanently to maintain the structural integrity of the vascular anastomosis. Thirdly, to establish a permanent, nonthrombogenic vessel, the innermost layer (the endothelium) should grow together for a continuous, uninterrupted lining of the entire vessel. Thus, it would be preferable to have a stapling instrument that would create vascular anastomoses that are everted, that is folded outward, or which create direct edge-to-edge coaptation without inversion.

At least one stapling instrument has been applied to performing vascular anastomoses during CABG surgery. This device, first adapted for use in CABG surgery by Dr. Vasilii I. Kolesov and later refined by Dr. Evgenii V. Kolesov (U.S. Pat. No. 4,350,160), was used to create an end-to-end anastomosis between the internal mammary artery (IMA) or a vein graft and one of the coronary arteries, primarily the left anterior descending coronary artery (LAD). Because the device could only perform end-to-end anastomoses, the coronary artery first had to be severed and dissected from the surrounding myocardium, and the exposed end everted for attachment. This technique limited the indications of the device to cases where the coronary artery was totally occluded, and therefore there was no loss of blood flow by completely severing the coronary artery downstream of the blockage to make the anastomosis. Consequently, this device is not applicable where the coronary artery is only partially occluded and is not at all applicable to making the proximal side-to-end anastomosis between a bypass graft and the aorta.

One attempt to provide a vascular stapling device for end-to-side vascular anastomoses is described in U.S. Pat. No. 5,234,447, issued to Kaster et al. for a Side-to-end Vascular Anastomotic Staple Apparatus. Kaster et al. provide a ring-shaped staple with staple legs extending from the proximal and distal ends of the ring to join two blood vessels together in an end-to-side anastomosis. However, Kaster et al. does not provide a complete system for quickly and automatically performing an anastomosis. The method of applying the anastomosis staple disclosed by Kaster et al. involves a great deal of manual manipulation of the staple, using hand operated tools to individually deform the distal tines of the staple after the graft has been attached and before it is inserted into the opening made in the aortic wall. One of the more difficult maneuvers in applying the Kaster et al. staple involves carefully everting the graft vessel over the sharpened ends of the staple legs, then piercing the evened edge of the vessel with the staple legs. Experimental attempts to apply this technique have proven to be very problematic because of difficulty in manipulating the graft vessel and the potential for damage to the graft vessel wall. For speed, reliability and convenience, it is preferable to avoid the need for complex maneuvers while performing the anastomosis. Further bending operations must then be performed on the staple legs. Once the distal tines of the staple have been deformed, it may be difficult to insert the staple through the aortotomy opening. Another disadvantage of the Kaster et al. device is that the distal tines of the staple pierce the wall of the graft vessel at the point where it is evened over the staple. Piercing the wall of the graft vessel potentially invites leaking of the anastomosis and may compromise the structural integrity of the graft vessel wall, serving as a locus for a dissection or even a tear, which could lead to catastrophic failure. Because the Kaster et al staple legs only apply pressure to the anastomosis at selected points, there is a potential for leaks between the staple legs. The distal tines of the staple are also exposed to the blood flow path at the anastomotic site where it is most critical to avoid the potential for thrombosis. There is also the potential that exposure of the medial layers of the graft vessel where the staple pierces the wall could be a site for the onset of intimal hyperplasia, which would compromise the long-term patency of the graft as described above. Because of these potential drawbacks, it is desirable to make the attachment to the graft vessel as atraumatic to the vessel wall as possible and to eliminate as much as possible the exposure of any foreign materials or any vessel layers other than a smooth uninterrupted intimal layer within the anastomosis site or within the graft vessel lumen.

A second approach to expediting and improving anastomosis procedures is through the use of anastomotic fittings for joining blood vessels together. One attempt to provide a vascular anastomotic fitting device for end-to-side vascular anastomoses is described in U.S. Pat. No. 4,366,819, issued to Kaster for an Anastomotic Fitting. This device is a four-part anastomotic fitting having a tubular member over which the graft vessel is evened, a ring flange which engages the aortic wall from within the aortic lumen, and a fixation ring and a locking ring which engage the exterior of the aortic wall. Another similar Anastomotic Fitting is described in U.S. Pat. No. 4,368,736, also issued to Kaster. This device is a tubular fitting with a flanged distal end that fastens to the aortic wall with an attachment ring, and a proximal end with a graft fixation collar for attaching to the graft vessel. These devices have a number of drawbacks. Firstly, the anastomotic fittings described expose the foreign material of the anastomotic device to the blood flow path within the arteries. This is undesirable because foreign materials within the blood flow path can have a tendency to cause hemolysis, platelet deposition and thrombosis. Immune responses to foreign material, such as rejection of the foreign material or auto-immune responses triggered by the presence of foreign material, tend to be stronger when the material is exposed to the bloodstream. As such, it is preferable that as much as possible of the interior surfaces of an anastomotic fitting that will be exposed to the blood flow path be covered with vascular tissue, either from the target vessel or from the graft vessel, so that a smooth, continuous, hemocompatible endothelial layer will be presented to the bloodstream. The anastomotic fitting described by Kaster in the '819 patent also has the potential drawback that the spikes that hold the graft vessel onto the anastomotic fitting are very close to the blood flow path, potentially causing trauma to the blood vessel that could lead to leaks in the anastomosis or compromise of the mechanical integrity of the vessels. Consequently, it is desirable to provide an anastomosis fitting that is as atraumatic to the graft vessel as possible. Any sharp features such as attachment spikes should be placed as far away from the blood flow path and the anastomosis site as possible so that there is no compromise of the anastomosis seal or the structural integrity of the vessels.

Another device, the 3M-Unilink device for end-to-end anastomosis (U.S. Pat. Nos. 4,624,257; 4,917,090; 4,917,091) is designed for use in microsurgery, such as for reattaching vessels severed in accidents. This device provides an anastomosis clamp that has two eversion rings which are locked together by a series of impaling spikes on their opposing faces. However, this device is awkward for use in end-to-side anastomosis and tends to deform the target vessel; therefore it is not currently used in CABG surgery. Due to the delicate process needed to insert the vessels into the device, it would also be unsuitable for port-access surgery.

In order to solve these and other problems, it is desirable to provide an anastomosis device which performs an end-to-side anastomosis between blood vessels or other hollow organs and vessels. It is also desirable to provide an anastomosis device which minimizes the trauma to the blood vessels while performing the anastomosis, which minimizes the amount of foreign materials exposed to the blood flow path within the blood vessels and which avoids leakage problems, and which promotes rapid endothelialization and healing. It is also desirable that the invention provide a complete system for quickly and automatically performing an anastomosis with a minimal amount of manual manipulation.

Anastomosis devices may be utilized to join biological tissues, and more particularly, joining tubular organs to create a fluid channel. The connections between the tubular organs or vessels may be made side to side, end to end and/or end to side. Typically, there is a graft vessel and a target vessel. The target vessel may be an artery, vein or any other conduit or fluid carrying vessel, for example, coronary arteries. The graft vessel may comprise a synthetic material, an autologus vessel, a homologus vessel or a xenograft. Anastomosis devices may comprise any suitable biocompatible materials, for example, metals, polymers and elastomers. In addition, there are a wide variety of designs and configurations for anastomosis devices depending on the type of connection to be made. Similarly to stents, anastomosis devices cause some injury to the target vessel, thereby provoking a response from the body. Therefore, as in the case with stents, there is the potential for smooth muscle cell proliferation which can lead to blocked connections. Accordingly, there is a need to minimize or substantially eliminate smooth muscle cell proliferation and inflammation at the anastomotic site. Rapamycin and/or other drugs, agents or compounds may be utilized in a manner analogous to stents as described above. In other words, at least a portion of the anastomosis device may be coated with rapamycin or other drug, agent and/or compound.

FIGS. 10-13 illustrate an exemplary anastomosis device 200 for an end to side anastomosis. The exemplary anastomosis device 200 comprises a fastening flange 202 and attached staple members 204. As stated above, the anastomosis device may comprise any suitable biocompatible material. Preferably, the anastomosis device 200 comprises a deformable biocompatible metal, such as a stainless steel alloy, a titanium alloy or a cobalt alloy. Also as stated above, a surface coating or surface coating comprising a drug, agent or compound may be utilized to improve the biocompatibility or other material characteristics of the device as well as to reduce or substantially eliminate the body's response to its placement therein.

In the exemplary embodiment, the fastening flange 202 resides on the interior surface 206 of the target vessel wall 208 when the anastomosis is completed. In order to substantially reduce the risk of hemolysis, thrombogenesis or foreign body reactions, the total mass of the fastening flange 202 is preferably as small as possible to reduce the amount of foreign material within the target vessel lumen 210.

The fastening flange 202 is in the form of a wire ring with an internal diameter, which when fully expanded, is slightly greater than the outside diameter of the graft vessel wall 214 and of the opening 216 made in the target vessel wall 208. Initially, the wire ring of the fastening flange 202 has a rippled wave-like shape to reduce the diameter of the ring so that it will easily fit through the opening 216 in the target vessel wall 208. The plurality of staple members 204 extend substantially perpendicular from the wire ring in the proximal direction. In the illustrative exemplary embodiment, there are nine staple members 204 attached to the wire ring fastening flange 202. Other variations of the anastomosis device 200 might typically have from four to twelve staple members 204 depending on the size of the vessels to be joined and the security of attachment required in the particular application. The staple members 204 may be integrally formed with the wire ring fastening flange 202 or the staple members 204 may be attached to the fastening flange 202 by welding, brazing or any other suitable joining method. The proximal ends 218 of the staple members 204 are sharpened to easily pierce the target vessel wall 208 and the graft vessel wall 214. Preferably, the proximal ends 218 of the staple members 204 have barbs 220 to improve the security of the attachment when the anastomosis device 200 is deployed. The anastomosis device 200 is prepared for use by mounting the device onto the distal end of an application instrument 222. The fastening flange 202 is mounted on an anvil 224 attached to the distal end of the elongated shaft 226 of the application instrument 222. The staple members 204 are compressed inward against a conical holder 228 attached to the instrument 222 proximal to the anvil 224. The staple members 204 are secured in this position by a cap 230 which is slidably mounted on the elongated shaft 226. The cap 230 moves distally to cover the sharpened, barbed proximal ends 218 of the staple members 204 and to hold them against the conical holder 228. The application instrument 222 is then inserted through the lumen 232 of the graft vessel 214. This may be done by inserting the application instrument 222 through the graft vessel lumen 232 from the proximal to the distal end of the graft vessel 214, or it may be done by back loading the elongated shaft 226 of the application instrument 222 into the graft vessel lumen 232 from the distal end to the proximal end, whichever is most convenient in the case. The anvil 224 and conical holder 228 on the distal end of the application instrument 222 with the anastomosis device 200 attached is extended through the opening 216 into the lumen 210 of the target vessel.

Next, the distal end 234 of the graft vessel wall 214 is everted against the exterior surface 236 of the target vessel wall 208 with the graft vessel lumen 232 centered over the opening 216 in the target vessel wall 208. The cap 230 is withdrawn from the proximal ends 218 of the staple members 204, allowing the staple members 204 to spring outward to their expanded position. The application instrument 222 is then drawn in the proximal direction so that the staple members pierce the target vessel wall 208 surrounding the opening 216 and the everted distil end 234 of the graft vessel 214.

The application instrument 222 has an annular staple former 238 which surrounds the outside of the graft vessel 214. Slight pressure on the everted graft vessel wall from the annular staple former 238 during the piercing step assists in piercing the staple members 204 through the graft vessel wall 214. Care should be taken not to apply too much pressure with the annular staple former 238 at this point in the process because the staple members 204 could be prematurely deformed before they have fully traversed the vessel walls. If desired, an annular surface made of a softer material, such as an elastomer, can be provided on the application instrument 222 to back up the vessel walls as the staple members 204 pierce through them.

Once the staple members 204 have fully traversed the target vessel wall 208 and the graft vessel wall 214, the staple former 238 is brought down with greater force while supporting the fastening flange 202 with the anvil 224. The staple members 204 are deformed outward so that the sharpened, barbed ends 218 pierce back through the everted distil end 234 and into the target vessel wall 208 to form a permanent attachment. To complete the anastomosis, the anvil 224 is withdrawn through the graft vessel lumen 232. As the anvil 224 passes through the wire ring fastening flange 202, it straightens out the wave-like ripples so that the wire ring flange 202 assumes its full expanded diameter. Alternately, the wire ring fastening flange 202 may be made of a resilient material so that the flange 202 may be compressed and held in a rippled or folded position until it is released within the target vessel lumen 210, whereupon it will resume its full expanded diameter. Another alternate construction would be to move the anastomosis device of a shape-memory alloy so that the fastening flange may be compressed and inserted through the opening in the target vessel, whereupon it would be returned to its full expanded diameter by heating the device 200 to a temperature above the shape-memory transition temperature.

In the above-described exemplary embodiment, the staple members 204 and/or the wire ring fastening flange 202 may be coated with any of the above-described agents, drugs or compounds such as rapamycin to prevent or substantially reduce smooth muscle wall proliferation.

Figure 14:
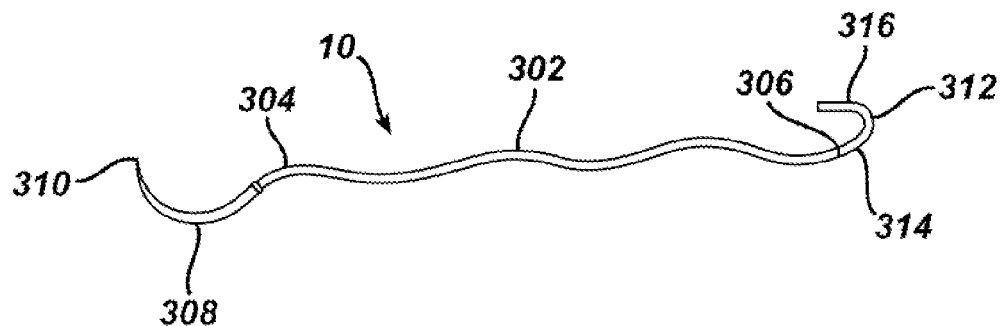
FIG. 14 is a side view of an apparatus for joining anatomical structures together, according to an exemplary embodiment of the invention.

FIG. 14 illustrates an alternate exemplary embodiment of an anastomosis device. FIG. 14 is a side view of an apparatus for joining at least two anatomical structures, according to another exemplary embodiment of the present invention. Apparatus 300 includes a suture 302 having a first end 304 and a second end 306, the suture 302 being constructed for passage through anatomical structures in a manner to be described subsequently. Suture 302 may be formed from a wide variety of materials, for example, monofilament materials having minimal memory, including polypropylene or polyamide. Any appropriate diameter size may be used, for example, through 8-0. Other suture types and sizes are also possible, of course, and are equally contemplated by the present invention.

A needle 308 preferably is curved and is disposed at the first end 304 of the suture 302. A sharp tip 310 of needle 308 enables easy penetration of various anatomical structures and enables the needle 308 and the suture 302 to readily pass therethrough. The needle 308 may be attached to the suture 302 in various ways, for example, by swedging, preferably substantially matching the outer diameter of the needle 308 and the suture 302 as closely as possible.

Apparatus 300 also includes a holding device 312 disposed at the second end 306 of the suture 302. The holding device 312 includes first and second limbs 314, 316, according to the illustrated exemplary embodiment, and preferably is of greater stiffness than the suture 302. The first limb 314 may be connected to suture 302 in a number of ways, for example, by swedging, preferably substantially matching the outside diameter of the suture 302 and the holding device 312 as closely as possible. The holding device 312 includes a staple structure comprising a bendable material that preferably is soft and malleable enough to crimp and hold its crimped position on the outside of an anastomosis. Such materials may include titanium or stainless steel. The holding device 312 may be referred to as a staple, according to the illustrated embodiment, and the suture 302 and the needle 308 a delivery system for staple 312.

FIG. 14 illustrates one of the many possible initial configurations of holding device 312, i.e. the configuration the holding device 312 is in upon initial passage through the anatomical structures and/or at a point in time beforehand. As will be described, the holding device 312 is movable from the initial configuration to a holding configuration, in which holding device 312 holds the anatomical structures together. According to the illustrated exemplary embodiments, the holding device 312 assumes the holding configuration when it is bent or crimped, as shown in FIG. 19 (further described below).

The holding device 312 preferably is substantially V-shaped or substantially U-shaped, as illustrated, but may assume a wide variety of shapes to suit particular surgical situations and/or surgeon preference. For example, one of limbs 314, 316 may be straight and the other curved, or limbs 314, 316 may be collinear. The holding device 312 preferably is as smooth and round in cross-section as the needle 308. Further, the diameters of the needle 308, the suture 302, and the holding device 312 preferably are substantially identical, especially the needle 308 and the holding device 312, to avoid creating holes in the anatomical structures that are larger than the diameter of the staple 312. Such holes likely would cause bleeding and/or leakage.

Figure 15:
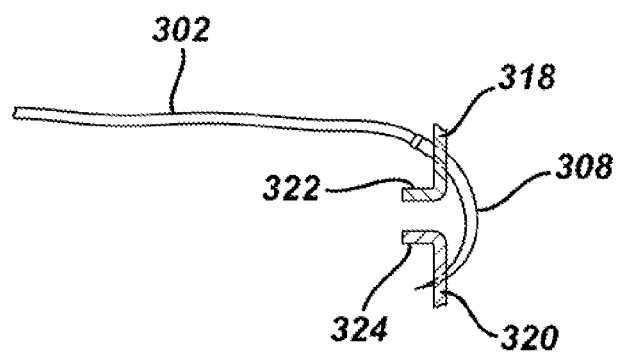
FIG. 15 is a cross-sectional view showing a needle portion of the FIG. 14 apparatus passing through edges of anatomical structures, according to an exemplary embodiment of the invention.
Figure 16:
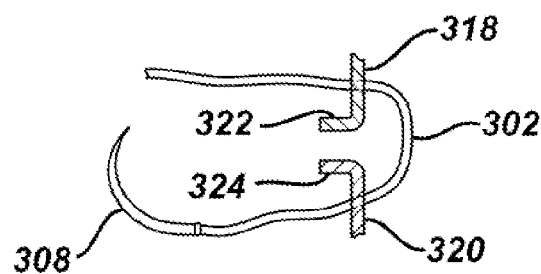
FIG. 16 is a cross-sectional view showing the FIG. 14 apparatus pulled through an anastomosis, according to an exemplary embodiment of the invention.
Figure 17:
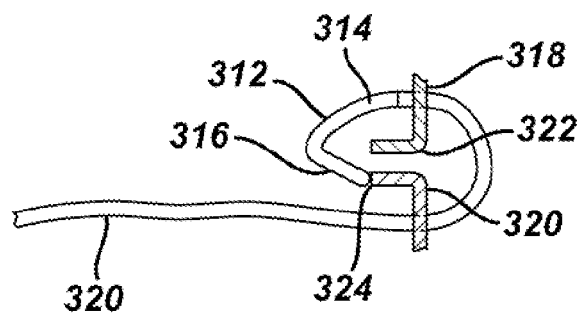
FIG. 17 is a cross-sectional view showing a staple of the FIG. 14 apparatus being placed into proximity with the anatomical structures, according to an exemplary embodiment of the invention
Figure 18:
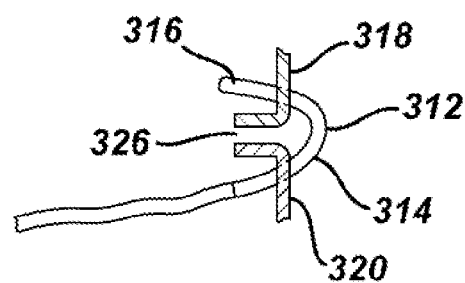
FIG. 18 is a cross-sectional view showing a staple of the FIG. 14 apparatus being engaged on both sides of the anastomosis, according to an exemplary embodiment of the invention.
Figure 19:
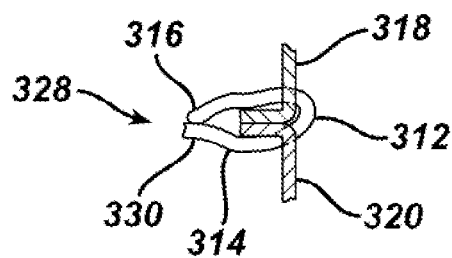
FIG. 19 is a cross-sectional view showing a staple after it has been crimped to join the anatomical structures, according to an exemplary embodiment of the invention.

A method of using apparatus 300 is illustrated in FIGS. 15-19. First, as illustrated in FIG. 15, the needle 308 passes through anatomical structures 318, 320, which are, for example, vascular structures. Specifically, according to the illustrated exemplary embodiment, the needle 308 passes through the edges 322, 324 of vascular structures 318, 320. Then, as shown in FIG. 16, the needle 308 pulls suture 302 into and through both structures 318, 320. The staple 312 then is pulled into desired proximity with structures 318, 320, as shown in FIGS. 17-19, such that it is engaged on both sides of the illustrated anastomosis and associated lumen 326. According to one exemplary embodiment, traction is placed on suture 302 to hook staple 312 into position.

As illustrated in FIG. 19 and as referenced earlier, the staple 312 then is moved from its initial configuration to a holding or crimped configuration 328, in which anatomical structures 318, 320 are joined together to effect an anastomosis between them. The staple 312 creates a substantially three hundred sixty-degree loop at the edge of the anastomosis, with crimped portion 330 outside lumen 321. A wide variety of tools and/or mechanisms may be used to crimp the staple 312 into its holding configuration, for example, in the manner of closure of a vascular clip. The same tool, or an alternative tool, may then be used to separate the staple 312 from the suture 302, for example, by cutting.

Thus, the staple 312 holds vascular structures 318, 320 together from inside the vascular structures, as well as from outside, unlike the many prior art staples that secure opposed structures only externally. This achieves a number of advantages, as described above. Not only does a better approximation result, but crimping a staple is simpler than tying one or more knots and is also less likely traumatic on tissue. Staple closure with a single crimp provides less tension on an anastomosis, for example, than a knot requiring several throws. Embodiments of the invention are especially advantageous in minimally invasive surgical situations, as knot-tying with, for example, a knot pusher in a minimally invasive setting through a small port is particularly tedious and can require up to four or five throws to prevent slippage. Crimping a staple through the port, as with embodiments of the invention, is far simpler and eliminates much of the difficulty.

According to one exemplary embodiment, the surgeon achieves a precise approximation of the vascular or other structures with preferably a limited number of staples or other holding devices, and then completes the anastomosis with biologic glue or laser techniques. The holding devices, for example, two or more in number, may be used to orient or line up the structures initially and thus used as a "pilot" for guiding the completion of the anastomosis.

In the above described exemplary embodiment, the holding device 312 may be coated with any of the above-described drugs, agents or compounds such as rapamycin to prevent or substantially reduce smooth muscle cell proliferation.

As described above, various drugs, agents or compounds may be locally delivered via medical devices. For example, rapamycin and heparin may be delivered by a stent to reduce restenosis, inflammation, and coagulation. Various techniques for immobilizing the drugs, agents or compounds are discussed above, however, maintaining the drugs, agents or compounds on the medical devices during delivery and positioning is critical to the success of the procedure or treatment. For example, removal of the drug, agent or compound coating during delivery of the stent can potentially cause failure of the device. For a self-expanding stent, the retraction of the restraining sheath may cause the drugs, agents or compounds to rub off the stent. For a balloon expandable stent, the expansion of the balloon may cause the drugs, agents or compounds to simply delaminate from the stent through contact with the balloon or via expansion. Therefore, prevention of this potential problem is important to have a successful therapeutic medical device, such as a stent.

There are a number of approaches that may be utilized to substantially reduce the above-described concern. In one exemplary embodiment, a lubricant or mold release agent may be utilized. The lubricant or mold release agent may comprise any suitable biocompatible lubricious coating. An exemplary lubricious coating may comprise silicone. In this exemplary embodiment, a solution of the silicone base coating may be introduced onto the balloon surface, onto the polymeric matrix, and/or onto the inner surface of the sheath of a self-expanding stent delivery apparatus and allowed to air cure. Alternately, the silicone based coating may be incorporated into the polymeric matrix. It is important to note, however, that any number of lubricious materials may be utilized, with the basic requirements being that the material be biocompatible, that the material not interfere with the actions/effectiveness of the drugs, agents or compounds and that the material not interfere with the materials utilized to immobilize the drugs, agents or compounds on the medical device. It is also important to note that one or more, or all of the above-described approaches may be utilized in combination.

Figure 20:
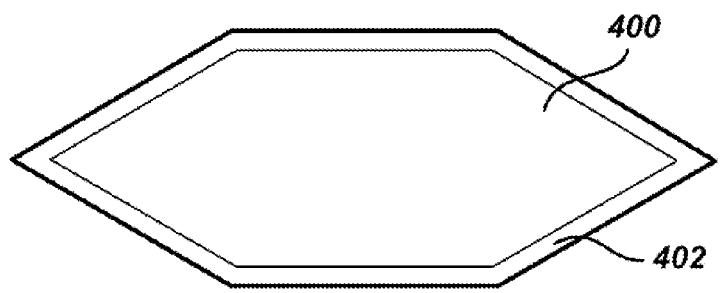
FIG. 20 is a cross-sectional view of a balloon having a lubricious coating affixed thereto in accordance with the present invention.

Referring now to FIG. 20, there is illustrated a balloon 400 of a balloon catheter that may be utilized to expand a stent in situ. As illustrated, the balloon 400 comprises a lubricious coating 402. The lubricious coating 402 functions to minimize or substantially eliminate the adhesion between the balloon 400 and the coating on the medical device. In the exemplary embodiment described above, the lubricious coating 402 would minimize or substantially eliminate the adhesion between the balloon 400 and the heparin or rapamycin coating. The lubricious coating 402 may be attached to and maintained on the balloon 400 in any number of ways including but not limited to dipping, spraying, brushing or spin coating of the coating material from a solution or suspension followed by curing or solvent removal step as needed.

Materials such as synthetic waxes, e.g. diethyleneglycol monostearate, hydrogenated castor oil, oleic acid, stearic acid, zinc stearate, calcium stearate, ethylenebis (stearamide), natural products such as paraffin wax, spermaceti wax, carnuba wax, sodium alginate, ascorbic acid and flour, fluorinated compounds such as perfluoroalkanes, perfluorofatty acids and alcohol, synthetic polymers such as silicones e.g. polydimethylsiloxane, polytetrafluoroethylene, polyfluoroethers, polyalkylglycol e.g. polyethylene glycol waxes, and inorganic materials such as talc, kaolin, mica, and silica may be used to prepare these coatings. Vapor deposition polymerization e.g. parylene-C deposition, or RF-plasma polymerization of perfluoroalkenes and perfluoroalkanes can also be used to prepare these lubricious coatings.

Figure 21:
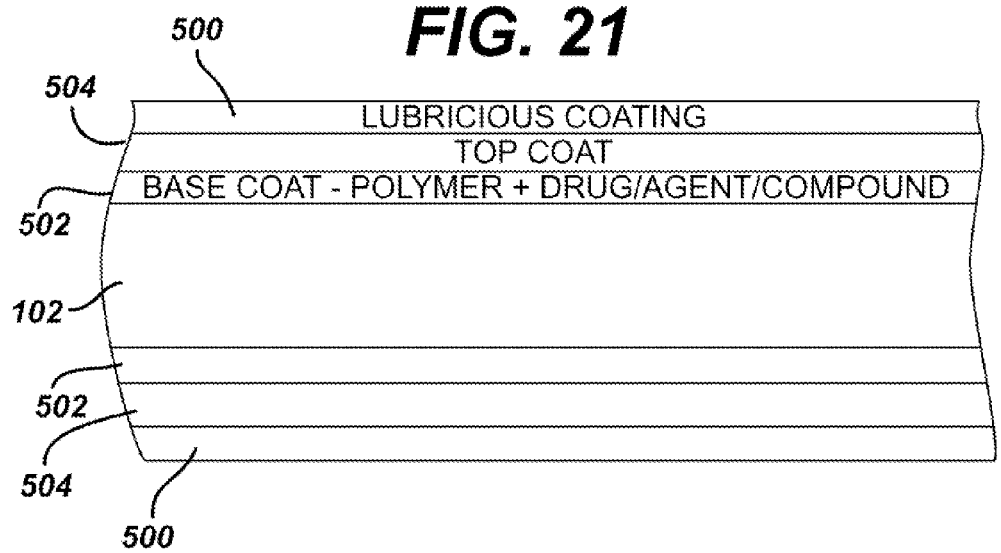
FIG. 21 is a cross-sectional view of a band of the stent in FIG. 1 having a lubricious coating affixed thereto in accordance with the present invention.

FIG. 21 illustrates a cross-section of a band 102 of the stent 100 illustrated in FIG. 1. In this exemplary embodiment, the lubricious coating 500 is immobilized onto the outer surface of the polymeric coating. As described above, the drugs, agents or compounds may be incorporated into a polymeric matrix. The stent band 102 illustrated in FIG. 21 comprises a base coat 502 comprising a polymer and rapamycin and a top coat 504 or diffusion layer 504 also comprising a polymer. The lubricious coating 500 is affixed to the top coat 502 by any suitable means, including but not limited to spraying, brushing, dipping or spin coating of the coating material from a solution or suspension with or without the polymers used to create the top coat, followed by curing or solvent removal step as needed. Vapor deposition polymerization and RF-plasma polymerization may also be used to affix those lubricious coating materials that lend themselves to this deposition method, to the top coating. In an alternate exemplary embodiment, the lubricious coating may be directly incorporated into the polymeric matrix.

Figure 22:
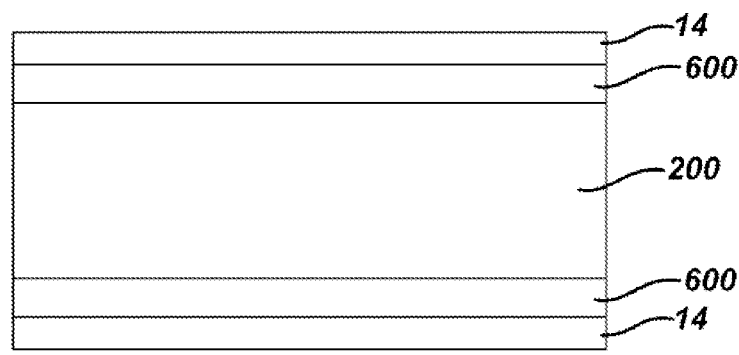
FIG. 22 is a partial cross-sectional view of a self-expanding stent in a delivery device having a lubricious coating in accordance with the present invention.

If a self-expanding stent is utilized, the lubricious coating may be affixed to the inner surface of the restraining sheath. FIG. 22 illustrates a partial cross-sectional view of self-expanding stent 200 within the lumen of a delivery apparatus sheath 14. As illustrated, a lubricious coating 600 is affixed to the inner surfaces of the sheath 14. Accordingly, upon deployment of the stent 200, the lubricious coating 600 preferably minimizes or substantially eliminates the adhesion between the sheath 14 and the drug, agent or compound coated stent 200.

Figure 23:
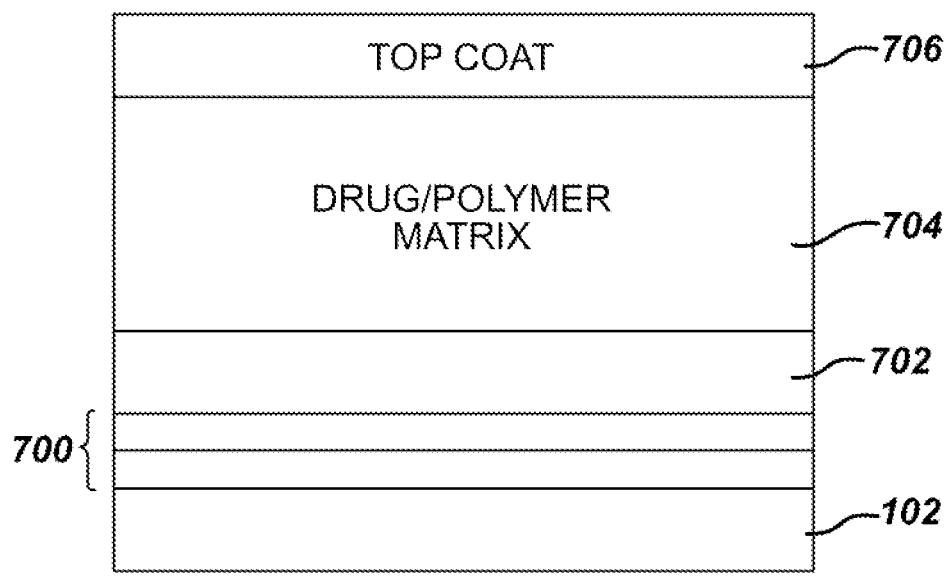
FIG. 23 is a cross-sectional view of a band of the stent in FIG. 1 having a modified polymer coating in accordance with the present invention.

In an alternate approach, physical and/or chemical cross-linking methods may be applied to improve the bond strength between the polymeric coating containing the drugs, agents or compounds and the surface of the medical device or between the polymeric coating containing the drugs, agents or compounds and a primer. Alternately, other primers applied by either traditional coating methods such as dip, spray or spin coating, or by RF-plasma polymerization may also be used to improve bond strength. For example, as shown in FIG. 23, the bond strength can be improved by first depositing a primer layer 700 such as vapor polymerized parylene-C on the device surface, and then placing a secondary layer 702 which comprises a polymer that is similar in chemical composition to the one or more of the polymers that make up the drug-containing matrix 704, e.g., polyethylene-co-vinyl acetate or polybutyl methacrylate but has been modified to contain cross-linking moieties. This secondary layer 702 is then cross-linked to the primer after exposure to ultra-violet light. It should be noted that anyone familiar with the art would recognize that a similar outcome could be achieved using cross-linking agents that are activated by heat with or without the presence of an activating agent. The drug-containing matrix 704 is then layered onto the secondary layer 702 using a solvent that swells, in part or wholly, the secondary layer 702. This promotes the entrainment of polymer chains from the matrix into the secondary layer 702 and conversely from the secondary layer 702 into the drug-containing matrix 704. Upon removal of the solvent from the coated layers, an interpenetrating or interlocking network of the polymer chains is formed between the layers thereby increasing the adhesion strength between them. A top coat 706 is used as described above.

A related difficulty occurs in medical devices such as stents. In the drug-coated stents crimped state, some struts come into contact with each other and when the stent is expanded, the motion causes the polymeric coating comprising the drugs, agents or compounds to stick and stretch. This action may potentially cause the coating to separate from the stent in certain areas. The predominant mechanism of the coating self-adhesion is believed to be due to mechanical forces. When the polymer comes in contact with itself, its chains can tangle causing the mechanical bond, similar to Velcro®. Certain polymers do not bond with each other, for example, fluoropolymers. For other polymers, however, powders may be utilized. In other words, a powder may be applied to the one or more polymers incorporating the drugs, agents or other compounds on the surfaces of the medical device to reduce the mechanical bond. Any suitable biocompatible material which does not interfere with the drugs, agents, compounds or materials utilized to immobilize the drugs, agents or compounds onto the medical device may be utilized. For example, a dusting with a water soluble powder may reduce the tackiness of the coatings surface and this will prevent the polymer from sticking to itself thereby reducing the potential for delamination. The powder should be water-soluble so that it does not present an emboli risk.

The powder may comprise an anti-oxidant, such as vitamin C, or it may comprise an anti-coagulant, such as aspirin or heparin. An advantage of utilizing an anti-oxidant may be in the fact that the anti-oxidant may preserve the other drugs, agents or compounds over longer periods of time.

It is important to note that crystalline polymers are generally not sticky or tacky. Accordingly, if crystalline polymers are utilized rather than amorphous polymers, then additional materials may not be necessary. It is also important to note that polymeric coatings without drugs, agents and/or compounds may improve the operating characteristics of the medical device. For example, the mechanical properties of the medical device may be improved by a polymeric coating, with or without drugs, agents and/or compounds. A coated stent may have improved flexibility and increased durability. In addition, the polymeric coating may substantially reduce or eliminate galvanic corrosion between the different metals comprising the medical device. The same holds true for anastomosis devices.

As stated above, for a self-expanding stent, the retraction of the restraining sheath may cause the drugs, agents or compounds to rub off the stent. Accordingly, in an alternate exemplary embodiment, the stent delivery device may be modified to reduce the potential of rubbing off the coating. This is especially important for long stents, for example, long rapamycin coated stents. In addition, there is also the potential of damaging the stent itself when the delivery sheath is retracted during stent deployment. Accordingly, the stent delivery device may be modified to substantially reduce the forces acting on certain areas of the stent by distributing the forces to more areas of the stent. The stent and stent delivery system described herein are intended to be merely illustrative in nature and those skilled in the art will recognize that the designs disclosed may be incorporated into any number of stents and stent delivery systems.

Figure 35:
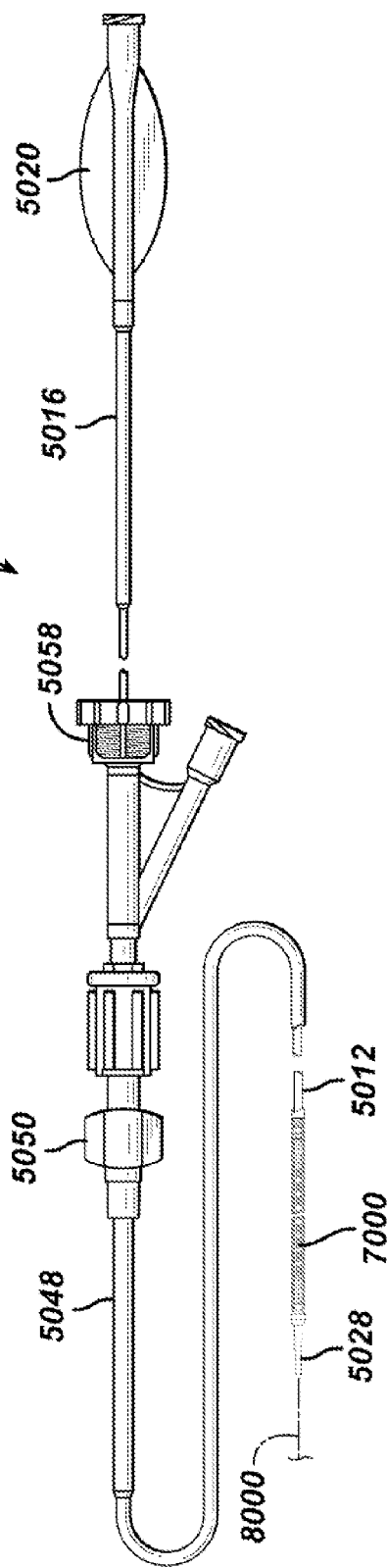
FIG. 35 is a simplified elevational view of a stent delivery apparatus made in accordance with the present invention.
Figure 36:
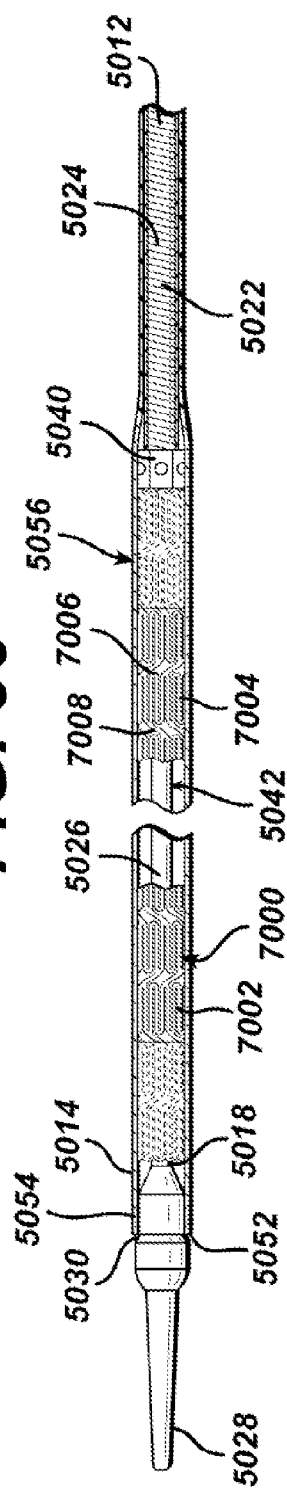
FIG. 36 is a view similar to that of FIG. 35 but showing an enlarged view of the distal end of the apparatus having a section cut away to show the stent loaded therein.

FIGS. 35 and 36 illustrate an exemplary self-expanding stent delivery apparatus 5010 in accordance with the present invention. Apparatus 5010 comprises inner and outer coaxial tubes. The inner tube is called the shaft 5012 and the outer tube is called the sheath 5014. A self-expanding stent 7000 is located within the sheath 5014, wherein the stent 7000 makes frictional contact with the sheath 5014 and the shaft 5012 is disposed coaxially within a lumen of the stent 7000.

Shaft 5012 has proximal and distal ends 5016 and 5018 respectively. The proximal end 5016 of the shaft 5012 has a Luer guidewire hub 5020 attached thereto. As seen best from FIG. 44, the proximal end 5016 of the shaft 5012 is preferably a ground stainless steel hypotube. In one exemplary embodiment, the hypotube is stainless steel and has a 0.042 inch outside diameter at its proximal end and then tapers to a 0.036 inch outside diameter at its distal end. The inside diameter of the hypotube is 0.032 inch throughout its length. The tapered outside diameter is utilized to gradually change the stiffness of the hypotube along its length. This change in the hypotube stiffness allows for a more rigid proximal end or handle end that is needed during stent deployment. If the proximal end is not stiff enough, the hypotube section extending beyond the Tuohy Borst valve described below could buckle as the deployment forces are transmitted. The distal end of the hypotube is more flexible allowing for better track-ability in tortuous vessels. The distal end of the hypotube also needs to be flexible to minimize the transition between the hypotube and the coil section described below.

As will be described in greater detail below, shaft 5012 has a body portion 5022, wherein at least a section thereof is made from a flexible coiled member 5024, looking very much like a compressed or closed coil spring. Shaft 5012 also includes a distal portion 5026, distal to body portion 5022, which is preferably made from a coextrusion of high-density polyethylene and Nylon®. The two portions 5022 and 5026 are joined together by any number of means known to those of ordinary skill in the art including heat fusing, adhesive bonding, chemical bonding or mechanical attachment.

As best seen from FIG. 37, the distal portion 5026 of the shaft 5012 has a distal tip 5028 attached thereto. Distal tip 5028 may be made from any number of suitable materials known in the art including polyamide, polyurethane, polytetrafluoroethylene, and polyethylene including multi-layer or single layer construction. The distal tip 5028 has a proximal end 5030 whose diameter is substantially the same as the outer diameter of the sheath 5014 which is immediately adjacent thereto. The distal tip 5028 tapers to a smaller diameter from its proximal end 5030 to its distal end 5032, wherein the distal end 5032 of the distal tip 5028 has a diameter smaller than the inner diameter of the sheath 5014.

The stent delivery apparatus 5010 glides over a guide wire 8000 (shown in FIG. 35) during navigation to the stent deployment site. As used herein, guidewire may also refer to similar guiding devices which have a distal protection apparatus incorporated herein. One preferred distal protection device is disclosed in published PCT Application 98/33443, having an international filing date of Feb. 3, 1998. As discussed above, if the distal tip 5028 is too stiff it will overpower the guide wire path and push the guide wire 8000 against the lumen wall and in some very tortuous settings the stent delivery apparatus 5010 could prolapse the wire. Overpowering of the wire and pushing of the apparatus against the lumen wall can prevent the device from reaching the target area because the guide wire will no longer be directing the device. Also, as the apparatus is advanced and pushed against the lumen wall, debris from the lesion can be dislodged and travel upstream causing complications to distal vessel lumens. The distal tip 5028 is designed with an extremely flexible leading edge and a gradual transition to a less flexible portion. The distal tip 5028 may be hollow and may be made of any number of suitable materials, including 40D Nylon®. Its flexibility may be changed by gradually increasing the thickness of its cross-sectional diameter, whereby the diameter is thinnest at its distal end, and is thickest at its proximal end. That is, the cross-sectional diameter and wall thickness of the distal tip 5028 increases as you move in the proximal direction. This gives the distal end 5032 of the distal tip 5028 the ability to be directed by the guidewire prior to the larger diameter and thicker wall thickness, less flexible portion, of the distal tip 5028 overpowering the guidewire. Over-powering the wire, as stated above, is when the apparatus, due to its stiffness, dictates the direction of the device instead of following the wire.

The guidewire lumen 5034 has a diameter that is matched to hug the recommended size guide wire so that there is a slight frictional engagement between the guidewire 8000 and the guidewire lumen 5034 of distal tip 5028. The distal tip 5028 has a rounded section 5036 between its distal portion 5032 and its proximal portion 5030. This helps prevent the sheath 5014 from slipping distally over the distal tip 5028, and thereby exposing the squared edges of the sheath 5014 to the vessel, which could cause damage thereto. This improves the device's "pushability." As the distal tip 5028 encounters resistance it does not allow the sheath 5014 to ride over it thereby exposing the sheath's 5014 square cut edge. Instead the sheath 5014 contacts the rounded section 5036 of the distal tip 5028 and thus transmits the forces applied to the distal tip 5028. The distal tip 5028 also has a proximally tapered section 5038 which helps guide the distal tip 5028 through the deployed stent 7000 without providing a sharp edge that could grab or hang up on a stent strut end or other irregularity in the lumen inner diameter.

Attached to distal portion 5026 of shaft 5012 is a stop 5040, which is proximal to the distal tip 5028 and stent 7000. Stop 5040 may be made from any number of suitable materials known in the art, including stainless steel, and is even more preferably made from a highly radio-opaque material such as platinum, gold tantalum, or radio-opaque filled polymer. The stop 5040 may be attached to shaft 5012 by any suitable means, including mechanical or adhesive bonding, or by any other means known to those skilled in the art. Preferably, the diameter of stop 5040 is large enough to make sufficient contact with the loaded stent 7000 without making frictional contact with the sheath 5014. As will be explained subsequently, the stop 5040 helps to "push" the stent 7000 or maintain its relative position during deployment, by preventing the stent 7000 from migrating proximally within the sheath 5014 during retraction of the sheath 5014 for stent deployment. The radio-opaque stop 5040 also aides in positioning the stent 7000 within the target lesion area during deployment within a vessel, as is described below.

A stent bed 5042 is defined as being that portion of the shaft 5012 between the distal tip 5028 and the stop 5040 (FIG. 36). The stent bed 5042 and the stent 7000 are coaxial so that the distal portion 5026 of the shaft 5012 comprising the stent bed 5042 is located within the lumen of stent 7000. The stent bed 5042 makes minimal contact with the stent 7000 because of the space which exists between the shaft 5012 and the sheath 5014. As the stent 7000 is subjected to temperatures at the austenite phase transformation it attempts to recover to its programmed shape by moving outwardly in a radial direction within the sheath 5014. The sheath 5014 constrains the stent 7000 as will be explained in detail subsequently. Distal to the distal end of the loaded stent 7000 attached to the shaft 5012 is a radio-opaque marker 5044 which may be made of platinum, iridium coated platinum, gold tantalum, stainless steel, radio-opaque filled polymer or any other suitable material known in the art.

Figure 44:
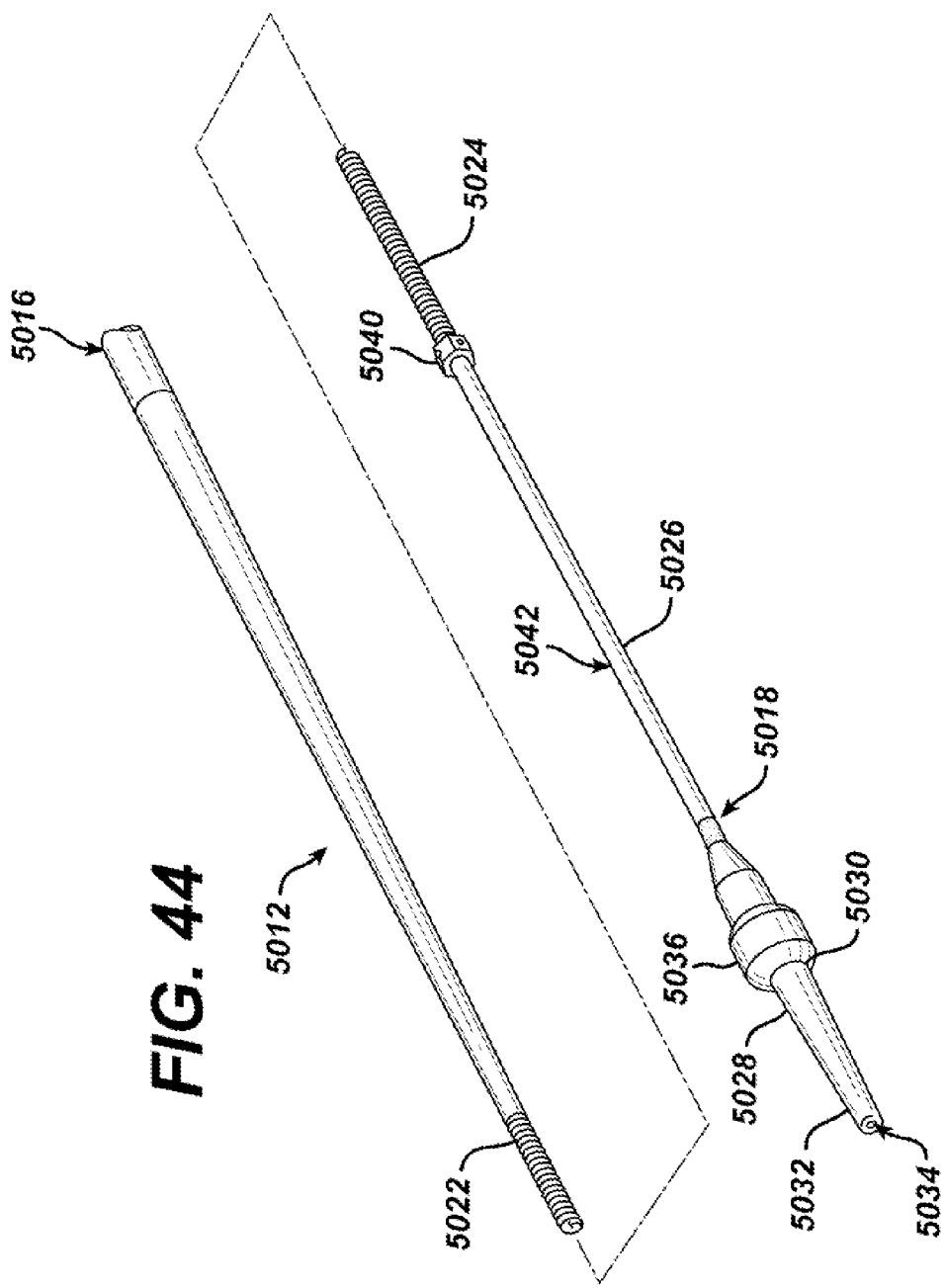
FIG. 44 is a simplified elevational view of a shaft for a stent delivery apparatus made in accordance with the present invention.

As seen from FIGS. 36, 37 and 44, the body portion 5022 of the shaft 5012 is made from a flexible coiled member 5024, similar to a closed coil or compressed spring. During deployment of the stent 7000, the transmission of compressive forces from the stop 5040 to the Luer guidewire hub 5020 is an important factor in deployment accuracy. A more compressive shaft 5012 results in a less accurate deployment because the compression of the shaft 5012 is not taken into account when visualizing the stent 7000 under fluoroscopic imaging. However, a less compressive shaft 5012 usually means less flexibility, which would reduce the ability of the apparatus 5010 to navigate through tortuous vessels. A coiled assembly allows both flexibility and resistance to compression. When the apparatus 5010 is being navigated through the arteries, the shaft 5012 is not in compression and therefore the coiled member 5024 is free to bend with the delivery path. As one deploys the stent 7000, tension is applied to the sheath 5014 as the sheath 5014 is retracted over the encapsulated stent 7000. Because the stent 7000 is self-expanding it is in contact with the sheath 5014 and the forces are transferred along the stent 7000 and to the stop 5040 of the shaft 5012. This results in the shaft 5012 being under compressive forces. When this happens, the flexible coiled member 5024, no gaps between the coil members, transfers the compressive force from one coil to the next.

The flexible coiled member 5024 further includes a covering 5046 that fits over the flexible coiled member 5024 to help resist buckling of the coiled member 5024 in both bending and compressive modes. The covering 5046 is an extruded polymer tube and is preferably a soft material that can elongate slightly to accommodate bending of the flexible coiled member 5024, but does not allow the coils to ride over each other. Covering 5046 may be made from any number of suitable materials including coextrusions of Nylon® and high-density polyethylene, polyurethane, polyamide, polytetrafluoroethylene, etc. The extrusion is also attached to the stop 5040. Flexible coiled member 5024 may be made of any number of materials known in the art including stainless steel, Nitinol, and rigid polymers. In one exemplary embodiment, flexible coiled member 5024 is made from a 0.003 inch thick by 0.010 inch wide stainless steel ribbon wire. The wire may be round, or more preferably flat to reduce the profile of the flexible coiled member 5024.

Sheath 5014 is preferably a polymeric catheter and has a proximal end 5048 terminating at a sheath hub 5050 (FIG. 35). Sheath 5014 also has a distal end 5052 which terminates at the proximal end 5030 of distal tip 5028 of the shaft 5012, when the stent 7000 is in an un-deployed position as shown in FIG. 36. The distal end 5052 of sheath 5014 includes a radio-opaque marker band 5054 disposed along its outer surface (FIG. 35). As will be explained below, the stent 7000 is fully deployed when the marker band 5054 is proximal to radio-opaque stop 5040, thus indicating to the physician that it is now safe to remove the delivery apparatus 5010 from the body.

As detailed in FIG. 36, the distal end 5052 of sheath 5014 includes an enlarged section 5056. Enlarged section 5056 has larger inside and outside diameters than the inside and outside diameters of the sheath 5014 proximal to enlarged section 5056. Enlarged section 5056 houses the pre-loaded stent 7000, the stop 5040 and the stent bed 5042. The outer sheath 5014 tapers proximally at the proximal end of enlarged section 5056 to a smaller size diameter. This design is more fully set forth in co-pending U.S. application Ser. No. 09/243,750 filed on Feb. 3, 1999, which is hereby incorporated herein by reference. One particular advantage to the reduction in the size of the outer diameter of sheath 5014 proximal to enlarged section 5056 is in an increase in the clearance between the delivery apparatus 5010 and the guiding catheter or sheath that the delivery apparatus 5010 is placed through. Using fluoroscopy, the physician will view an image of the target site within the vessel, before and after deployment of the stent, by injecting a radio-opaque solution through the guiding catheter or sheath with the delivery apparatus 5010 placed within the guiding catheter. Because the clearance between the sheath 5014, and the guiding catheter is increased by tapering or reducing the outer diameter of the sheath 5014 proximal to enlarged section 5056, higher injection rates may be achieved, resulting in better images of the target site for the physician. The tapering of sheath 5014 provides for higher injection rates of radio-opaque fluid, both before and after deployment of the stent.

Figure 45:
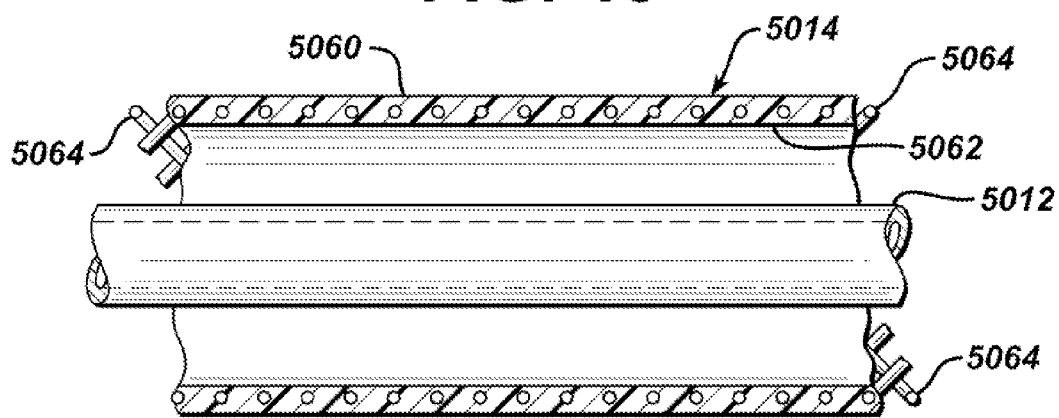
FIG. 45 is a partial cross-sectional view of the shaft and sheath of the stent delivery apparatus in accordance with the present invention.

A problem encountered with earlier self-expanding stent delivery systems is that of the stent becoming embedded within the sheath in which it is disposed. Referring to FIG. 45, there is illustrated a sheath construction which may be effectively utilized to substantially prevent the stent from becoming embedded in the sheath as well as provide other benefits as described in detail below. As illustrated, the sheath 5014 comprises a composite structure of at least two layers and preferably three layers. The outer layer 5060 may be formed from any suitable biocompatible material. Preferably, the outer layer 5060 is formed from a lubricious material for ease of insertion and removal of the sheath 5014. In a preferred embodiment, the outer layer 5060 comprises a polymeric material such as Nylon®. The inner layer 5062 may also be formed from any suitable biocompatible material. For example, the inner layer 5062 may be formed from any number of polymers including polyethylene, polyamide or polytetrafluroethylene. In a preferred embodiment, the inner layer 5062 comprises polytetrafluroethylene. Polytetrafluroethylene is also a lubricious material which makes stent delivery easier, thereby preventing damage to the stent 7000. The inner layer 5062 may also be coated with another material to increase the lubricity thereof for facilitating stent deployment. Any number of suitable biocompatible materials may be utilized. In an exemplary embodiment, silicone based coatings may be utilized. Essentially, a solution of the silicone based coating may be injected through the apparatus and allowed to cure at room temperature. The amount of silicone based coating utilized should be minimized to prevent transference of the coating to the stent 7000. Sandwiched between the outer and inner layers 5060 and 5062, respectively, is a wire reinforcement layer 5064. The wire reinforcement layer 5064 may take on any number of configurations. In the exemplary embodiment, the wire reinforcement layer 5064 comprises a simple under and over weave or braiding pattern. The wire used to form the wire reinforcement layer 5064 may comprise any suitable material and any suitable cross-sectional shape. In the illustrated exemplary embodiment, the wire forming the wire reinforcement layer 5064 comprises stainless steel and has a substantially circular cross-section. In order to function for its intended purpose, as described in detail below, the wire has a diameter of 0.002 inches.

The three layers 5060, 5062, and 5064 comprising the sheath 5014 collectively enhance stent deployment. The outer layer 5060 facilitates insertion and removal of the entire apparatus 5010. The inner layer 5062 and the wire reinforcement layer 5064 function to prevent the stent 7000 from becoming embedded in the sheath 5014. Self-expanding stents such as the stent 7000 of the present invention tend to expand to their programmed diameter at a given temperature. As the stent attempts to undergo expansion, it exerts a radially outward directed force and may become embedded in the sheath 5014 restraining it from expanding. Accordingly, the wire reinforcing layer 5064 provides radial or hoop strength to the inner layer 5062 thereby creating sufficient resistance to the outwardly directed radial force of the stent 7000 within the sheath 5014. The inner layer 5062, also as discussed above, provides a lower coefficient of friction surface to reduce the forces required to deploy the stent 7000 (typically in the range from about five to eight pounds). The wire reinforcement layer 5064 also provides tensile strength to the sheath 5014. In other words, the wire reinforcement layer 5064 provides the sheath 5014 with better pushability, i.e., the ability to transmit a force applied by the physician at a proximal location on the sheath 5014 to the distal tip 5028, which aids in navigation across tight stenotic lesions within the vasculature. Wire reinforcement layer 5064 also provides the sheath 5014 with better resistance to elongation and necking as a result of tensile loading during sheath retraction for stent deployment.

The sheath 5014 may comprise all three layers along its entire length or only in certain sections, for example, along the length of the stent 7000. In a preferred embodiment, the sheath 5014 comprises all three layers along its entire length.

Prior art self-expanding stent delivery systems did not utilize wire reinforcement layers. Because the size of typical self-expanding stents is relatively large, as compared to balloon expandable coronary stents, the diameter or profile of the delivery devices therefore had to be large as well. However, it is always advantageous to have delivery systems which are as small as possible. This is desirable so that the devices can reach into smaller vessels and so that less trauma is caused to the patient. However, as stated above, the advantages of a thin reinforcing layer in a stent delivery apparatus outweighs the disadvantages of slightly increased profile.

Figure 46:
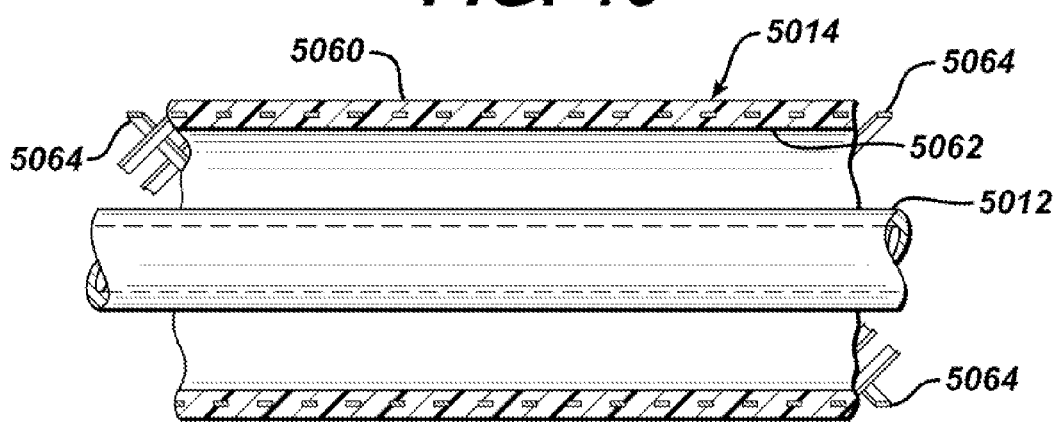
FIG. 46 is a partial cross-sectional view of the shaft and modified sheath of the stent delivery system in accordance with the present invention.

In order to minimize the impact of the wire reinforcement layer on the profile of the apparatus 5010, the configuration of the wire reinforcement layer 5064 may be modified. For example, this may be accomplished in a number of ways, including changing the pitch of the braid, changing the shape of the wire, changing the wire diameter and/or changing the number of wires utilized. In a preferred embodiment, the wire utilized to form the wire reinforcement layer comprises a substantially rectangular cross-section as illustrated in FIG. 46. In utilizing a substantially rectangular cross-section wire, the strength features of the reinforcement layer 5064 may be maintained with a significant reduction in the profile of the delivery apparatus. In this preferred embodiment, the rectangular cross-section wire has a width of 0.003 inches and a height of 0.001 inches. Accordingly, braiding the wire in a similar manner to FIG. 45, results in a fifty percent decrease in the thickness of the wire reinforcement layer 5064 while maintaining the same beneficial characteristics as the 0.002 round wire. The flat wire may comprise any suitable material, and preferably comprises stainless steel.

In another alternate exemplary embodiment, the sheath of the delivery system may comprise an inner layer or coating on its inner surface which substantially prevents the stent from becoming embedded therein while increasing the lubricity thereof. This inner layer or coating may be utilized with the sheaths illustrated in FIGS. 45 and 46 or as an alternative means to decrease the stent deployment forces. Given the thinness of the coating, as described in more detail below, the overall profile of the delivery system will be minimally impacted if at all. In addition to increasing the strength of the sheath and making it more lubricious, the coating is extremely biocompatible which is important since it does make contact with blood, albeit at least temporarily.

Essentially, in the exemplary embodiment, a hard and lubricious coating is applied to or affixed to the inner surface of the sheath of the self-expanding delivery system. The coating provides a number of advantages over currently utilized self-expanding stent delivery systems. For example, the coating provides a hard surface against which the stent exerts a radially outward directed force. As described above, self-expanding stents have a constant outward force of expansion when loaded into the delivery system. This constant and relatively high radially outward directed force can force the polymeric materials that comprise the sheath of the delivery system to creep and allow the stent to become embedded into the polymer surface. As stent platforms are developed with larger diameter stents and subsequently higher radially outward directed forces, the occurrence of this phenomenon will increase. Consequently, embedding increases the force required to deploy the stent because it causes mechanical resistance to the movement of the stent inside the delivery system, thereby preventing accurate deployment and causing potential damage to the stent. In addition, the coating is lubricious, i.e. it has a low coefficient of friction. A lubricious coating, as stated above, functions to further reduce the force required to deploy the stent, thereby increasing the facility by which the stents are delivered and deployed by physicians. This is especially important with respect to newer larger diameter stent designs and/or drug/polymer coated stent designs that have either increased radial forces, increased profile or increased overall diameter. A lubricious coating is particularly advantageous with respect to drug/polymer coated stents. Accordingly, the coating functions to prevent the stent from embedding in the sheath of the delivery system prior to deployment and reducing the friction between the sheath and the stent, both of which will reduce the deployment forces.

Various drugs, agents or compounds may be locally delivered via medical devices such as stents. For example, rapamycin and/or heparin may be delivered by a stent to reduce restenosis, inflammation and coagulation. Various techniques for immobilizing the drugs, agents or compounds onto the stent are known; however, maintaining the drugs, agents or compounds on the stent during delivery and positioning is critical to the success of the procedure or treatment. For example, removal of the drug, agent or compound during delivery of the stent can potentially cause failure of the device. For a self-expanding stent, the retraction of the restraining sheath may cause the drugs, agents or compounds to rub off the stent. Therefore, prevention of this potential problem is important to have successful therapeutic medical devices such as stents.

Figure 47:
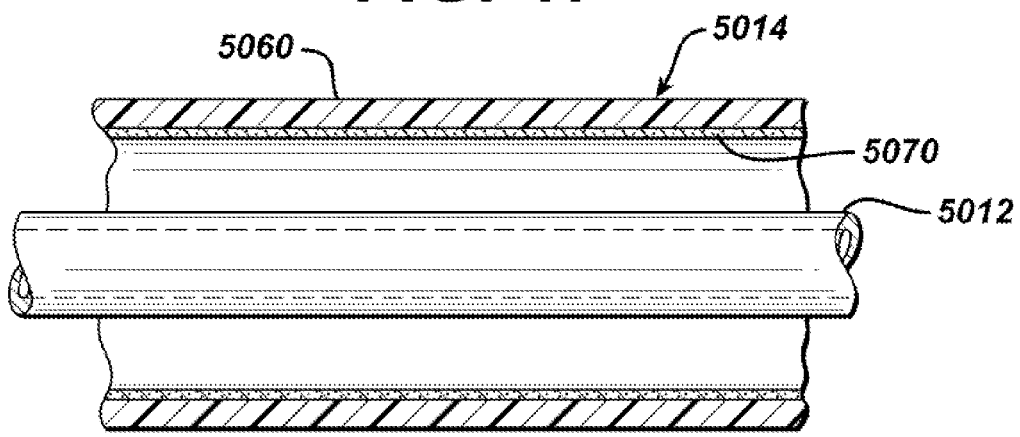
FIG. 47 is a partial cross-sectional view of the shaft and modified sheath of the stent delivery system in accordance with the present invention.

FIG. 47 illustrates a partial cross-sectional view of the shaft and modified sheath of the stent delivery system in accordance with an exemplary embodiment of the present invention. As shown, a coating or layer of material 5070 is affixed or otherwise attached to the inner circumference of the sheath 5014. As stated above, the coating or layer of material 5070 comprises a hard and lubricious substance. In a preferred embodiment, the coating 5070 comprises pyrolytic carbon. Pyrolytic carbon is a well-known substance that is utilized in a wide variety of implantable medical prostheses and is most commonly utilized in cardiac valves, as it combines high strength with excellent tissue and blood compatibility.

Pyrolytic carbon's usefulness in the implantable medical device area is a result of its unique combination of physical and chemical characteristics, including chemical inertness, isotrophy, low weight, compactness and elasticity. Pyrolytic carbon belongs to a specific family of turbostratic carbons which are similar to the structure of graphite. In graphite, the carbon atoms are covalently bonded in planar hexagonal arrays that are stacked in layers with relatively weak inter-layer bonding. In turbostratic carbons, the stacking sequence is disordered and distortions may exist within each of the layers. These structural distortions in the layers are responsible for the superior ductility and durability of pyrolytic carbon. Essentially, the microstructure of pyrolytic carbon makes the material durable, strong and wear resistant. In addition, pyrolytic carbon is highly thromboresistant and has inherent cellular biocompatability with blood and soft tissue.

The pyrolytic carbon layer 5070 may be deposited along the entire length of the sheath 5014 or only in proximity to the stent bed 5042, illustrated in FIGS. 36 and 37. In a preferred embodiment, the pyrolytic carbon layer 5070 is affixed to the sheath 5014 in the region of the stent bed 5042. The pyrolytic carbon layer 5070 may be deposited or affixed to the inner circumference utilizing any number of known techniques that are compatible or usable with the polymeric materials comprising the sheath 5014. The thickness of the pyrolytic carbon layer 5070 is selected such that it prevents or substantially reduces the possibility of the stent becoming embedded in the sheath 5014 without decreasing the flexibility of the sheath 5014 or increasing the profile of the self-expanding stent delivery system. As described above, it is important that the sheath be both flexible and pushable to navigate tortuous pathways within the body. In addition, it is always desirable to reduce the profile of percutaneously delivered devices.

As stated above, pyrolytic carbon surfaces are recognized as biocompatible, especially with respect to blood contact applications. This is, however, only a minor benefit in terms of stent delivery applications because the location of the pyrolytic carbon layer 5070 within the sheath 5014 is only minimally exposed to blood and is only within the body for a duration sufficient to deliver a stent.

The pyrolytic carbon layer 5070 may be affixed to the lumen of the sheath in any number of ways as mentioned above. In one exemplary embodiment, the pyrolytic carbon layer 5070 may be directly affixed to the lumen of the sheath 5014. In another exemplary embodiment, the pyrolytic carbon layer 5070 may be indirectly applied to the lumen of the sheath 5014 by first applying it to a variety of substrates, also utilizing any number of known techniques. Regardless of whether the pyrolytic carbon layer 5070 is deposited directly onto the sheath 5014 or first onto a substrate, any number of known techniques may be utilized, for example, chemical vapor deposition. In chemical vapor deposition, the carbon material is deposited from gaseous hydrocarbon compounds on suitable underlying substrates, e.g. carbon materials, metals, ceramics as well as other materials, at temperatures ranging from about 1000K to about 2500K. At these temperatures, one can understand the need to possibly utilize substrates. Any suitable biocompatible, durable and flexible substrate may be utilized and then affixed to the lumen of the sheath 5014 utilizing well-known techniques such as adhesives. As stated above, profile and flexibility are important design characteristics; accordingly, the type of substrate material chosen and/or its thickness should be considered. It is important to note that a wide range of microstructures, e.g. isotropic, lamellor, substrate-nucleated and a varied content of remaining hydrogen can occur in pyrolytic carbons, depending on the deposition conditions, including temperature, type, concentration and flow rates of the source gas and surface area of the underlying substrate.

Other techniques which may be utilized to affix the pyrolytic carbon layer 5070 directly onto the sheath 5014 or onto a substrate include pulsed laser ablation deposition, radio frequency plasma modification, physical vapor deposition as well as other known techniques. In addition to pyrolytic carbon, other materials that might be beneficial in providing similar properties include diamond-like carbon coatings, silane/silicon glass like surfaces and thin ceramic coatings such as alumina, hydroxyapatite and titania.

In an alternate exemplary embodiment, the pyrolytic carbon coating may be applied with a controlled finite porosity as briefly described above. This controlled finite porosity provides two distinct advantages. First, the porosity may serve to reduce the contact surface area if the stent with the pyrolytic carbon coating 5070, thereby reducing the friction between the stent and the inner lumen of the sheath 5014. Second, lubricious materials such as biocompatible oils, waxes and powders could be infused or impregnated within the porous surface of the coating thereby providing a reservoir of lubricious material further reducing the frictional coefficient.

FIGS. 35 and 36 show the stent 7000 as being in its fully un-deployed position. This is the position the stent is in when the apparatus 5010 is inserted into the vasculature and its distal end is navigated to a target site. Stent 7000 is disposed around the stent bed 5042 and at the distal end 5052 of sheath 5014. The distal tip 5028 of the shaft 5012 is distal to the distal end 5052 of the sheath 5014. The stent 7000 is in a compressed state and makes frictional contact with the inner surface of the sheath 5014.

When being inserted into a patient, sheath 5014 and shaft 5012 are locked together at their proximal ends by a Tuohy Borst valve 5058. This prevents any sliding movement between the shaft 5012 and sheath 5014, which could result in a premature deployment or partial deployment of the stent 7000. When the stent 100 reaches its target site and is ready for deployment, the Tuohy Borst valve 5058 is opened so that the sheath 5014 and shaft 5012 are no longer locked together.

Figure 39:
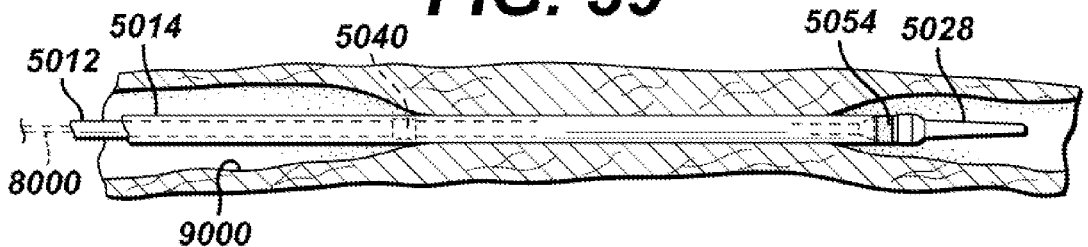
FIG. 39 through 43 are partial cross-sectional views of the apparatus of the present invention sequentially showing the deployment of the self-expanding stent within the vasculature.
Figure 40:
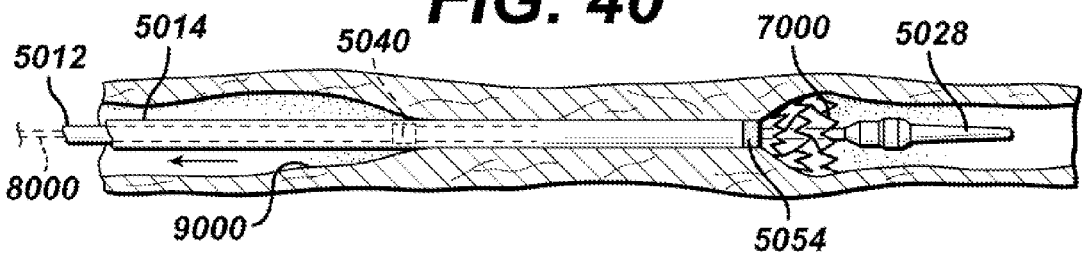
Figure 41:
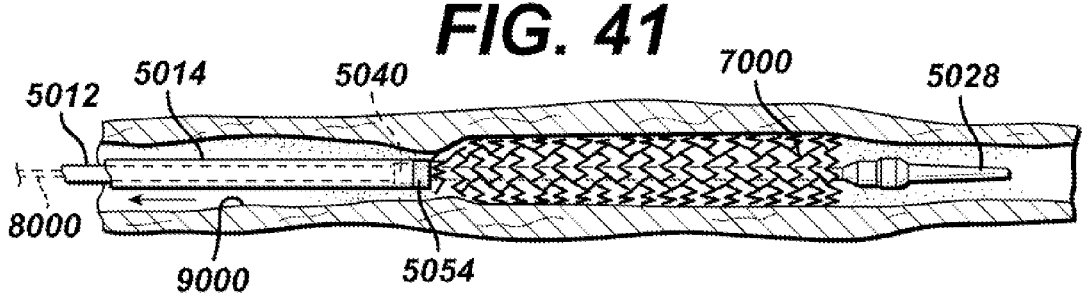
Figure 42:
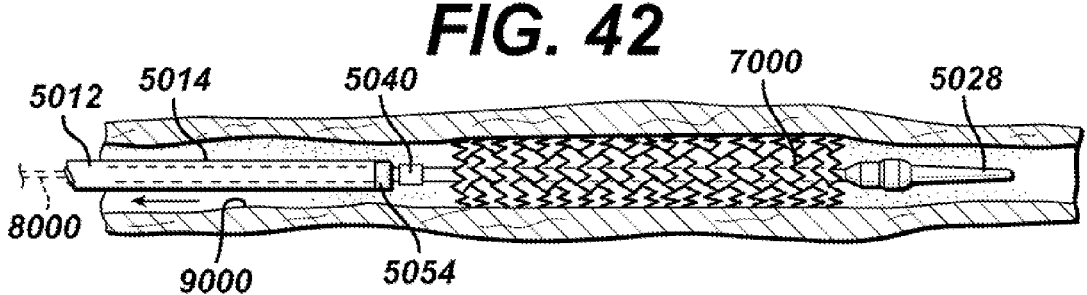

The method under which delivery apparatus 5010 deploys stent 7000 may best be described by referring to FIGS. 39-43. In FIG. 39, the delivery apparatus 5010 has been inserted into a vessel 9000 so that the stent bed 5042 is at a target diseased site. Once the physician determines that the radio-opaque marker band 5054 and stop 5040 on shaft 5012 indicating the ends of stent 7000 are sufficiently placed about the target disease site, the physician would open Tuohy Borst valve 5058. The physician would then grasp the Luer guidewire hub 5020 of shaft 5012 so as to hold shaft 5012 in a fixed position. Thereafter, the physician would grasp the Tuohy Borst valve 5058, attached proximally to sheath 5014, and slide it proximal, relative to the shaft 5012 as shown in FIGS. 40 and 41. Stop 5040 prevents the stent 7000 from sliding back with sheath 5014, so that as the sheath 5014 is moved back, the stent 7000 is effectively "pushed" out of the distal end 5052 of the sheath 5014, or held in position relative to the target site. Stent 7000 should be deployed in a distal to proximal direction to minimize the potential for creating emboli with the diseased vessel 9000. Stent deployment is complete when the radio-opaque band 5054 on the sheath 5014 is proximal to radio-opaque stop 5040, as shown in FIG. 42. The apparatus 5010 can now be withdrawn through stent 7000 and removed from the patient.

Figure 43:
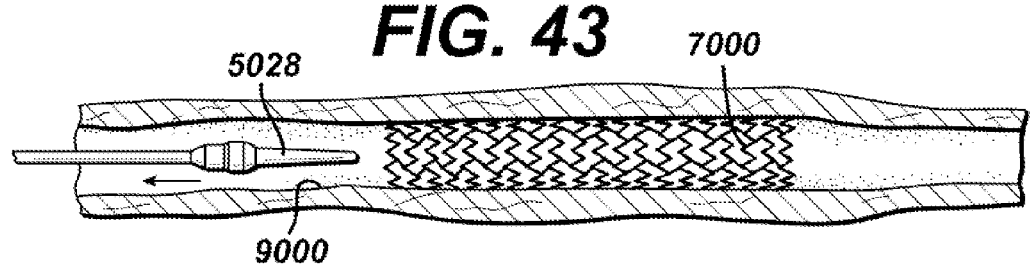

FIGS. 36 and 43 show a preferred embodiment of a stent 7000, which may be used in conjunction with the present invention. Stent 7000 is shown in its unexpanded compressed state, before it is deployed, in FIG. 36. Stent 7000 is preferably made from a superelastic alloy such as Nitinol. Most preferably, the stent 7000 is made from an alloy comprising from about 50.5 percent (as used herein these percentages refer to atomic percentages) Ni to about 60 percent Ni, and most preferably about 55 percent Ni, with the remainder of the alloy Ti. Preferably, the stent 7000 is such that it is superelastic at body temperature, and preferably has an Af in the range from about twenty-one degrees C. to about thirty-seven degrees C. The superelastic design of the stent makes it crush recoverable which, as discussed above, can be used as a stent or frame for any number of vascular devices for different applications.

Stent 7000 is a tubular member having front and back open ends a longitudinal axis extending there between. The tubular member has a first smaller diameter, FIG. 30, for insertion into a patient and navigation through the vessels, and a second larger diameter for deployment into the target area of a vessel. The tubular member is made from a plurality of adjacent hoops 7002 extending between the front and back ends. The hoops 7002 include a plurality of longitudinal struts 7004 and a plurality of loops 7006 connecting adjacent struts, wherein adjacent struts are connected at opposite ends so as to form a substantially S or Z shape pattern. Stent 7000 further includes a plurality of curved bridges 7008, which connect adjacent hoops 7002. Bridges 7008 connect adjacent struts together at bridge to loop connection points which are offset from the center of a loop.

The above described geometry helps to better distribute strain throughout the stent, prevents metal to metal contact when the stent is bent, and minimizes the opening size between the features, struts, loops and bridges. The number of and nature of the design of the struts, loops and bridges are important factors when determining the working properties and fatigue life properties of the stent. Preferably, each hoop has between twenty-four to thirty-six or more struts. Preferably the stent has a ratio of number of struts per hoop to strut length (in inches) which is greater than two hundred. The length of a strut is measured in its compressed state parallel to the longitudinal axis of the stent.

In trying to minimize the maximum strain experienced by features, the stent utilizes structural geometries which distribute strain to areas of the stent which are less susceptible to failure than others. For example, one vulnerable area of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge to loop connection points. One way to accomplish this is to utilize the largest possible radii while maintaining feature widths, which are consistent with applied forces. Another consideration is to minimize the maximum open area of the stent. Efficient utilization of the original tube from which the stent is cut increases stent strength and it's ability to trap embolic material.

As set forth above, stents coated with combinations of polymers and drugs, agents and/or compounds may potentially increase the forces acting on the stent during stent deployment. This increase in forces may in turn damage the stent. For example, as described above, during deployment, the stent is forced against a stop to overcome the force of sliding the outer sheath back. With a longer stent, e.g. greater than 200 mm, the forces exerted on the end of the stent during sheath retraction may be excessive and could potentially cause damage to the end of the stent or to other sections of the stent. Accordingly, a stent delivery device which distributes the forces over a greater area of the stent would be beneficial.

Figure 48:
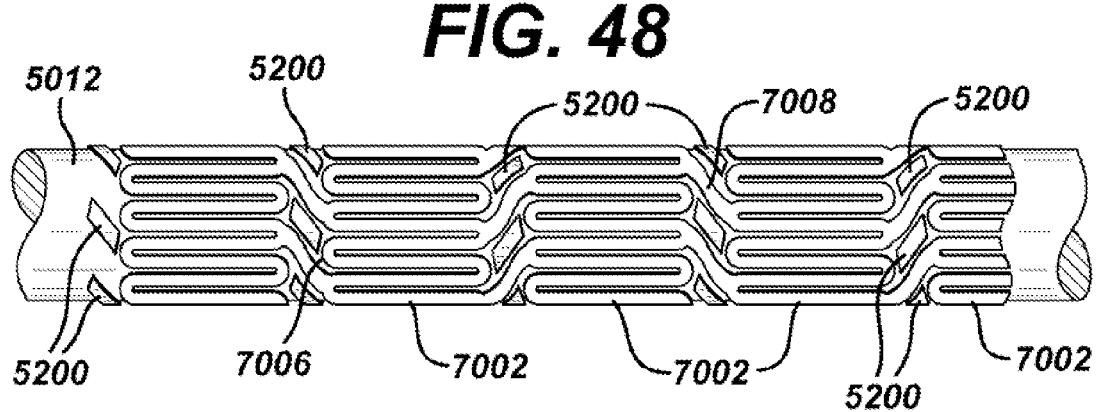
FIG. 48 is a partial cross-sectional view of a modified shaft of the stent delivery system in accordance with the present invention.

FIG. 48 illustrates a modified shaft 5012 of the stent delivery section. In this exemplary embodiment, the shaft 5012 comprises a plurality of raised sections 5200. The raised sections 5200 may comprise any suitable size and geometry and may be formed in any suitable manner. The raised sections 5200 may comprise any suitable material, including the material forming the shaft 5012. The number of raised sections 5200 may also be varied. Essentially, the raised sections 5200 may occupy the open spaces between the stent 7000 elements. All of the spaces may be filled or select spaces may be filled. In other words, the pattern and number of raised sections 5200 is preferably determined by the stent design. In the illustrated embodiment, the raised sections or protrusions 5200 are arranged such that they occupy the spaces formed between adjacent loops 7006 on adjacent hoops 7002 and between the bridges 7008.

The raised sections 5200 may be formed in any number of ways. For example, the raised sections 5200 may be formed using a heated clamshell mold or a waffle iron heated die approach. Either method allows for the low cost mass production of inner shafts comprising protrusions.

The size, shape and pattern of the raised sections 5200 may be modified to accommodate any stent design. The height of each of the raised sections 5200 is preferably large enough to compensate for the slight gap that exists between the inner shaft 5012 and the outer sheath 5014. The height, H, of the raised sections or protrusions 5200 on the shaft 5012 should preferably be, at a minimum, greater than the difference in radius between the outside diameter of the shaft 5012, IM(r), and the inside diameter of the sheath 5014, OM(r), minus the wall thickness of the device or stent 7000, WT. The equation representing this relationship is given by $$H > (OM(r) - IM(r)) - WT.$$

For example, if the shaft 5012 has an outside diameter of 0.08 inches, the sheath 5014 has an inside diameter of 0.1 inches, and the wall thickness of the stent 7000 is 0.008 inches, then the height of the raised sections or protrusions 5200 is $$H > \left(\frac{0.100}{2} - \frac{0.080}{2}\right) - 0.008,$$

$$H > 0.002 \text{ inches}.$$

It is important to note that the height of the raised sections 5200 should preferably be less than the difference between the radius of the sheath and the radius of the shaft unless the protrusions 5200 are compressible.

Although each raised section 5200 is small, the number of raised sections 5200 may be large and each of the raised sections 5200 apply a small amount of force to different parts of the stent 7002, thereby distributing the force to deploy the stent 7000 and preventing damage to the stent 7000 particularly at its proximal end. The raised sections 5200 also protect the stent 7000 during loading of the stent 7000 into the delivery system. Essentially, the same forces that act on the stent 7000 during deployment act on the stent 7000 during loading. The longitudinal flexibility of the stent necessitates that as little force as possible is placed on the stent as it is released or deployed to ensure repeatable foreshortening and accurate placement. Essentially, it is preferable that longitudinal movement of the stent 7000 be eliminated or substantially reduced during deployment thereby eliminating or substantially reducing compression of the stent. Without the raised sections 5200, as the stent 7000 is being deployed, the compressive forces will compress the delivery system as well as the stent 7000. This compressive energy will be released upon deployment, reducing the chances of accurate placement of the stent 7000 and contributing to the possibility of stent "jumping." With the raised sections 5200, the stent 7000 is less likely to move, thereby eliminating or substantially reducing compression.

In an alternate exemplary embodiment, once the stent is positioned on the shaft of the delivery device, the stent may be heated and externally pressurized to make a mirror-like imprint in the inner shaft of the delivery system. The imprint provides a three-dimensional surface which allows the stent to maintain its position as the sheath is retracted. The three-dimensional imprint may be made using heat alone, pressure alone or with a separate device.

Any of the above-described medical devices may be utilized for the local delivery of drugs, agents and/or compounds to other areas, not immediately around the device itself. In order to avoid the potential complications associated with systemic drug delivery, the medical devices of the present invention may be utilized to deliver therapeutic agents to areas adjacent to the medical device. For example, a rapamycin coated stent may deliver the rapamycin to the tissues surrounding the stent as well as areas upstream of the stent and downstream of the stent. The degree of tissue penetration depends on a number of factors, including the drug, agent or compound, the concentrations of the drug and the release rate of the agent. The same holds true for coated anastomosis devices.

The drug, agent and/or compound/carrier or vehicle compositions described above may be formulated in a number of ways. For example, they may be formulated utilizing additional components or constituents, including a variety of excipient agents and/or formulary components to affect manufacturability, coating integrity, sterilizability, drug stability, and drug release rate. Within exemplary embodiments of the present invention, excipient agents and/or formulary components may be added to achieve both fast-release and sustained-release drug elution profiles. Such excipient agents may include salts and/or inorganic compounds such as acids/bases or buffer components, anti-oxidants, surfactants, polypeptides, proteins, carbohydrates including sucrose, glucose or dextrose, chelating agents such as EDTA, glutathione or other excipients or agents.

It is important to note that any of the above-described medical devices may be coated with coatings that comprise drugs, agents or compounds or simply with coatings that contain no drugs, agents or compounds. In addition, the entire medical device may be coated or only a portion of the device may be coated. The coating may be uniform or non-uniform. The coating may be discontinuous.

As described above, any number of drugs, agents and/or compounds may be locally delivered via any number of medical devices. For example, stents and anastomosis devices may incorporate coatings comprising drugs, agents and/or compounds to treat various disease states and reactions by the body as described in detail above. Other devices which may be coated with or otherwise incorporate therapeutic dosages of drugs, agents and/or compounds include stent-grafts, which are briefly described above, and devices utilizing stent-grafts, such as devices for treating abdominal aortic aneurysms as well as other aneurysms, e.g. thoracic aorta aneurysms.

Figure 24:
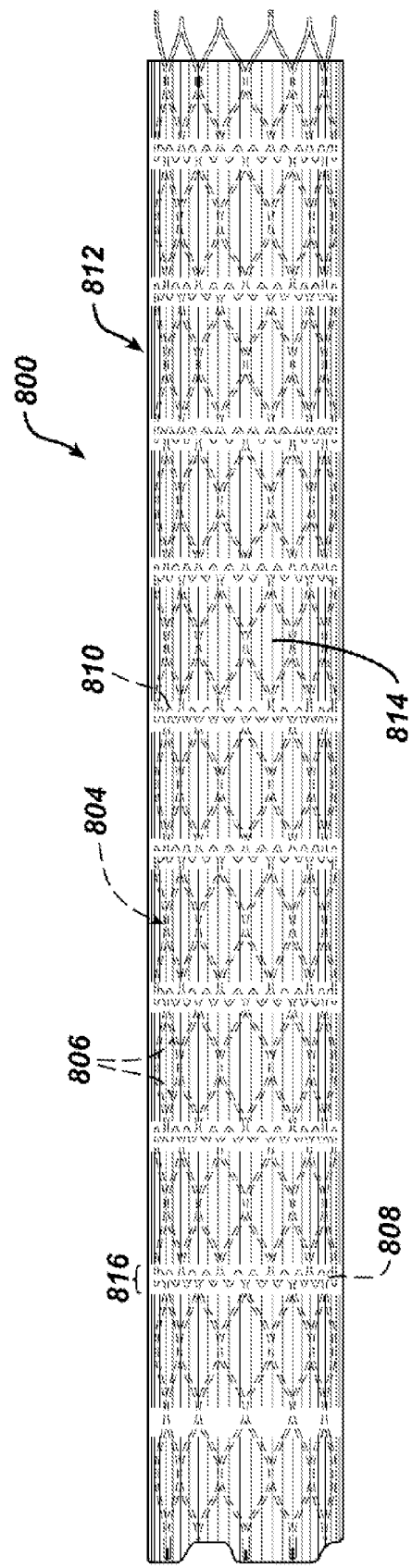
FIG. 24 is a side elevation of an exemplary stent-graft in accordance with the present invention.

Stent-grafts, as the name implies, comprise a stent and a graft material attached thereto. FIG. 24 illustrates an exemplary stent-graft 800. The stent-graft 800 may comprise any type of stent and any type of graft material as described in detail subsequently. In the illustrated exemplary embodiment, the stent 802 is a self-expanding device. A typical self-expanding stent comprises an expandable lattice or network of interconnected struts. In preferred embodiments of the invention, the lattice is fabricated, e.g. laser cut, from an integral tube of material.

In accordance with the present invention, the stent may be variously configured. For example, the stent may be configured with struts or the like that form repeating geometric shapes. One skilled in the art will readily recognize that a stent may be configured or adapted to include certain features and/or to perform a certain function(s), and that alternate designs may be used to promote that feature or function.

In the exemplary embodiment of the invention illustrated in FIG. 24, the matrix or struts of stent 802 may be configured into at least two hoops 804, each hoop 804 comprising a number of struts 806 formed into a diamond shape, having approximately nine diamonds. The stent 802 may further include a zigzag shaped ring 808 for connecting adjacent hoops to one another. The zigzag shaped rings 808 may be formed from a number of alternating struts 810, wherein each ring has fifty-four struts.

An inner or outer surface of the stent 802 may be covered by or support a graft material. Graft material 812 may be made from any number of materials known to those skilled in the art, including woven or other configurations of polyester, Dacron®, Teflon®, polyurethane porous polyurethane, silicone, polyethylene, terephthalate, expanded polytetrafluoroethylene (ePTFE) and blends of various materials.

The graft material 812 may be variously configured, preferably to achieve predetermined mechanical properties. For example, the graft material may incorporate a single or multiple weaving and/or pleating patterns, or may be pleated or unpleated. For example, the graft material may be configured into a plain weave, a satin weave, include longitudinal pleats, interrupted pleats, annular or helical pleats, radially oriented pleats, or combinations thereof. Alternately, the graft material may be knitted or braided. In the embodiments of the invention in which the graft material is pleated, the pleats may be continuous or discontinuous. Also, the pleats may be oriented longitudinally, circumferentially, or combinations thereof.

As illustrated in FIG. 24, the graft material 812 may include a plurality of longitudinal pleats 814 extending along its surface, generally parallel to the longitudinal axis of the stent-graft 800. The pleats 814 allow the stent-graft 800 to collapse around its center, much as it would be when it is delivered into a patient. This provides a relatively low profile delivery system, and provides for a controlled and consistent deployment therefrom. It is believed that this configuration minimizes wrinkling and other geometric irregularities. Upon subsequent expansion, the stent-graft 800 assumes its natural cylindrical shape, and the pleats 814 uniformly and symmetrically open.

In addition, the pleats 814 help facilitate stent-graft manufacture, in that they indicate the direction parallel to the longitudinal axis, allowing stent to graft attachment along these lines, and thereby inhibiting accidental twisting of the graft relative to the stent after attachment. The force required to push the stent-graft 800 out of the delivery system may also be reduced, in that only the pleated edges of the graft make frictional contact with the inner surface of the delivery system. One further advantage of the pleats 814 is that blood tends to coagulate generally uniformly in the troughs of the pleats 814, discouraging asymmetric or large clot formation on the graft surface, thereby reducing embolus risk.

As shown in FIG. 24, the graft material 812 may also include one or more, and preferably a plurality of, radially oriented pleat interruptions 816. The pleat interruptions 816 are typically substantially circular and are oriented perpendicular to longitudinal axis. Pleat interruptions 816 allow the graft and stent to bend better at selective points. This design provides for a graft material that has good crimpability and improved kink resistance.

The foregoing graft materials may be braided, knitted or woven, and may be warp or weft knitted. If the material is warp knitted, it may be provided with a velour, or towel like surface; which is believed to speed the formation of blood clots, thereby promoting the integration of a stent-graft or stent-graft component into the surrounding cellular structure.

A graft material may be attached to a stent or to another graft material by any number of structures or methods known to those skilled in the art, including adhesives, such as polyurethane glue; a plurality of conventional sutures of polyvinylidene fluoride, polypropylene, Dacron®, or any other suitable material; ultrasonic welding; mechanical interference fit; and staples.

The stent 802 and/or graft material 812 may be coated with any of the above-described drugs, agents and/or compounds. In one exemplary embodiment, rapamycin may be affixed to at least a portion of the graft material 812 utilizing any of the materials and processes described above. In another exemplary embodiment, rapamycin may be affixed to at least a portion of the graft material 812 and heparin or other anti-thrombotics may be affixed to at least a portion of the stent 802. With this configuration, the rapamycin coated graft material 812 may be utilized to minimize or substantially eliminate smooth muscle cell hyperproliferation and the heparin coated stent may substantially reduce the chance of thrombosis.

The particular polymer(s) utilized depends on the particular material upon which it is affixed. In addition, the particular drug, agent and/or compound may also affect the selection of polymer(s). As set forth above, rapamycin may be affixed to at least a portion of the graft material 812 utilizing the polymer(s) and processes described above. In another alternate exemplary embodiment, the rapamycin or any other drug, agent and/or compound may be directly impregnated into the graft material 812 utilizing any number of known techniques.

Figure 25:
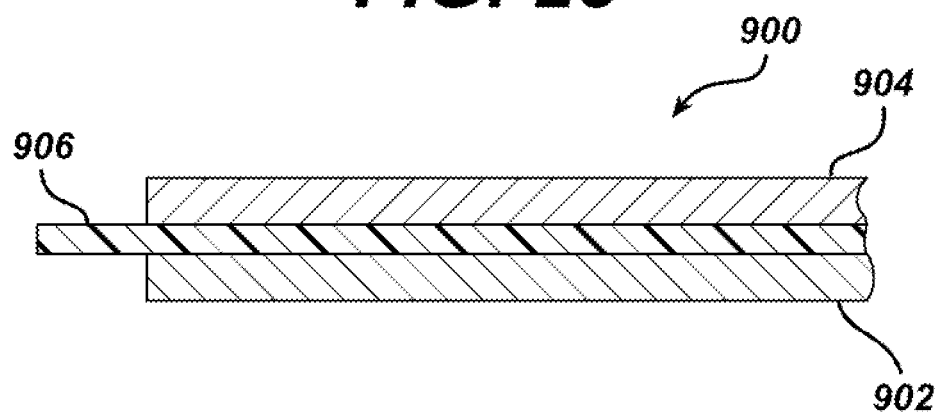
FIG. 25 is a fragmentary cross-sectional view of another alternate exemplary embodiment of a stent-graft in accordance with the present invention.

In yet another alternate exemplary embodiment, the stent-graft may be formed from two stents with the graft material sandwiched therebetween. FIG. 25 is a simple illustration of a stent-graft 900 formed from an inner stent 902, an outer stent 904 and graft material 906 sandwiched therebetween. The stents 902, 904 and graft material 906 may be formed from the same materials as described above. As before, the inner stent 902 may be coated with an anti-thrombotic or anti-coagulant such as heparin while the outer stent 904 may be coated with an anti-proliferative such as rapamycin. Alternately, the graft material 906 may be coated with any of the above described drugs, agents and/or compounds, as well as combinations thereof, or all three elements may be coated with the same or different drugs, agents and/or compounds.

Figure 26:
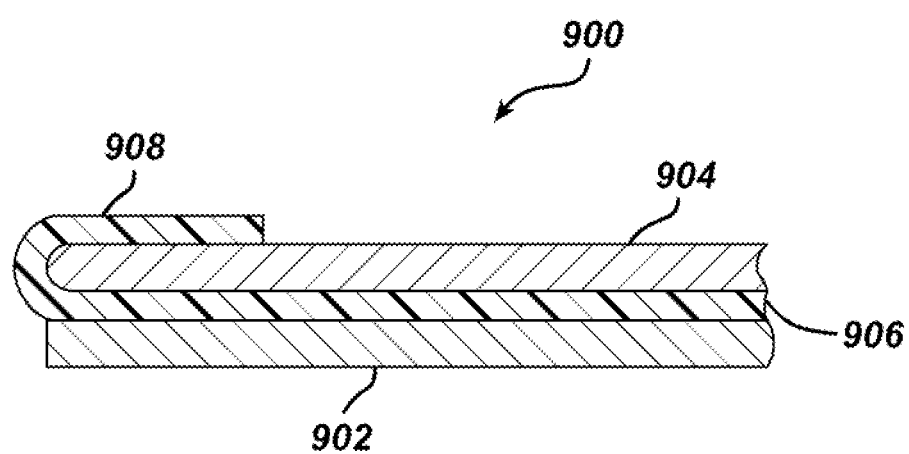
FIG. 26 is a fragmentary cross-sectional view of another alternate exemplary embodiment of a stent-graft in accordance with the present invention.

In yet another alternate exemplary embodiment, the stent-graft design may be modified to include a graft cuff. As illustrated in FIG. 26, the graft material 906 may be folded around the outer stent 904 to form cuffs 908. In this exemplary embodiment, the cuffs 908 may be loaded with various drugs, agents and/or compounds, including rapamycin and heparin. The drugs, agents and/or compounds may be affixed to the cuffs 908 utilizing the methods and materials described above or through other means. For example, the drugs, agents and/or compounds may be trapped in the cuffs 908 with the graft material 906 acting as the diffusion barrier through which the drug, agent and/or compound elutes. The particular material selected as well as its physical characteristics would determine the elution rate. Alternately, the graft material 906 forming the cuffs 908 may be coated with one or more polymers to control the elution rate as described above.

Stent-grafts may be utilized to treat aneurysms. An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type 1 aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal approach has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital, and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, percutaneous, e.g., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. The delivery procedure typically involves advanced angiographic techniques performed through vascular accesses gained via surgical cutdown of a remote artery, such as the common femoral or brachial arteries. Over a guidewire, the appropriate size introducer will be placed. The catheter and guidewire are passed through the aneurysm, and, with the appropriate size introducer housing a stent-graft, the stent-graft will be advanced along the guidewire to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure requires surgical repair. Some procedures may require additional surgical techniques, such as hypogastric artery embolization, vessel ligation, or surgical bypass, in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and re-configurable while maintaining acute and long term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

Figure 27:
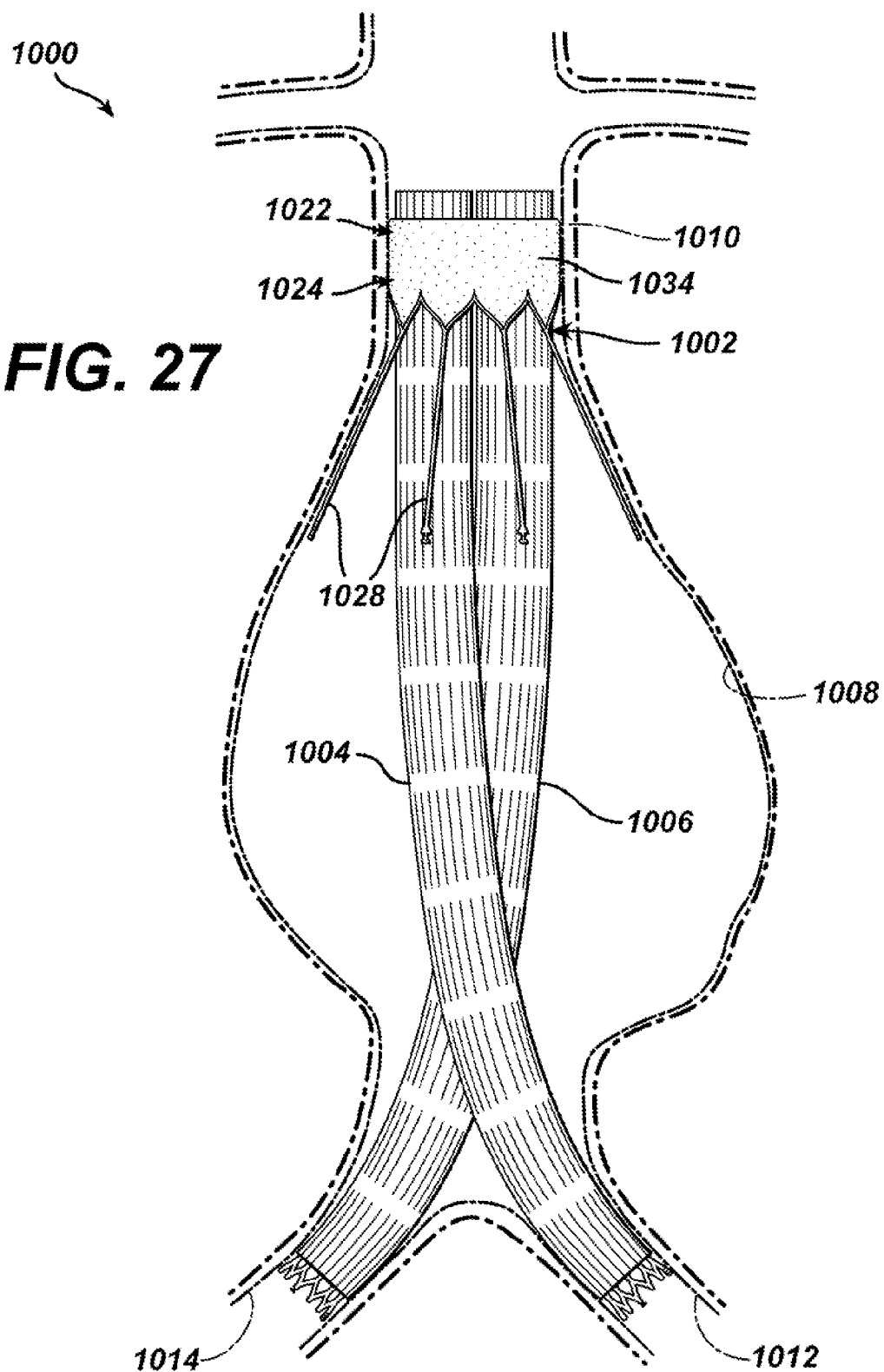
FIG. 27 is an elevation view of a fully deployed aortic repair system in accordance with the present invention.

As stated above, one or more stent-grafts may be utilized to treat aneurysms. These stent-grafts or endoprostheses may comprise any number of materials and configurations. FIG. 27 illustrates an exemplary system for treating abdominal aortic aneurysms. The system 1000 includes a first prosthesis 1002 and two second prostheses 1004 and 1006, which in combination, bypass an aneurysm 1008. In the illustrated exemplary embodiment, a proximal portion of the system 1000 may be positioned in a section 1010 of an artery upstream of the aneurysm 1008, and a distal portion of the system 1000 may be positioned in a downstream section of the artery or a different artery such as iliacs 1012 and 1014.

A prosthesis used in a system in accordance with the present invention typically includes a support, stent or lattice of interconnected struts defining an interior space or lumen having an open proximal end and an open distal end. The lattice also defines an interior surface and an exterior surface. The interior and/or exterior surfaces of the lattice, or a portion of the lattice, may be covered by or support at least one gasket material or graft material.

In preferred embodiments of the invention, a prosthesis is moveable between an expanded or inflated position and an unexpanded or deflated position, and any position therebetween. In some exemplary embodiments of the invention, it may be desirable to provide a prosthesis that moves only from fully collapsed to fully expanded. In other exemplary embodiments of the invention, it may be desirable to expand the prosthesis, then collapse or partially collapse the prosthesis. Such capability is beneficial to the surgeon to properly position or re-position the prosthesis. In accordance with the present invention, the prosthesis may be self-expanding, or may be expandable using an inflatable device, such as a balloon or the like.

Referring back to FIG. 27, the system 1000 is deployed in the infrarenal neck 1010 of the abdominal aorta, upstream of where the artery splits into first and second common iliac arteries 1012, 1014. FIG. 27 shows the first prosthesis or stent gasket 1002 positioned in the infrarenal neck 1010; two second prostheses, 1004, 1006, the proximal ends of which matingly engage a proximal portion of stent gasket 1002, and the distal ends of which extend into a common iliac artery 1012 or 1014. As illustrated, the body of each second prosthesis forms a conduit or fluid flow path that passes through the location of the aneurysm 1008. In preferred embodiments of the invention, the components of the system 1000 define a fluid flow path that bypasses the section of the artery where the aneurysm is located.

The first prosthesis includes a support matrix or stent that supports a sealing material or foam, at least a portion of which is positioned across a biological fluid flow path, e.g., across a blood flow path. In preferred embodiments of the invention, the first prosthesis, the stent, and the sealing material are radially expandable, and define a hollow space between a proximal portion of the prosthesis and a distal portion of the prosthesis. The first prosthesis may also include one or more structures for positioning and anchoring the prosthesis in the artery, and one or more structures for engaging and fixing at least one second prosthesis in place, e.g., a bypass prosthesis.

The support matrix or stent of the first prosthesis may be formed of a wide variety of materials, may be configured in a wide variety of shapes, and their shapes and uses are well known in the art. Exemplary prior art stents are disclosed in U.S. Pat. No. 4,733,665 (Palmaz); U.S. Pat. No. 4,739,762 (Palmaz); and U.S. Pat. No. 4,776,337 (Palmaz), each of the foregoing patents being incorporated herein by reference.

In preferred embodiments of the invention, the stent of the first prosthesis is a collapsible, flexible, and self-expanding lattice or matrix formed from a metal or metal alloy, such as nitinol or stainless steel. Structures formed from stainless steel may be made self-expanding by configuring the stainless steel in a predetermined manner, for example, by twisting it into a braided configuration. More preferably, the stent is a tubular frame that supports a sealing material. The term tubular, as used herein, refers to any shape having a sidewall or sidewalls defining a hollow space or lumen extending therebetween; the cross-sectional shape may be generally cylindrical, elliptic, oval, rectangular, triangular, or any other shape. Furthermore, the shape may change or be deformable as a consequence of various forces that may press against the stent or prosthesis.

The sealing material or gasket member supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The sealing material or gasket member may comprise any suitable material. Exemplary materials preferably comprise a biodurable and biocompatible material, including but are not limited to, open cell foam materials and closed cell foam materials. Exemplary materials include polyurethane, polyethylene, polytetrafluoroethylene; and other various polymer materials, preferably woven or knitted, that provide a flexible structure, such as Dacron®. Highly compressible foams are particularly preferred, preferably to keep the crimped profile low for better delivery. The sealing material or foam is preferably substantially impervious to blood when in a compressed state.

The sealing material may cover one or more surfaces of the stent i.e., may be located along an interior or exterior wall, or both, and preferably extends across the proximal end or a proximal portion of the stent. The sealing material helps impede any blood trying to flow around the first prosthesis, e.g., between the first prosthesis and the arterial wall, and around one or more bypass prostheses after they have been deployed within the lumen of the first prosthesis (described in more detail below).

In preferred embodiments of the invention, the sealing material stretches or covers a portion of the proximal end of the stent and along at least a portion of the outside wall of the stent.

In some embodiments of the invention, it may be desirable for the portion of the sealing material covering the proximal portion of the stent to include one or more holes, apertures, points, slits, sleeves, flaps, weakened spots, guides, or the like for positioning a guidewire, for positioning a system component, such as a second prosthesis, and/or for engaging, preferably matingly engaging, one or more system components, such as a second prosthesis. For example, a sealing material configured as a cover or the like, and having a hole, may partially occlude the stent lumen.

These openings may be variously configured, primarily to conform to its use. These structures promote proper side by side placement of one or more, preferably multiple, prostheses within the first prosthesis, and, in some embodiments of the invention, the sealing material may be configured or adapted to assist in maintaining a certain shape of the fully deployed system or component. Further, these openings may exist prior to deployment of the prosthesis, or may be formed in the prosthesis as part of a deployment procedure. The various functions of the openings will be evident from the description below. In exemplary embodiments of the invention, the sealing material is a foam cover that has a single hole.

The sealing material may be attached to the stent by any of a variety of connectors, including a plurality of conventional sutures of polyvinylidene fluoride, polypropylene, Dacron®, or any other suitable material and attached thereto. Other methods of attaching the sealing material to the stent include adhesives, ultrasonic welding, mechanical interference fit and staples.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

First prosthesis is typically deployed in an arterial passageway upstream of an aneurysm, and functions to open and/or expand the artery, to properly position and anchor the various components of the system, and, in combination with other components, seal the system or portions thereof from fluid leaks. For example, the sealing prosthesis may be deployed within the infrarenal neck, between an abdominal aortic aneurysm and the renal arteries of a patient, to assist in repairing an abdominal aortic aneurysm.

Figure 28:
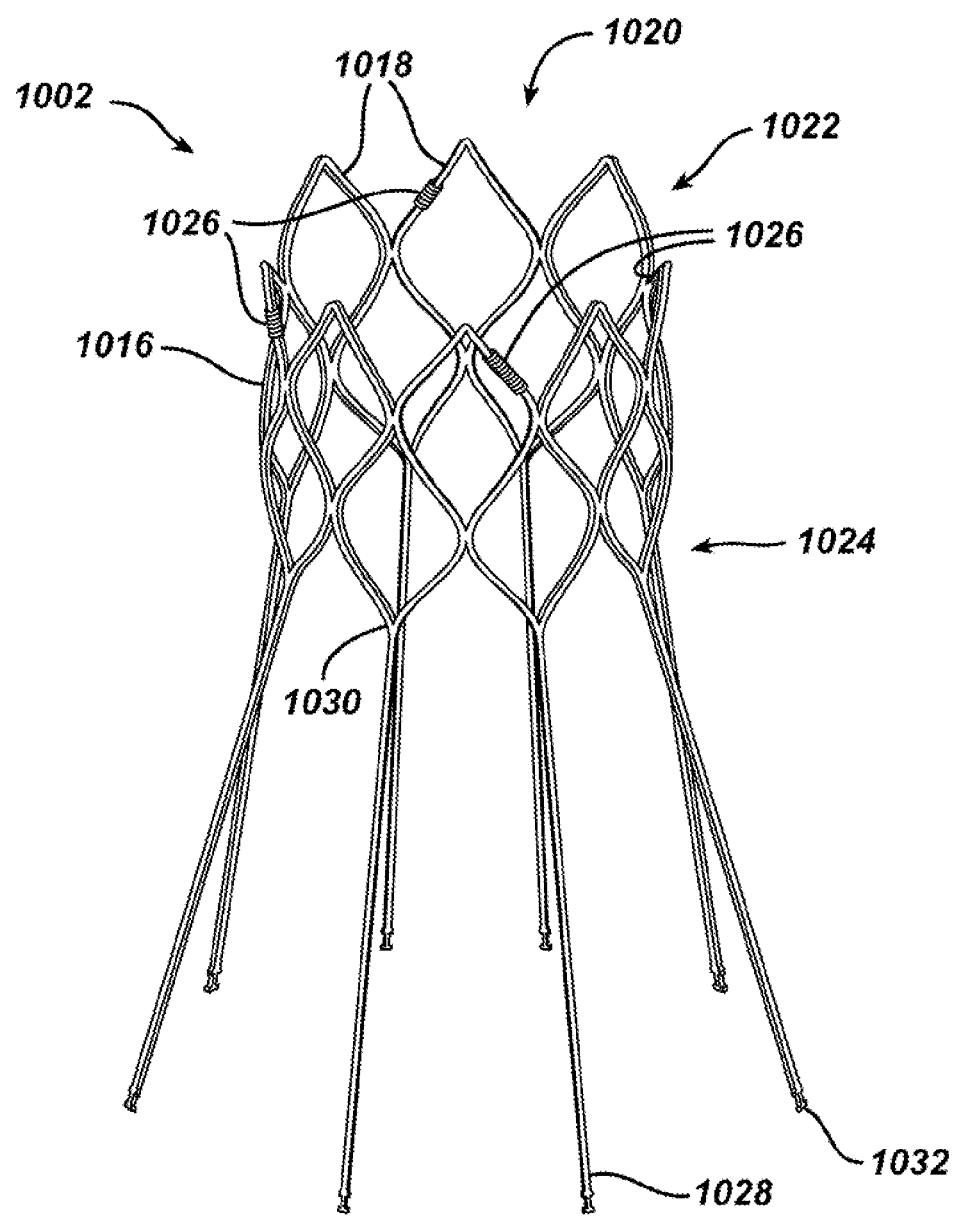
FIG. 28 is a perspective view of a stent for a first prosthesis, shown for clarity in an expanded state, in accordance with the present invention.
Figure 29:
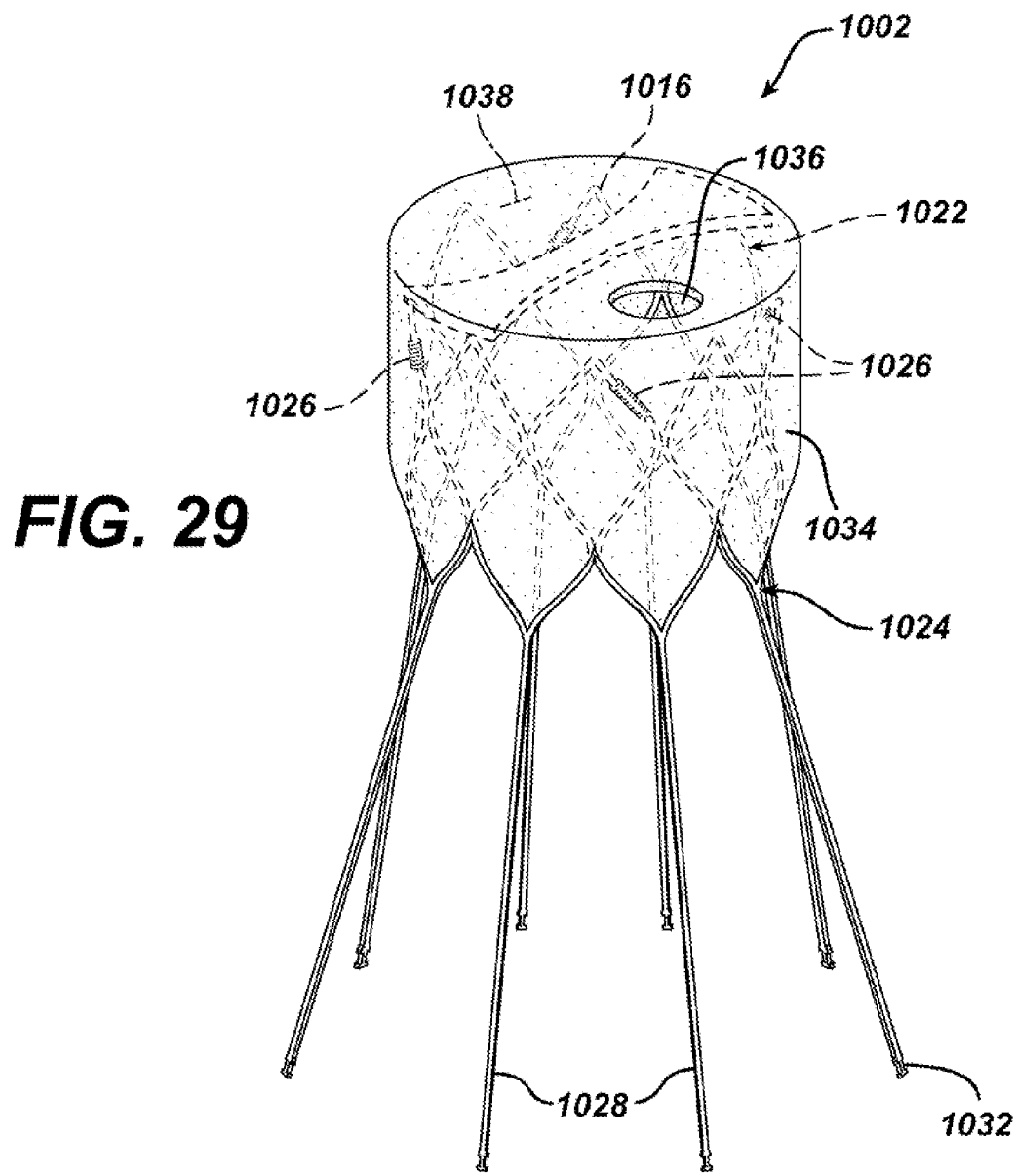
FIG. 29 is a perspective view of a first prosthesis having a stent covered by a gasket material in accordance with the present invention.

FIGS. 27-29 show an exemplary sealing prosthesis of the present invention. Sealing prosthesis 1002 includes a cylindrical or oval self-expanding lattice, support, or stent 1016, typically made from a plurality of interconnected struts 1018. Stent 1016 defines an interior space or lumen 1020 having two open ends, a proximal end 1022 and a distal end 1024. One or more markers 1026 may be optionally disposed in or on the stent between the proximal end 1022 and the distal end 1024.

Stent 1016 may further include at least two but preferably eight (as shown in FIG. 28) spaced apart longitudinal legs 1028. Preferably, there is a leg extending from each apex 1030 of diamonds formed by struts 1018. At least one leg, but preferably each leg, includes a flange 1032 adjacent its distal end which allows for the stent 1016 to be retrievable into its delivery apparatus after partial or nearly full deployment thereof so that it can be turned, or otherwise repositioned for proper alignment.

FIG. 29 shows the sealing material 1034 covering the proximal end 1022 of stent gasket 1002. In the exemplary embodiment shown in FIG. 29, sealing prosthesis 1002 includes a sealing material 1034 having a first opening or hole 1036 and a second opening or slit 1038. The gasket material covers at least a portion of the interior or exterior of the stent, and most preferably covers substantially all of the exterior of the stent. For example, gasket material 1034 may be configured to cover stent 1016 from the proximal end 1022 to the distal end 1024, but preferably not covering longitudinal legs 1028.

The sealing material 1034 helps impede any blood trying to flow around bypass prostheses 1004 and 1006 after they have been deployed (as shown in FIG. 27) and from flowing around the stent gasket 1002 itself. For this embodiment, sealing material 1034 is a compressible member or gasket located along the exterior of the stent 1016 and at least a portion of the interior of the stent 1016.

The second prostheses 1004 and 1006 may comprise stent-grafts such as described with respect to FIG. 24 and may be coated with any of the drugs, agents and/or compounds as described above. In other words, the stent and/or the graft material may be coated with any of the above-described drugs, agents and/or compounds utilizing any of the above-described polymers and processes. The stent gasket 1002 may also be coated with any of the above-described drugs, agents and/or compounds. In other words, the stent and/or sealing material may be coated with any of the above-described drugs, agents and/or compounds utilizing any of the above-described polymers and processes. In particular, rapamycin and heparin may be of importance to prevent smooth muscle cell hyperproliferation and thrombosis. Other drugs, agents and/or compounds may be utilized as well. For example drugs, agents and/or compounds which promote re-endotheliazation may be utilized to facilitate incorporation of the prosthesis into the living organism. Also, embolic material may be incorporated into the stent-graft to reduce the likelihood of endo leaks.

It is important to note that the above-described system for repairing abdominal aortic aneurysms is one example of such a system. Any number of aneurysmal repair systems comprising stent-grafts may be coated with the appropriate drugs, agents and/or compounds, as well as combinations thereof. For example, thoracic aorta aneurysms may be repaired in a similar manner. Regardless of the type of aneurysm or its position within the living organism, the components comprising the repair system may be coated with the appropriate drug, agent and/or compound as described above with respect to stent-grafts.

A difficulty associated with the treatment of aneurysms, specifically abdominal aortic aneurysms, is endoleaks. An endoleak is generally defined as the persistence of blood flow outside of the lumen of the stent-graft, but within the aneurysmal sac or adjacent vascular segment being treated with the stent-graft. Essentially, endoleaks are caused by one of two primary mechanisms, wherein each mechanism has a number of possible modalities. The first mechanism involves the incomplete sealing or exclusion of the aneurysmal sac or vessel segment. The second mechanism involves retrograde flow. In this type of endoleak, blood-flow into the aneurysmal sac is reversed due to retrograde flow from patent collateral vessels, particularly the lumbar arteries or the inferior mesenteric artery. This type of endoleak may occur even when a complete seal has been achieved around the stent-grafts. It is also possible that an endoleak may develop due to stent-graft failure, for example, a tear in the graft fabric.

Endoleaks may be classified by type. A type I endoleak is a perigraft leak at the proximal or distal attachment sites of the stent-grafts. Essentially, this type of endoleak occurs when a persistent perigraft channel of blood flow develops due to an ineffective or inadequate seal at the ends of the stent-graft. There are a number of possible causes of a type I endoleak, including improper sizing of the stent-graft, migration of the stent-graft, incomplete stent-graft expansion and an irregular shape of the arterial lumen. A type II endoleak is persistent collateral blood flow into the aneurysmal sac from a patent branch of the aorta. Essentially, the pressure in the aneurysmal sac is lower than the collateral branches, thereby causing a retrograde blood flow. Sources of type II endoleaks include the accessory renal arteries, the testicular arteries, the lumbar arteries, the middle sacral artery, the inferior mesenteric artery and the spinal artery. A type III endoleak may be caused by a structural failure of the abdominal aortic aneurysm repair system or its components, for example, the stent-grafts. A type III endoleak may also be caused by a junction failure in systems employing modular components. Sources of type III endoleaks include tears, rips or holes in the fabric of the stent-graft, improper sizing of the modular components and limited overlap of the modular components. A type IV endoleak is blood flow through the graft material itself. The blood flow through the pores of the graft material or through small holes in the fabric caused by the staples or sutures attaching the graft material to the stent. Blood flow through the pores typically occurs with highly porous graft fabrics. A type V endoleak or endotension is a persistent or recurrent pressurization of the aneurysmal sac without any radiologically detectable endoleak. Possible causes of a type V endoleak include pressure transmission by thrombus, highly porous graft material, or the adjacent aortic lumen.

There are a number of possible treatment options for each type of endoleak described above. The particular treatment option depends mainly upon the cause of endoleak and the options are not always successful. The present invention is directed to a modification of existing endovascular abdominal aortic aneurysm repair systems or devices, such as the exemplary devices described herein, that is intended to eliminate or substantially reduce the incidence of endoleaks.

The modification comprises coating at least a portion of the various components comprising an abdominal aortic aneurysm repair system with drugs, agents and/or compounds which promote wound healing as described below. For example, portions of the exemplary system 1000, illustrated in FIG. 27, may be coated with one or more drugs, agents and/or compounds that induce or promote the wound healing process, thereby reducing or substantially reducing the risk of endoleaks. It may be particularly advantageous to coat the ends of the two second prostheses 1004 and 1006 and the entire first prosthesis 1002, as these are the most likely regions for endoleaks. However, coating the entire stent-graft, i.e. graft material and stent, may prove beneficial depending upon the type of endoleak. Since it is not always possible to stop endoleaks utilizing currently available methods, the use of wound healing agents, delivered locally, in accordance with the present invention may serve to effectively stop or prevent acute and chronic endoleaks. It is important to note that the present invention may be utilized in combination with any abdominal aortic aneurysm repair system, or with any other type of graft component where leakage is a potential problem. The present invention may be utilized in conjunction with type I, III, IV and V endoleaks.

Normal wound healing essentially occurs in three stages or phases, which have a certain degree of overlap. The first phase is cellular migration and inflammation. This phase lasts for several days. The second phase is the proliferation of fibroblasts for two to four weeks with new collagen synthesis. The third phase is remodeling of the scar and typically lasts from one month to a year. This third phase includes collagen cross linking and active collagen turnover.

As stated above, there are certain drugs, agents and/or compounds that may be delivered locally to the repair site, via the repair system, that promotes wound healing which in turn may eliminate or substantially reduce the incidence of endoleaks. For example, increased collagen production early in wound healing leads to greater wound strength. Accordingly, collagen may be combined with the repair system to increase wound strength and promote platelet aggregation and fibrin formation. In addition, certain growth factors may be combined with the repair system to promote platelet aggregation and fibrin formation as well as to increase wound strength.

Platelet-derived Growth Factor induces mitoses and is the major mitogen in serum for growth in connective tissue. Platelet Factor 4 is a platelet released protein that promotes blood clotting by neutralizing heparin. Platelet-derived Growth Factor and Platelet Factor 4 are important in inflammation and repair. They are active for human monocytes, neutrophils, smooth muscle cells, fibroblasts and inflammation cells. Transforming Growth Factor-β is a part of a complex family of polypeptide hormones or biological factors that are produced by the body to control growth, division and maturation of blood cells by the bone marrow. Transforming Growth Factor-β is found in tissues and platelets, and is known to stimulate total protein, collagen and DNA content in wound chambers implanted in vivo. Transforming Growth Factor-β in combination with collagen has been shown to be extremely effective in wound healing.

A series of reactions take place in the body whenever a blood clot begins to form. A major initiator of these reactions is an enzyme system called the Tissue Factor/VIIa complex. Accordingly, Tissue Factor/VIIa may be utilized to promote blood clot formation and thus enhance wound healing. Other agents which are known to initiate thrombus formation include thrombin, fibrin, plasminogin-activator initiator, adenosine diphosphate and collagen.

The use of these drugs, agents and/or compounds in conjunction with the various components of the repair system may be used to eliminate or substantially reduce the incidence of endoleaks through the formation of blood clots and wound healing.

The stent and/or graft material comprising the components of the system 1000 may be coated with any of the above-described drugs, agents and/or compounds. The above-described drugs, agents and/or compounds may be affixed to a portion of the components or to all of the components utilizing any of the materials and processes described above. For example, the drugs, agents and/or compounds may be incorporated into a polymeric matrix or affixed directly to various portions of the components of the system.

The particular polymer(s) utilized depends on the particular material upon which it is affixed. In addition, the particular drug, agent and/or compound may also affect the selection of polymer(s).

As described above, other implantable medical devices that may be coated with various drugs, agents and/or compounds include surgical staples and sutures. These medical devices may be coated with any of the above-described drugs, agents and/or compounds to treat various conditions and/or to minimize or substantially eliminate the organisms' reaction to the implantation of the device.

Figure 30:
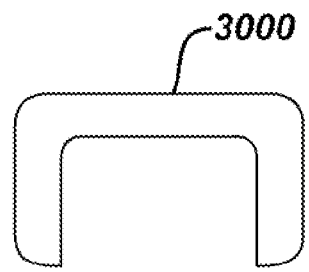
FIG. 30 is a diagrammatic representation of an uncoated surgical staple in accordance with the present invention.
Figure 31:
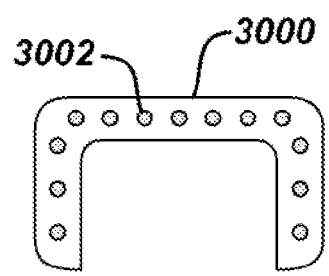
FIG. 31 is a diagrammatic representation of a surgical staple having a multiplicity of through-holes in accordance with the present invention.

FIG. 30 illustrates an uncoated or bare surgical staple 3000. The staple 3000 may be formed from any suitable biocompatible material having the requisite strength requirements for a given application. Generally, surgical staples comprise stainless steel. FIG. 31 illustrates an exemplary embodiment of a surgical staple 3000 comprising a multiplicity of through-holes 3002, which preferably contain one or more drugs, agents and/or compounds as described above. The one or more drugs, agents and/or compounds may be injected into the through-holes 3002 with or without a polymeric mixture. For example, in one exemplary embodiment, the through-holes 3002 may be sized such that the one or more drugs, agents and/or compounds may be injected directly therein and elute at a specific rate based upon the size of the through-holes 3002. In another exemplary embodiment, the one or more drugs, agents and/or compounds may be mixed with the appropriate polymer, which controls the elution rate, and injected into or loaded into the through-holes 3002. In yet another alternate exemplary embodiment, the one or more drugs, agents and/or compounds may be injected into or loaded into the though-holes 3002 and then covered with a polymer to control the elution rate.

Figure 32:
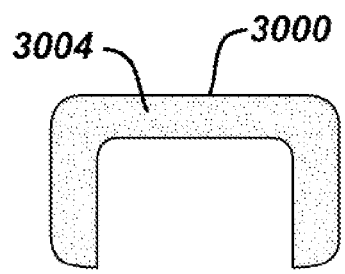
FIG. 32 is a diagrammatic representation of a surgical staple having a coating on the outer surface thereof in accordance with the present invention.

FIG. 32 illustrates an exemplary embodiment of a surgical staple 3000 comprising a coating 3006 covering substantially the entire surface thereof. In this embodiment, the one or more drugs, agents and/or compounds may be directly affixed to the staple 3000 utilizing any number of known techniques including spraying or dipping, or the one or more drugs, agents and/or compounds may be mixed with or incorporated into a polymeric matrix and then affixed to the staple 3000. Alternately, the one or more drugs, agents and/or compounds may be directly affixed to the surface of the staple 3000 and then a diffusion barrier may be applied over the layer of one or more drugs, agents and/or compounds.

Although any number of drugs, agents and/or compounds may be used in conjunction with the surgical staple 3000 to treat a variety of conditions and/or to minimize or substantially eliminate the organisms' reaction to the implantation of the staple 3000, in a preferred embodiment, the surgical staple 3000 is coated with an anti-proliferative. The advantage of such a device is that the anti-proliferative coating would function as a prophylactic defense against neo-intimal hyperplasia. As described above, neo-intimal hyperplasia often happens at the site of what the body perceives to be injuries, for example, anastomatic sites, either tissue to tissue or tissue to implant, which are often sites of hyperplastic events. By utilizing a staple that comprises an anti-proliferative agent, the incidence of neo-intimal hyperplasia may be substantially reduced or eliminated.

Rapamycin is a known anti-proliferative that may be utilized on or in the surgical staple 3000 and may be incorporated into any of the above-described polymeric materials. An additional benefit of utilizing rapamycin is its action as an anti-inflammatory. The dual action not only functions to reduce neo-intimal hyperplasia but inflammation as well. As used herein, rapamycin includes rapamycin, sirolimus, everolimus and all analogs, derivatives and conjugates that bind FKBP12, and other immunophilins and possesses the same pharmacologic properties as rapamycin including inhibition of MTOR.

In yet another alternate exemplary embodiment, the surgical staple 3000 may be fabricated from a material, such as a polymeric material, which incorporates the one or more drugs, agents, and/or compounds. Regardless of the particular embodiment, the elution rate of the one or more drugs, agents and/or compounds may be controlled as described above.

Figure 33:
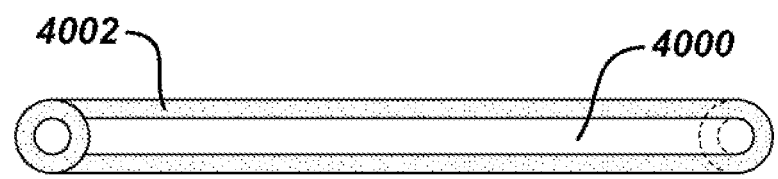
FIG. 33 is a diagrammatic representation of a section of suture material having a coating thereon in accordance with the present invention.

Referring now to FIG. 33, there is illustrated a section of suture material 4000. The suture 4000 may comprise any suitable material commonly utilized in the fabrication of both absorbable or non-absorbable sutures. As illustrated, the suture 4000 comprises a coating 4002 of one or more drugs, agents and/or compounds. As in the coating on the surgical staple 3000, the one or more drugs, agents and/or compounds may be applied directly to the suture 4000 or it may be mixed or incorporated into a polymeric matrix and then affixed to the suture 4000. Also as described above, the one or more drugs, agents and/or compounds may be affixed to the suture 4000 and then a diffusion barrier or top coating may be affixed to the one or more drugs, agents and/or compounds to control the elution or release rate.

Figure 34:
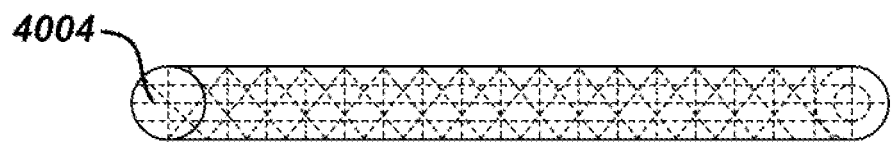
FIG. 34 is a diagrammatic representation of a section of suture material having a coating impregnated into the surface thereof in accordance with the present invention.

FIG. 34 illustrates a section of suture material 4000 impregnated with one or more drugs, agents and/or compounds 4004. The one or more drugs, agents, and/or compounds may be directly impregnated into the suture material 4000, incorporated into a polymeric matrix and then impregnated into the suture material 4000. Alternately, the one or more drugs, agents and/or compounds may be impregnated into the suture material 4000 and then covered with a polymeric material.

In yet another alternate exemplary embodiment, the suture 4000 may be formed from a material, for example, a polymeric material that incorporates the one or more drugs, agents and/or compounds. For example, the one or more drugs, agents, and/or compounds may be mixed within the polymer matrix and then extruded and/or formed by a dip method to form the suture material.

The particular polymer(s) utilized depend on the particular material upon which it is affixed. In addition, the particular drug, agent, and/or compound may also affect the selection of polymers. Rapamycin may be utilized with poly(vinylidenefluoride)/hexafluoropropylene.

The introduction of medical devices into a living organism, and more particularly into the vasculature of a living organism, provokes a response by the living organism. Typically the benefit provided by the medical device far exceeds any complications associated with the living organism's response. Endothelialization is one preferable manner or means for making devices fabricated from synthetic materials more blood compatible. The endothelium is a single layer of endothelial cells that forms the lining of all blood vessels. The endothelium regulates exchanges between blood and surrounding tissues and is surrounded by a basal lamina, i.e. extracellular matrix that separates epithelia layers and other cell types, including fat and muscle cells from connective tissue.

Endothelial cells cover or line the inner surface of the entire vascular system, including the heart, arteries, veins, capillaries and everything in between. Endothelial cells control the passage of materials and the transit of white blood cells into and out of the blood stream. While the larger blood vessels comprise multiple layers of different tissues, the smallest blood vessels consist essentially of endothelial cells and a basal lamina. Endothelial cells have a high capacity to modify or adjust their numbers and arrangement to suit local requirements. Essentially, if it were not for endothelial cells multiplying and remodeling, the network of blood vessel/tissue growth and repair would be impossible.

Even in an adult living organism, endothelial cells throughout the vascular system retain a capacity for cell division and movement. For example, if one portion of a vein or artery is missing endothelial cells through damage or disease, neighboring endothelial cells proliferate and migrate to the affected area in order to cover the exposed surface. Endothelial cells not only repair areas of missing endothelial cells, they are capable of creating new blood vessels. In addition, and directly related to the present invention, newly formed endothelial cells will cover implantable medical devices, including stents and other similar devices.

As stated above, endothelialization is a means for making devices fabricated from synthetic materials more blood compatible and thus more acceptable to the living organism. For the introduction of certain medical devices anywhere in the vasculature, one goal is the reduction of the thrombogenicity of the medical device. This is device specific, for example, certain medical devices would require thrombus formation for healing and fixation. Therefore, the endothelialization of these specific medical devices is preferable. The source of autologous endothelial cells is crucial and thus an amplification step is preferable to obtain enough cells to cover the entire exposed surface of the medical device regardless of the complexity of design of the medical device. Accordingly, it would be preferable to coat the medical device or provide some localized means for the introduction of a chemical, agent, drug, compound and/or biological element for the promotion or proliferation of endothelial cells at the site of the implant.

In accordance with one exemplary embodiment, implantable intraluminal medical devices, such as stents, may be affixed with, in any of the above described manners, with vascular endothelial growth factor, VEGF, which acts selectively on endothelial cells. Vascular endothelial growth factor and its various related isoforms may be affixed directly to any of the medical devices illustrated and described herein by any of the means described herein. For example, VEGF may be incorporated into a polymeric matrix or affixed directly to the medical device.

Other factors that promote the stimulation of endothelial cells include members of the fibroblast growth factor family. Various agents that accelerate cellular migration may increase endothelialization, including agents that upregulate integrins. Nitric oxide may promote endothelialization. In addition, pro-angiogenic agents may stimulate endothelialization.

Alternately, the medical device may be fabricated from a material which by its physical material characteristics promotes the migration of endothelial towards the device. Essentially, since the living organism creates endothelial cells, any material or coating that attracts endothelial cells would be preferable.

It is generally known in the art that the application of a topcoat of a biocompatible material, for example, a polymer, may be utilized to control the elution of a therapeutic dosage of a pharmaceutical drug, agent and/or compound, or combinations thereof, from a medical device base coating, for example, a stent base coating. The basecoat generally comprises a matrix of one or more drugs, agents and/or compounds and a biocompatible material such as a polymer. The control over elution results from either a physical barrier, a chemical barrier, or a combination physical and chemical barrier supplied by the topcoat material. When the topcoat material acts as a physical barrier, the elution is controlled by varying the thickness of the topcoat, thereby changing the diffusion path length for the drugs, agents and/or compounds to diffuse out of the basecoat matrix. Essentially, the drugs, agents and/or compounds in the basecoat matrix diffuse through the interstitial spaces in the topcoat. Accordingly, the thicker the topcoat, the longer the diffusion path, and conversely, the thinner the topcoat, the shorter the diffusion path. It is important to note that both the basecoat and the topcoat thickness may be limited by the desired overall profile of the medical device. For action as a chemical barrier, the topcoat preferably comprises a material that is less compatible with the drugs, agents and/or compounds to substantially prevent or slow the diffusion, or is less compatible with the basecoat matrix to provide a chemical barrier the drugs, agents and/or compounds must cross prior to being released. It is important to note that the concentration of the drugs, agents and/or compounds may affect diffusion rate; however, the concentration of the drugs, agents and/or compounds is dictated to a certain extent by the required therapeutic dosage as described herein.

In one exemplary embodiment, a medical device such as a stent, may utilize a polymeric material that acts primarily as a chemical barrier for the control of elution of rapamycin from the stent. As used herein, rapamycin includes rapamycin, sirolimus, everolimus and all analogs, derivatives and conjugates that bind FKBP12, and other immunophilins and possesses the same pharmacologic properties as rapamycin including inhibition of mTOR. In this exemplary embodiment, the coating comprises a basecoat drug, agent and/or compound and polymer matrix with a topcoat that includes only a polymer. The topcoat polymer and the basecoat polymer are immiscible or incompatible, thereby creating the chemical barrier. Comparisons, however, are made with basecoat and topcoats comprising the exact same polymers or with polymers containing the same constituents in different ratios. Although the primary control mechanism is the chemical barrier, the topcoat also provides a limited physical barrier, as will be described subsequently.

In this exemplary embodiment, the basecoat may comprise any suitable fluoropolymer and the topcoat may comprise any suitable acrylate or methacrylate. In preferred embodiments, the basecoat drugs, agent and/or compound/polymer matrix comprises the copolymer polyvinylidenefluoride-co-hexafluoropropylene (PVDF/HFP) as described above in detail. The copolymers utilized in this exemplary basecoat embodiment comprises vinylidenefluoride copolymerized with hexafluoropropylene in the weight ratio of sixty weight percent vinyldenefluoride to forty weight percent hexafluoropropylene. The topcoat polymer may, as described above, comprise any suitable acrylate or methacrylate. In the preferred embodiment, the topcoat polymer comprises poly(n-butylmethacrylate) or BMA.

PVDF/HFP and BMA are immiscible or incompatible polymers that when mixed and precipitated from solution utilizing known techniques will undergo phase separation. It is this incompatibility that allows a topcoat of an acrylic polymer to act as both a chemical barrier (primary mechanism) and physical barrier (secondary mechanism) to the release of a drug, agent and/or compound, such as rapamycin, from the basecoat matrix.

The combination of a PVDF/HFP basecoat and a BMA topcoat offers a number advantages over other combinations, including increased durability, increased lubriciousness and increased elution rate control. PVDF/HFP is a flexible polymer. Flexible polymers result in more durable medical device coatings as they tend to move or give as the stent or other device undergoes deformations. Poly(n-butylmethacrylate) or BMA is a more thermoplastic polymer rather than a more elastomeric polymer, and therefore more rigid than PVDF/HFP. A more rigid polymer equates to a harder surface and a harder surface is a more lubricious surface. The lubriciousness of the polymer topcoat is important during device delivery and deployment as described in detail herein. A lubricious coating is particularly advantageous in the delivery of self-expanding stents which typically require the retraction of a delivery sheath. If the coating were not lubricious, the retraction of the delivery sheath may remove a position of the coating, including the drugs, agents and/or compounds contained therein. Lubricious coatings are also advantageous for balloon expandable stents where stent/balloon separation during deployment may also remove coating. Acrylic polymers utilized in conjunction with fluoropolymers are excellent chemical and physical barriers as described above and thus provide increase elution rate control.

Although the coatings in this exemplary embodiment may be utilized on any number of implantable medical devices as described herein, the exemplary coating embodiments described below are utilized in conjunction with nickel-titanium self-expanding stents.

Figure 49:
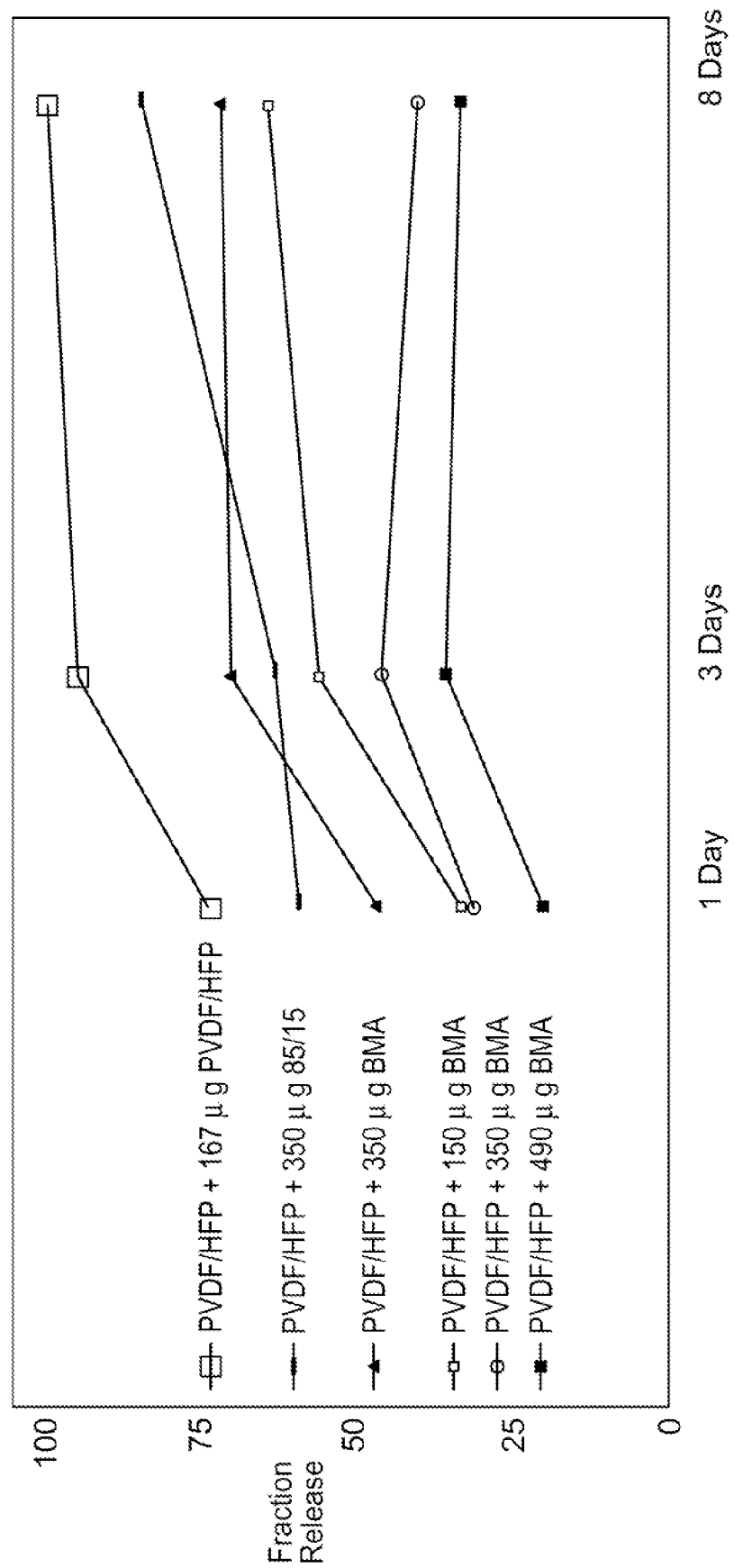
FIG. 49 indicates the fraction or percentage of rapamycin released over time from various polymeric coatings during in vivo testing in accordance with the present invention.

Referring now to FIG. 49, there is illustrated in vivo drug release curves for a number of fluoropolymer/fluoropolymer and fluoropolymer/acrylic coating formulations. The in vivo procedure involved evaluating the elution characteristics of rapamycin eluting stents with a number of polymer coating formulations for both the basecoat and the topcoat. Pigs are an established animal species for intravascular stent studies and accepted for such studies by the appropriate regulatory agencies. This in vivo study utilized male pigs of the species Sus Scrofa and strain Yoorkshire pigs. S.M.A.R.T.™ stents, available from Cordis Corporation, were placed into the iliac and femoral arteries, PALMAZ® GENESIS™ stents, available from Cordis Corporation, were placed in the renal arteries and CYPHER™ stents, available from Cordis Corporation, were placed in the coronary arteries. Once third of the pigs were euthanized on each of days 2, 4 and 8 and the stents and surrounding vessels were explanted and analyzed for drug content.

The data presented in FIG. 49 represents the release of rapamycin in vivo from coated S.M.A.R.T.™ stents, which as described herein, are nickel-titanium stents twenty millimeters in length. The ratio by weight of rapamycin to polymer is thirty/seventy for each PVDF/HFP basecoat and thirty-three/sixty-seven for the polyethylene-co-vinylacetate/poly(n-butylmethacrylate) (EVA/BMA) basecoat. Curve 4902 represents the elution release rate for a stent coated with a PVDF/HFP (sixty/forty weight ratio of VDF:HFP) and rapamycin basecoat with a one hundred sixty-seven microgram PVDF/HFP (sixty/forty weight ratio of VDF:HFP) topcoat. Curve 4904 represents the elution release rate for a stent coated with a PVDF/HFP (sixty/forty weight ratio of VDF:HFP) and rapamycin basecoat with a three hundred fifty microgram PVDF/HFP (eighty-five/fifteen weight ratio of VDF:HFP) topcoat. Curve 4906 represents the elution release rate for a stent coated with an EVA/BMA and rapamycin basecoat (thirty-three percent EVA, thirty-three percent BMA and thirty-three percent rapamycin) with a three hundred fifty microgram BMA topcoat. Curve 4908 represents the elution release rate for a stent coated with a PVDF/HFP (sixty/forty weight ratio of VDF:HFP) and rapamycin basecoat with a one hundred fifty microgram BMA topcoat. Curve 4910 represents the elution release rate for a stent coated with a PVDF/HFP (sixty/forty weight ratio of VDF:HFP) and rapamycin basecoat with a three-hundred fifty microgram BMA topcoat. Curve 4912 represents the elution release rate for a stent coated with a PVDF/HFP (sixty/forty weight ratio of VDF:HFP) and rapamycin basecoat with a four hundred ninety microgram BMA topcoat.

The data represented in FIG. 49 provides an understanding of the elution rate of rapamycin from various coating combinations. A PVDF/HFP basecoat with a PVDF/HFP topcoat provides a minor physical barrier to drug elution, and a minimal chemical barrier because the basecoat and topcoat are chemically identical. A topcoat of BMA on a basecoat of EVA/BMA provides a physical barrier because of the compatibility between the EVA/BMA drug matrix and the BMA topcoat chemistries. The BMA topcoat provides a slightly more effective barrier to elution because of the difference in basecoat matrix (EVA/BMA) and topcoat (BMA only) chemistries. The most substantial barrier to the elution of rapamycin, however, is observed with a PVDF/HFP basecoat matrix and a BMA topcoat because of the chemical barrier that results from the incompatible polymer chemistries. Even within the chemical barrier, however, changes in the topcoat thickness or density, still provide additional levels of physical barriers to drug elution, resulting in a coating system that provides both a chemical and a physical barrier to control release of a pharmaceutical compound as indicated in curves 4908, 4910 and 4912.

The idea of utilizing incompatible polymer chemistries in conjunction with varying the thickness of the topcoat in accordance with the present invention takes advantage of what may normally be viewed as a negative aspect of chemical incompatibility to achieve a desired effect. As indicated in curve 4912, the peak elution release at three days is substantially less than fifty percent, whereas the peak elution release at three days for a PVDF/HFP basecoat and a PVDF/HFP topcoat is substantially greater than seventy-five percent as indicated in curve 4902.

Although demonstrated here with specific examples of a PVDF/HFP (sixty-forty weight ratio of VDF:HFP) copolymer and a BMA polymer, the concept would apply to any polymer in the family of fluoropolymers in combination with any polymer in the family of acrylics (poly(alkyl) acrylate and poly(alkyl)meth)acrylate).

Figure 50:
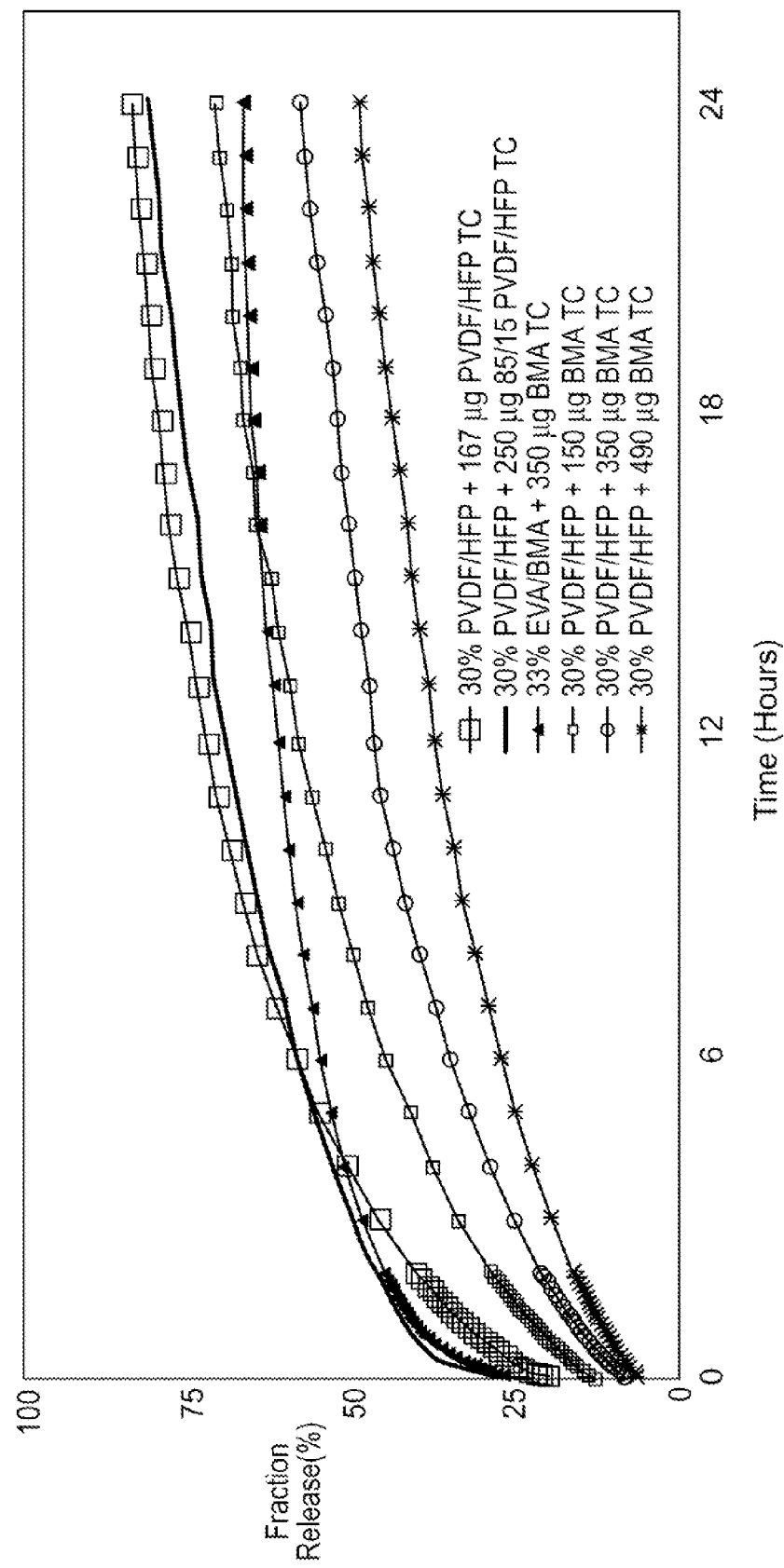
FIG. 50 indicates the fraction or percentage of rapamycin released over time from various polymeric coatings during in vitro testing in accordance with the present invention.

Referring to FIG. 50, there is illustrated in vitro drug release curves for the same fluoropolymer/acrylic coating formulations described above with respect to FIG. 49. In in vitro testing procedures, the stents are exposed to continuous flow of a surfactant media for a period of twenty-four hours. The exposure of the media causes elution of the drug, agent and/or compound (rapamycin in this instance) from the stents. The flow of media is directed through an ultraviolet/visible spectrophotometer, and the concentration of rapamycin eluting from the stent is determined as a function of time. Calculations are made based on the fraction of rapamycin released compared to the total drug content, as determined from a drug content assay on stents from the same lot.

The results from the in vitro testing are similar to the results from the in vivo testing. Essentially, a review of 5002, 5004, 5006, 5008, 5010 and 5012 indicate that once again, the most substantial barrier to the elution of rapamycin is observed with a PVDF/HFP basecoat matrix and a BMA topcoat because of the chemical barrier that results from the incompatible polymer chemistries and the physical barrier provided by the thicker topcoat as shown by curve 5012.

It is also interesting to note that a stent coated with a PVDF/HFP (sixty/forty weight ratio of VDF:HFP) basecoat matrix and a BMA topcoat is more durable than a stent coated with a PVDF/HFP (sixty/forty weight ratio of VDF: HFP) basecoat matrix and a PVDF/HFP (sixty/forty weight ratio of VDF:HFP) topcoat.

The design of a coated implantable medical device that elutes a therapeutic drug, agent and/or compound requires the balancing of a number of design factors. For example, the addition of a coating to an implantable medical device alters the profile of the device which in turn may have an impact on device delivery. More specifically, the addition of a coating on a stent increases the diameter of the stent, which in turn may make delivery more difficult. Accordingly, it may be preferable to minimize the thickness of the coating while increasing the concentration of the therapeutic drug, agent and/or compound. Increasing the concentration of the therapeutic drug, agent and/or compound may increase its elution rate into the surrounding tissue or bloodstream. Increasing the elution rate may in turn deplete the drug, agent and/or compound prematurely. Therefore, the present invention provides a mechanism whereby drug, agent and/or compound concentrations may be increased while maintaining control over the elution rate and maintaining a lower profile. Essentially, the chemical and physical barrier provided by the topcoat in the two layer approach provides a means for increasing drug, agent and/or compound concentrations, if preferable, maintaining a lower profile, if preferable, and maintaining more precise control over elution rates.

In addition, it is important to emphasize the multiple layers; multiple polymer approach offers the advantages of durability, flexibility and lubriciousness that a single layer approach may not be able to provide.

Vascular diseases include diseases that affect areas containing blood vessels. For example, stenosis is a narrowing or constricting of arterial lumen in a living organism (e.g., a human) usually due to atherosclerosis/coronary heart disease (CHD). Restenosis is a recurrence of stenosis after a percutaneous intervention such as angioplasty and stenting. The underlying mechanisms of restenosis comprise a combination of effects from vessel recoil, negative vascular remodeling, thrombus formation and neointimal hyperplasia. It has been shown that restenosis after balloon angioplasty is mainly due to vessel remodeling and neointimal hyperplasia and after stenting is mainly due to neo-intimal hyperplasia.

Treatment for stenosis and restenosis varies. Stenosis caused by CHD often affects quality of life and can lead to stroke, heart attack, sudden death and loss of limbs or function of a limb stemming from the stenosis. The recanalization of blood vessels may also be needed to treat individuals suffering from stenosis and restenosis. Coronary bypass can be utilized to revascularize the heart and restore normal blood flow. In other cases, balloon angioplasty may be conducted to increase the lumen size of affected areas. Overall, these treatments address the problems associated with stenosis, but they can also create the problem of restenosis that can result in recurrence of cardiac symptoms and mortality. Moreover, these treatments are not curative in nature, and therefore generally are not utilized until significant disease progression has occurred.

One type of stenosis is atherosclerosis. Atherosclerosis affects medium and large arteries and is characterized by a patchy, intramural thickening that encroaches on the arterial lumen and, in most severe form, causes obstruction. The atherosclerotic plaque consists of an accumulation of intracellular and extracellular lipids, smooth muscle cells and connective tissue matrix. The earliest lesion of atherosclerosis is the fatty streak that evolves into a fibrous plaque coating the artery. Atherosclerotic vessels have reduced systolic expansion and abnormal wave propagation. Treatment of atherosclerosis is usually directed at its complications, for example, arrhythmia, heart failure, kidney failure, stroke, and peripheral arterial occlusion.

More particularly, atherosclerosis is a thickening and hardening of the arteries and is generally believed to be caused by the progressive buildup of fatty substances, for example, cholesterol, cellular debris, inflammatory cells, calcium and other substances in the inner lining or intima of the arteries. The buildup of these substances may in turn stimulate cells in the walls of the affected arteries to produce additional substances that result in the further recruitment of cells.

Atherosclerosis is a slow, complex disease process that typically starts in childhood and progresses as the individual ages. The rate of progression may be affected by a number of factors, including blood cholesterol levels, diabetes, obesity, physical inactivity, high blood pressure and tobacco use. This buildup in commonly referred to as plaque and may grow large enough to significantly reduce blood flow through the affected arteries.

Essentially, the deposits of the various substances set forth above, and the proliferation of additional cellular substances or constituents caused thereby, substantially enlarge the intima, which in turn reduces luminal cross-sectional area of the affected arteries, which in turn reduces the oxygen supply to one or more organs. The deposits or plaque may also rupture and form thrombi that can completely obstruct blood flow in the affected artery or break free and embolize in another part of the body. If either of these events occurs, the individual may suffer a myocardial infarction if the artery affected perfuses the heart or a stroke if the artery affected supplies blood to the brain. If the artery affected supplies blood to a limb or appendage, gangrene may result.

Conventional wisdom holds that myocardial infarction originates from severe blockages created by atherosclerosis. Increase deposition of lipids in the arteries and ensuing tissue reaction leads to a narrowing of the affected artery or arteries, which in turn, can result in angina and eventual coronary occlusion, sudden cardiac death or thrombotic stroke. More recent research, however, is leading to a shift in understanding atherosclerosis. Researchers now believe that at least some coronary artery disease is an inflammatory process, in which inflammation causes plaque buildup or progression and rupture. These plaques which are prone to rupture, commonly referred to as vulnerable plaques, do not obstruct flow in the affected artery or arteries per se, but rather, much like an abscess, they may be ingrained in the arterial wall so that they are difficult to detect. Essentially, these vulnerable plaques cannot be seen by conventional angiography and/or fluoroscopy, and they do not typically cause symptoms of ischemia. Techniques for determining the presence of vulnerable plaques are, however, improving as discussed subsequently.

For a variety of reasons, these so-called vulnerable plaques are more likely to erode or rupture, creating emboli and exposed tissue surfaces that are highly thrombogenic. Accordingly, it is now accepted that the majority of cases of acute myocardial infarction, sudden cardiac death and thrombotic stroke result from the disruption of vulnerable atherosclerotic plaques leading to thrombosis. Therefore, these vulnerable plaques are more life-threatening than other plaques and may be responsible for as much as sixty to eighty percent of all myocardial infarctions.

More specifically, unstable or vulnerable plaques are inflammatory vascular lesions that develop in atherosclerotic blood vessels. Vulnerable plaques are characterized by active inflammation, cellular hyperplasia and variable degrees of lumen obstruction. Morphologically, vulnerable plaques comprise a fibrous cap in contact with the lumen of the vessel overlying a core of lipid and cellular material. Vulnerable plaque lesions are not typically obstructive, in contrast to chronic stable plaques that produce ischemic symptoms. For that reason, they are not easily detected.

The hallmark of vulnerable plaques is active inflammation with significant inflammatory cell infiltration, predominantly T-lymphocytes and macrophage, causing the generation of proteolytic enzymes that essentially digest the wall of the fibrous cap thereby inducing plaque instability and eventually plaque rupture. Plaque rupture exposes highly thrombogenic material in the lipid core to flowing blood leading to the rapid development of occlusive thrombi. Ruptured vulnerable plaque, as stated above, is the primary cause of acute coronary and cerebral syndromes. These include unstable angina, myocardial infarction, both Q-wave and non-Q-wave myocardial infarction, cerebral stroke and transient cerebral ischemia. In other words, ruptured vulnerable plaque accounts for a significant percentage of cardiovascular morbidity and mortality.

Given the lack of currently available effective technologies for detecting vulnerable plaque, the treatment of vulnerable plaque is typically initiated only after the plaque has ruptured and clinical symptoms have developed. Detection technologies currently under investigation include refined magnetic resonance imaging, thermal sensors that measure the temperature of the arterial wall on the premise that the inflammatory process generates heat, elasticity sensors, intravascular ultrasound, optical coherence tomography, contrast agents, and near-infrared and infrared light. As better diagnostic methods evolve to identify vulnerable plaque lesions before they rupture, it becomes possible to treat discrete lesions before dangerous clinical symptoms occur. The treatment of vulnerable plaque, however, is preferably as described below.

There are two fundamental physiologic processes ongoing in active vulnerable plaque, inflammation and lipid accumulation and metabolism. Inflammation is an ongoing process which includes the inflammation of the fibrous cap and creating a cap vulnerable to rupture. Lipid metabolism is the formation of an active lipid pool or core comprising a pliable, cholesterolemic lipid material susceptible to rupture. The inflammation process is the acute phase and the lipid metabolism is the chronic phase of vulnerable plaque disease.

A stent or other scaffold structure designed to maintain vessel patency and comprising a multilaminate coating architecture that includes one or more therapeutic agents, drugs, and/or compounds for treating both the inflammation and lipid metabolism processes, may be utilized to effectively treat vulnerable plaques. In one exemplary embodiment, a stent comprising a coating having a two tier release profile may be utilized to treat both the acute and chronic phases of vulnerable plaque. For example, anti-inflammatory therapeutic agents, such as corticosteroids, non-steroidal anti-inflammatories, acetylsalicyclic acid, acetaminophen and ibuprofen may be incorporated into the coating architecture for "fast release" and shorter overall duration to address the acute phase of vulnerable plaque disease and lipid lowering or lipid modifying agents may be incorporated into the coating architecture for "slow release" and longer overall duration to address the chronic phase of vulnerable plaque disease. The stent/drug architecture may utilize a variety of non-resorbable or resorbable polymers to control, modulate and/or optimize the delivery profile for optimal physiologic effect. In other words, specific therapeutic drugs and/or compound delivery profiles may be utilized in conjunction with the stent to treat all aspects of vulnerable plaques, for example, fast release anti-inflammatory drugs, agents and/or compounds to address the inflammatory rupture of the fibrous cap and slow release lipid lowering or lipid modifying drugs, agents and/or compounds to affect the size and composition of the vulnerable plaque lipid pool.

The stent may comprise any suitable scaffold structure, including balloon expandable stents, constructed from stainless steel or other metal alloys, and/or self-expanding stents, constructed from nitinol or other shape memory metal alloys. Alternately, the stent may be made from non-metallic materials, such as ceramics and/or polymers, which may be biodegradable. The biodegradable stent would serve as a temporary scaffold and eventually dissolve over a period of time raging from days or weeks to months and years. The stent would be mounted on a delivery catheter and delivered percutaneously through the lumen of a blood vessel to the site of the vulnerable plaque lesion as described in detail above with respect to treating restenosis. The stent, as described above, is designed to maintain vessel patency and also provide structural support to the weakened or potentially weakened fibrous cap and prevent it from rupturing. The stent also provides a means for preventing further encroachment by the lesion.

Recent research has uncovered that different sex hormones may have different effects on vascular function. For example, gender differences in cardiovascular disease have largely been attributed to the protective effects of estrogen in women; premenopausal women have a lower incidence of Coronary Heart Disease. In particular, estrogen has well-known beneficial effects on lipid profile. More importantly, estrogen may directly affect vascular reactivity, which is an important component of atherosclerosis. Recent epidemiological studies suggest that hormone replacement therapy (HRT) may reduce the risk of coronary-artery disease in post-menopausal women. More particularly, many epidemiological studies suggest that estrogen replacement therapy (ERT) may be cardioprotective in postmenopausal women. The beneficial effects of these hormone therapies may also be applicable to males. Unfortunately the systemic use of estrogen has limitations due to the possible hyperplastic effects of estrogen on the uterus and breast in women, and the feminizing effects in males.

The mechanisms for these beneficial effects are probably multifactorial. Estrogen is known to favorably alter the atherogenic lipid profile and may also have a direct action on blood vessel walls. Estrogen can have both rapid and long-term effects on the vasculature including the local production of coagulation and fibrinolytic factors, antioxidants and the production of other vasoactive molecules, such as nitric oxide and prostaglandins, all of which are known to influence the development of vascular disease.

Experimental work suggests that estrogen can also act on the endothelium and smooth muscle cells either directly or via estrogen receptors in both men and women. This appears to have an inhibitory effect on many steps in the atherosclerotic process. With respect to the interventional cardiology, estrogen appears to inhibit the response to balloon injury to the vascular wall. Estrogen can repair and accelerate endothelial cell growth in-vitro and in-vivo. Early restoration of endothelial cell integrity may contribute to the attenuation of the response to injury by increasing the availability of nitric oxide. This in turn can directly inhibit the proliferation of smooth muscle cells. In experimental studies, estrogen has been shown to inhibit the proliferation and migration of smooth muscle cells in response to balloon injury. Estrogen has also proved to inhibit adventitial fibroblast migration, which may in turn have an effect on negative remodeling.

Accordingly, in addition to the drugs described herein, the local or regional administration of an estrogen, a rapamycin and/or a combination thereof may be utilized in the treatment or stabilization of vulnerable plaque lesions. Estrogen as utilized herein shall include 17 beta-estradiol (chemically described as 1,3,5(10)-estradien-3, 17 beta-diol having the chemical notation $C_{18}H_{24}O_2$), synthetic or natural analogs or derivatives of 17 beta-estradiol with estrogenic activity, or biologically active metabolites of 17 beta-estradiol, such as 2 methoxy estradiol. 17 beta-estradiol is a natural estrogen produced in the body itself. Accordingly, there should be no biocompatibility issues when 17 beta-estradiol is administered locally, regionally or systemically.

17 beta-estradiol is generally regarded as the most potent female hormone. It is generally known that premenopausal women have a lower incidence of coronary heart disease than other individuals and that these women produce higher levels of 17 beta-estradiol. 17 beta-estradiol has been referred to as a natural vasculoprotective agent providing a vasculoprotective effect mediated via a number of cellular mechanisms. It has been determined that 17 beta-estradiol may inhibit smooth muscle cell proliferation and migration, promote re-endothelialization, and restore normal endothelial function following vascular injury. In addition, 17 beta-estradiol is known to have pleomorphic properties, i.e. the ability to occur in various distinct forms, anti-atherogenic properties, anti-inflammatory properties and antioxidant properties.

Accordingly, 17 beta-estradiol may be combined with rapamycin to treat vulnerable plaque. The treatment of vulnerable plaque may be achieved through the combined effect of two therapeutic agents acting synergistically through different mechanisms to reduce smooth muscle proliferation, inflammation and atherosclerosis.

The one or more therapeutic drugs, agents and/or compounds utilized in combination with the stent would preferably prevent neointimal hyperplasia that is commonly encountered in stenting and which could lead to restenosis and device failure as described in detail above. In addition, the same or additional therapeutic drugs, agents and/or compounds would preferably stabilize or passivate the lesion by reducing local inflammation and preventing further erosion of the fibrous cap. The one or more therapeutic drugs, agents and/or compounds may be delivered in a polymer matrix coating applied to the stent struts or embedded into the material forming the stent itself and would release into the vessel wall over a predetermined period of time, preferably utilizing the dual profile release rate as briefly described above.

In treating both restenosis following vascular injury and treating vulnerable plaque, it may be advantageous to provide for the regional delivery of various drugs, agents and/or compounds in addition to the local delivery of various drugs, agents and/or compounds as described herein. The drugs, agents, and/or compounds delivered regionally may be the same as those delivered locally or they may be different. Regional delivery, as used herein, shall mean delivery to an area greater than the area covered by a local delivery device such as those disclosed herein, including stents and other implantable medical devices. For example, an infusion catheter may be utilized to administer a predetermined therapeutic dosage or range of dosages of one or more drugs, agents and/or compounds to a number of sites proximate to the disease site, for example, stenotic or vulnerable plaque lesions. Essentially, the drug or drugs may be administered proximal to the lesion, distal to the lesion, directly into the lesion or any combination thereof. The drug or drugs may be administered in any number of ways, including adventitial injection. The dosage and number of injection sites depends on a number of factors, including the type of drug, agent and/or compound, the diffusion characteristics of the drug, agent and/or compound and the area in the body that is to be treated. In practice, the drug, agent and/or compound is injected into the adventitial tissue proximal and/or distal to the lesion, as well as the adventitial tissue surrounding the lesion, and then distributes axially and longitudinally away from the site of injection.

As set forth herein, drug coated stents may be utilized in the treatment and/or prevention of restenosis and vulnerable plaque. The stents may be coated with any number of drugs or combinations of drugs as described herein. For example, rapamycin alone or in combination, may be locally delivered from a stent or other implantable medical devices. In this exemplary embodiment, the same or different drugs may also be regionally delivered via a catheter-based device. Essentially, the catheter-based device may be utilized to deliver additional quantities of the drug or drugs associated with the local delivery device or completely different drugs. The regional delivery of drugs may be beneficial for a number of reasons, including higher dose quantities and broader coverage areas. In addition, certain drugs may be more efficacious in injectable form rather than dissolved or suspended in a polymeric coating. Also, drug therapies may be tailored to the individual patient.

In addition to rapamycin, other drugs that may be regionally delivered for the treatment of vulnerable plaque include non-steroidal anti-inflammatories such as aspirin and celecoxib, steroidal agents such as estrogen, metabolic agents such as troglitazone and anti-coagulants such as enoxaparin, probucol, hirudin and apo-A1$_{MILANO}$. Accordingly, these drugs may be utilized alone or in combination with rapamycin.

Any number of catheter-based devices may be utilized for regional drug delivery. In one exemplary embodiment, the drug delivery device comprises a microfabricated surgical device for interventional procedures or microneedle. The device is the EndoBionics MicroSyringe™ Infusing Catheter available from EndoBionics, Inc., San Leandros Calif. and may be generally characterized set forth below.

The microneedle is inserted substantially normal to the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel is terminated, and the actuator is controlled to cause the microneedle to be thrust outwardly, substantially perpendicular to the central axis of a vessel, for instance, in which the catheter has been inserted.

Figure 73A:
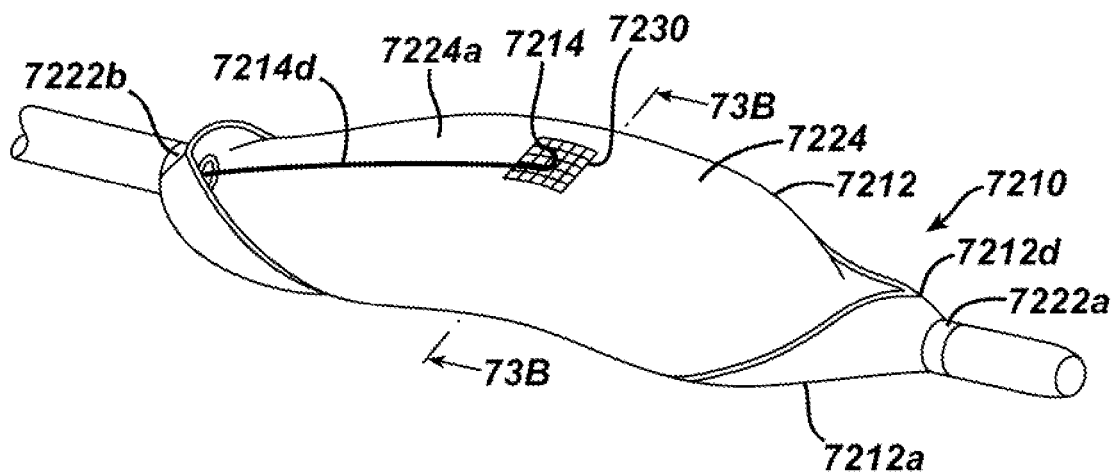
FIG. 73A is a schematic, perspective view of a microfabricated surgical device for interventional procedures in an actuated condition in accordance with the present invention.
Figure 73B:
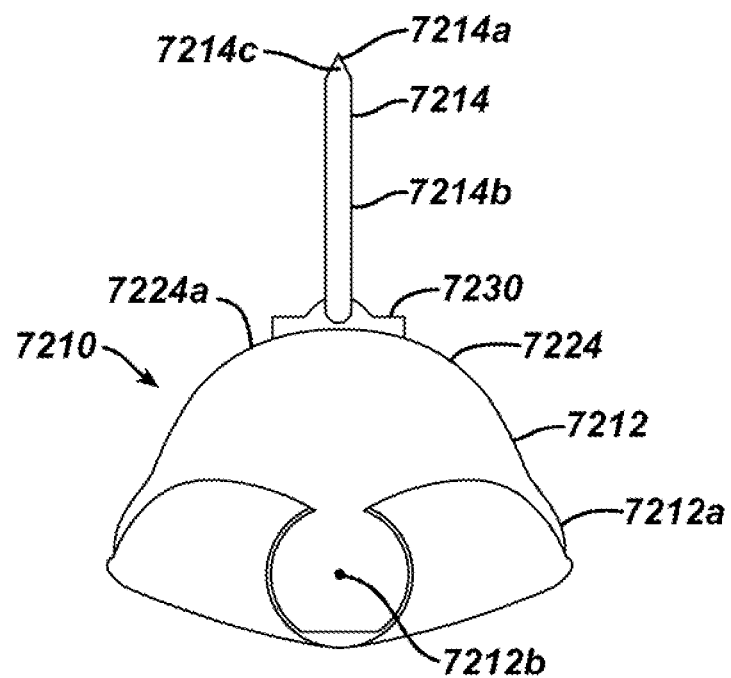
FIG. 73B is a schematic view along line 73B-73B of FIG. 73A.

As shown in FIGS. 72A-73B, a microfabricated surgical device 7210 includes an actuator 7212 having an actuator body 7212*a* and a central longitudinal axis 7212*b*. The actuator body more or less forms a C-shaped outline having an opening or slit 7212*d* extending substantially along its length. A microneedle 7214 is located within the actuator body, as discussed in more detail below, when the actuator is in its unactuated condition (furled state), as illustrated in FIG. 72B. The microneedle is moved outside the actuator body when the actuator is operated to be in its actuated condition (unfurled state), as illustrated in FIG. 73B.

The actuator may be capped at its proximal end 7212*e* and distal end 7212*f* by a lead end 7216 and a tip end 7218, respectively, of a therapeutic catheter 7220. The catheter tip end serves as a means of locating the actuator inside a blood vessel by use of a radio opaque coatings or markers. The catheter tip also forms a seal at the distal end 7212*f* of the actuator. The lead end of the catheter provides the necessary interconnects (fluidic, mechanical, electrical or optical) at the proximal end 7212*e* of the actuator.

Retaining rings 7222*a* and 7222*b* are located at the distal and proximal ends, respectively, of the actuator. The catheter tip is joined to the retaining ring 7222*a*, while the catheter lead is joined to retaining ring 7222*b*. The retaining rings are made of a thin, on the order of ten to one hundred microns, substantially rigid material, such as Parylene (types C, D or N), or a metal, for example, aluminum, stainless steel, gold, titanium or tungsten. The retaining rings form a rigid substantially C-shaped structure at each end of the actuator. The catheter may be joined to the retaining rings by, for example, a butt-weld, an ultra-sonic weld, integral polymer encapsulation or an adhesive such as an epoxy.

The actuator body further comprises a central, expandable section 7224 located between retaining rings 7222*a* and 7222*b*. The expandable section 7224 includes an interior open area 7226 for rapid expansion when an activating fluid is supplied to that area. The central section 7224 is made of a thin, semi-rigid or rigid, expandable material, such as a polymer, for instance, Parylene (types C, D or N), silicone, polyurethane or polyimide. The central section 7224, upon actuation, is expandable somewhat like a balloon-device.

The central section is capable of withstanding pressures of up to about one-hundred atmospheres upon application of the activating fluid to the open area 7226. The material from which the central section is made of is rigid or semi-rigid in that the central section returns substantially to its original configuration and orientation (the unactuated condition) when the activating fluid is removed from the open area 7226. Thus, in this sense, the central section is very much unlike a balloon which has no inherently stable structure.

The open area 7226 of the actuator is connected to a delivery conduit, tube or fluid pathway 7228 that extends from the catheter's lead end to the actuator's proximal end. The activating fluid is supplied to the open area via the delivery tube. The delivery tube may be constructed of Teflon® or other inert plastics. The activating fluid may be a saline solution or a radio-opaque dye.

The microneedle 7214 may be located approximately in the middle of the central section 7224. However, as discussed below, this is not necessary, especially when multiple microneedles are used. The microneedle is affixed to an exterior surface 7224*a* of the central section. The microneedle is affixed to the surface 7224*a* by an adhesive, such as cyanoacrylate. Alternatively, the microneedle may be joined to the surface 7224*a* by a metallic or polymer mesh-like structure 7230, which is itself affixed to the surface 7224*a* by an adhesive. The mesh-like structure may be made of, for instance, steel or nylon.

The microneedle includes a sharp tip 7214*a* and a shaft 7214*b*. The microneedle tip can provide an insertion edge or point. The shaft 7214*b* can be hollow and the tip can have an outlet port 7214*c*, permitting the injection of a pharmaceutical or drug into a patient. The microneedle, however, does not need to be hollow, as it may be configured like a neural probe to accomplish other tasks. As shown, the microneedle extends approximately perpendicularly from surface 7224*a*. Thus, as described, the microneedle will move substantially perpendicularly to an axis of a vessel or artery into which it has been inserted, to allow direct puncture or breach of vascular walls.

The microneedle further includes a pharmaceutical or drug supply conduit, tube or fluid pathway 7214*d* which places the microneedle in fluid communication with the appropriate fluid interconnect at the catheter lead end. This supply tube may be formed integrally with the shaft 7214*b*, or it may be formed as a separate piece that is later joined to the shaft by, for example, an adhesive such as an epoxy.

The needle 7214 may be a 30-gauge, or smaller, steel needle. Alternatively, the microneedle may be microfabricated from polymers, other metals, metal alloys or semiconductor materials. The needle, for example, may be made of Parylene, silicon or glass.

Figure 74:
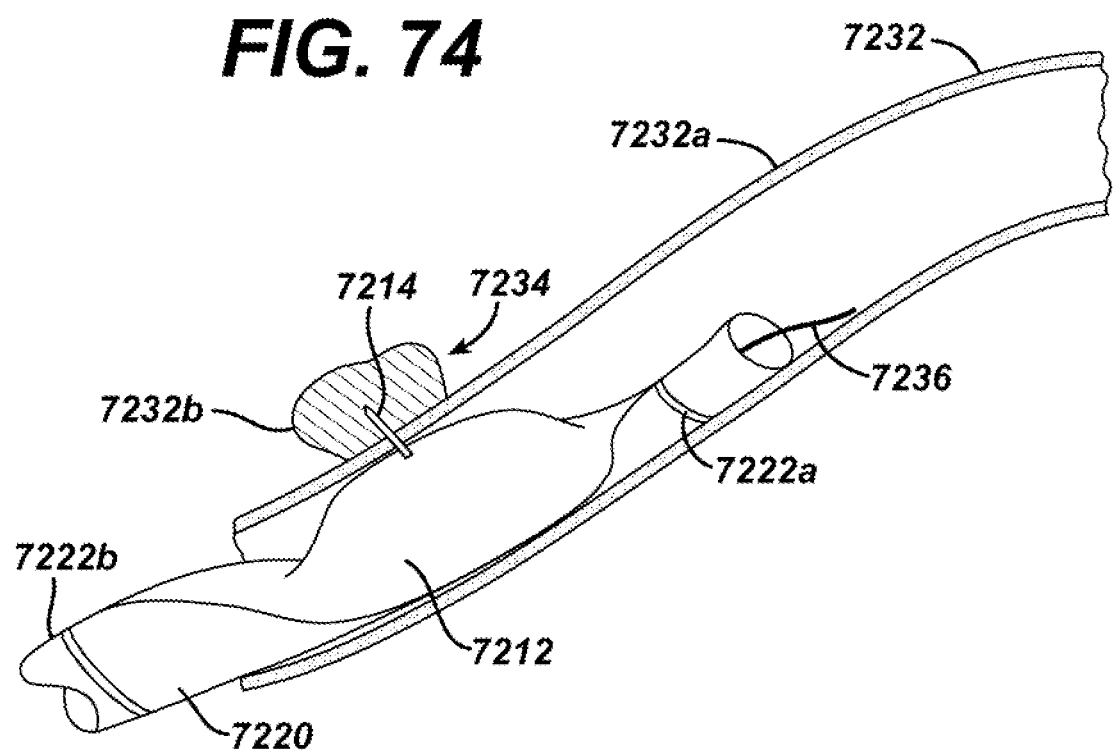
FIG. 74 is a schematic, perspective view of the microfabricated surgical device of the present invention inserted into a patient's vasculature.

The catheter 7220, in use, is inserted through an artery or vein and moved within a patient's vasculature, for instance, a vein 7232, until a specific, targeted region 7234 is reached, as illustrated in FIG. 74. As is well known in catheter-based interventional procedures, the catheter 7220 may follow a guide wire 7236 that has previously been inserted into the patient. Optionally, the catheter 7220 may also follow the path of a previously-inserted guide catheter (not shown) that encompasses the guide wire. In either case, the actuator is hollow and has a low profile and fits over the guide wire.

During maneuvering of the catheter 7220, well-known methods of fluoroscopy or magnetic resonance imaging (MRI) can be used to image the catheter and assist in positioning the actuator 7212 and the microneedle 7214 at the target region. As the catheter is guided inside the patient's body, the microneedle remains unfurled or held inside the actuator body so that no trauma is caused to the vascular walls.

After being positioned at the target region 7234, movement of the catheter is terminated and the activating fluid is supplied to the open area 7226 of the actuator, causing the expandable section 7224 to rapidly unfurl, moving the microneedle 7214 in a substantially perpendicular direction, relative to the longitudinal central axis 7212*b* of the actuator body 7212*a*, to puncture a vascular wall 7232*a*. It may take only between approximately one-hundred milliseconds and two seconds for the microneedle to move from its furled state to its unfurled state.

The ends of the actuator at the retaining rings 7222*a* and 7222*b* remain rigidly fixed to the catheter 7220. Thus, they do not deform during actuation. Since the actuator begins as a furled structure, its so-called pregnant shape exists as an unstable buckling mode. This instability, upon actuation, produces a large scale motion of the microneedle approximately perpendicular to the central axis of the actuator body, causing a rapid puncture of the vascular wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle, in fact, travels so quickly and with such force that it can enter perivascular tissue 7232*b* as well as vascular tissue. Additionally, since the actuator is "parked" or stopped prior to actuation, more precise placement and control over penetration of the vascular wall are obtained.

After actuation of the microneedle and delivery of the pharmaceutical to the target region via the microneedle, the activating fluid is exhausted from the open area 7226 of the actuator, causing the expandable section 7224 to return to its original, furled state. This also causes the microneedle to be withdrawn from the vascular wall. The microneedle, being withdrawn, is once again sheathed by the actuator.

As set forth above, the microneedle or other catheter-based delivery systems may be utilized to deliver one or more drugs, agents and/or compounds, including rapamycin, to the site of atherosclerotic plaque. This type of regional delivery may be utilized alone or in combination with an implantable medical device with the same or different drugs affixed thereto. The one or more drugs, agents and/or compounds are preferably delivered to the adventitial space proximate the lesion.

As described herein, there are a number of advantages to the local or regional delivery of certain drugs, agents and/or compounds via means other than or in addition to delivery from an implantable medical device. However, the efficacy of the drugs, agents and/or compounds may, to a certain extent, depend on the formulation thereof.

It is typically very difficult to create solution dosage forms of water insoluble and lipohilic (having an affinity for and/or tending to combine with lipids) drugs such as rapamycin without resorting to substantial quantities of surfactants, co-solvents and the like. Often times, these excipients (inert substance that acts as a vehicle), such as Tween 20 and 80, Cremophor and polyethylene glycol (PEG) come with varying degrees of toxicity to the surrounding tissue. Accordingly, the use of organic co-solvents such as dimethol sulfoxide (DMSO), N-methylpyrrolidone (NMP) and ethanol need to be minimized to reduce the toxicity of the solvent. Essentially, the key for a liquid formulation of a water insoluble drug is to find a good combination of excipient and co-solvent, and an optimal range of the additives in the final dosage form to balance the improvement of drug solubility and necessary safety margins.

As the outstanding results from clinical trials of recent drug eluting stents such as the Cypher® and Taxus® drug eluting stents demonstrated, a prolonged local high concentration and tissue retention of a potent anti-inflammatory and anti-neoplastic agent released from a stent coating can substantially eliminate the neointimal growth following an angioplasty procedure. Rapamycin, released from the Cypher® stent has consistently demonstrated superior efficacy against restenosis after stent implantation as compared to a bare metal stent. However, there are clinical situations where a non-stent approach for the local delivery or regional delivery may be advantageous, including bifurcated junctions, small arteries and the restenosis of previously implanted stents. Accordingly, there may exist a need for potent therapeutics that only need to be deposited locally or regionally and the drug will exert its pharmacological functions mainly through its good lipophilic nature and long tissue retention property.

A locally or regionally delivered solution of a potent therapeutic agent, such as rapamycin, offers a number of advantages over a systemically delivered agent or an agent delivered via an implantable medical device. For example, a relatively high tissue concentration may be achieved by the direct deposition of the pharmaceutical agent in the arterial wall. Depending on the location of the deposition, a different drug concentration profile may be achieved than through that of a drug eluting stent. In addition, with a locally or regionally delivered solution, there is no need for a permanently implanted device such as a stent, thereby eliminating the potential side affects associated therewith, such as inflammatory reaction and long term tissue damage. It is, however, important to note that the locally or regionally delivered solution may be utilized in combination with drug eluting stents or other coated implantable medical devices. Another advantage of solution or liquid formulations lies in the fact that the adjustment of the excipients in the liquid formulation would readily change the drug distribution and retention profiles. In addition, the liquid formulation may be mixed immediately prior to the injection through a pre-packaged multi-chamber injection device to improve the storage and shelf life of the dosage forms.

In accordance with exemplary embodiments of the present invention, a series of liquid formulations were developed for the local or regional delivery of water insoluble compounds such as sirolimus and its analogs, including CCI-779, ABT-578 and everolimus, through weeping balloons and catheter injection needles. Sirolimus and its analogs are rapamycins, and rapamycin as used herein, includes rapamycin and all analogs, derivatives and congeners that bind FKBP12 and possess the same pharmacologic properties as rapamycin. These liquid formulations increase the apparent solubility of the pharmacologically active but water insoluble compounds by two to four orders of magnitude as compared to the solubility limits of the compounds in water. These liquid formulations rely on the use of a very small amount of organic solvents such as Ethanol (typically less than two percent) and a larger amount of safe amphiphilic (of or relating to a molecule having a polar, water soluble group attached to a non-polar, water insoluble hydration chain) excipients such as polyethylene glycol (PEG 200, PEG 400) and vitamin E TPGS to enhance the solubility of the compounds. These liquid formulations of highly water insoluble compounds are stable and readily flowable at room temperature. Certain excipients, such as Vitamin E TPGS and BHT may be utilized to enhance the storage stability of sirolimus compounds through their anti-oxidation properties.

Table 9, shown below, summarizes the concentrations of the excipient, the co-solvents and the drug for four different liquid formulations in accordance with exemplary embodiments of the present invention. The concentrations of each constituent were determined by liquid chromatography and are presented as weight by volume figures. As may be seen from Table 9, a 4 mg/ml concentration of sirolimus was achieved with an ethanol concentration of two percent, a water concentration of twenty-five percent and a PEG 200 concentration of seventy-five percent. The concentration of ethanol is preferably two or less percent so as to avoid ethanol becoming an active ingredient in the formulation.

TABLE 9

|  | Formulation B1 | Formulation A1 |
| --- | --- | --- |
| Sirolimus conc. (mg/mL) | 1.79 | 1.0 |
| EtOH conc. (%) | 3.83 | 2 |
| H2O conc. (%) | 7.7 | 25 |
| PEG 200 conc. (%) | 88.5 | 73 |
| Sirolimus conc. (mg/mL) | 2.0 | 4 |
| EtOH conc. (%) | 2.0 | 2.0 |
| H2O conc. (%) | 25 | 25 |
| PEG 200 conc. (%) | 75 | 75 |

As set forth above, a liquid formulation comprising 4 mg/ml of sirolimus may be achieved utilizing PEG 200 as the excipient and ethanol and water as the co-solvents. This concentration of sirolimus is about four hundred to about one thousand times higher than the solubility of sirolimus in water. The inclusion of an effective co-solvent, PEG 200, ensures that the high concentration of sirolimus does not start to precipitate out of solution until diluted five to ten fold with water. The high concentration of sirolimus is necessary to maintain an effective and high local concentration of sirolimus after delivery to the site. The liquid formulations are flowable at room temperature and are compatible with a number of delivery devices. Specifically, each of these formulations were successfully injected through an infusion catheter designated by the brand name CRESCENDO™ from Cordis Corporation, Miami, Fla., as described in more detail subsequently, and the EndoBionics Micro Syringe™ Infusion Catheter available from EndoBionics, Inc., San Leandros, Calif., as described in more detail above, in porcine studies.

In another exemplary embodiment, the liquid formulation of sirolimus comprises water and ethanol as co-solvents and Vitamin E TPGS as the excipient. The liquid formulation was created utilizing the following process. Two hundred milligrams of sirolimus and two grams of ethanol were added to a pre-weighed twenty milliliter scintillation vial. The vial was vortexed and sonicated until the sirolimus was completely dissolved. Approximately six hundred milligrams of Vitamin E TPGS was then added to the solution of ethanol and sirolimus. The vial was vortexed again until a clear yellowish solution was obtained. Nitrogen gas was then used to reduce the amount of ethanol in the vial to approximately two hundred twenty-nine milligrams. In a separate vial, three hundred milligrams of Vitamin E TPGS was dissolved in eleven milliliters of purified water while undergoing vortexing. The Vitamin E TPGS and water solution was then added to the first vial containing the sirolimus, Vitamin E TPGS and ethanol. The first vial was then vortexed vigorously and continuously for three minutes. The resulting sirolimus solution was clear with a foam on top. The foam gradually disappeared after sitting at room temperature. An HPLC assay of sirolimus indicated that the sirolimus concentration in the final solution was 15 mg/ml. The final solution had an ethanol concentration of less than two percent, which as stated above is important so as to maintain ethanol as an inactive ingredient. Accordingly, utilizing Vitamin E TPGS as the excipient rather than PEG, resulted in a higher concentration of sirolimus in the final formulation.

Table 10, as shown below, summarizes the composition and visual observations for aqueous formulations of sirolimus utilizing ethanol, Vitamin E TPGS and water at different ratios. The solutions represented by the data contained in Table 10 were generated using essentially the same procedure as described above, except that the ratios between sirolimus and Vitamin E TPGS were varied.

All of the above preparations except for number five remained as stable solutions at both room temperature and under refrigerated condition. The results in Table 10 indicate that, Vitamin E TPGS may be utilized over a wide range of concentrations to increase the solubility of sirolimus in an aqueous solution.

In another exemplary embodiment, a liquid formulation of CCI-779, a sirolimus analog, is prepared utilizing ethanol, Vitamin E TPGS and water. This liquid formulation was made under similar conditions as to that described above. Because of its better solubility in ethanol, only 0.8 grams of ethanol was used to dissolve two hundred milligrams of CCI-779 as opposed to the two grams of sirolimus. After the amount of ethanol was reduced to approximately two hundred thirty milligrams, eleven milliliters of purified water containing three hundred milligrams of Vitamin E TPGS was added to the vial of ethanol and CCI-779. The combined solution was vortexed for three minutes and resulted in a clear solution. An HPLC assay of CCI-779 indicated that the concentration of CCI-779 in the final solution was 15 mg/ml. The concentration of ethanol in the final solution was less than two percent. Accordingly, the results are substantially identical to that achieved for the sirolimus.

As stated above, a number of catheter-based delivery systems may be utilized to deliver the above-described liquid formulations. One such catheter-based system is the CRESCENDO™ infusion catheter. The CRESCENDO™ infusion catheter is indicated for the delivery of solutions, such as heparinized saline and thrombolytic agents selectively to the coronary vasculature. The infusion catheter may also be utilized for the delivery of the liquid formulations, including the liquid solution of sirolimus, described herein. The infusion region includes an area comprised of two inflatable balloons with multiple holes at the catheter's distal tip. The infusion region is continuous with a lumen that extends through the catheter and terminates at a Luer port in the proximal hub. Infusion of solutions is accomplished by hand injection through an infusion port. The catheter also comprises a guidewire lumen and a radiopaque marker band positioned at the center of the infusion region to mark its relative position under fluoroscopy.

In yet another alternate exemplary embodiment, Probucol may be utilized alone or in combination with other drugs, such as a rapamycin to treat restenosis, vulnerable plaque, abdominal aortic aneurysms and stroke. Rapamycin, its analogs, derivatives and conjugates have been demonstrated to be highly effective for treating restenosis following angioplasty. Rapamycin may also have potent actions for other vascular disease processes such as vulnerable plaque and aneurysms. Rapamycin acts to reduce lymphocyte and smooth muscle cell proliferation by arresting cells in the G1 phase of the cell cycle through the inhibition of the mammalian target of rapamycin. Syubsequent activity of cell

TABLE 10

| Group # | Sirolimus mg | Vitamin E TPGS, mg | Ethanol mg | 13.3 ml water containing Vitamin E TPGS, mg | Observation of final solution |
| --- | --- | --- | --- | --- | --- |
| 1 | 202.7 | 642 | 230 | 320 | Clear |
| 2 | 205.2 | 631 | 260 | 330 | Clear |
| 3 | 201.1 | 618 | 260 | 600 | Clear |
| 4 | 204.1 | 625 | 260 | 590 | Clear |
| 5 | 203.3 | 618 | 250 | 1400 | Hazy to clear, Viscous |
| 6 | 204.5 | 630 | 250 | 1420 | Clear, viscous | cycle-associated protein kineases is blocked by the downstream effects of rapamycin on the mammalian target of rapamycin. Although the local delivery of rapamycin is highly effective in reducing restenosis, further reductions in neointernal hyperplasica would benefit certain patient populations. Therefore, the combination of rapamycin with another antiproliferative agent within a stent coating or via other local drug delivery techniques could reduce further fibroproliferative vascular responses secondary to procedures involving vascular injury.

Probucol exerts a positive effect on vascular remodeling. By utilizing probucol to promote vascular remodeling in accordance with the present invention, favorable results may be obtained in treating such diseases and conditions as restenosis following transluminal coronary angioplasty, intimal smooth muscle cell hyperplasia, vascular occlusion, or restenosis following transluminal angioplasty or atherectomy procedures performed on the coronary, iliac femoral, renal or carotid arteries.

Figure 89A:
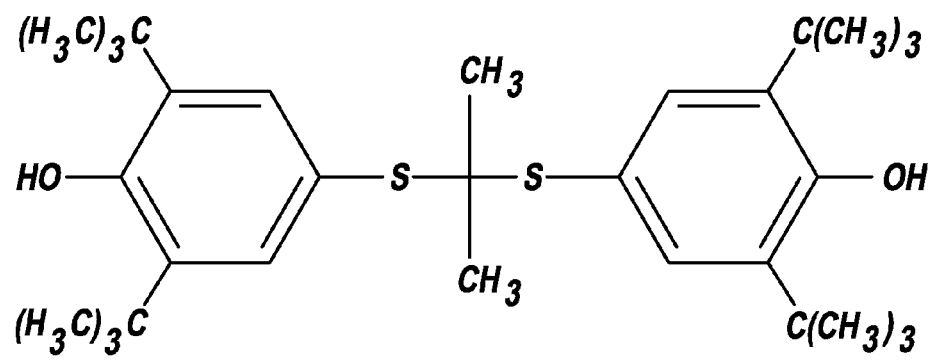
FIGS. 89a and 89b illustrate the structure of probucol and butylated hydroxytolucene in accordance with the present invention.
Figure 89B:
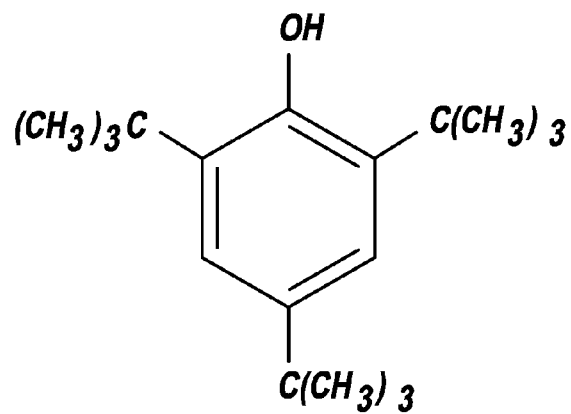

Probucol remains essentially the only conventional drug that reduces restenosis after coronary angioplasty. It has weak cholesterol lowering effect and antioxidant properties. Recent studies indicate that probucol exerts its anti-restenotic effects by promoting functional re-endothelialization. Probucol's antioxidant effects are largely expected because it is structurally equivalent to two molecules of an established antioxidant; namely, butylated hydroxyloluene (BHT) as illustrated in FIGS. 89a and b. Probucol's antioxidant properties are potentially useful for a wide range of vascular diseases where oxidation processes are implicated. Such oxidative processes include vulnerable plaque, myocardial infarction, stroke and aneurysms.

On the basis of "oxidation hypothesis," the oxidation of LDL in the artery is an early initiating event and contributes to atherogenesis. Probucol may exert its protective function via its antioxidant activities independently of lowering cholesterol. Several studies demonstrated that Probucol inhibits atherosclerosis and copper-induced ex vivo oxidation of LDL in non-human primates and Watanabe hyperlipidermia rabbits under cholesterol-clamped conditions. Probucol may also decrease vascular superoxide production, leading to improved endothelial functions.

In addition, probucol inhibits the proliferation of vascular smooth muscle cells (VSMCs) in vivo and in vitro, and it promotes the proliferation of endothelial cells in vitro. Probucol was also shown to be anti-inflammatory by down-regulating endothelial expression of adhesion molecules and decreases tissue macrophages, secretion of interleukin-1 from macrophages, and expression of tumor necrosis factor-alpha in the vessel wall.

All of these properties make probucol potentially an ideal drug candidate for a wide range of vascular diseases, preferably when it is delivered locally for a prolonged period of time. As rapamycin and probucol act through divergent antiproliferative mechanisms, it is possible that these agents, when combined on a singe delivery mechanism, such as a drug eluting stent, may potentiate each others' antirestenotic activities. Probucol may also improve the stability of rapamycin during storage and in vivo use through its strong antioxidant effects.

The present invention concerns methods and devices for promoting vascular remodeling. By the present invention, vascular remodeling is accomplished by the systemic or local administration of the drug, probucol; 4,4'-([1-methyl-ethylidene)bis(thio)]bis-[2,6-bis(1,1-dimethylethyl)phenol] alone or in combination with one or more other therapeutic agents. The preparation of probucol has been described in U.S. Pat. No. 3,576,883 and its use as a cholesterol-lowering agent has also been described in U.S. Pat. No. 3,862,332. Its use to inhibit angiographic and clinical restenosis, i.e., death from cardiac cause, acute myocardial infarction, recurrence or exacerbation of angina pectoris and the need for revascularization (coronary bypass surgery or reangioplasty) post-coronary angioplasty by promoting positive vascular remodeling has not previously been described. By using probucol to promote vascular remodeling by the method of the present invention, favorable results may be obtained in treating diseases and conditions such as restenosis following balloon angioplasty, directional or rotational atherectomy, laser angioplasty and post-stent implantation. Promoting positive vascular remodeling would be favorable not only for interventions performed in the coronary arteries but also when these procedures are performed in any vascular structure, i.e., peripheral vessels (iliac, femoral etc.), renal, mesenteric, or carotid arteries, etc. Furthermore, promoting positive vascular remodeling would be favorable in the long-term treatment of patients with ischemic syndromes as seen in coronary artery disease, peripheral vascular disease, mesenteric vascular disease, cerebro-vascular disease, etc. The benefit of a positive vascular remodeling agent would also be desirable for the treatment of conditions such as chronic arterial hypertension, post-heart transplant, post-bypass surgery, etc.

Five small clinical studies have suggested that probucol started before angioplasty may prevent restenosis (Circulation 1991; 84: II-299 (abstract), Clin Ther 1993; 15:374-382, Jpn Heart J 1996; 37:327-32, Am Heart J 1996; 132:23-29, J Am Coll Cardiol 1997; 30:855-62). Recently, we have shown in the MultiVitamins and Probucol (MVP) randomized clinical trial that probucol, a drug with strong antioxidant properties, given alone reduced angiographic lumen loss by sixty-eight percent, restenosis rate per segment by forty-seven percent and the need for repeat angioplasty at 6 month by fifty-eight percent compare to placebo. These results have been recently published (Multivitamins and probucol in the prevention of restenosis after coronary angioplasty: Results of the MVP randomized trial. N Engl J Med 1997; 365-372) and the publication is incorporated herein by reference. It was not possible to determine with angiography alone whether probucol acted via inhibition of tissue hyperplasia or improvement in vascular remodeling. Determination of this mechanistic question was necessary to help identify the appropriate targets in the periangioplasty period and, as taught by the present invention, lead to more effective strategies to prevent restenosis. In addition, the invention enables the skilled practitioner to use probucol in conjunction with other percutaneous coronary interventions such as stenting if it is deemed appropriate.

Serial intravascular ultrasound (IVUS) examinations have been performed in a consecutive series of patients involved in the MVP trial. By providing tomographic views of coronary arteries with high resolution, IVUS allows quantitative assessment of changes in arterial lumen and wall dimensions. We were therefore able in this study to determine the pathophysiology of coronary restenosis after balloon angioplasty in patients systematically undergoing follow-up IVUS examination and determine the effect of probucol on tissue hyperplasia and vascular remodeling after coronary angioplasty.

Study Design and Population

The present invention concerns the IVUS substudy from the MVP restenosis trial. MVP was a double-blind placebo-controlled randomized clinical trial with four study groups. The protocol was approved by the Montreal Heart Institute institutional review board. The MVP study design, inclusion and exclusion criteria have been previously described (N Engl J Med 1997; 365-372). Briefly, patients referred for elective coronary angioplasty were evaluated at least 30 days prior to their scheduled procedure. Eligible patients were asked to provide written informed consent. Patients were eligible if they were scheduled to undergo standard balloon angioplasty on at least one native coronary artery and had at least one de novo target lesion with luminal narrowing of fifty percent or more by caliper measurements.

Beginning thirty days prior to scheduled angioplasty, patients were randomly assigned to receive either probucol alone, multivitamins alone, the combination of probucol and multivitamins, or placebo. Probucol 500 mg or matched placebo was administered twice daily. The multivitamin complex, consisting of vitamin E 700 IU, vitamin C 500 mg and beta-carotene 30,000 IU, or matched placebo was also administered in one tablet twice daily. All patients received an extra dose of probucol 1000 mg and/or vitamin E 2000 IU and/or matched placebos twelve hours before angioplasty, according to randomization assignment. After angioplasty, all successfully dilated patients who did not present a periprocedural complication were maintained on their assigned study regimen until follow-up angiography was performed. All patients received aspirin 325 mg daily started at least thirty days before procedure and continued for the study period. Balloon angioplasty was performed according to standard techniques. Intracoronary nitroglycerin (0.3 mg) was given for each target artery for both pre- and post-dilatation angiography and at follow-up. The sequence of contrast injections with the exact degree of angulation was recorded and used for every angiogram. Coronary arteriograms (pre-, post-procedure, and final follow-up) were analyzed together using the Coronary Measurement System (CMS), as previously reported. Patient follow-up included clinical evaluation, exercise treadmill testing, blood chemistry, pill count and drug level measurements, and dietary assessment and intervention. Patients were readmitted for follow-up coronary angiography at five to seven months. Patients in whom arteriography was performed for clinical reasons before the fifth month returned for repeat angiographic examination at five to seven months if no definite angiographic restenosis was present on at least one dilated site. During follow-up, patients with recurrence or exacerbation of anginal symptoms were treated with medical therapy or revascularization procedures (reangioplasty or Coronary Bypass Surgery) as clinically indicated. Patients with angiographic restenosis (lesion>50%. at follow-up) without clinical evidence of ischemia were not subjected to further interventional procedures.

The MVP study was stopped prematurely by an independent monitoring board after three hundred-seventeen patients had entered the trial because one treatment had a significant effect on the primary (angiographic) efficacy endpoint. one hundred-eleven patients underwent IVUS examination of the angioplasty site after final balloon inflation at baseline and constituted the initial population for the IVUS study.

IVUS Instrumentation and Examination

IVUS examinations were performed using 30 MHZ, 3.5 French mechanical (1800 rpm) ultrasound catheters (Boston Scientific, Natick, Mass.) and a dedicated imaging console (Hewlett Packard, Andover, Mass.) (Curr Opin Cardiol 1994; 9:627-633). In six patients, both examinations were performed using 20 MHZ, 3.5 French 64-element IVUS catheters (Endosonics, Pleasanton, Calif.). IVUS studies were first performed after coronary angioplasty (after final balloon inflation) and then after follow-up angiography (before any subsequent intervention) and were always preceded by administration of intracoronary nitroglycerin (0.3 mg). IVUS imaging was monitored by an experienced cardiologist, but the angioplasty operator was blinded to ultrasound results to avoid altering standard balloon angioplasty practice. The IVUS catheter was advanced distal to the dilated site to an easily recognizable landmark, most often a side branch, which was noted and used for follow-up IVUS examination. One angiographic view was recorded on videotape before beginning pullback of the IVUS catheter. Slow manual pullbacks (approximately 0.5 mm/sec) were performed up to the guiding catheter and the ultrasound images recorded onto 0.5 inch S-VHS videotape for off-line analysis, with a detailed running audio commentary describing the location of the ongoing IVUS interrogation including the angioplasty site. Simultaneous high-resolution fluoroscopic images were recorded on the IVUS imaging screen during pullbacks to constantly know the location of the IVUS transducer. The operator was allowed to pause at sites of interest (e.g., angioplasty site, side branches) and contrast injections were performed when necessary to identify major and selected minor side branches, to accurately define the position of the IVUS catheter in relation to the angioplasty site and to improve delineation of the lumen-intima interface. Gain settings were carefully optimized during the initial assessment and changed only if required due to suboptimal image quality.

Quantitative IVUS Measurements

Figure 90:
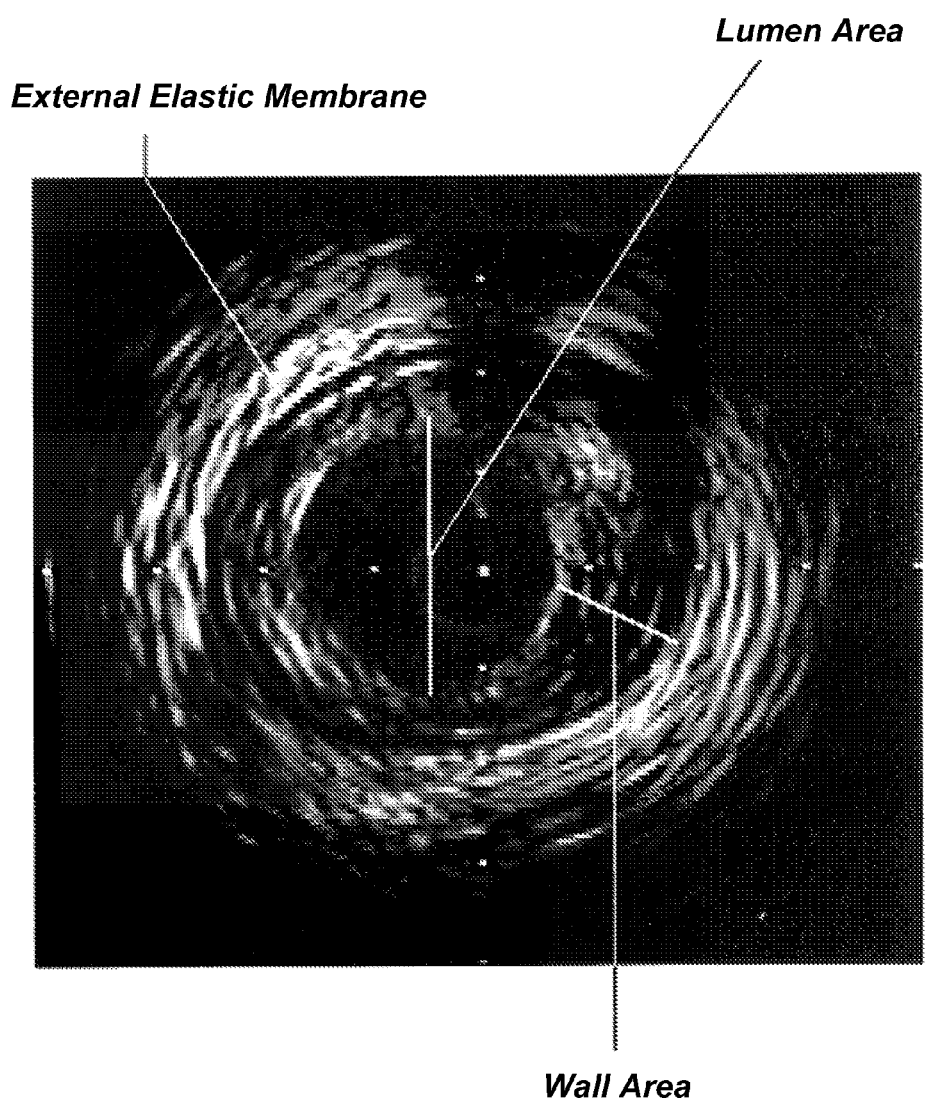
FIG. 90 shows a tomographic section of a coronary artery (single frame of an IVUS study). The lumen area, the wall or plaque area and the external elastic membrane are identified.

All the IVUS images were interpreted by experienced technicians supervised by a cardiologist blinded to treatment assignment. The post-angioplasty and follow-up studies were analyzed side by side. Great care was taken to ensure that the same and correct anatomic slice was measured in both IVUS studies. The fluoroscopic and angiographic images and audio commentary were used to determine the axial location of the ultrasound transducer and of IVUS landmarks relative to the angioplasty site and to side branches. IVUS landmarks (side branches, veins, calcifications, fibrotic deposits) were used to allow matching of the anatomic slice in both studies using frame by frame review of the images. The anatomic cross-section selected for serial analysis was the one at the angioplasty site with the smallest lumen area at follow-up. The corresponding anatomic slice was then identified on the post-angioplasty study. The images were digitized and quantitative analysis performed using custom-developed software for geometric computations (NIH Image 1.59). Quantitative analysis consisted in measurements of lumen area and the area within the external elastic membrane (EEM) (FIG. 90). The external elastic membrane was defined as the border between the hypoechoic media zone and the surrounding echobright adventitia. Wall area was calculated as the difference between EEM and lumen areas. When the plaque encompassed the IVUS catheter, the lumen area was assumed to be the size of the catheter.

Measurement of the EEM area may be difficult in the presence of extensive calcifications, because of acoustic shadowing of deeper structures. Two strategies were used to circumvent this problem (J Am Coll Cardiol 1997; 29:268-274). Considering that coronary arterial cross-sections are relatively circular, extrapolation of the EEM level was directly performed when each arc of calcification at the selected site did not shadow more than 60 degrees of the adventitial circumference. In addition, study of the anatomic slices just proximal and just distal to a selected calcified site was also performed when necessary to escape the shadowing and to identify the EEM correctly.

Statistical Methods

Statistical analysis was performed for all patients who underwent both baseline and follow-up examinations. The same analyses were performed for compliant patients only (efficacy analysis). Measurements are reported as mean.+−.1 SD. The relations between changes in lumen, wall and EEM areas within study groups were tested using least squares linear regression analyses and Pearson's correlation coefficients. IVUS measurements were analyzed between groups with a two-way analysis of covariance (Fleiss J L. The design and analysis of clinical experiments. New York: John Wiley and Sons, 1986; 186-194) on follow-up areas, controlling for post-angioplasty area and for potential prognostic factors and extracting treatment effects and interactions. The IVUS measurements were analyzed per segment by the generalized estimating equations (GEE) technique (Biometrika 1986; 73:13-22), which takes into account potential dependence between segments in the same patient.

Results

Of the one hundred-seven patients who underwent IVUS examination of the angioplasty site immediately after intervention, eleven were not studied at follow-up for different reasons. Two patients underwent both IVUS studies but extensive calcifications precluded quantitative IVUS measurements at the selected angioplasty site. Thus, ninety-four patients constituted our study population and were distributed in the four groups as follows: twenty-one received probucol alone, twenty-five multivitamins alone, twenty probucol plus multivitamins and twenty-eight received only placebo. Selected demographic, clinical and angiographic characteristics of the four groups are shown in Table 11 shown below. There were no statistically significant baseline differences between study groups. Six patients were not adequately compliant to study medications (1, 2, 2 and 1 in the probucol, vitamins, combined treatment and placebo groups). There were also no baseline differences between groups when compliant patients only were evaluated.

Natural History of Restenosis: IVUS Results in the Placebo Group

Table 12 shown below summarizes IVUS results for the placebo alone group and for the 3 active treatment groups. At baseline (immediately after angioplasty) in the placebo group, lumen, wall and EEM areas were 4.52.+−.1.39 mm.sup.2, 8.85.+−.3.01 mm.sup.2, and 13.37.+−.3.45 mm.sup.2, respectively. At follow-up, these values were 3.31.+−.1.44 mm.sup.2, 10.35.+−.3.95 mm.sup.2, and 13.66.+−.4.18 mm.sup.2. Thus, lumen area at follow-up decreased by −1.21.+−.1.88 mm.sup.2, and wall and EEM areas increased by 1.50.+−.2.50 mm.sup.2 and 0.29.+−.2.93 mm.sup.2. The change in lumen area correlated more strongly with the change in EEM area r=0.53, p=0.002) than with the change in wall area r=−0.13, p=0.49).

Figure 91:
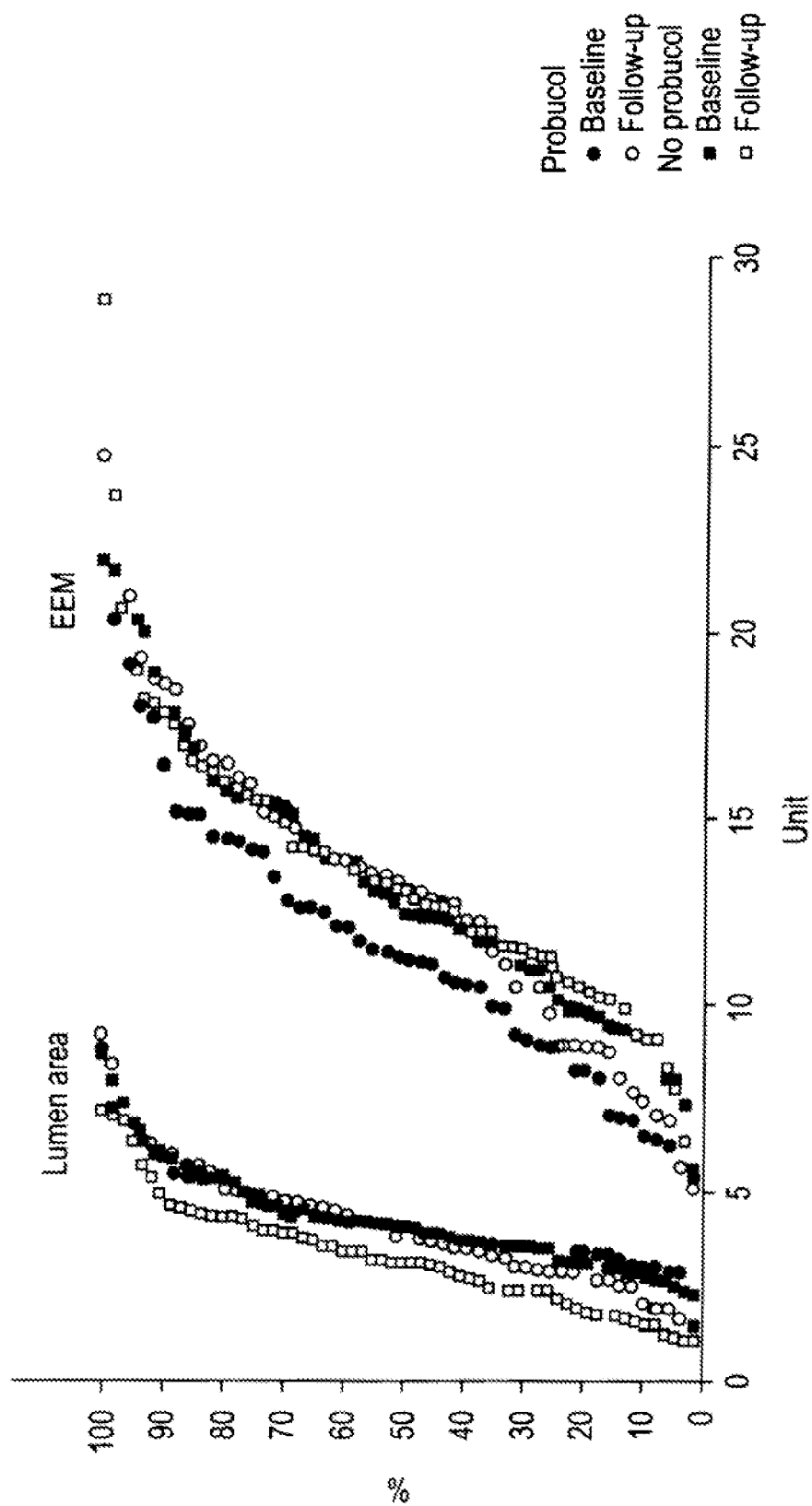
FIG. 91 represents the cumulative frequency curves of the lumen and EEM areas observed by IVUS in all study groups.

Effects of Probucol and Vitamins on Tissue Hyperplasia and Vascular Remodeling: IVUS Results in the Four Study Groups Lumen area at follow-up was 3.31.+−.1.44 mm.sup.2 in the placebo group, 3.24.+−.1.58 mm.sup.2 for vitamins only, 3.85.+−.1.39 mm.sup.2 for combined treatment and 4.47.+−.1.93 mm.sup.2 for probucol alone (p=0.002 for probucol versus no probucol; p=0.84 for vitamins versus no vitamins). Follow-up wall area was 10.35.+−.3.95 mm.sup.2 for the placebo group, 10.02.+−.3.40 mm.sup.2 in the vitamins only group, 8.52.+−.3.49 mm.sup.2 for combined treatment and 9.46.+−.4.36 mm.sup.2 for probucol alone (p=0.27 for probucol versus no probucol and 0.18 for vitamins versus no vitamins). EEM area at follow-up was 13.66.+−.4.18 mm.sup.2 in patients receiving placebo alone, 13.26.+−.3.80 mm.sup.2 for vitamins only, 12.37.+−.3.70 mm.sup.2 for combined treatment and 13.93.+−.4.74 mm.sup.2 for those treated with probucol only (p=0.005 for probucol versus no probucol; p=0.36 for vitamins versus no vitamins). FIG. 91 represents the cumulative frequency curves of the lumen and EEM areas observed on IVUS in all study groups.

Figure 92:
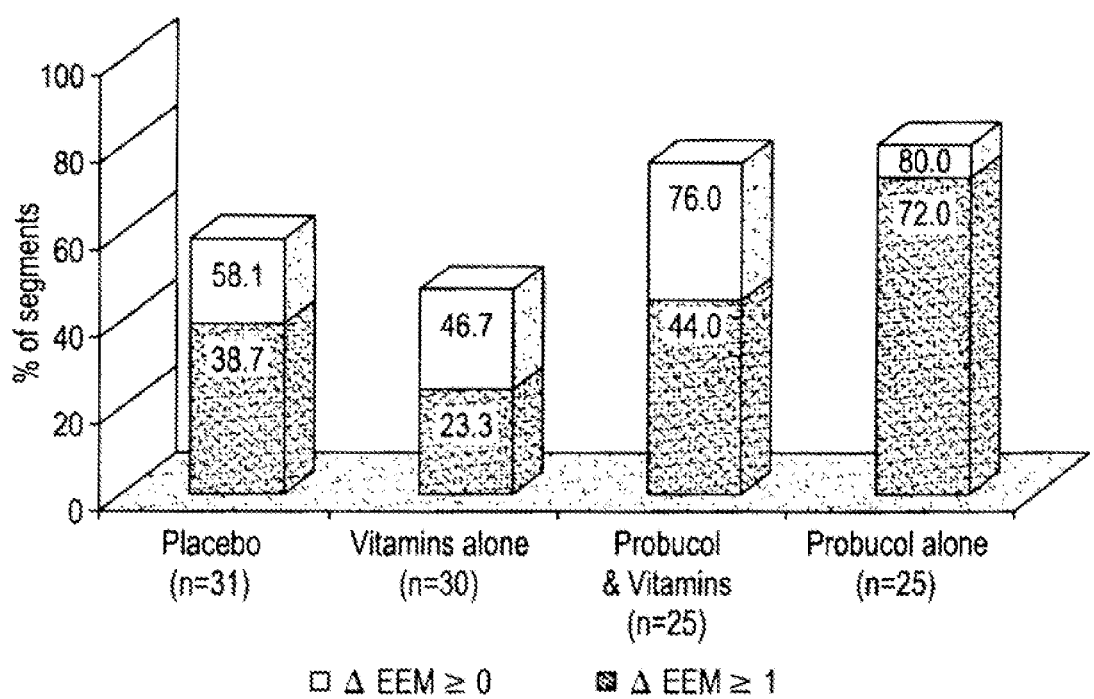
FIG. 92 shows the proportion of segments for each treatment group showing an increase in the external elastic membrane surface area between baseline and follow-up. Lower bars depict the proportion of segments showing a growth greater or equal to 1 mm$^2$.

Lumen loss was 1.21.+−.1.88 mm.sup.2 in the placebo group, 0.83.+−.1.22 mm.sup.2 for vitamins alone, 0.25.+−.1.17 mm.sup.2 for combined treatment and 0.15.+−.1.70 mm.sup.2 for patients receiving probucol alone (p=0.002 for probucol versus no probucol and p=0.84 for vitamins versus no vitamins). The change in wall area was 1.50.+−.2.50 mm.sup.2, 0.93.+−.2.26 mm.sup.2, 1.41.+−.1.45 mm.sup.2 and 1.89.+−.1.87 mm.sub.2, respectively (p=NS). EEM area increased at follow-up by 0.29.+−.2.93 mm.sup.2 in the placebo group, 0.09.+−.2.33 mm.sub.2 in the vitamins only group, 1.17.+−.1.61 mm.sup.2 for combined treatment and 1.74.+−.1.80 mm.sup.2 for the probucol alone group (p=0.005 for probucol versus no probucol and p=0.36 for vitamins versus no vitamins). An increase in EEM area of at least 1 mm.sup.2 at follow-up occurred in 38.7% of patients given placebo alone, in 23.3% in the vitamins only group, 44.0% in the combined treatment group, and 72.0% of patients taking probucol (FIG. 92). Table 13 shows the changes in lumen, wall and EEM areas for compliant patients only.

TABLE 11

BASELINE DEMOGRAPHIC, CLINICAL AND ANGIOGRAPHIC CHARACTERISTICS OF THE FOUR STUDY GROUPS

|  | Placebo Alone | Vitamins Alone | Probucol + Vitamins | Probucol Alone |
|---|---|---|---|---|
| Patients | 28 | 25 | 20 | 21 |
| Age (yrs) (means ± SD) | 59.5 ± 8.8 | 58.1 ± 11.1 | 57.1 ± 8.9 | 56.1 ± 7.8 |
| Female (%) | 28.6 | 8.0 | 30.0 | 9.5 |
| Ever Smoked (%) | 17.9 | 8.0 | 25.0 | 4.8 |
| Current Smoker (%) | 7.1 | 28.0 | 15.0 | 19.1 |
| Hist. Of Diabetes (%) | 7.1 | 0 | 20.0 | 20.0 |
| Hist. Of Hypertension (%) | 42.9 | 52.0 | 50.0 | 14.3 |

TABLE 11-continued

BASELINE DEMOGRAPHIC, CLINICAL AND ANGIOGRAPHIC CHARACTERISTICS OF THE FOUR STUDY GROUPS

| | Placebo Alone | Vitamins Alone | Probucol + Vitamins | Probucol Alone |
|---|---|---|---|---|
| CCS angenia Class (%) | | | | |
| I | 0 | 4.0 | 10.0 | 14.3 |
| II | 53.6 | 56.0 | 65.0 | 66.7 |
| III | 28.6 | 24.0 | 10.0 | 14.3 |
| IV | 0 | 0 | 0 | 0 |
| Prior MI (%) | 32.1 | 52.0 | 50.0 | 52.4 |
| Prior CABG (%) | 7.1 | 0 | 5.0 | 0 |
| Prior PTCA(%) | 7.1 | 8.0 | 15.0 | 4.8 |
| No. of Diseased Vessels (%) | | | | |
| 1 | 39.3 | 36.0 | 445.0 | 33.3 |
| 2 | 39.3 | 48.0 | 25.0 | 42.9 |
| 3 | 21.4 | 16.0 | 30.0 | 23.8 |
| Target Vessels (%) | | | | |
| Left anterior descending | 54.8 | 56.7 | 33.0 | 40.0 |
| Left circumflex | 16.1 | 20.0 | 24.0 | 36.0 |
| Right coronary artery | 29.0 | 23.3 | 32.0 | 24.0 |
| Maximum Pressure (mean ± SD) | 10.8 ± 2.2 | 10.8 ± 3.2 | 10.3 ± 2.7 | 10.1 ± 2.1 |
| Total Inflation Time (sec) | 513.8 ± 236 | 496 ± 205 | 438 ± 209 | 516 ± 277 |
| Balloon to Artery Ratio | 1.04 ± 0.17 | 1.02 ± 0.10 | 1.06 ± 0.22 | 1.09 ± 0.11 |

CABG: Coronary artery bypass graft
MI: Myocardial infarction
PTCA: Percutaneous transluminal coronary angioplasty
*p = 0.042 based on Chi-squared test

TABLE 12

SERIAL INTRAVASCULAR ULTRASOUND RESULTS*

| | Placebo Alone (n = 31) | Vitamin Alone (n = 30) | Probucol & Vitamins (n = 25) | Probucol Alone (n = 25) | P value Probucol vs No Probucol | P value Vitamins vs. No Vitamins |
|---|---|---|---|---|---|---|
| After Angioplasty | | | | | | |
| Lumen area ($mm^2$) | 4.52 ± 1.39 | 4.08 ± 1.41 | 4.10 ± 0.95 | 4.62 ± 1.59 | 0.7885 | 0.0544 |
| EEM area ($mm^2$) | 13.37 ± 3.45 | 13.17 ± 3.90 | 11.21 ± 3.25 | 12.20 ± 4.66 | 0.0261 | 0.4258 |
| Wall area ($mm^2$) | 8.85 ± 3.01 | 9.09 ± 3.28 | 7.11 ± 2.75 | 7.57 ± 3.98 | 0.0071 | 0.8930 |
| Follow-up | | | | | | |
| Lumen area ($mm^2$) | 3.31 ± 1.44 | 3.24 ± 1.58 | 3.85 ± 1.39 | 4.47 ± 1.93 | 0.0022 | 0.8449 |
| EEM area ($mm^2$) | 13.85 ± 4.18 | 13.26 ± 3.80 | 12.37 ± 3.70 | 13.93 ± 4.74 | 0.0055 | 0.3590 |
| Wall area ($mm^2$) | 10.35 ± 3.95 | 10.02 ± 3.40 | 8.52 ± 3.49 | 9.46 ± 4.36 | 0.2739 | 0.1795 |
| Follow-up Post PTCA | | | | | | |
| Lumen area ($mm^2$) | −1.21 ± 1.88 | −0.83 ± 1.22 | −0.25 ± 1.17 | −0.15 ± 1.70 | 0.0022 | 0.8449 |
| EEM area ($mm^2$) | 0.29 ± 2.93 | 0.09 ± 2.33 | 1.17 ± 1.61 | 1.74 ± 1.80 | 0.0055 | 0.3590 |
| Wall area ($mm^2$) | 1.50 ± 2.50 | 0.93 ± 2.26 | 1.41 ± 1.45 | 1.89 ± 1.87 | 0.2739 | 0.1795 |

*Per segment analysis using the GEE technique

TABLE 13

EFFICACY ANALYSIS IN COMPLIANT PATIENT

| Follow-up Post PTCA | Placebo Alone (n = 30) | Vitamin Alone (n = 28) | Probucol & Vitamins (n = 23) | Probucol Alone (n = 25) | P value Probucol vs No Probucol | P value Vitamins vs. No Vitamins |
|---|---|---|---|---|---|---|
| Lumen area (mm$^2$) | −1.21 ± 1.88 | −0.83 ± 1.22 | −0.25 ± 1.17 | −0.15 ± 1.70 | 0.0022 | 0.8449 |
| EEM area (mm$^2$) | 0.29 ± 2.93 | 0.09 ± 2.33 | 1.17 ± 1.61 | 1.74 ± 1.80 | 0.0055 | 0.3590 |
| Wall area (mm$^2$) | 1.50 ± 2.50 | 0.93 ± 2.26 | 1.41 ± 1.45 | 1.89 ± 1.87 | 0.2739 | 0.1795 |

There was no statistically significant drug interaction in the factorial design. However, considering potential underpowering to detect such an interaction, post-hoc analyses comparing each group separately and adjusted for a possible interaction were performed. Results remained significant for all ultrasound endpoints between the probucol alone and placebo groups.

Probucol is one of the first pharmacological interventions shown to prevent coronary restenosis after balloon angioplasty. However, its mechanism of action and its efficacy as a vascular remodeling agent has never been studied. In the MVP study, probucol therapy initiated thirty days before and given alone for six months after angioplasty resulted in reductions, of sixty-eight percent in angiographic lumen loss, forty-seven percent in restenosis rate per segment and fifty-eight percent in the need for repeat angioplasty when compared to placebo. Whether probucol acted via prevention of tissue hyperplasia, improvement in vascular remodeling, or both, could not be adequately addressed by angiography and required the use of IVUS. It was desirable to determine the mechanism of action of probucol in order to develop better strategies against restenosis. These strategies are unequivocally needed. Indeed, although probucol drastically reduced angiographic lumen loss in the MVP study, restenosis still occurred in over twenty percent of patients given probucol alone. Furthermore, the positive results found with stents have predominantly been obtained in patients with large coronary arteries, i.e., 3.0 mm in diameter or more (N Engl J Med 1994; 331:489-495, N Engl J Med 1994; 331:496-5). In a subset analysis of patients randomized in the BENESTENT trial and having interventions performed on small vessels (<3.0 mm), the benefits noted in the patients with larger vessels (>3.0 mm) were not seen (Semin Intervent Cardiol 1996; 1:255-262). In the stented population, smaller vessel size was associated with a higher stent/vessel ratio, a greater relative gain and a greater subsequent loss index, and a higher risk of adverse cardiac events within six months of the procedure.

Before learning how probucol acted in the MVP study, it was first desirable to clarify the mechanisms of lumen loss and restenosis after balloon angioplasty in the placebo group. In these control patients, the increase in wall area (mean: 1.50 mm.sup.2) was greater than the decrease in lumen area (−1.21 mm.sup.2) with a slight increase of the EEM area (0.29 mm.sup.2). However, the change in lumen area correlated better with the change in EEM area than with the change in wall area. Taken together, these results indicate that the direction (enlargement [positive] or constriction [negative]) and extent (e.g., inadequate or adequate compensatory enlargement) of vascular remodeling in response to the tissue hyperplasia that occurs after balloon angioplasty determine the magnitude of lumen loss at follow-up.

Animal studies have yielded various results on the relative importance of remodeling and tissue hyperplasia in the pathogenesis of restenosis. Animal models, however, have different proliferative and thrombogenic responses to arterial trauma, and plaque content is often significantly different than what is found in human atherosclerotic stenoses requiring angioplasty. One additional limitation is that wall and EEM (or internal elastic lamina) areas were never measured serially with the same method in a given animal artery.

Although clinical studies have revealed that remodeling occurs in humans after different interventions, relative changes in wall and EEM areas have varied. Mintz, et al. observed that seventy-three percent of late lumen loss after intervention was explained by a decrease in EEM area (Circulation 1996; 94:35-43). As acknowledged by the authors, however, the study involved a mix of primary and restenotic lesions on which different interventions were performed. Balloon angioplasty was performed alone in only a small minority of patients, and follow-up examination was largely driven by the presence of symptoms. An underestimation of the increase in plaque area may also have occurred because of the larger acoustic size (i.e., physical catheter size+central artifact) of the catheters that were used in that study. Preliminary data from the SURE study now appear to show that most of the lumen loss from immediately after to six months after balloon angioplasty (−1.51 mm.sup.2) was not caused by a decrease in EEM area (−0.46 mm.sup.2) (J Am Coll Cardiol 1996; 27:41A).

Whereas data from this and other studies support the conclusion that lumen loss after balloon angioplasty is caused by the combination of inadequate or deleterious vessel remodeling and tissue hyperplasia, probucol in the MVP study significantly reduced lumen loss by improving vascular remodeling but it did not modify the post-angioplasty increase in wall area. When compared to non-probucol treated patients, those receiving probucol showed a reduction in lumen loss by eighty percent or 0.79 mm.sup.2 when assessed by IVUS. When compared to the placebo group only, the reduction in lumen loss with probucol given alone was eighty-eight percent or 1.06 mm.sup.2. A striking improvement in compensatory vessel enlargement was responsible for probucol's favorable effect on lumen loss. There was an enlargement in EEM area of 1.74 mm.sup.2 from immediately after angioplasty to follow-up in patients treated with probucol alone compared with 0.29 mm.sup.2 in patients given placebo. This represents a seven hundred-thirty percent increase in vessel enlargement in patients given probucol only. Five other clinical studies, smaller than MVP, have also observed the antirestenotic effect of probucol using angiography (Circulation 1991; 84:II-299 (abstract), Clin Ther 1993; 15:374-382, Jpn Heart J 1996;

37:327-32, Am Heart J 1996; 132:23-29, J Am Coll Cardiol 1997; 30:855-62). In addition, a better arterial response after balloon injury has been demonstrated with probucol in animal studies (Circulation 1993; 88:628-637, Proc Natl Acad Sci 1992; 89:11312-11316). Other antioxidants were also specifically shown in animals to improve vascular remodeling after angioplasty (Arterioscle Thromb Vasc Biol 1995; 15:156-165). Thus, results from the MVP trial and from these other studies provide strong support for the central role of oxidative processes in the pathophysiology of restenosis Oxygen free radicals generated by damaged endothelium, activated platelets and neutrophils at the angioplasty site (Mayo Clin Proc 1988; 63:381-389) can induce chain reactions which result in endothelial dysfunction (Nature 1990; 344:160-162) and LDL oxidation (N Engl J Med 1989; 320:915-924). Macrophages activated by oxidized LDL and dysfunctional endothelium can then release several cytokines and growth factors promoting matrix remodeling and smooth muscle cell proliferation. Matrix degradation by metalloproteinases precedes or accompanies early formation of new extracellular matrix (Circ Res 1994; 75:650-658) after angioplasty and also is a crucial step before smooth muscle cell migration and proliferation (Circ Res 1994; 75:539-545, Biochem J 1992; 288:93-99). Interestingly, it has recently been shown that oxygen free radicals can modulate matrix remodeling by activating metalloproteinases (J Clin Invest 1996; 98:2572-2579). The same events that lead to an increase in wall area after angioplasty, i.e., matrix formation and smooth muscle cell proliferation, are likely involved in the process of vascular remodeling. Smooth muscle cell contraction (Crit Care Med 1988; 16:899-908), along with cross-linking of collagen fibers (J Am Coll Cardiol 1995; 25:516-520), may limit compensatory vessel enlargement in response to tissue hyperplasia and may even result in vascular constriction. Again, nonenzymatic cross-linking of collagen typically involves oxidation processes (FASEB J 1992; 6:2439-2449). In addition, chronic flow-dependent changes in vessel size may be limited by endothelial dysfunction (Science 1986; 231:405-407).

Not being bound by any theory, the powerful chain-breaking antioxidant effects of probucol (Am J Cardiol 1986; 57:16H-21) may have prevented endothelial dysfunction (J Lipid Res 1991; 32:197-204, N Engl J Med 1995; 332:488-493), LDL oxidation (J Clin Invest 1986; 77:641-644) and macrophage and metalloproteinase activation in the MVP study. This could have limited smooth muscle cell activation, migration, proliferation and contraction, and matrix degradation and deposition of new collagen and other fibers. By ultimately limiting smooth muscle cell contraction, collagen formation and cross-linking, and endothelial dysfunction through its antioxidant effects, probucol can modify vascular remodeling and allow greater vessel enlargement. The hypocholesterolemic effect of probucol is weak and unlikely by itself to be responsible for the positive MVP results. However, specific inhibition by probucol of secretion of interleukin-1 (Am J Cardiol 1988; 62:77B-81B) may have decreased secretion of metalloproteinases (Circ Res 1994; 75:181-189) and modified matrix remodeling.

Figure 93:
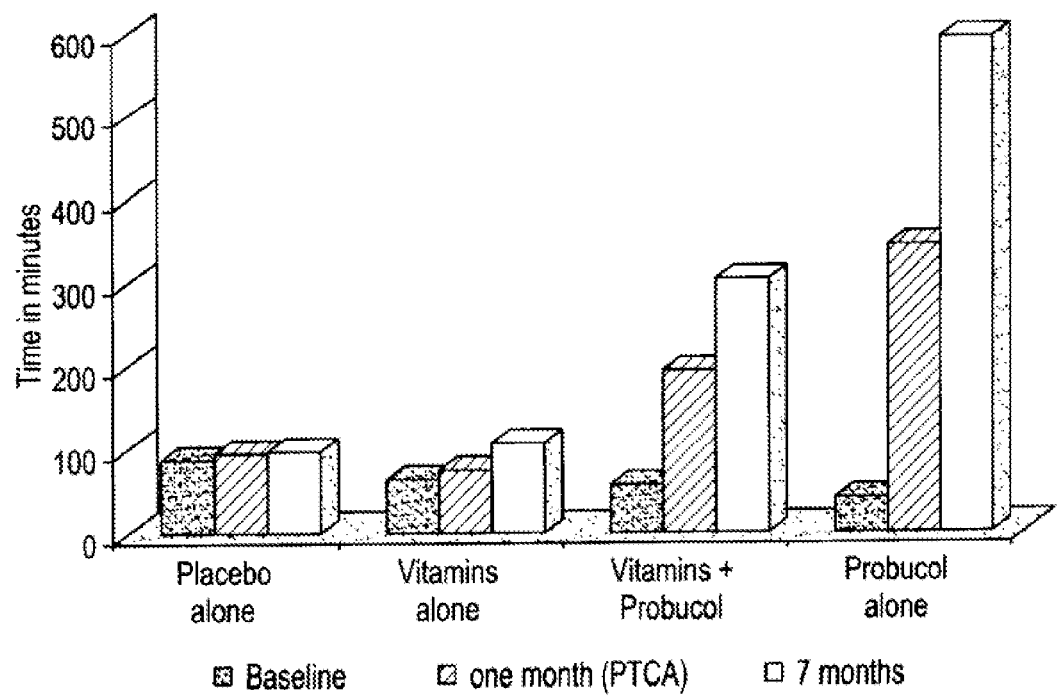
FIG. 93 shows the lag phase for LDL peroxidation for all four treatment groups at baseline, one month and seven months post-treatment initiation

Similar to what was observed clinically and angiographically, multivitamins had no significant effect on IVUS endpoints. It is not clear why multivitamins did not prevent restenosis whereas probucol did. Dietary intervention and smoking habits were similar in all groups. Probucol may simply be a more powerful antioxidant than the combination of vitamins. To this regard, preliminary results from the continuous spectrophotometric monitoring of diene conjugates in LDL after the addition of copper ions to the isolated lipoprotein ex vivo (Free Radic Res Commun 1989; 6:67-75) of MVP patients are noteworthy. FIG. 93 shows the lag phase for LDL peroxidation for all four treatment groups at baseline, one month and seven months post-treatment initiation. Although LDL trapped in the arterial intima encounters a very complex environment, compared with the simple set-up of oxidation resistance assays, our results would suggest that probucol treatment for one month provided a significantly greater protection against LDL oxidation than vitamins alone or the combination of probucol and vitamins. Although the described (Science 1984; 224:569-73) pro-oxidant effects of high doses of multivitamin was not evident ex vivo in the vitamins alone group, it does not exclude the possibility that it may have played a role in vivo. Alternatively, the effect of probucol on interleukin-1 and on reverse cholesterol transfer may have contributed to this result.

Lumen loss after balloon angioplasty is shown to be due to inadequate vessel remodeling in response to tissue hyperplasia. We have shown using IVUS that probucol exerts its antirestenotic effects in humans by improving vascular remodeling after angioplasty. The disclosure describes the positive vascular remodeling effects of probucol using the balloon angioplasty procedure as an example. Probucol, the first pharmacologic agent demonstrated to have positive vascular remodeling capabilities, or any other similar agent to be described in the future for that matter, would be useful in a variety of clinical conditions associated with arterial wall injury. Such conditions could be of natural origin or iatrogenic. More specifically, natural conditions may include hypertensive disorders, vascular disorders affecting the coronaries, the peripheral arteries, the cerebral arteries, the pulmonary arteries, the vascular supply to the kidneys, and any other organ in the abdominal cavity, etc. Iatrogenic conditions for which probucol or a positive vascular remodeling agent may be beneficial could include conditions such as post-coronary intervention, i.e., balloon angioplasty, directional or rotational atherectomy, laser-assisted angioplasty, post-radiation therapy, or coronary stenting or any other intervention which may be associated with vascular injury which will lead to intimal proliferation or negative vascular remodeling (constriction). The potential benefit of a positive vascular remodeling agent would not be limited to the coronary tree. Similar vascular injury in the renal, carotid, vertebral, mesenteric, peripheral vascular bed would also benefit from such an agent. In other conditions, such as post-bypass surgery, the conduit utilized for bypass (vein or artery) would also benefit from a vascular remodeling agent. Such an agent could favor the development (growth) of the graft immediately post-surgery and/or prevent its occlusion due to intimal hyperplasia or atherosclerotic process. Patients with renal failure treated with hemodialysis through an arteriovenous fistula frequently show intimal proliferation and progressive disease of their shunt, which eventually will occlude. Vascular remodeling agent may be beneficial and prolong the life of the shunt. Post-organ transplant, vascular damage and intimal proliferation, which may lead to vascular obstruction and graft damage, is a frequent problem that may also benefit from the use of a vascular remodeling agent. In addition, vascular remodeling agent could play a role in the treatment of patients with a condition such as primary pulmonary hypertension.

So far, the present invention and its applications have only been described for the vascular system. It is intended to encompass with these claims the use of such an agent for any condition where a structure surrounded by a muscular wall will benefit from having its wall remodeled (expansion) so doing creating a larger conduit or cavity.

Probucol or the agent with positive vascular remodeling properties could be administered systemically or locally. Systemic administration may be accomplished with intravenous/intra-arterial injection (bolus injection or longer perfusion) orally (any forms of oral delivery systems), subcutaneously (injection, pallet, slow release, etc.), percutaneously (patch, cream, gel, etc.) with short-acting or long-acting (slow release) delivery profile. A local delivery system would include any device intended to locally delivery probucol or a similar agent (i.e., local delivery catheter, coated or impregnated stent, local infusion device, etc.).

Probucol, alone or in combination with any of the drugs and or agents described herein may be utilized with any of the devices described herein.

Diabetes is a disease in which the body fails to provide enough insulin (type 1 diabetes) or cannot properly use the insulin it makes (type 2 diabetes). Insulin is a hormone that is required to convert sugar, starches and other foods into energy for normal cellular activity or function. In healthy individuals insulin is released or secreted from the beta cells of the Islets of Langerhans, located in the pancreas, after ingesting food and/or drink and it signals insulin-sensitive tissues in the body, for example, muscle, to absorb glucose thereby lowering blood glucose levels in the blood.

Approximately five to ten percent of the population diagnosed with diabetes has type 1 diabetes. As briefly described above and as known in the medical art, type 1 diabetes results from the body's inability to produce enough or even any insulin. Therefore, without sufficient insulin, glucose cannot enter the cells of the body to provide the required metabolic fuel. The remaining ninety to ninety-five percent of the population diagnosed with diabetes have type 2 diabetes. As briefly described above and as known in the medical art, type 2 diabetes results from insulin resistance combined with relative insulin deficiency. Insulin resistance is a condition in which normal amounts of insulin are inadequate to produce a normal insulin response from muscle, liver and fats cells in the body. Insulin resistance in muscle cells reduces glucose uptake and insulin resistance in liver cells reduces glucose storage with the combined effect leading to elevated blood glucose levels resulting in various deleterious effects, including metabolic diseases. Insulin resistance in fat cells results in the hydrolysis of stored triglycerides which elevates free fatty acids in the blood which in turn causes other deleterious effects.

Atherogenic dyslipidemia or diabetic dyslipidemia is a condition associated with insulin resistance that is characterized by high levels of triglycerides, high levels of low-density lipoproteins and low levels of high-density lipoproteins. Evidence suggests that the high levels of triglycerides, the high levels of low-density lipoproteins and the low levels of high-density lipoproteins contribute to atherosclerosis, i.e. fatty buildup in the artery walls. Essentially, atherosclerosis begins with damage to the inner layer or endothelium of the artery and is followed by plaque buildup that may in turn stimulate the cells that comprise the artery to produce substances that may lead to further plaque buildup. The initial damage is at least partially caused by the lipid imbalance described above. This process significantly increases the thickness of the endothelium and may eventually develop to a point where the plaque buildup ruptures. Once the plaque ruptures, there is a chance that blood clots may form and block off the flow of blood through the diseased artery. The lack of blood flow may be to a major organ such as the heart, thereby causing a myocardioinfarction, or the brain, thereby causing a stroke.

In cellular biology, peroxisome proliferators-activated receptors or PPARs are a group of nuclear transcription factor isoforms that are closely connected to cellular metabolism and cell differentiation. To date, three types of PPARs have been identified. PPAR-alpha is expressed in certain tissues, including the liver, the kidneys, the heart, in muscle and in adipose. PPAR-gamma, although transcribed by the same gene, exists in three forms. PPAR-gamma 1 is expressed in virtually all tissues, including the heart, muscle, the colon, the kidneys, the pancreas and the spleen. PPAR-gamma 2 is expressed mainly in adipose tissue. PPAR-gamma 3 is expressed in macrophages, the large intestine and white adipose tissue. PPAR-delta is expressed in a variety of tissues, including the brain, adipose and skin.

PPAR-gamma is a target of the drug class of thiazolidinediones or TZDs currently utilized in the treatment of diabetes mellitus and other diseases that are a product of or associated with insulin resistance. Glitazones, a chemical class of thiazolidinediones, including troglitazone, pioglitazone and rosiglitazone, activate PPAR-gamma receptors in body tissues to exert multiple metabolic effects, the most well known being increased insulin sensitivity; however, glitazones also appear to have direct anti-inflammatory and anti-proliferative effects in vascular tissue through the activation of PPAR-gamma receptors located in the vascular tissues including endothelial cells (EC), smooth muscle cells (SMC), and the inflammatory cells.

Experimental and clinical data accumulated over the last decade suggests that PPAR-gamma activators, such as thiazolidinediones (insulin sensitizers), may exert direct modulatory function in the vasculature in addition to their known and currently effectively utilized metabolic effects. PPAR-gamma is expressed in all vascular cells, as briefly described above, where its activators exhibit anti-inflammatory and anti-atherogenic properties, thereby suggesting that PPAR-gamma ligands may influence critical processes in all phases of atherosclerosis. For instance, thiazolidinediones may inhibit neointimal formation by inhibiting cell cycle (G1-S) in vascular SMCs. Thiazolidinediones my inhibit metalloprotease (MMP) production, particularly MMP 9 that can cause vulnerable plaque erosion. Thiazolidinediones may improve the vascular blood flow. Thiazolidinediones may reduce inflammation by inhibiting adhesion molecule up-regulation (ICAM and VCAM). Thiazolidinediones may also up-regulate nitric oxide (eNOS) production in the endothelial cell (EC). Nitric Oxide serves to prevent thrombosis and is a vasodilator. Thiazolidinedione may also increase adiponectin production by fat cells, which improve insulin effects.

Therefore, in accordance with another exemplary embodiment, thiazolidinediones may be utilized alone or in combination with one or more agents, including mTOR inhibitors for the localized treatment of vascular disease. This exemplary embodiment may be particularly effective for the treatment of individuals with vascular disease caused by or contributed to by type 2 diabetes. Thiazolidinediones are currently utilized in the treatment of type 2 diabetes by reducing peripheral insulin resistance thereby lowering blood glucose levels. This type of treatment involves the systemic delivery of thiazolidinediones. However, based on the clinical data suggesting a direct modulatory effect or function in the vasculature, thiazolidinediones may be delivered locally at much lower doses for the treatment of vascular disease, including restenosis and vulnerable plaque.

The systemic toxicities of thiazolidinediones associated with large and repeated doses may be obviated by the local application at low doses.

In this exemplary embodiment, an implantable medical device such as a stent may be utilized to deliver thiazolidinediones directly to a localized area in proximity to the stent or other implantable medical device. Preferably, the thiazolidinediones may be delivered in combination with mTOR inhibitors, such as rapamycins. Rapamycins, as described herein in detail, may be utilized to effectively treat restenosis. As described herein, rapamycins may be applied to stents or other implantable devices for local delivery. The rapamycins may be affixed to the stents in any number of ways, including being directly applied to the stents, encased in reservoirs or mixed in polymers and then applied to the stents. Also as described herein, the rapamycins may be combined with one or more other agents that work through the same or different mechanisms to achieve a synergistic effect.

The local delivery of thiazolidinediones via a stent or other implantable medical device offers a number of advantages over systemic delivery. Potential systemic toxicity of thiazolidinediones may be eliminated by direct local administration of low sustained doses from a stent while maintaining therapeutic benefit. In addition, thiazolidinediones have been shown to inhibit neointimal formation by inhibiting the cell cycle at the G1-S phase in vascular smooth muscle cells, to inhibit metalloprotease (MMP) production, particularly MMP-9 that may cause vulnerable plaque erosion, to improve micro vascular blood flow, to reduce inflammation by inhibiting adhesion molecule upregulation, to upregulate nitric oxide production in endothelial cells and directly increases adiponectin production by fat cells which improves insulin effects. Accordingly, the combination of mTOR inhibitors with thiazolidinediones for local delivery would provide a synergistic effect in the treatment of vascular disease in type 2 diabetic patients.

In this exemplary embodiment, the delivery mechanism for the two therapeutic agents should preferably be designed to release the two therapeutic agents over different periods of time. In a preferred exemplary embodiment, a substantial portion of the mTOR inhibitor is configured to be released over a period of time of less than or equal to sixty days for the reasons described herein. The release duration or profile may be controlled in any number of ways, including those set forth herein, for example, agent concentration and/or polymer construct, including the use of topcoats and incompatible polymers as described herein. In one exemplary embodiment, a polymeric vehicle may be designed to release the mTOR inhibitor through the elution of the mTOR inhibitor through the polymeric material comprising the vehicle. In another alternate exemplary embodiment a biodegradable polymeric vehicle may be utilized. In this exemplary embodiment, the mTOR inhibitor is released as the polymeric material degrades. In yet another alternate exemplary embodiment, a topcoat comprising the same or different polymeric material may be utilized to achieve the desired elution rate.

As the thiazolidinediones work differently than the mTOR inhibitors, their myriad therapeutic effects may be best utilized by designing an optimal release duration and release rate in the vascular tissues. For instance, the release rate of the thiazolidinediones may be advantageously designed to be different than that of the mTOR inhibitor. Given that the thiazolidinediones work by modulating both cellular functions and cellular metabolism, the thiazolidinediones will be beneficial for treatment of both the acute and chronic phases of vascular disease. Accordingly, the release duration or release rate of the thiazolidinediones should be greater than sixty days, and more preferably greater than ninety days and even more preferably grater than one hundred eighty days. It is preferable that a substantial amount of the thiazolidinediones remains on the device for as long as possible to treat the chronic phase as well as the acute phase of the vascular disease. Once again, this release rate may be achieved in any number of ways including drug concentration and polymeric material constructs. For example, the thiazolidinediones and the mTOR inhibitor may be incorporated into different layers of the same polymeric material or into different polymers that are layered onto one another. In yet another alternate exemplary embodiment, one or more additional therapeutic agents may be affixed onto the device as an additional barrier for drug elution. For example, heparin or other antithrombotic agents may be utilized as a control mechanism and for its therapeutic effect. The various polymers and agents described herein may be utilized to create a release construct that will allow the desired release profiles. In yet another alternate exemplary embodiment, a topcoat comprising the same or different polymeric material may be utilized to achieve the desired elution rate. Alternately, incompatible polymers may be utilized to provide a means for controlling the elution rate via chemical and physical barriers as described in detail herein.

Figure 94:
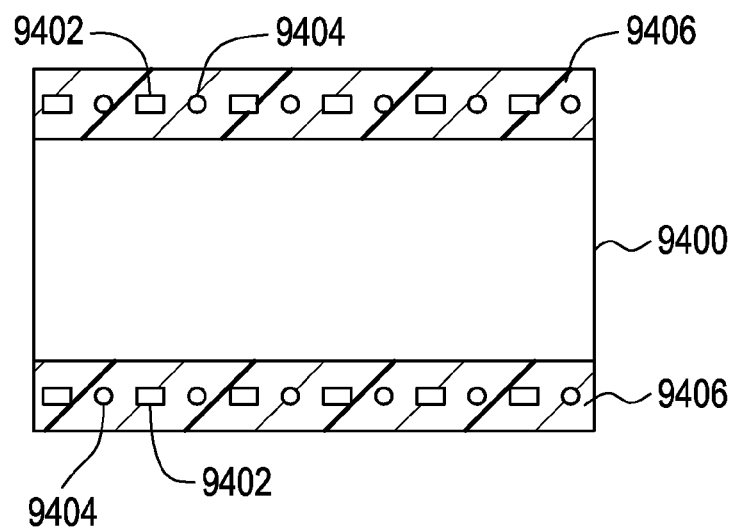
FIG. 94 is a cross-sectional view of a band of a stent in FIG. 1 having drug coatings for treating vascular disease in type 2 diabetic patients in accordance with a first exemplary embodiment of the invention.
Figure 95:
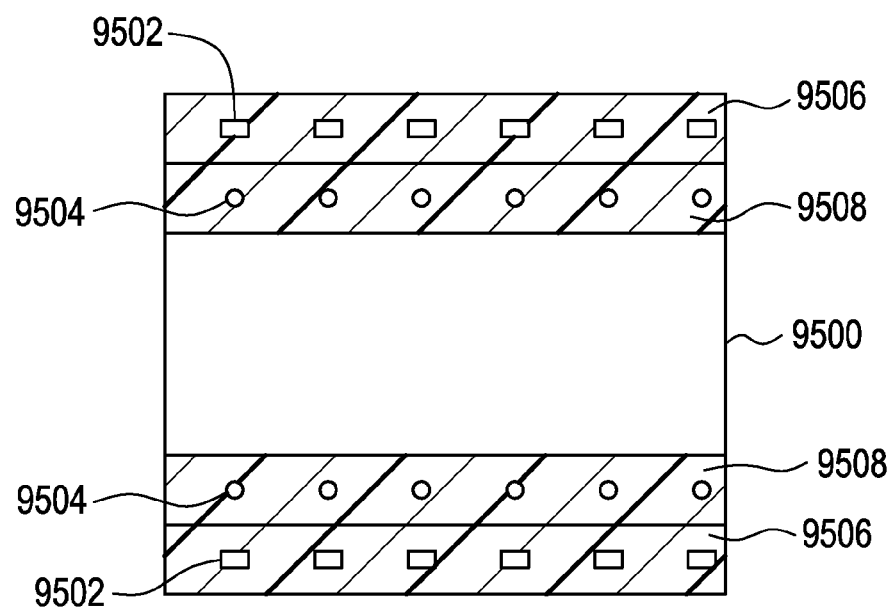
FIG. 95 is a cross-sectional view of a band of a stent in FIG. 1 having drug coatings for treating vascular disease in type 2 diabetic patients in accordance with a second exemplary embodiment of the invention.
Figure 96:
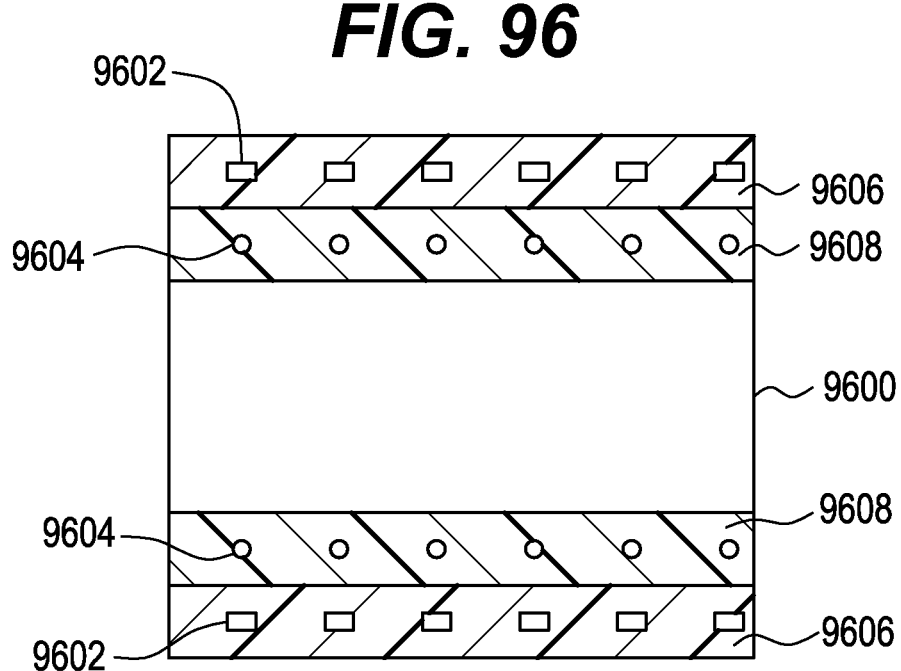
FIG. 96 is a cross-sectional view of a band of a stent in FIG. 1 having drug coatings for treating vascular disease in type 2 diabetic patients in accordance with a third exemplary embodiment of the invention.
Figure 97:
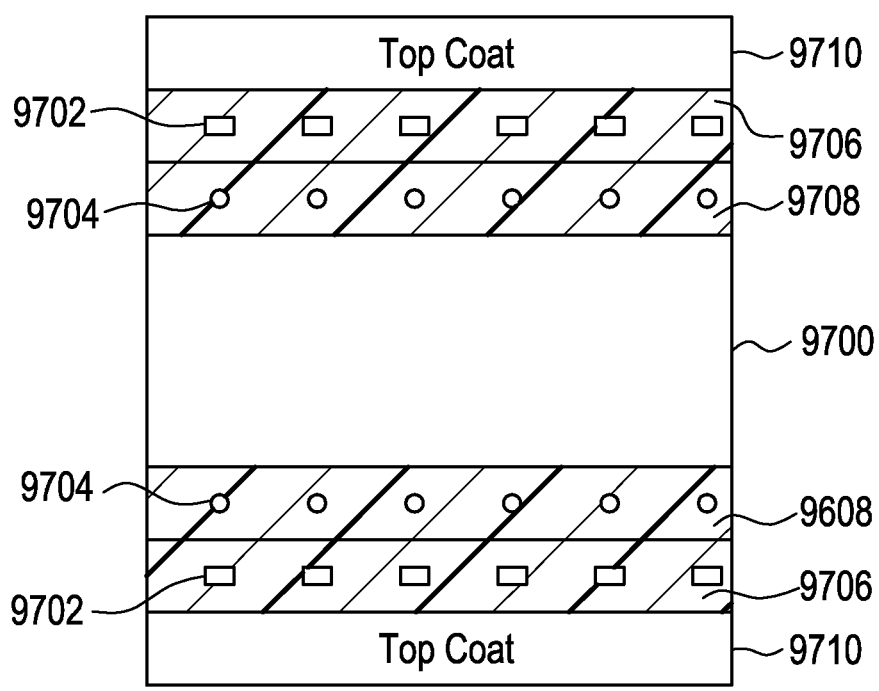
FIG. 97 is a cross-sectional view of a band of a stent in FIG. 1 having drug coatings for treating vascular disease in type 2 diabetic patients in accordance with a fourth exemplary embodiment of the invention.
Figure 98:
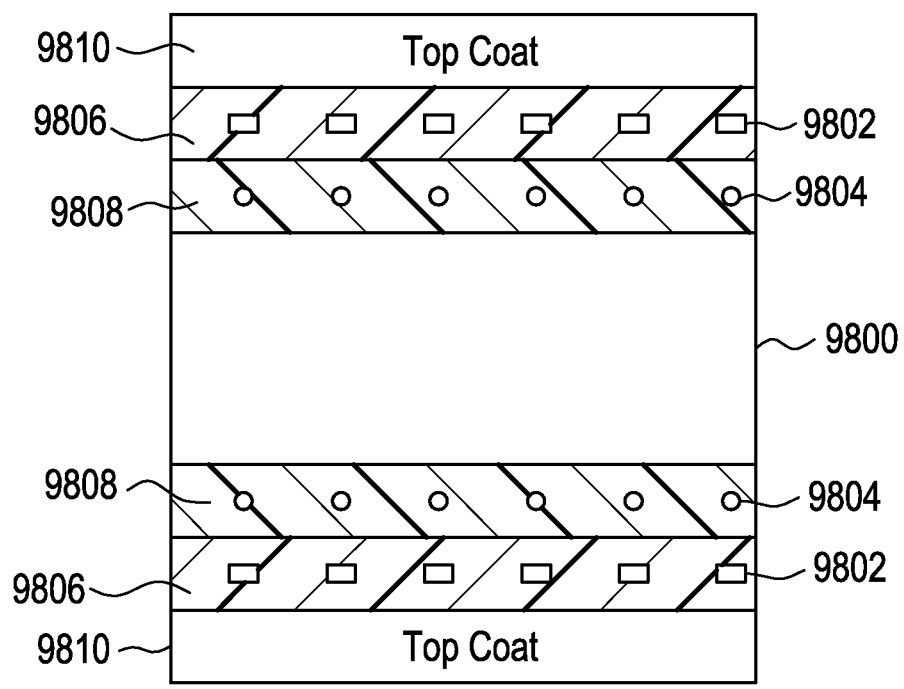
FIG. 98 is a cross-sectional view of a band of a stent in FIG. 1 having drug coatings for treating vascular disease in type 2 diabetic patients in accordance with a fifth exemplary embodiment of the invention.

FIGS. 94 through 98 illustrate some basic exemplary delivery constructs. For example, FIG. 94 illustrates the mTOR inhibitor 9402 and the thiazolidinedione 9404 mixed in the same polymeric material in a single layer 9406 and affixed to a stent 9400 or other medical device via the methods and materials described herein. FIG. 95 illustrates the mTOR inhibitor 9502 and the thiazolidinedione 9504 in the same polymeric material but in different layers 9506 and 9508 and affixed to a stent 9500 or other medical device via the methods and materials described herein. In this exemplary embodiment, the thiazolidinedione 9504 is positioned in the inner layer 9508, which is below the outer layer 9506 comprising the mTOR inhibitor 9502 so as to potentially aid in controlling the elution rate of the thiazolidinedione 9504. FIG. 96 illustrates the mTOR inhibitor 9602 and the thiazolidinedione 9604 in different layers 9606 and 9608, with each layer comprising a different polymeric material, and affixed to a stent 9600 or other medical device via the methods and materials described herein. Once again, the mTOR inhibiting containing layer 9606 is the outer layer thereby potentially aiding in the control of the elution of the thiazolidinedione 9604 from the inner layer 9608. FIG. 97 illustrates the mTOR inhibitor 9702 and the thiazolidinedione 9704 in the same polymeric material but in different layers 9706 and 9708 with a top coat 9710 of one or more additional agents or another polymeric material and affixed to a stent 9700 or other medical device via the methods and materials described herein. The topcoat 9710 may serve any number of functions, including elution control, drug protection, deliverability and/or therapeutic benefit. The topcoat 9710 may comprise any biocompatible material or therapeutic agent. FIG. 98 illustrates the mTOR inhibitor 9802 and the thiazolidinedione 9804 in different layers 9806 and 9808 comprising different polymers with a top coat of one or more additional agents or another polymeric material 9810 and affixed to a stent 9800 or other medical device via the methods and materials described herein. It is important to note that the figures are only exemplary representations of the numerous configurations possible.

The design of a coated implantable medical device that elutes a therapeutic drug, agent and/or compound requires the balancing of a number of design factors. For example, the addition of a coating to an implantable medical device alters the profile of the device, which in turn may have an impact on device delivery. More specifically, the addition of a coating on a stent increases the diameter of the stent, which in turn may make delivery more difficult. Accordingly, it may be preferable to minimize the thickness of the coating while increasing the concentration of the therapeutic drug, agent and/or compound. Increasing the concentration of the therapeutic drug, agent and/or compound may increase its elution rate into the surrounding tissue or bloodstream. Increasing the elution rate may in turn deplete the drug, agent and/or compound prematurely. Accordingly, utilizing the various designs disclosed herein, a balance resulting in the proper therapeutic release profile may be achieved. The above-mentioned principles also apply to the design of a medical device that elutes multiple drugs, including the combination of a thiazolidinedione compound and an mTOR inhibitor. In addition, there are more factors to be considered in the design of such a combination drug device such as potential drug-drug interactions, drug stability in the device, etc.

The particular polymer(s) utilized depends on the particular material upon which it is affixed. In addition, the particular drug, agent and/or compound may also affect the selection of polymer(s).

The concentration of the mTOR inhibitor, sirolimus, is described in detail herein. Typically, for a standard eighteen-millimeter length stent, the amount of the sirolimus is in the range from about fifty to about one hundred fifty micrograms. For the thiazolidinedione, the desired loading amount for the standard eighteen-millimeter length stent is in the range from fifty to about 1 milligram. Greater amounts may be utilized depending on a number of factors, including the overall size of the device and deliverability of the device. In addition, greater amounts may be locally delivered through other means such as perfusion catheters as described herein.

The stent may comprise any suitable scaffold structure, including balloon expandable stents, constructed from stainless steel or other metal alloys such as cobalt-chromium alloys, and/or self-expanding stents, constructed from nitinol or other shape memory metal alloys. Alternately, the stent may be made from a biodegradable magnesium or iron based metal alloy. Alternately, the stent may be made from non-metallic materials, such as ceramics and/or polymers, which may be biodegradable. The biodegradable stent would serve as a temporary scaffold and eventually dissolve over a period of time raging from days or weeks to months and years. The stent would be mounted on a delivery catheter and delivered percutaneously through the lumen of a blood vessel to the diseased site. In addition, the stent may be constructed with a plurality of through holes in which one or more therapeutic agents or combinations thereof may be loaded. Accordingly, an exemplary embodiment of such a stent is described below.

Figure 99:
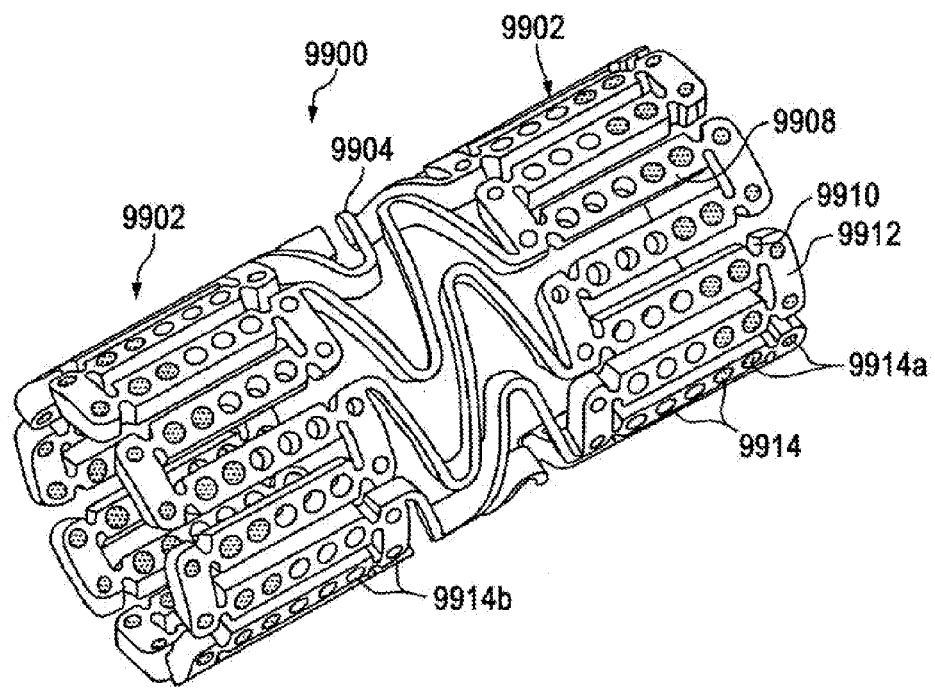
FIG. 99 is an isometric view of an expandable medical device with a beneficial agent at the ends in accordance with the present invention.

FIG. 99 illustrates an expandable medical device having a plurality of holes containing a beneficial agent for delivery to tissue by the expandable medical device. The expandable medical device 9900 illustrated in FIG. 99 is cut from a tube of material to form a cylindrical expandable device. The expandable medical device 9900 includes a plurality of cylindrical sections 9902 interconnected by a plurality of bridging elements 9904. The bridging elements 9904 allow the tissue supporting device to bend axially when passing through the torturous path of vasculature to a deployment site and allow the device to bend axially when necessary to match the curvature of a lumen to be supported. Each of the cylindrical tubes 9902 is formed by a network of elongated struts 9908 which are interconnected by ductile hinges 9910 and circumferential struts 9912. During expansion of the medical device 9900 the ductile hinges 9910 deform while the struts 9908 are not deformed. Further details of one example of the expandable medical device are described in U.S. Pat. No. 6,241,762 which is incorporated herein by reference in its entirety.

As illustrated in FIG. 99, the elongated struts 9908 and circumferential struts 9912 include openings 9914, some of which contain a beneficial agent for delivery to the lumen in which the expandable medical device is implanted. In addition, other portions of the device 9900, such as the bridging elements 9904, may include openings, as discussed below with respect to FIG. 103. Preferably, the openings 9914 are provided in non-deforming portions of the device 9900, such as the struts 9908, so that the openings are non-deforming and the beneficial agent is delivered without risk of being fractured, expelled, or otherwise damaged during expansion of the device. A further description of one example of the manner in which the beneficial agent may be loaded within the openings 9914 is described in U.S. patent application Ser. No. 09/948,987, filed Sep. 7, 2001, which is incorporated herein by reference in its entirety.

The exemplary embodiments of the present invention illustrated may be further refined by using Finite Element Analysis and other techniques to optimize the deployment of the beneficial agents within the openings 9914. Basically, the shape and location of the openings 9914, may be modified to maximize the volume of the voids while preserving the relatively high strength and rigidity of the struts with respect to the ductile hinges 9910. According to one preferred exemplary embodiment of the present invention, the openings have an area of at least $5 \times 10^{-6}$ square inches, and preferably at least $7 \times 10^{-6}$ square inches. Typically, the openings are filled about fifty percent to about ninety-five percent full of beneficial agent.

The various exemplary embodiments of the present invention described herein provide different beneficial agents in different openings in the expandable device or beneficial agent in some openings and not in others. The particular structure of the expandable medical device may be varied without departing from the spirit of the invention. Since each opening is filled independently, individual chemical compositions and pharmacokinetic properties may be imparted to the beneficial agent in each opening.

One example of the use of different beneficial agents in different openings in an expandable medical device or beneficial agents in some openings and not in others, is in addressing edge effect restenosis. As discussed above, current generation coated stents may have a problem with edge effect restenosis or restenosis occurring just beyond the edges of the stent and progressing around the stent and into the interior luminal space.

The causes of edge effect restenosis in first generation drug delivery stents are currently not well understood. It may be that the region of tissue injury due to angioplasty and/or stent implantation extends beyond the diffusion range of current generation beneficial agents such as paclitaxel and rapamycin, which tend to partition strongly in tissue. A similar phenomenon has been observed in radiation therapies in which low doses of radiation at the edges of stent have proven stimulatory in the presence of an injury. In this case, radiating over a longer length until uninjured tissue is irradiated solved the problem. In the case of drug delivery stents, placing higher doses or higher concentrations of beneficial agents along the stent edges, placing different agents at the stent edges which diffuse more readily through the tissue, or placing different beneficial agents or combinations of beneficial agents at the edges of the device may help to remedy the edge effect restenosis problem.

FIG. 99 illustrates an expandable medical device 9900 with "hot ends" or beneficial agent provided in the openings 9914a at the ends of the device in order to treat and reduce edge effect restenosis. The remaining openings 9914b in the central portion of the device may be empty (as shown) or may contain a lower concentration of beneficial agent.

Other mechanisms of edge effect restenosis may involve cytotoxicity of particular drugs or combinations of drugs. Such mechanisms could include a physical or mechanical contraction of tissue similar to that seen in epidermal scar tissue formation, and the stent might prevent the contractile response within its own boundaries, but not beyond its edges. Further, the mechanism of this latter form of restenosis may be related to sequelae of sustained or local drug delivery to the arterial wall that is manifest even after the drug itself is no longer present in the wall. That is, the restenosis may be a response to a form of noxious injury related to the drug and/or the drug carrier. In this situation, it might be beneficial to exclude certain agents from the edges of the device.

Figure 100:
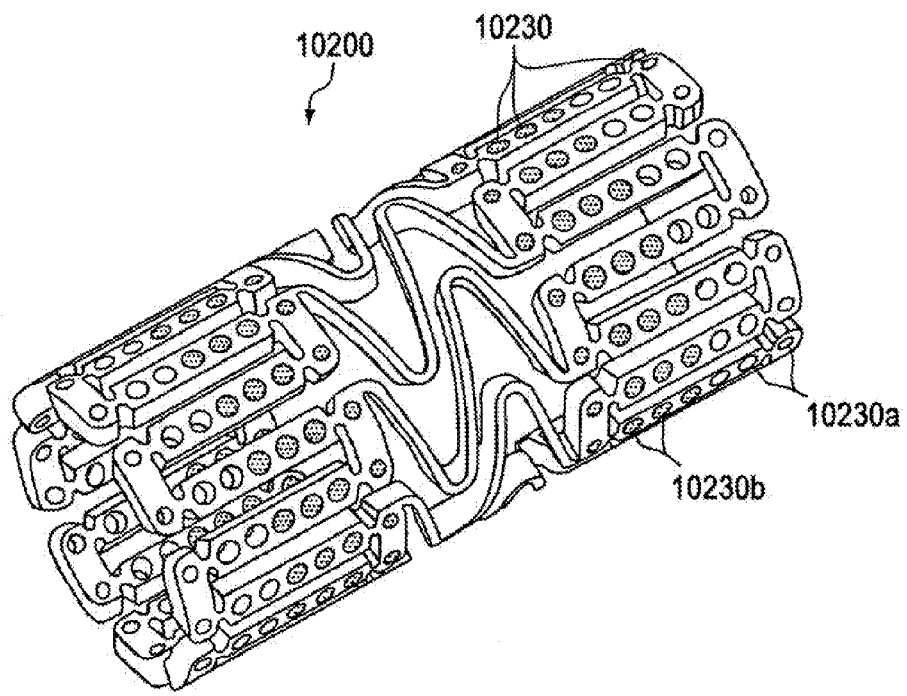
FIG. 100 is an isometric view of an expandable medical device with a beneficial agent at a central portion and no beneficial agent at the ends in accordance with the present invention.

FIG. 100 illustrates an alternate exemplary embodiment of an expandable medical device 10200 having a plurality of openings 10230 in which the openings 10230b in a central portion of the device are filled with a beneficial agent and the openings 10230a at the edges of the device remain empty. The device of FIG. 100 is referred to as having "cool ends."

In addition to use in reducing edge effect restenosis, the expandable medical device 10200 of FIG. 100 may be used in conjunction with the expandable medical device 9900 of FIG. 99 or another drug delivery stent when an initial stenting procedure has to be supplemented with an additional stent. For example, in some cases the device 9900 of FIG. 99 with "hot ends" or a device with uniform distribution of drug may be implanted improperly. If the physician determines that the device does not cover a sufficient portion of the lumen a supplemental device may be added at one end of the existing device and slightly overlapping the existing device. When the supplemental device is implanted, the device 10200 of FIG. 2 is used so that the "cool ends" of the medical device 10200 prevent double-dosing of the beneficial agent at the overlapping portions of the devices 9900, 10200.

Figure 101:
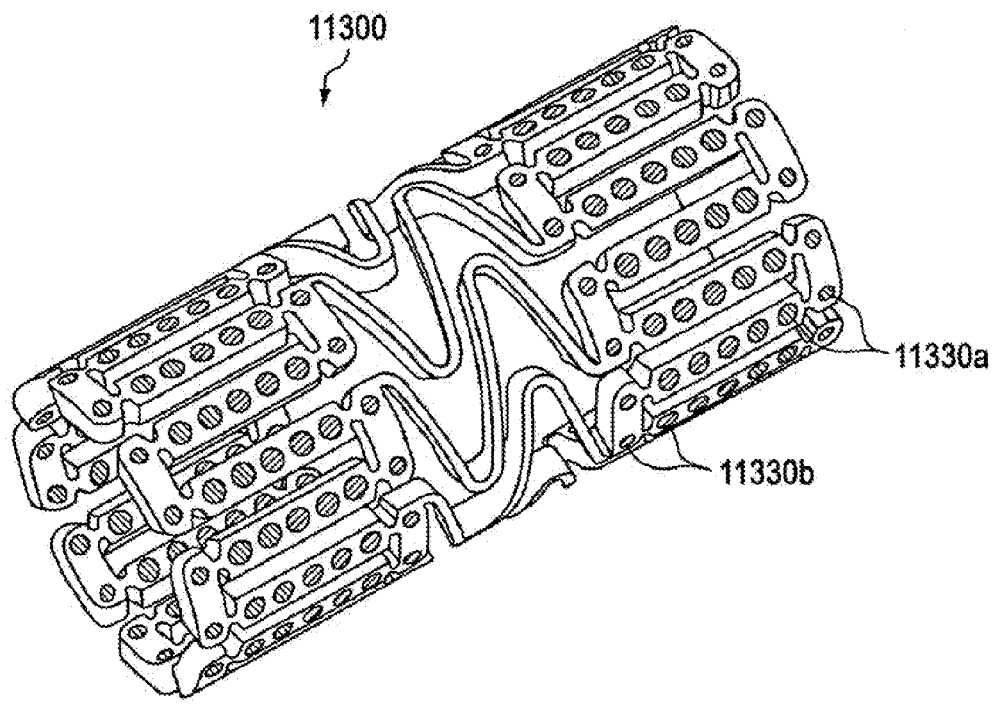
FIG. 101 is an isometric view of an expandable medical device with different beneficial agents in different holes in accordance with the present invention.

FIG. 101 illustrates a further alternate exemplary embodiment of the invention in which different beneficial agents are positioned in different holes of an expandable medical device 11300. A first beneficial agent is provided in holes 11330a at the ends of the device and a second beneficial agent is provided in holes 11330b at a central portion of the device. The beneficial agent may contain different drugs, the same drugs in different concentrations, or different variations of the same drug. The exemplary embodiment of FIG. 101 may be used to provide an expandable medical device 11300 with either "hot ends" or "cool ends."

Preferably, each end portion of the device 11300 which includes the holes 11330a comprising the first beneficial agent extends at least one hole and up to about fifteen holes from the edge. This distance corresponds to about 0.005 to about 0.1 inches from the edge of an unexpanded device. The distance from the edge of the device 11300 which includes the first beneficial agent is preferably about one section, where a section is defined between the bridging elements.

Different beneficial agents comprising different drugs may be disposed in different openings in the stent. This allows the delivery of two or more beneficial agents from a single stent in any desired delivery pattern. Alternately, different beneficial agents comprising the same drug in different concentrations may be disposed in different openings. This allows the drug to be uniformly distributed to the tissue with a non-uniform device structure.

The two or more different beneficial agents provided in the devices described herein may comprise (1) different drugs; (2) different concentrations of the same drug; (3) the same drug with different release kinetics, i.e., different matrix erosion rates; or (4) different forms of the same drug. Examples of different beneficial agents formulated comprising the same drug with different release kinetics may use different carriers to achieve the elution profiles of different shapes. Some examples of different forms of the same drug include forms of a drug having varying hydrophilicity or lipophilicity.

In one example of the device 11300 of FIG. 101, the holes 11330a at the ends of the device are loaded with a first beneficial agent comprising a drug with a high lipophilicity while holes 11330b at a central portion of the device are loaded with a second beneficial agent comprising the drug with a lower lipophilicity. The first high lipophilicity beneficial agent at the "hot ends" will diffuse more readily into the surrounding tissue reducing the edge effect restenosis.

The device 11300 may have an abrupt transition line at which the beneficial agent changes from a first agent to a second agent. For example, all openings within 0.05 inches of the end of the device may comprise the first agent while the remaining openings comprise the second agent. Alternatively, the device may have a gradual transition between the first agent and the second agent. For example, a concentration of the drug in the openings may progressively increase (or decrease) toward the ends of the device. In another example, an amount of a first drug in the openings increases while an amount of a second drug in the openings decreases moving toward the ends of the device.

Figure 102:
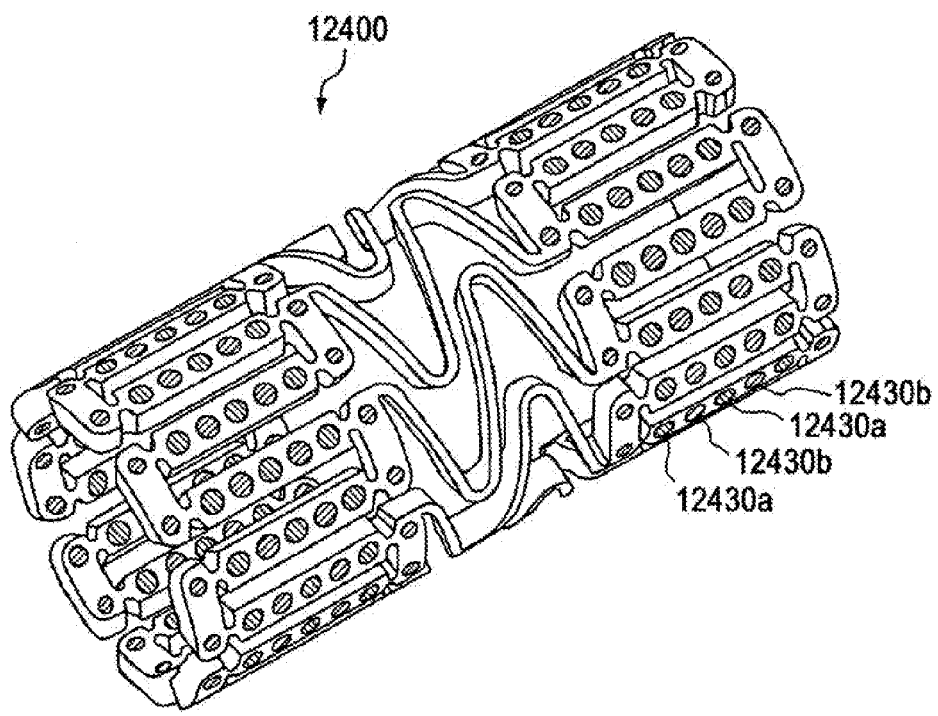
FIG. 102 is an isometric view of an expandable medical device with different beneficial agents in alternating holes in accordance with the present invention.

FIG. 102 illustrates a further alternate exemplary embodiment of an expandable medical device 12400 in which different beneficial agents are positioned in different openings 12430a, 12430b in the device in an alternating or interspersed manner. In this manner, multiple beneficial agents may be delivered to tissue over the entire area or a portion of the area supported by the device. This exemplary embodiment will be useful for delivery of multiple beneficial agents where combination of the multiple agents into a single composition for loading in the device is not possible due to interactions or stability problems between the beneficial agents.

In addition to the use of different beneficial agents in different openings to achieve different drug concentrations at different defined areas of tissue, the loading of different beneficial agents in different openings may be used to provide a more even spatial distribution of the beneficial agent delivered in instances where the expandable medical device has a non-uniform distribution of openings in the expanded configuration.

The use of different drugs in different openings in an interspersed or alternating manner allows the delivery of two different drugs which may not be deliverable if combined within the same polymer/drug matrix composition. For example, the drugs themselves may interact in an undesirable way. Alternatively, the two drugs may not be compatible with the same polymers for formation of the matrix or with the same solvents for delivery of the polymer/drug matrix into the openings.

Further, the exemplary embodiment of FIG. 102 having different drugs in different openings in an interspersed arrangement provide the ability to deliver different drugs with very different desired release kinetics from the same medical device or stent and to optimize the release kinetic depending on the mechanism of action and properties of the individual agents. For example, the water solubility of an agent greatly affects the release of the agent from a polymer or other matrix. A highly water soluble compound will generally be delivered very quickly from a polymer matrix, whereas, a lipophilic agent will be delivered over a longer time period from the same matrix. Thus, if a hydrophilic agent and a lipophilic agent are to be delivered as a dual drug combination from a medical device, it is difficult to achieve a desired release profile for these two agents delivered from the same polymer matrix.

The system of FIG. 102 allows the delivery of a hydrophilic and a lipophilic drug easily from the same stent. Further, the system of FIG. 102 allows the delivery two agents at two different release kinetics and/or administration periods. Each of the initial release in the first twenty-four hours, the release rate following the first twenty-four hours, the total administration period and any other characteristics of the release of the two drugs may be independently controlled. For example the release rate of the first beneficial agent can be arranged to be delivered with at least forty percent (preferably at least fifty percent) of the drug delivered in the first twenty-four hours and the second beneficial agent may be arranged to be delivered with less than twenty percent (preferably less than ten percent) of the drug delivered in the first twenty-four hours. The administration period of the first beneficial agent may be about three weeks or less (preferably two weeks or less) and the administration period of the second beneficial agent may be about four weeks or more.

Restenosis or the recurrence of occlusion post-intervention, involves a combination or series of biological processes. These processes include the activation of platelets and macrophages. Cytokines and growth factors contribute to smooth muscle cell proliferation and upregulation of genes and metalloproteinases lead to cell growth, remodeling of extracellular matrix, and smooth muscle cell migration. A drug therapy which addresses a plurality of these processes by a combination of drugs may be the most successfully antirestenotic therapy. The present invention provides a means to achieve such a successful combination drug therapy.

The examples discussed below illustrate some of the combined drug systems which benefit from the ability to release different drugs in different holes or openings. One example of a beneficial system for delivering two drugs from interspersed or alternating holes is the delivery of an anti-inflammatory agent or an immunosuppressant agent in combination with an antiproliferative agent or an antimigratory agent. Other combinations of these agents may also be used to target multiple biological processes involved in restenosis. The anti-inflammatory agent mitigates the initial inflammatory response of the vessel to the angioplasty and stenting and is delivered at a high rate initially followed by a slower delivery over a time period of about two weeks to match the peak in the development of macrophages which stimulate the inflammatory response. The antiproliferative agent is delivered at a relatively even rate over a longer time period to reduce smooth muscle cell migration and proliferation.

In addition to the examples that are be given below, the following chart illustrates some of the useful two drug combination therapies which may be achieved by placing the drugs into different openings in the medical device.

|  | PTX | 2-Cda | Epothilone D | Imatinibmesylate Gleevec | Rapamycin analog | Pimecrolimus |
|---|---|---|---|---|---|---|
| PTX | x |  |  | x |  | x |
| 2-CdA |  | x | x | x | x | x |
| Epothilone D |  |  |  | x |  |  |
| Imatinibmesylate Gleevec |  |  |  |  | x | x |
| Rapamycin analog |  |  |  |  |  |  |
| Pimecrolimus |  |  |  |  |  |  |
| PKC-412 |  |  |  |  |  |  |
| Dexamethasone |  |  |  |  |  |  |
| Farglitazar |  |  |  |  |  |  |
| Insulin |  |  |  |  |  |  |
| VIP |  |  |  |  |  |  |
| ApoA-I milano |  |  |  |  |  |  |

|  | PKC-412 | Dexamethasone | Farglitazar | Insulin | VIP | ApoA-I milano |
|---|---|---|---|---|---|---|
| PTX | x | x |  | x | x | x |
| 2-CdA | x |  | s |  |  |  |
| Epothilone D | x | x |  | x | x | x |
| Imatinibmesylate Gleevec | x | x |  |  |  |  |
| Rapamycin analog | x | x |  | x | x | x |
| Pimecrolimus | x | x |  | x | x | x |
| PKC-412 |  | x |  | x | x | x |
| Dexamethasone |  |  |  |  | x | x |
| Farglitazar |  |  |  |  | x | x |
| Insulin |  |  |  |  | x |  |
| VIP |  |  |  |  |  | x |
| ApoA-I milano |  |  |  |  |  |  |

The placement of the drugs in different openings allows the release kinetics to be tailored to the particular agent regardless of the hydrophobicity or lipophobicity of the drug. Examples of some arrangements for delivery of a lipophilic drug at a substantially constant or linear release rate are described in WO 04/110302 published on Dec. 23, 2004, which is incorporated herein by reference in its entirety. Examples of some of the arrangements for delivery of hydrophilic drug are described in WO 04/043510, published on May 27, 2004 which is incorporated herein by reference in its entirety. The hydrophilic drugs listed above include CdA, Gleevec, VIP, insulin, and ApoA-1 milano. The lipophilic drugs listed above include paclitaxel, Epothilone D, rapamycin, pimecrolimus, PKC-412 and Dexamethazone. Farglitazar is partly liphophillic and partly hydrophilic.

In addition to the delivery of multiple of drugs to address different biological processes involved in restenosis, the present invention may deliver two different drugs for treatment of different diseases from the same stent. For example, a stent may deliver an anti-proliferative, such as paclitaxel or a limus drug from one set of openings for treatment of restenosis while delivering a myocardial preservative drug, such as insulin, from other openings for the treatment of acute myocardial infarction.

Figure 103:
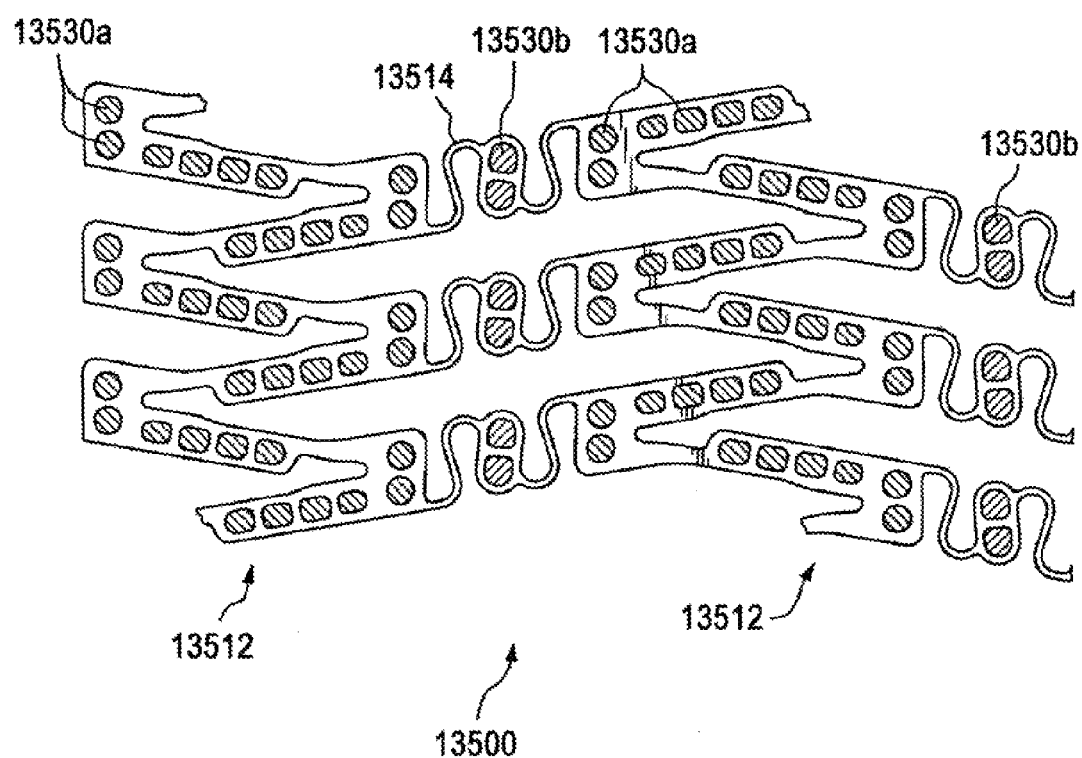
FIG. 103 is an enlarged side view of a portion of an expandable medical device with beneficial agent openings in the bridging elements in accordance with the present invention.

In many of the known expandable devices and for the device illustrated in FIG. 103 the coverage of the device 13500 is greater at the cylindrical tube portions 13512 of the device than at the bridging elements 13514. Coverage is defined as the ratio of the device surface area to the area of the lumen in which the device is deployed. When a device with varying coverage is used to deliver a beneficial agent contained in openings in the device, the beneficial agent concentration delivered to the tissue adjacent the cylindrical tube portions 13512 is greater that the beneficial agent delivered to the tissue adjacent the bridging elements 13514. In order to address this longitudinal variation in device structure and other variations in device coverage which lead to uneven beneficial agent delivery concentrations, the concentration of the beneficial agent may be varied in the openings at portions of the device to achieve a more even distribution of the beneficial agent throughout the tissue. In the case of the exemplary embodiment illustrated in FIG. 103, the openings 13530*a* in the tube portions 13512 include a beneficial agent with a lower drug concentration than the openings 13530*b* in the bridging elements 13514. The uniformity of agent delivery may be achieved in a variety of manners including varying the drug concentration, the opening diameter or shape, the amount of agent in the opening (i.e., the percentage of the opening filed), the matrix material, or the form of the drug.

Figure 104:
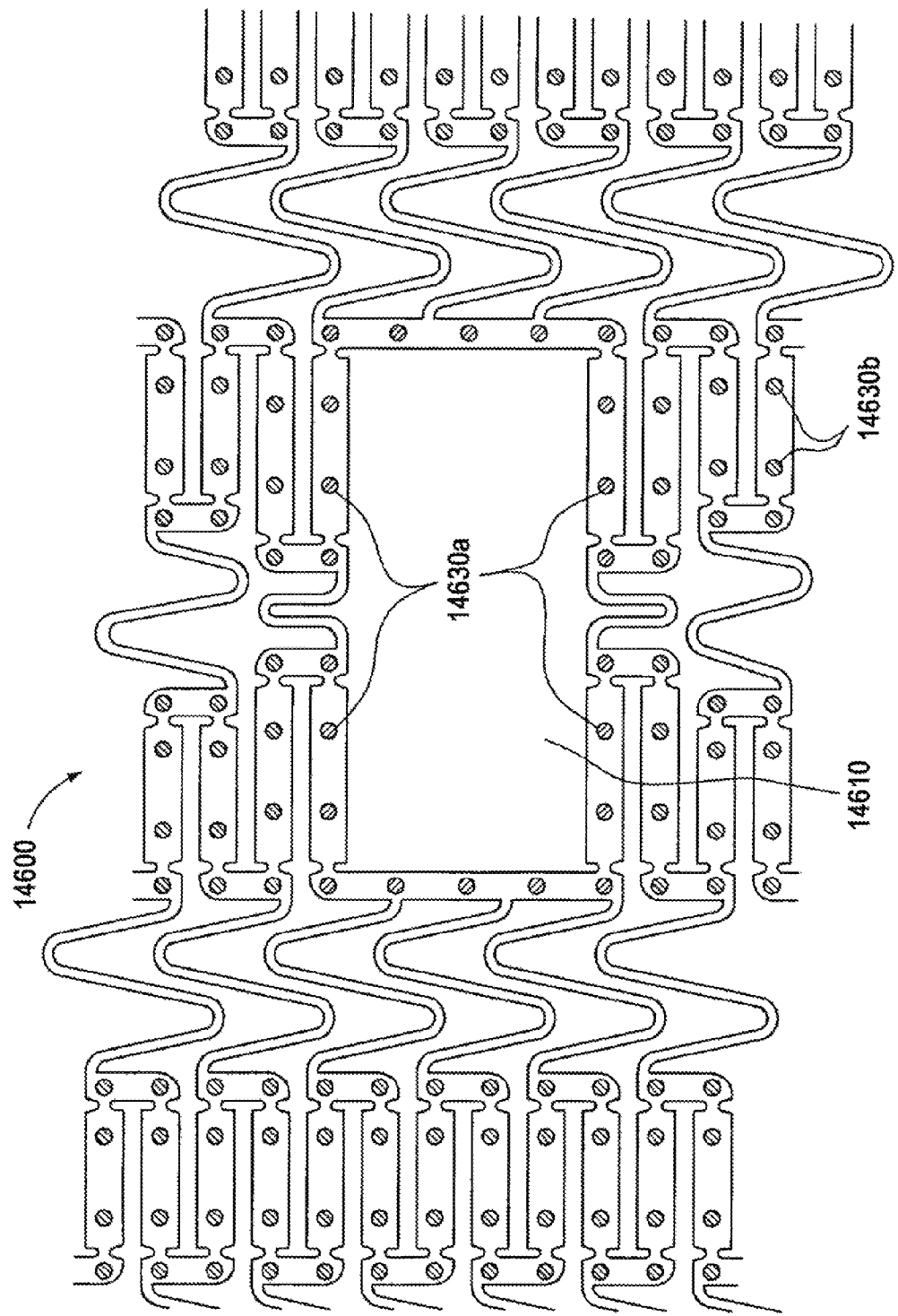
FIG. 104 is an enlarged side view of a portion of an expandable medical device with a bifurcation opening in accordance with the present invention.

Another example of an application for the use of different beneficial agents in different openings is in an expandable medical device 14600, as illustrated in FIG. 104, configured for use at a bifurcation in a vessel. Bifurcation devices include a side hole 14610 which is positioned to allow blood flow through a side branch of a vessel. One example of a bifurcation device is described in U.S. Pat. No. 6,293,967 which is incorporated herein by reference in its entirety. The bifurcation device 14600 includes the side hole feature 14610 interrupting the regular pattern of beams which form a remainder of the device. Since an area around a bifurcation is a particularly problematic area for restenosis, a concentration of an antiproliferative drug may be increased in openings 14630*a* at an area surrounding the side hole 14610 of the device 14600 to deliver increased concentrations of the drug where needed. The remaining openings 14630*b* in an area away from the side opening contain a beneficial agent with a lower concentration of the antiproliferative. The increased antiproliferative delivered to the region surrounding the bifurcation hole may be provided by a different beneficial agent containing a different drug or a different beneficial agent containing a higher concentration of the same drug.

In addition to the delivery of different beneficial agents to the mural or abluminal side of the expandable medical device for treatment of the vessel wall, beneficial agents may be delivered to the luminal side of the expandable medical device to prevent or reduce thrombosis. Drugs which are delivered into the blood stream from the luminal side of the device may be located at a proximal end of the device or a distal end of the device.

The methods for loading different beneficial agents into different openings in an expandable medical device may include known techniques such as dipping and coating and also known piezoelectric micro-jetting techniques. Micro-injection devices may be computer controlled to deliver precise amounts of two or more liquid beneficial agents to precise locations on the expandable medical device in a known manner. For example, a dual agent jetting device may deliver two agents simultaneously or sequentially into the openings. When the beneficial agents are loaded into through openings in the expandable medical device, a luminal side of the through openings may be blocked during loading by a resilient mandrel allowing the beneficial agents to be delivered in liquid form, such as with a solvent. The beneficial agents may also be loaded by manual injection devices.

Example 8

Figure 105:
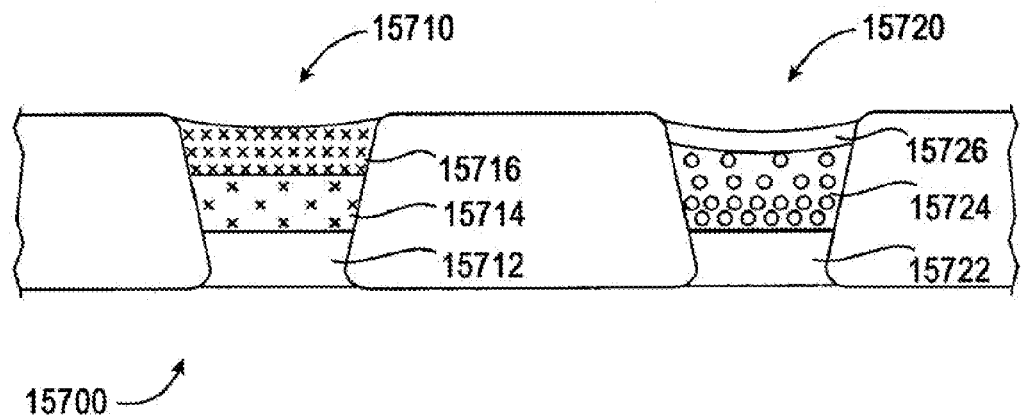
FIG. 105 is a cross sectional view of an expandable medical device having a combination of a first agent, such as an anti-inflammatory agent, in a first plurality of holes and a second agent, such as an anti-proliferative agent, in a second plurality of holes in accordance with the present invention.

FIG. 105 illustrates a dual drug stent 15700 having an anti-inflammatory agent and an antiproliferative agent delivered from different holes in the stent to provide independent release kinetics of the two drugs which are specifically programmed to match the biological processes of restenosis. According to this example, the dual drug stent includes an anti-inflammatory agent pimecrolimus in a first set of openings 15710 in combination with the antiproliferative agent paclitaxel in a second set of openings 15720. Each agent is provided in a matrix material within the holes of the stent in a specific inlay arrangement designed to achieve the release kinetics illustrated in FIG. 106. Each of the drugs are delivered primarily murally for treatment of restenosis.

As illustrated in FIG. 105, pimecrolimus is provided in the stent for directional delivery to the mural side of the stent by the use of a barrier 15712 at the luminal side of the hole. The barrier 15712 is formed by a biodegradable polymer. The pimecrolimus is loaded within the holes in a manner which creates a release kinetics having dual phases. A first phase of the release of pimecrolimus is provided by a murally located region 15716 of the matrix which has a fast release formulation including pimecrolimus and biodegradable polymer (PLGA) with a high percentage of drug, such as about ninety percent drug to about ten percent polymer. A second phase of the release is provided by a central region 15714 of the matrix with pimecrolimus and biodegradable polymer (PLGA) in a ratio of about fifty percent drug to fifty percent polymer. As may be seen on the graph of FIG. 106, the first phase of the pimecrolimus release delivers about fifty percent of the loaded drug in about the first swenty-four hours. The second phase of the release delivers the remaining fifty percent over about two weeks. This release is specifically programmed to match the progression of the inflammatory process following angioplasty and stenting. In addition to or as an alternative to changing the drug concentration between the two regions to achieve the two phase release, different polymers or different comonomer ratios of the same polymer may be used in two drug different regions to achieve the two different release rates.

Figure 106:
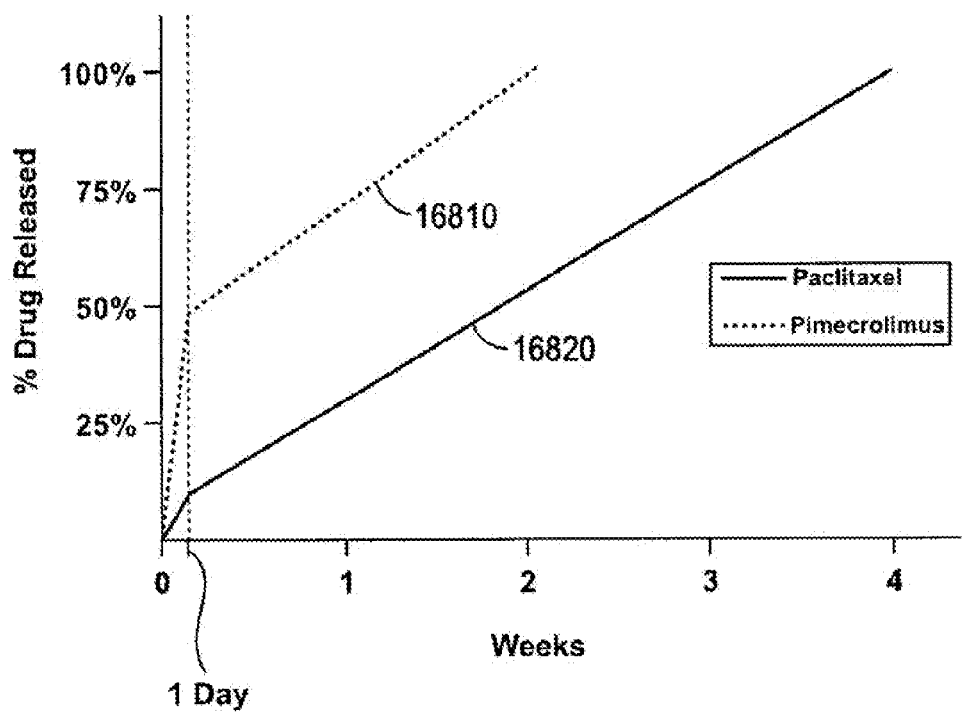
FIG. 106 is a graph of the release rates of one example of an anti-inflammatory and an anti-proliferative delivered by the expandable medical device of FIG. 105 in accordance with the present invention.

The paclitaxel is loaded within the openings 15720 in a manner which creates a release kinetic having a substantially linear release after the first approximately twenty-four hours, as illustrated in FIG. 106. The paclitaxel openings 15720 are loaded with three regions including a base region 15722 of primarily polymer with minimal drug at a luminal side of the hole, a central region 15724 with paclitaxel and polymer (PLGA) provided in a concentration gradient, and a cap region 15726 with primarily polymer which controls release of the paclitaxel. The paclitaxel is released with an initial release in the first day of about five to about fifteen percent of the total drug load followed by a substantially linear release for about twenty to ninety days. Additional examples of arrangements for paclitaxel in the holes with a concentration gradient are described in WO 04/110302 set forth above.

FIG. 105 illustrates the drug, barrier, and cap regions as distinct regions within the openings for ease of illustration. It should be understood that these regions indistinct and formed by a blending of the different areas. Thus, although the barrier layers are primarily polymer without drug, depending on the manufacturing processes employed, some small amount of drug of the subsequent region can be incorporation into the barrier region.

The amount of the drugs delivered varies depending on the size of the stent. For a three mm by six mm stent the amount of pimecrolimus is about fifty to about three micrograms preferably about one hundred to about two hundred fifty micrograms. The amount of paclitaxel delivered from this stent is about five to about fifty micrograms preferably about ten to about thirty micrograms. In one example, about two hundred micrograms of pimecrolimus and about twenty micrograms of paclitaxel are delivered. The drugs may be located in alternating holes in the stent. However, in view of the large difference in the doses to be delivered between the two drugs, it may be desirable to place the paclitaxel in every third of fourth hole in the stent. Alternatively, the holes for delivery of the low dose drug (paclitaxel) may be made smaller than the holes for the high dose.

The polymer/drug inlays are formed by computer controlled piezoelectric injection techniques as described in WO 04/026182 published on Apr. 1, 2004, which is incorporated herein by reference in its entirety. The inlays of the first agent may be formed first followed by the inlays of the second agent using the piezoelectric injector. Alternatively, the system of WO 04/02182 may be equipped with dual piezoelectric dispensers for dispensing the two agents at the same time.

Example 9

According to this example, the dual drug stent includes the Gleevec in the first set of openings 15710 in combination with the antiproliferative agent paclitaxel in the second set of openings 15720. Each agent is provided in a matrix material within the holes of the stent in a specific inlay arrangement designed to achieve the release kinetics illustrated in FIG. 106.

The Gleevec is delivered with a two phase release including a high initial release in the first day and then a slow release for one to two weeks. The first phase of the Gleevec release delivers about fifty percent of the loaded drug in about the first twenty-four hours. The second phase of the release delivers the remaining fifty percent over about one-two weeks. The paclitaxel is loaded within the openings 15720 in a manner which creates a release kinetics having a substantially linear release after the first approximately twenty-four hours, as illustrated in FIG. 106 and as described above in Example 8.

The amount of the drugs delivered varies depending on the size of the stent. For a three mm by six mm stent the amount of Gleevec is about two hundred to about five hundred micrograms, preferably about three hundred to about four hundred micrograms. The amount of paclitaxel delivered from this stent is about five to about fifty micrograms, preferably about ten to about thirty micrograms. As in Example 8, the drugs may be located in alternating holes in the stent or interspersed in a non-alternating manner. The polymer/drug inlays are formed in the manner described in Example 8.

Example 10

According to this example, the dual drug stent includes the PKC-412 (a cell growth regulator) in the first set of openings in combination with the antiproliferative agent paclitaxel in the second set of openings. Each agent is provided in a matrix material within the holes of the stent in a specific inlay arrangement designed to achieve the release kinetics discussed below.

The PKC-412 is delivered at a substantially constant release rate after the first approximately twenty-four hours, with the release over a period of about four to sixteen weeks, preferably about six to twelve weeks. The paclitaxel is loaded within the openings in a manner which creates a release kinetic having a substantially linear release after the first approximately twenty-four hours, with the release over a period of about four to sixteen weeks, preferably about six to twelve weeks.

The amount of the drugs delivered varies depending on the size of the stent. For a three mm by six mm stent the amount of PKC-412 is about one hundred to about four hundred micrograms, preferably about one hundred fifty to about two hundred fifty micrograms. The amount of paclitaxel delivered from this stent is about five to about fifty micrograms, preferably about ten to about thirty micrograms. As in Example 8, the drugs may be located in alternating holes in the stent or interspersed in a non-alternating manner. The polymer/drug inlays are formed in the manner described in Example 8.

Therapeutic Agents

The present invention relates to the delivery of anti-restenotic agents including paclitaxel, rapamycin, cladribine (CdA), and their derivatives, as well as other cytotoxic or cytostatic agents and microtubule stabilizing agents. Although anti-restenotic agents have been primarily described herein, the present invention may also be used to deliver other agents alone or in combination with anti-restenotic agents. Some of the therapeutic agents for use with the present invention which may be transmitted primarily luminally, primarily murally, or both and may be delivered alone or in combination include, but are not limited to, antiproliferatives, antithrombins, immunosuppressants including sirolimus, antilipid agents, anti-inflammatory agents, antineoplastics, antiplatelets, angiogenic agents, anti-angiogenic agents, vitamins, antimitotics, metalloproteinase inhibitors, NO donors, estradiols, anti-sclerosing agents, and vasoactive agents, endothelial growth factors, estrogen, beta blockers, AZ blockers, hormones, statins, insulin growth factors, antioxidants, membrane stabilizing agents, calcium antagonists, retenoid, bivalirudin, phenoxodiol, etoposide, ticlopidine, dipyridamole, and trapidil alone or in combinations with any therapeutic agent mentioned herein. Therapeutic agents also include peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, ACE inhibitors, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting, and vasodilation.

Anti-inflammatories include but are not limited to nonsteroidal anti-inflammatories (NSAID), such as aryl acetic acid derivatives, e.g., Diclofenac; aryl propionic acid derivatives, e.g., Naproxen; and salicylic acid derivatives, e.g., Diflunisal. Anti-inflammatories also include glucocoriticoids (steroids) such as dexamethasone, aspirin, prednisolone, and triamcinolone, pirfenidone, meclofenamic acid, tranilast, and nonsteroidal anti-inflammatories. Anti-inflammatories may be used in combination with antiproliferatives to mitigate the reaction of the tissue to the antiproliferative.

The agents may also include anti-lymphocytes; anti-macrophage substances; immunomodulatory agents; cyclooxygenase inhibitors; anti-oxidants; cholesterol-lowering drugs; statins and angiotens in converting enzyme (ACE); fibrinolytics; inhibitors of the intrinsic coagulation cascade; antihyperlipoproteinemics; and anti-platelet agents; anti-metabolites, such as 2-chlorodeoxy adenosine (2-CdA or cladribine); immuno-suppressants including sirolimus, everolimus, tacrolimus, etoposide, and mitoxantrone; anti-leukocytes such as 2-CdA, IL-1 inhibitors, anti-CD116/CD18 monoclonal antibodies, monoclonal antibodies to VCAM or ICAM, zinc protoporphyrin; anti-macrophage substances such as drugs that elevate NO; cell sensitizers to insulin including glitazones; high density lipoproteins (HDL) and derivatives; and synthetic facsimile of HDL, such as lipator, lovestatin, pranastatin, atorvastatin, simvastatin, and statin derivatives; vasodilators, such as adenosine, and dipyridamole; nitric oxide donors; prostaglandins and their derivatives; anti-TNF compounds; hypertension drugs including Beta blockers, ACE inhibitors, and calcium channel blockers; vasoactive substances including vasoactive intestinal polypeptides (VIP); insulin; cell sensitizers to insulin including glitazones, P par agonists, and metformin; protein kinases; antisense oligonucleotides including resten-NG; antiplatelet agents including tirofiban, eptifibatide, and abciximab; cardio protectants including, VIP, pituitary adenylate cyclase-activating peptide (PACAP), apoA-I milano, amlodipine, nicorandil, cilostaxone, and thienopyridine; cyclooxygenase inhibitors including COX-1 and COX-2 inhibitors; and petidose inhibitors which increase glycolitic metabolism including omnipatrilat. Other drugs which may be used to treat inflammation include lipid lowering agents, estrogen and progestin, endothelin receptor agonists and interleukin-6 antagonists, and Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic surfactants may be used. Examples of nonionic excipients include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEO) and polyvinyl pyrrolidone (PVP); carboxylic acids including D-lactic acid, glycolic acid, and propionic acid; surfactants with affinity for hydrophobic interfaces including n-dodecyl-.beta.-D-maltoside, n-octyl-.beta.-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; (PC) CM-PEG; cholic acid; sodium dodecyl sulfate (SDS); docusate (AOT); and taumocholic acid.

In accordance with another exemplary embodiment, a stent or intraluminal scaffold as described herein, may be coated with an anti-thrombotic agent in addition to one or more therapeutic agents deposited in the holes or openings. In one exemplary embodiment, the stent may be fabricated with the openings therein and prior to the addition or deposition of other therapeutic agents into the openings, an anti-thrombotic agent, with or without a carrier vehicle (polymer or polymeric matrix) may be affixed to the stent or a portion thereof. In this exemplary embodiment, the luminal and abluminal surfaces of the stent may be coated with the anti-thrombotic agent or coating, as well as the surfaces of the walls of the openings. In an alternative exemplary embodiment, a stent may first be coated with an anti-thrombotic agent or coating and then the openings may be fabricated. In this exemplary embodiment, only the luminal and abluminal surfaces would have the anti-thrombotic agent or coating and not the walls of the openings. In each of these embodiments any number of anti-thrombotic agents may be affixed to all or portions of the stents. In addition, any number of known techniques may be utilized to affix the anti-thrombotic agent to the stent such as that utilized with the HEPACOAT™ on the Bx Velocity® Coronary Stent from Cordis Corporation. Alternatively, the stents may be manufactured with a rough surface texture or have a microtexture to enhance cell attachment and endothelialization, independently of or in addition to the anti-thrombotic coating. In addition, any number of therapeutic agents may be deposited into the openings and different agents may be utilized in different regions of the stent.

As described above, it is important to note that any number of drugs and or agents may be utilized in accordance with the present invention including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)II$_b$III$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, and growth factor signal transduction kinase inhibitors.

Figure 107A:
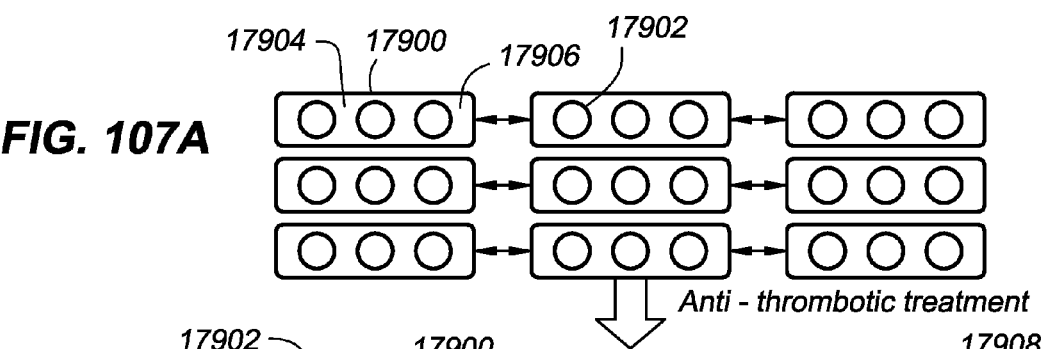
FIGS. 107A, 107B, 107C are partial diagrammatic representations of an alternate exemplary embodiment of an expandable medical device in accordance with the present invention.
Figure 107B:
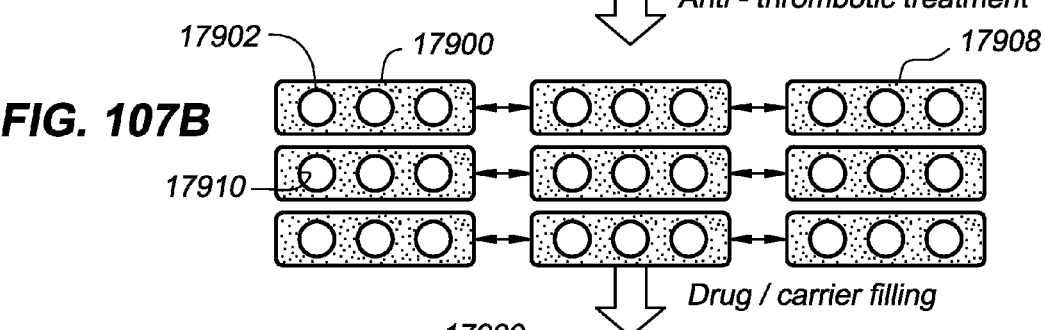
Figure 107C:
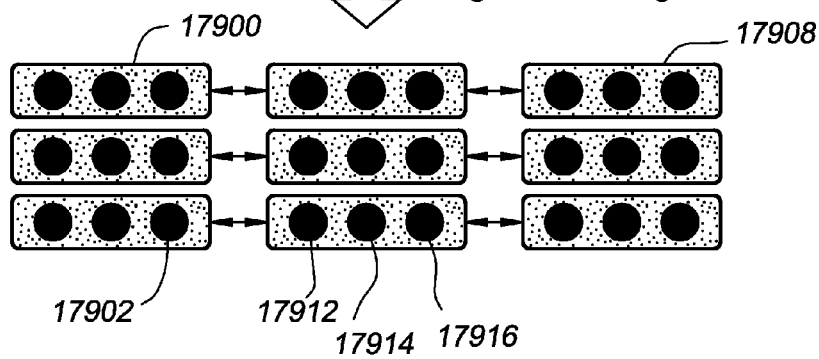

Referring now to FIGS. 107A, 107B and 107C, there is illustrated a diagrammatic representation of a portion of a stent.

As illustrated in FIG. 107A the stent 17900 comprises a plurality of substantially circular openings 17902. In this exemplary embodiment, the plurality of substantially circular openings 17902 extend through the wall of the stent 17900. In other words, the plurality of substantially circular openings 17902 extend from the abluminal surface of the stent 17904 to the abluminal surface of the stent 17906, wherein the wall thickness is defined as the distance between the luminal and abluminal surfaces. In other embodiments, however, the openings need not extend through the wall of the stent 17900. For example, the openings or reservoirs may extend partially from either the luminal or abluminal surfaces or both. The stent 17900 in FIG. 107A has untreated surfaces 17904 and 17906 and empty openings 17902.

In FIG. 107B, at least one surface has been coated with a therapeutic agent 17908. The therapeutic agent preferably comprises an anti-thrombotic agent such as heparin; however, any anti-thrombotic agent may be utilized. The anti-thrombotic agent may be affixed utilizing any technique as briefly described above. In this exemplary embodiment, both the abluminal and luminal surfaces have an anti-thrombotic agent affixed thereto. In addition, as there is nothing in the plurality of substantially circular openings 17902 at this juncture, the walls of the openings 17902 may also have some anti-thrombotic agent affixed thereto. The amount of anti-thrombotic agent affixed to the walls of the openings 910 depends on how the agent is affixed. For example, if the agent is affixed by dip coating, the walls of the openings will have more agent affixed thereto than if the agent is affixed utilizing a spray coating technique. As described herein, in this exemplary embodiment, all exposed surfaces have a substantial anti-thrombotic coating affixed thereto; however, in alternate exemplary embodiments, only specific surfaces may have an anti-thrombotic affixed thereto. For example, in one exemplary embodiment, only the surface in contact with the blood may be treated with the anti-thromobotic agent. In yet another alternate exemplary embodiment, one or both surfaces may be coated with the anti-thrombotic agent while the walls of the openings are not. This may be accomplished in a number of ways including plugging the openings prior to coating or creating the openings after the anti-thrombotic agent is affixed.

FIG. 107C illustrates a completed stent in accordance with this exemplary embodiment. As illustrated in this figure, the plurality of substantially circular openings 17902 have been filled with one or more therapeutic agents for treating vascular diseases such as restenosis and inflammation or any other dieses as described herein. Each opening 17902 may be filled with the same therapeutic agent or different agents as described in detail above. As illustrated in the figure, these different agents 17912, 17914 and 17916 are used in a particular pattern; however, as detailed above, any combination is possible as well as utilizing a singe agent with different concentrations. The drugs, such as a rapamycin, may be deposited in the openings 17902 in any suitable manner. Techniques for depositing the agent include micropippetting and/or ink-jet filling methods. In one exemplary embodiment, the drug filling may be done so that the drug and/or drug/polymer matrix in the opening will be below the level of the stent surfaces so that there is no contact with the surrounding tissue. Alternately, the openings may be filled so that the drug and/or drug/polymer matrix may contact the surrounding tissue. In addition, the total dose of each of the drugs, if multiple drugs are utilized, may be designed with maximal flexibility. Additionally, the release rate of each of the drugs may be controlled individually. For example, the openings near the ends may contain more drugs to treat edge restenosis.

In accordance with this exemplary embodiment, the hole or openings may be configured not only for the most efficacious drug therapy, but also for creating a physical separation between different drugs. This physical separation may aid in preventing the agents from interacting.

As used herein, rapamycin includes rapamycin and all analogs, derivatives and conjugates that bind to FKBP12, and other immunophilins and possesses the same pharmacologic properties as rapamycin including inhibition of TOR. In addition, all drugs and agents described herein in their analogs, derivatives and conjugates.

In accordance with another exemplary embodiment, a polymeric construct comprising a layer-by-layer arrangement of stereospecific polymers may be utilized as drug or therapeutic agent depot carriers or coatings for use in conjunction with medical devices. Medical devices as utilized herein means any of the devices described herein for local or regional drug delivery. Essentially, this polymeric construct may be utilized with any of the therapeutic agents or combinations thereof described herein, with any of the drug delivery devices described herein and with any of the implantable medical devices described herein. In addition, as intimated above, the polymeric construct may be utilized as a coating for coating some or all of the surfaces of an implantable medical device or as a carrier for filling reservoirs in implantable medical devices. The polymeric construct may take on any number of forms as is described in detail below.

In one exemplary embodiment the construct is formed from alternating layers of chemically identical, biodegradable polymers with different optical rotations. In this exemplary embodiment the biodegradable polymers are poly(D-lactic acid) (PDLA) and poly(L-lactic acid)(PLLA). Poly(D-lactic acid) is synthesized from stereo-specific RR-lactide dimer using a catalyst that maintains the chiral configurations during the ring-opening polymerization (ROP) process. Conversely, poly(L-lactic acid) is synthesized from SS-lactide dimer using a ROP process. The ROP conditions are known to those skilled also in the relevant art. These alternating layers in close proximity to one another form a sterocomplex that provides for superior results with respect to the local and regional drug and/or therapeutic agent delivery. In other words, the identical chemical properties of the two stereo-specific polymers with variable physical properties enable a broad range of therapeutic agent stability and release controls. In addition, changes in the rheological properties of these sterocomplexed biodegradable polymers make these materials denser and lead to the use of a thinner coating thickness and potentially lower molecular weight polymer while achieving equal or better results than non-sterocomplexed polymers. These thinner coatings preferably should improve the long term biocompatibility of the coating and shorten the resorption time. Essentially, the layered poly(D-lactic acid) and poly(L-lactic acid) create sterocomplexes in situ that provide better control of therapeutic agent release pharmakinetics with a smaller amount of drug carrier matrix.

Figure 108A:
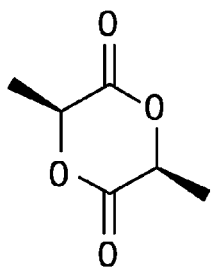
FIGS. 108A, 108B and 108C are exemplary lactide dimmers utilized in the synthesis of stereo-specific polylactides in accordance with the present invention.
Figure 108B:
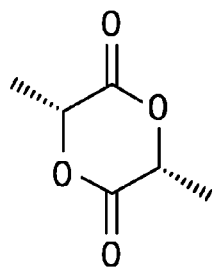
Figure 108C:
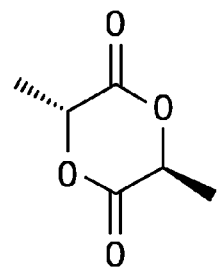

Polymer-polymer complexes may be formed upon the mixing of polymers of different chemical compositions under suitable conditions. These complexes include a polyelectrolyte complex between a polycation and a polyanion, a hydrogen bonding complex between a poly(carboxylic acid) and a polyether or polyol and a charge transfer complex between a polymeric donor and acceptor. However, only limited instances are known wherein a complex formation may occur between polymers of identical composition but different steric structures. The first such believed complex was observed by Ikada, Y., et al., Sterocomplex formation Between Enantiomeric poly(lactides), Marcomolecter, 1987, 20, 904-906, in 1987 between poly(L-lactic acid) and poly(D-lactic acid). It is known that polymers made from D, L-lactide are amorphous and optically inactive, while polymers made from L-lactide and D-lactide are partially crystalline and optically active. The L-lactide polymer is more crystalline than a D-lactide based polymer and may be more hydrophobic and thus degrade more slowly as a result. Ikada's study also demonstrated that when equal moles of poly(L-lactic acid) and poly(D-lactic acid) are mixed, the polymer blend has a single melting point of two-hundred thirty degrees C. which is higher than either of the individual melting points, approximately one hundred eighty degrees C. The crystalline structure of poly(L-lactide) made from SS-lactide as shown in FIG. 108A, consists of left-handed helical chains and poly(D-lactide), made from RR-lactide as shown in FIG. 108B, has a right-handed helical crystalline structure. FIG. 108C illustrates a meso-lactide which when polymerized results in an amorphous, racemic polymer.

Figure 109:
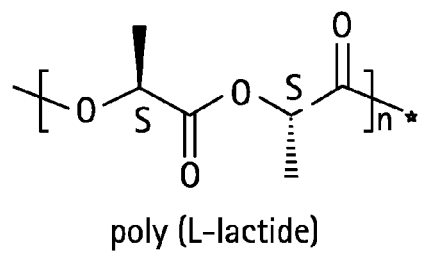
FIG. 109 illustrates a poly L-lactide in accordance with the present invention.
Figure 110:
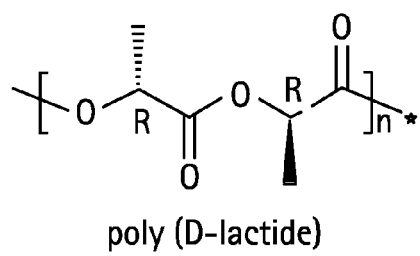
FIG. 110 illustrates a poly D-lactide in accordance with the present invention.

The observations made by Ikada et al. may have significant implications when these lactide dimers are utilized in the synthesis of stereospecific polylactide as illustrated in FIGS. 109 poly(L-lactide) and 110 poly(D-lactide). It is for the reasons described herein that the sterocomplex formed between poly(D-lactic acid) and poly(L-lactic acid) may be more effective in providing a control over drug elution with comparatively smaller quantity of the carrier or thinner coating or optionally lower molecular weight. The sterocomplex formed between poly(D-lactic acid) and poly(L-lactic acid) may result in greater physical stability due to its resultant higher melting temperature and may also result in better storage of the therapeutic agent or agents contained therein. In addition, the lower molecular weight of the poly(D-lactic acid) and the poly(L-lactic acid) utilized in the serocomplex is likely to result in a shortened resportion time and better biocompatibility compared to the higher molecular weight individual polymers.

An exemplary process to take advantage of such sterocomplexes of poly(D-lactic acid) and poly(L-lactic acid) comprises mixing one of the stereospecific and optically pure polylactic acids with a therapeutic agent or combination of agents and coat at least a portion of the surface of a medical device using a common coating method such as spray coating. Any type of coating technique may be utilized such as those described herein. The next step involves mixing another stereospecific and optically pure polylactic acid with opposite optical rotation with a therapeutic agent or combination of agents and coating on top of the previous layer, optionally while the previous layer is still "wet." These polymers of opposite stereospecificity will bind in situ to form a sterocomplex and hold the therapeutic agent or combination of therapeutic agents in place for local or regional drug delivery. The process described above may be repeated any number of times until a proper level of therapeutic agent or combination of therapeutic agents is achieved. A top layer or coating of any of the two optically active polymers or a combination thereof may be applied to further regulate the release rate of the therapeutic agent or combination of agents from the coatings.

This process may be applied to at least a portion of the surface or surfaces of any of the medical devices described herein utilizing any of the therapeutic agents described herein, or combinations thereof, and utilizing any of the coating techniques described herein. In addition, the above described process may be utilized with or without therapeutic agents.

In an alternative exemplary embodiment, the therapeutic agents may be added after each layer is coated on the device rather than be mixed with the polymeric layers.

In yet another alternate exemplary embodiment, the combination of the optically pure polylactides and/or therapeutic agents described above may be mixed and deposited into a receptacle, for example, a well, inside of a medical device to accomplish the layer-by-layer therapeutic agent leading configuration.

Figure 111A:
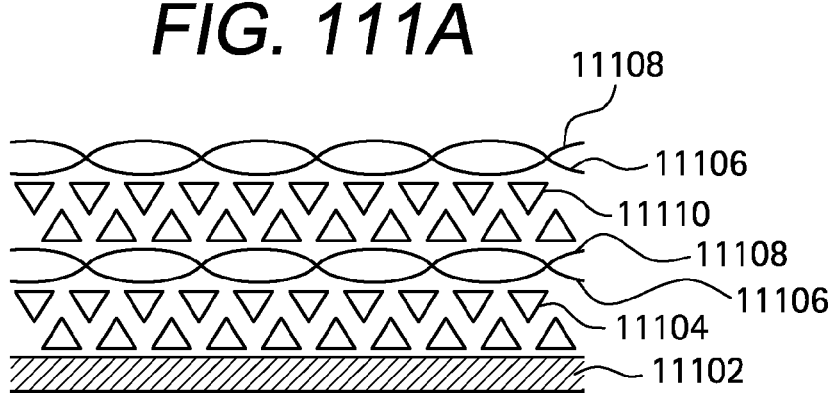
FIGS. 111A, 111B and 111C illustrate coating or deposition schemes utilizing alternating layer-by-layer polymers having identical chemical compositions but with different optical rotations with therapeutic agents in accordance with the present invention.
Figure 111B:
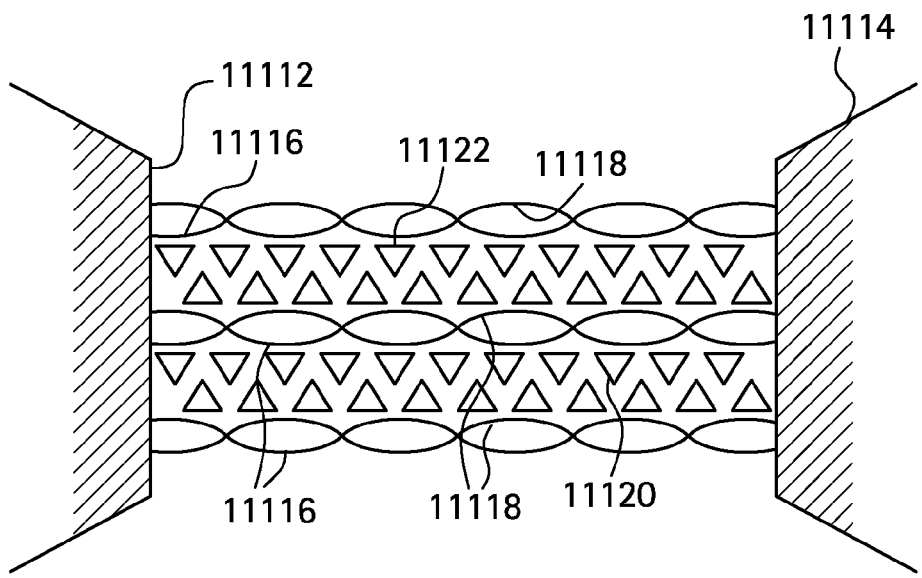
Figure 111C:
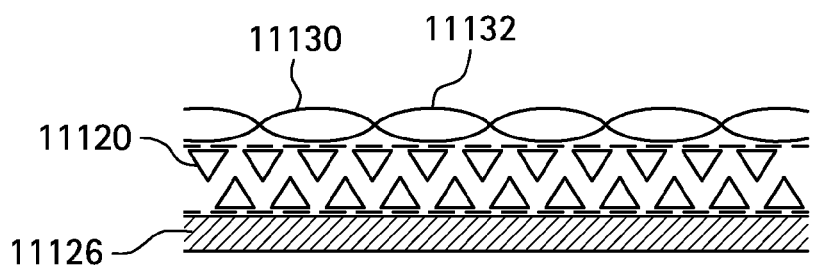

Referring to FIGS. 111A, 111B and 111C, there is illustrated the exemplary coating or deposition scheme utilizing an alternating layer-by-layer of poly(D-lactic acid) and poly(L-lactic acid) optionally with a therapeutic agent or agents interspersed therebetween. Specifically, in FIG. 111A there is illustrated a section 11102 of a medical device having the layer-by-layer sterocomplexed coating thereon. In this exemplary embodiment, one or more first therapeutic agents 11104 is mixed with poly(D-lactic acid) 11106 and affixed to the surface of the section 11102 of the medical device. A second layer comprising poly(L-lactic acid) 11108 is affixed to the first layer thereby forming the basic building block of the layer-by-layer construct. It is important to note that additional layers may be utilized, with the same or different therapeutic agents 1110 so long as chemically identical, but physically different polymers were utilized. As illustrated, one or more additional therapeutic agents 11110 are affixed to the polymer building block layer and then a second polymer building block layer comprising poly(D-lactic acid) 11106 and poly(L-lactic acid) 11108 is affixed thereto.

FIG. 111B illustrates a reservoir 11112 in a section 11114 of a medical device having the layer-by-layer sterocomplexed coating deposited therein. In this exemplary embodiment, a first bottom barrier layer consisting of poly(D-lactic acid) 11116 and poly(L-lactic acid) 11118 is laid down by a standard deposition method such as ink-jetting. Poly(D-lactic acid) and poly(L-lactic acid) may be pre-mixed in a common solvent and deposited into the reservoir, deposited sequentially to form the stereopcomplex barrier layer. The amount of poly(D-lactic acid) and poly(L-lactic acid) is preferably substantially the same. Subsequently poly(D-lactic acid) 11116 mixed with a therapeutic agent 11120 or combinations of therapeutic agents 11120 are deposited in the reservoir, followed by deposition of poly(D-lactic acid) 11118 to form in situ stereocomplex and drug polymer matrix. A second layer of stereocomplex of poly(D-lactic acid) and poly(L-lactic acid), optionally mixed with the same or different therapeutic agent 11122 may be deposited on the first layer, forming the layer-by-layer construct once again. Such alternating layers may be repeated for a number of times. Optional top barrier layers comprising poly(D-lactic acid) and poly(L-lactic acid) 1118 may be deposited to regulate drug release from the top side of the reservoir.

As set forth above, the therapeutic agent or agents may be mixed with the polymers or just deposited or coated in between the polymers.

FIG. 111C illustrates a layer-by-layer deposition of poly(D-lactic acid) 11130 and poly(L-lactic acid) 11132 utilized as a drug diffusion barrier for a therapeutic agent or combination of agents 11128 on the surface of a section 11126 of a medical device.

Figure 112A:
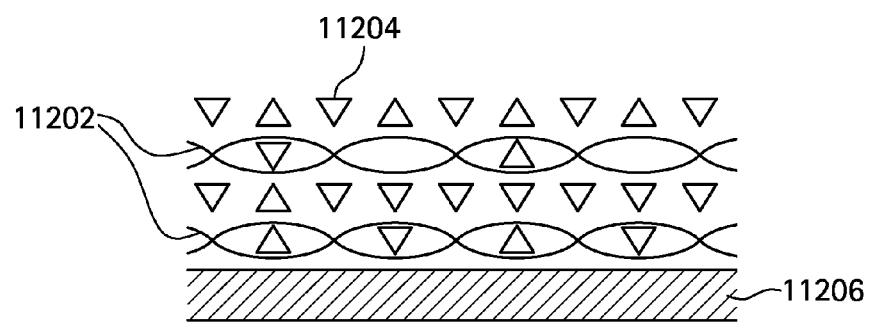
FIGS. 112A and 112B illustrate coating or deposition schemes utilizing solutions containing both poly(D-lactic acid) and poly(L-lactic acid) at a substantially one-to-one molar ratio in accordance with the present invention.
Figure 112B:
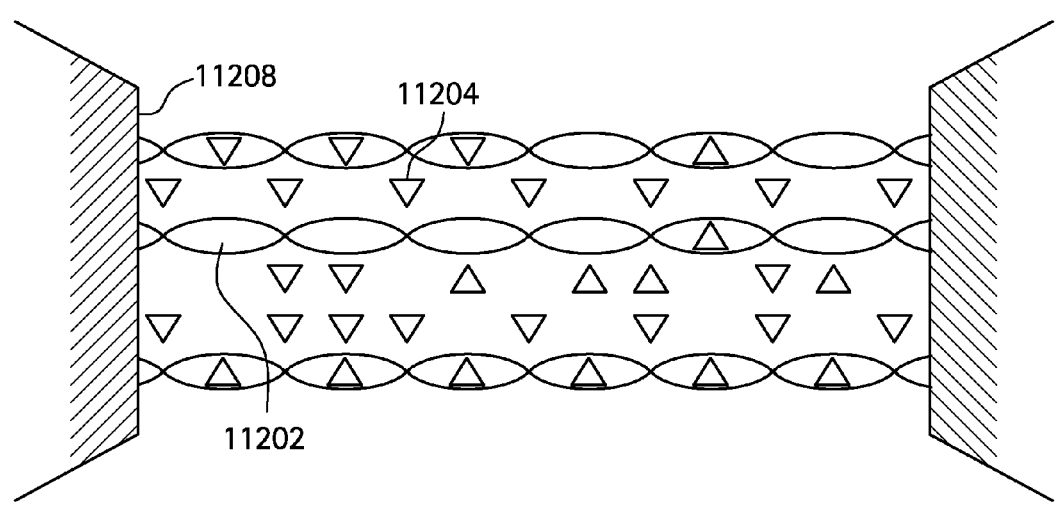

FIGS. 112A and 112B illustrate a coating or deposition scheme utilizing polymer solutions 11202 comprising both poly(D-lactic acid) and poly (L-lactic acid) at a substantially one to one molar ratio, optionally with a therapeutic agent or agents 11204 dispersed within the solution and affixed to a surface 11206 of a device or deposited in a reservoir 11208 of a device.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An implantable medical device consisting of:
   a metallic structure configured for implantation in an organ of the body;
   a solution of a first stereospecific and optically pure biodegradable polymer affixed to at least a portion of the metallic structure, and
   a solution of a second stereospecific and optically pure biodegradable polymer having an opposite optical rotation from that of the first stereospecific and optically pure biodegradable polymer, the solution of the second stereospecific and optically pure biodegradable polymer being affixed to the solution of the first stereospecific and optically pure biodegradable polymer, wherein the first and second solutions of stereospecific and optically pure biodegradable polymers are layered in a solution form on top of one another in an alternating fashion and bind in situ to form at least one stereo polymer complex layer that is substantially crystalline, wherein the stereo polymer complex layer consists of a pair of substantially even, alternate discrete layers of the first and second stereospecific and optically pure biodegradable polymers and wherein at least one therapeutic agent is interspersed beneath the at least one stereo polymer complex layer.

2. The implantable medical device according to claim 1, wherein the first and second stereospecific and optically pure biodegradable polymers are configured as a layer-by-layer complex and deposited in reservoirs in the structure.

3. The implantable medical device according to claim 1, wherein the structure is a stent.

4. The implantable medical device according to claim 1, wherein the first and second stereospecific and optically pure biodegradable polymers each are one of poly (D-lactic acid) and poly (L-lactic acid).

* * * * *